US010745385B2

United States Patent
Li et al.

(10) Patent No.: US 10,745,385 B2
(45) Date of Patent: Aug. 18, 2020

(54) COVALENT INHIBITORS OF KRAS

(71) Applicant: Araxes Pharma LLC, San Diego, CA (US)

(72) Inventors: Liansheng Li, San Diego, CA (US); Jun Feng, San Diego, CA (US); Tao Wu, Carlsbad, CA (US); Yuan Liu, San Diego, CA (US); Yi Wang, San Diego, CA (US); Pingda Ren, San Diego, CA (US); Yi Liu, San Diego, CA (US)

(73) Assignee: Araxes Pharma LLC, San Diego, CA (US)

( * ) Notice: Subject to any disclaimer, the term of this patent is extended or adjusted under 35 U.S.C. 154(b) by 0 days.

(21) Appl. No.: 15/989,015

(22) Filed: May 24, 2018

(65) Prior Publication Data
US 2019/0062313 A1 Feb. 28, 2019

Related U.S. Application Data

(60) Provisional application No. 62/511,163, filed on May 25, 2017, provisional application No. 62/625,889, filed on Feb. 2, 2018.

(51) Int. Cl.
| | |
|---|---|
| *C07D 403/14* | (2006.01) |
| *C07D 403/04* | (2006.01) |
| *A61P 35/00* | (2006.01) |
| *C07D 401/14* | (2006.01) |
| *C07D 413/14* | (2006.01) |
| *C07D 417/14* | (2006.01) |
| *C07D 405/14* | (2006.01) |
| *C07D 471/04* | (2006.01) |
| *C07D 487/08* | (2006.01) |

(52) U.S. Cl.
CPC ............ *C07D 403/14* (2013.01); *A61P 35/00* (2018.01); *C07D 401/14* (2013.01); *C07D 403/04* (2013.01); *C07D 405/14* (2013.01); *C07D 413/14* (2013.01); *C07D 417/14* (2013.01); *C07D 471/04* (2013.01); *C07D 487/08* (2013.01); *C07B 2200/07* (2013.01)

(58) Field of Classification Search
CPC .. C07D 401/14; C07D 403/04; C07D 403/14; C07D 405/14; C07D 413/14; C07D 417/14; C07D 471/04; C07D 487/08; C07B 2200/07; A61P 35/00
See application file for complete search history.

(56) References Cited

U.S. PATENT DOCUMENTS

| | | | |
|---|---|---|---|
| 3,702,849 | A | 11/1972 | Cronin et al. |
| 3,752,660 | A | 8/1973 | Little |
| 4,439,606 | A | 3/1984 | Du et al. |
| 4,649,219 | A | 3/1987 | Itoh et al. |
| 4,656,181 | A | 4/1987 | Sunkel et al. |
| 4,861,760 | A | 8/1989 | Mazuel et al. |
| 4,911,920 | A | 3/1990 | Jani et al. |
| 5,010,175 | A | 4/1991 | Rutter et al. |

(Continued)

FOREIGN PATENT DOCUMENTS

| | | |
|---|---|---|
| CN | 1267291 A | 9/2000 |
| CN | 104 418 860 B | 9/2016 |

(Continued)

OTHER PUBLICATIONS

McGregor et al., "Expanding the Scope of Electrophiles Capable of Targeting K-Ras Oncogenes," *Biochemistry* 56:3178-3183, 2017.
American Chemical Society, STN Database: Nov. 16, 1984, RN5530-21-2.
Appel et al., "Supramolecular Cross-Linked Networks via Host-Guest Complexation with Cucurbit[8]uril,"*J. Am. Chem. Soc.* 132(40):14251-14260, Jul. 2010.
Adibekian et al., "Optimization and characterization of a triazole urea dual inhibitor for lysophospholipase 1 (LYPLA1) and lysophospholipase 2 (LYPLA2)," *Probe Reports from the NIH Molecular Libraries Program*, 2011, 42 pages.
Al-Muhammed et al., "In-vivo studies on dexamethasone sodium phosphate liposomes," *J. Microencapsulation* 13(3):293-306, 1996.
Arkin et al., "Binding of small molecules to an adaptive protein—protein interface," *PNAS* 100(4):1603-1608, Feb. 2003.
Bachovchin et al., "Identification of selective inhibitors of uncharacterized enzymes by high-throughput screening with fluorescent activity-based probes," *Nat. Biotechnol* 27(7)387-394, 2009.

(Continued)

*Primary Examiner* — Sarah Pihonak
(74) *Attorney, Agent, or Firm* — Seed Intellectual Property Law Group LLP

(57) ABSTRACT

Compounds having activity as inhibitors of G12C mutant KRAS protein are provided. The compounds have the following structure (I):

or a pharmaceutically acceptable salt, stereoisomer, isotopic form or prodrug thereof, wherein $R^1$, $R^{2a}$, $R^{2b}$, $R^{2c}$, $R^{3a}$, $R^{3b}$, $R^{4a}$, $R^{4b}$, $R^5$, $L^1$, $L^2$, $L^3$, E, $m^1$, $m^2$ and * are as defined herein. Methods associated with preparation and use of such compounds, pharmaceutical compositions comprising such compounds and methods to modulate the activity of G12C mutant KRAS protein for treatment of disorders, such as cancer, are also provided.

54 Claims, No Drawings

(56) References Cited

U.S. PATENT DOCUMENTS

| | | |
|---|---|---|
| 5,033,252 A | 7/1991 | Carter |
| 5,052,558 A | 10/1991 | Carter |
| 5,212,162 A | 5/1993 | Missel et al. |
| 5,288,514 A | 2/1994 | Ellman |
| 5,323,907 A | 6/1994 | Kalvelage |
| 5,403,841 A | 4/1995 | Lang et al. |
| 5,538,848 A | 7/1996 | Livak et al. |
| 5,539,083 A | 7/1996 | Cook et al. |
| 5,593,853 A | 1/1997 | Chen et al. |
| 5,605,798 A | 2/1997 | Köster |
| 5,670,505 A | 9/1997 | Matsuo et al. |
| 5,731,352 A | 3/1998 | Lesieur et al. |
| 5,777,324 A | 7/1998 | Hillenkamp |
| 5,858,659 A | 1/1999 | Sapolsky et al. |
| 5,861,510 A | 1/1999 | Piscopio et al. |
| 5,863,949 A | 1/1999 | Robinson et al. |
| 5,919,626 A | 7/1999 | Shi et al. |
| 5,925,525 A | 7/1999 | Fodor et al. |
| 5,952,174 A | 9/1999 | Nikiforov et al. |
| 6,002,008 A | 12/1999 | Wissner et al. |
| 6,017,696 A | 1/2000 | Heller |
| 6,043,031 A | 3/2000 | Köster et al. |
| 6,045,996 A | 4/2000 | Cronin et al. |
| 6,051,380 A | 4/2000 | Sosnowski et al. |
| 6,068,818 A | 5/2000 | Ackley et al. |
| 6,214,872 B1 | 4/2001 | Robinson |
| 6,251,639 B1 | 6/2001 | Kurn |
| 6,511,993 B1 | 1/2003 | Dack et al. |
| 6,689,779 B2 | 2/2004 | Lee et al. |
| 6,903,118 B1 | 6/2005 | Biedermann et al. |
| 7,074,801 B1 | 7/2006 | Yoshida et al. |
| 7,595,397 B2 | 9/2009 | Zindell et al. |
| 7,879,863 B2 | 2/2011 | Tokumasu et al. |
| 8,399,454 B2 | 3/2013 | Bian et al. |
| 8,426,401 B2 | 4/2013 | Bian et al. |
| 8,466,288 B2 | 6/2013 | Aronov |
| 8,604,017 B2 | 12/2013 | Bian et al. |
| 8,697,684 B2 | 4/2014 | Bian et al. |
| 8,741,887 B2 | 6/2014 | Bian et al. |
| 8,759,333 B2 | 6/2014 | Connolly et al. |
| 9,126,952 B2 | 9/2015 | Mederski et al. |
| 9,227,978 B2 | 1/2016 | Ren et al. |
| 9,376,559 B2 | 6/2016 | Holtcamp et al. |
| 9,695,179 B2 | 7/2017 | Vankayalapati et al. |
| 9,745,319 B2 | 8/2017 | Ren et al. |
| 9,810,690 B2 | 11/2017 | Patricelli et al. |
| 9,840,516 B2 | 12/2017 | Li et al. |
| 9,862,701 B2 | 1/2018 | Li et al. |
| 9,926,267 B2 | 3/2018 | Ren et al. |
| 9,938,292 B2 | 4/2018 | Wu et al. |
| 9,988,357 B2 | 6/2018 | Mani et al. |
| 10,023,588 B2 | 7/2018 | Ostrem et al. |
| 10,111,874 B2 | 10/2018 | Janes et al. |
| 10,144,724 B2 | 12/2018 | Li et al. |
| 10,351,550 B2 | 7/2019 | Li et al. |
| 10,370,386 B2 | 8/2019 | Li et al. |
| 10,377,743 B2 | 8/2019 | Li et al. |
| 10,414,757 B2 | 9/2019 | Li et al. |
| 10,428,064 B2 | 10/2019 | Li et al. |
| 2002/0169300 A1 | 11/2002 | Waterman et al. |
| 2003/0022344 A1 | 1/2003 | Williams et al. |
| 2003/0166620 A1 | 9/2003 | Lee et al. |
| 2003/0171400 A1 | 9/2003 | Pikul et al. |
| 2004/0106634 A1 | 6/2004 | Satoh et al. |
| 2005/0012070 A1 | 1/2005 | Inoue et al. |
| 2005/0119266 A1 | 6/2005 | Shi et al. |
| 2005/0227997 A1 | 10/2005 | Noe et al. |
| 2006/0167044 A1 | 7/2006 | Arnaiz et al. |
| 2008/0004285 A1 | 1/2008 | De Jonghe et al. |
| 2008/0004348 A1 | 1/2008 | Yous et al. |
| 2008/0039450 A1 | 2/2008 | Jensen et al. |
| 2009/0036430 A1 | 2/2009 | De Jonghe et al. |
| 2009/0054402 A1 | 2/2009 | Wang et al. |
| 2009/0124636 A1 | 5/2009 | Barber et al. |
| 2009/0298075 A1 | 12/2009 | Travers et al. |
| 2010/0331300 A1 | 12/2010 | Bian et al. |
| 2011/0046370 A1 | 2/2011 | Sim et al. |
| 2011/0230476 A1 | 9/2011 | Niu et al. |
| 2011/0269244 A1 | 11/2011 | Petter et al. |
| 2011/0311447 A1 | 12/2011 | Tu et al. |
| 2011/0319290 A1 | 12/2011 | Raymond et al. |
| 2013/0012489 A1 | 1/2013 | Mederski |
| 2013/0029964 A1 | 1/2013 | Aoki et al. |
| 2013/0274252 A1 | 10/2013 | Pandey et al. |
| 2013/0302407 A1 | 11/2013 | Rao et al. |
| 2014/0288045 A1 | 9/2014 | Ren et al. |
| 2014/0315886 A1 | 10/2014 | Suzuki |
| 2015/0087628 A1 | 3/2015 | Ostrem et al. |
| 2015/0239900 A1 | 8/2015 | Li et al. |
| 2015/0283142 A1 | 10/2015 | Stern et al. |
| 2015/0374678 A1 | 12/2015 | Chamberlain et al. |
| 2016/0031898 A1 | 2/2016 | Ren et al. |
| 2016/0108019 A1 | 4/2016 | Li et al. |
| 2016/0159738 A1 | 6/2016 | Ren et al. |
| 2016/0166571 A1 | 6/2016 | Janes et al. |
| 2016/0297774 A1 | 10/2016 | Li et al. |
| 2016/0368930 A1 | 12/2016 | Ostrem et al. |
| 2017/0022184 A1 | 1/2017 | Li et al. |
| 2017/0131278 A1 | 5/2017 | Patricelli et al. |
| 2017/0190672 A1 | 7/2017 | Mani et al. |
| 2017/0197945 A1 | 7/2017 | Li et al. |
| 2017/0247376 A1 | 8/2017 | Li et al. |
| 2018/0015087 A1 | 1/2018 | Liu et al. |
| 2018/0086753 A1 | 3/2018 | Li et al. |
| 2018/0118757 A1 | 5/2018 | Li et al. |
| 2018/0127396 A1 | 5/2018 | Li et al. |
| 2018/0141927 A1 | 5/2018 | Li et al. |
| 2018/0155348 A1 | 6/2018 | Li et al. |
| 2018/0162812 A1 | 6/2018 | Ren et al. |
| 2018/0194748 A1 | 7/2018 | Li et al. |
| 2018/0246102 A1 | 8/2018 | Patricelli et al. |
| 2018/0273515 A1 | 9/2018 | Li et al. |
| 2018/0273523 A1 | 9/2018 | Li et al. |
| 2018/0282307 A1 | 10/2018 | Li et al. |
| 2018/0282308 A1 | 10/2018 | Li et al. |
| 2018/0319775 A1 | 11/2018 | Li et al. |
| 2019/0055211 A1 | 2/2019 | Li et al. |
| 2019/0062314 A1 | 2/2019 | Li et al. |
| 2019/0092767 A1 | 3/2019 | Li et al. |
| 2019/0127336 A1 | 5/2019 | Li et al. |
| 2019/0262342 A1 | 8/2019 | Janes et al. |
| 2019/0284144 A1 | 9/2019 | Li et al. |
| 2019/0345158 A1 | 11/2019 | Li et al. |
| 2019/0367489 A1 | 12/2019 | Li et al. |
| 2019/0382377 A1 | 12/2019 | Li et al. |
| 2019/0389796 A1 | 12/2019 | Ren et al. |
| 2019/0389851 A1 | 12/2019 | Li et al. |

FOREIGN PATENT DOCUMENTS

| | | |
|---|---|---|
| EP | 0 094 498 A2 | 11/1983 |
| EP | 0 606 046 A1 | 7/1994 |
| EP | 0 780 386 A1 | 6/1997 |
| EP | 0 818 442 A2 | 1/1998 |
| EP | 0 931 788 A2 | 7/1999 |
| EP | 0 655 442 B1 | 5/2001 |
| EP | 1 004 578 A1 | 5/2001 |
| EP | 1 348 434 A1 | 10/2003 |
| EP | 1 736 465 A1 | 12/2006 |
| EP | 2 133 334 A1 | 12/2009 |
| EP | 2 270 002 A1 | 1/2011 |
| EP | 2 889 291 A1 | 7/2015 |
| GB | 939516 A | 10/1963 |
| JP | 58-203966 A | 11/1983 |
| JP | 59-163372 A | 9/1984 |
| JP | 2005-502623 A | 1/2005 |
| JP | 2005-179557 A | 7/2005 |
| JP | 2007-16011 A | 1/2007 |
| JP | 2008-524154 A | 7/2008 |
| JP | 2013-516422 A | 5/2013 |
| JP | 2013-107855 A | 6/2013 |
| JP | 2013-522249 A | 6/2013 |
| WO | 86/01207 A1 | 2/1986 |
| WO | 90/05719 A1 | 5/1990 |

(56) References Cited

FOREIGN PATENT DOCUMENTS

| | | |
|---|---|---|
| WO | 91/19735 A1 | 12/1991 |
| WO | 92/00091 A1 | 1/1992 |
| WO | 93/20242 A1 | 10/1993 |
| WO | 96/05309 A2 | 2/1996 |
| WO | 96/13262 A1 | 5/1996 |
| WO | 96/27583 A1 | 9/1996 |
| WO | 96/33172 A1 | 10/1996 |
| WO | 97/00271 A1 | 1/1997 |
| WO | 97/30992 A1 | 8/1997 |
| WO | 98/03516 A1 | 1/1998 |
| WO | 98/07697 A1 | 2/1998 |
| WO | 98/30566 A1 | 8/1998 |
| WO | 98/33496 A1 | 8/1998 |
| WO | 98/33768 A1 | 8/1998 |
| WO | 98/34915 A1 | 8/1998 |
| WO | 98/35951 A2 | 8/1998 |
| WO | 98/43960 A1 | 10/1998 |
| WO | 98/34918 A1 | 12/1998 |
| WO | 98/57948 A1 | 12/1998 |
| WO | 99/29667 A1 | 2/1999 |
| WO | 99/31063 A1 | 6/1999 |
| WO | 99/52910 A1 | 6/1999 |
| WO | 99/32454 A1 | 7/1999 |
| WO | 99/07675 A1 | 10/1999 |
| WO | 99/52889 A1 | 10/1999 |
| WO | 99/67641 A1 | 12/1999 |
| WO | 00/39587 A1 | 7/2000 |
| WO | 01/68186 A2 | 9/2001 |
| WO | 02/04420 A1 | 1/2002 |
| WO | 02/080928 A1 | 10/2002 |
| WO | 02/088107 A1 | 11/2002 |
| WO | 03/004480 A2 | 1/2003 |
| WO | 2004/033427 A1 | 4/2004 |
| WO | 2004/074283 A1 | 9/2004 |
| WO | 2004/080976 A1 | 9/2004 |
| WO | 2005/070891 A2 | 8/2005 |
| WO | 2005/082892 A2 | 9/2005 |
| WO | 2006/066948 A1 | 6/2006 |
| WO | 2006/097261 A1 | 9/2006 |
| WO | 2006/135993 A1 | 12/2006 |
| WO | 2007/047146 A2 | 4/2007 |
| WO | 2007/095588 A1 | 8/2007 |
| WO | 2007/113226 A1 | 10/2007 |
| WO | 2007/144394 A2 | 12/2007 |
| WO | 2008/009078 A2 | 1/2008 |
| WO | 2008/028691 A1 | 3/2008 |
| WO | 2008/112440 A1 | 9/2008 |
| WO | 2010/027746 A2 | 3/2010 |
| WO | 2010/087399 A1 | 8/2010 |
| WO | 2010/121918 A1 | 10/2010 |
| WO | 2011/002816 A1 | 1/2011 |
| WO | 2011/031896 A2 | 3/2011 |
| WO | 2011/082285 A1 | 7/2011 |
| WO | 2011/093524 A1 | 8/2011 |
| WO | 2011/148922 A1 | 12/2011 |
| WO | 2011/153553 A2 | 12/2011 |
| WO | 2012/016082 A1 | 2/2012 |
| WO | 2012/041872 A1 | 4/2012 |
| WO | 2012/054716 A1 | 4/2012 |
| WO | 2012/061557 A2 | 5/2012 |
| WO | 2012/174489 A2 | 12/2012 |
| WO | 2013/064068 A1 | 5/2013 |
| WO | 2013/096151 A1 | 6/2013 |
| WO | 2013/106641 A1 | 7/2013 |
| WO | 2013/140148 A1 | 9/2013 |
| WO | 2013/155223 A1 | 10/2013 |
| WO | 2013/184757 A1 | 12/2013 |
| WO | 2014/011900 A2 | 1/2014 |
| WO | 2014/143659 A1 | 9/2014 |
| WO | 2014/152588 A1 | 9/2014 |
| WO | 2014/159837 A1 | 10/2014 |
| WO | 2014/201435 A1 | 12/2014 |
| WO | 2015/003166 A1 | 1/2015 |
| WO | 2015/017502 A1 | 2/2015 |
| WO | 2015/054572 A1 | 4/2015 |
| WO | 2015/108992 A1 | 7/2015 |
| WO | 2015/132799 A2 | 9/2015 |
| WO | 2015/143148 A1 | 9/2015 |
| WO | 2015/144001 A1 | 10/2015 |
| WO | 2015/184349 A2 | 12/2015 |
| WO | 2016/044772 A1 | 3/2016 |
| WO | 2016/049524 A1 | 3/2016 |
| WO | 2016/049565 A1 | 3/2016 |
| WO | 2016/049568 A1 | 3/2016 |
| WO | 2016/118951 A2 | 7/2016 |
| WO | 2016/164675 A1 | 10/2016 |
| WO | 2016/168540 A1 | 10/2016 |
| WO | 2017/015562 A1 | 1/2017 |
| WO | 2017/058902 A1 | 4/2017 |
| WO | 2017/058915 A1 | 4/2017 |
| WO | 2017/068412 A1 | 4/2017 |
| WO | 2017/070256 A2 | 4/2017 |
| WO | WO-2017087528 A1 * | 5/2017 ........... C07D 401/14 |
| WO | 2017/172979 A1 | 10/2017 |
| WO | 2018/140512 A1 | 8/2018 |

OTHER PUBLICATIONS

Banker et al. (eds.), *Modern Pharmaceutics*, New York, Marcel Dekker, Inc., 1996, pp. 451 and 596. (3 pages).
Barbe et al., "Highly Chemoselective Metal-Free Reduction of Tertiary Amides," *J. Am. Chem. Soc.* 130:18-19, 2008.
Bégué et al., "Ions α-Cetocarbenium. Influence De La Structure Sur L'Evolution Des Ions α-Cetocyclohexylcarbenium," *Tetrahedron* 31(20):2505-2511, 1975. (English Abstract Only).
Berge et al., "Pharmaceutical Salts," *Journal of Pharmaceutical Sciences* 66(1):1-19, 1977.
CAS RN 1390243-63-6, Aug. 12, 2012, "Benzenesulfonamide, N-[1-[(1-methyl-1H-pyrrol-2-yl)carbonyl]-4-piperidinyl]-".
CAS RN 1346522-30-2, Nov. 29, 2011, "Methanone, [4-(phenylsulfonyl)-1-piperazinyl][5-(2-thienyl)-1H-pyrazol-3-yl]-".
CAS RN 1394801-07-0, Sep. 18, 2012, "2-Pentenamide, N-[1-(2-ethoxybenzoyl)-4-piperidinyl]-2-methyl-".
CAS RN 1312005-01-8, Jul. 7, 2011, "2-Penten-1-one, 1-[-(2,3-dimethoxybenzoyl)-1-piperazinyl]-2-methyl-".
CAS RN 1252566-45-2, Nov. 10, 2010, "2-Pentenamide, N-[1-(2-fluorobenzoyl)-4-piperidinyl]-2-methyl-".
CAS RN 1156156-36-3, Jun. 12, 2009, "2-Propen-1-one, 1-(4-benzoyl-1-piperazinyl)-".
Chemcats Chemical Abstract, Accession No. 1301347730, Sep. 9, 2015, 2 pages.
Chemocare, "Taxol," retrieved from http://www.chemocare.com/chemotherapy/drug-info/Taxol.aspx on Feb. 22, 2017, 3 pages.
Cho et al., "An Unnatural Biopolymer," *Science* 261:1303-1305, Sep. 1993.
Chonn et al., "Recent advances in liposomal drug-delivery systems," *Current Opinion in Biotechnology* 6:698-708, 1995.
Choong et al., "Identification of Potent and Selective Small-Molecule Inhibitors of Caspase-3 through the Use of Extended Tethering and Structure-Based Drug Design," *J. Med. Chem.* 45:5005-5022, 2002.
Cox et al., "Durging the undruggable RAS: Mission Possible?," *Nat. Rev. Drug Discov.* 13(11):828-851, 2014.
DeWitt et al., ""Diversomers": An approach to nonpeptide, nonoligomeric chemical diversity," *Proc. Natl. Acad. Sci.* 90:6909-6913, Aug. 1993.
Duncan et al., "N-Dialkylaminoalkybiphenylamines as Antimalarial and Atischistosomal Agents," *Journal of Medicinal Chemistry* 12:25-29, Jan. 1969.
Erlanson et al., "Site-directed ligand discovery," *Proc. Natl Acad. Sci. U.S.A.* 97(17):9367-9372, Aug. 2000.
Forbes et al., "COSMIC 2005," *British Journal of Cancer* 94:318-322, 2006.
Furka et al., "General method for rapid synthesis of multicomponent peptide mixtures," *Int. J. Peptide Protein Res.* 37:487-493, 1991.
Gorfe et al., "Mapping the Nucleotide and Isoform-Dependent Structural and Dynamical Features of Ras Proteins," *Structure* 16:885-896, Jun. 2008.

(56) References Cited

OTHER PUBLICATIONS

Haggam et al., "Facile synthesis of some condensed 1,3-thiazines and thiazoles under conventional conditions: antitumor activity," *Research on Chemical Intermediates* 43(11):6299-6315, 2017.
Hall et al., "The Effect of $Mg^{2+}$ on Guanine Nucleotide Exchange Rate of $p21^{N\text{-}ras}$" *The Journal of Biological Chemistry* 261(24):10963-10965, 1986.
Hall et al., "The structural basis for the transition from Ras-GTP to Ras-GDP," *PNAS* 99(19):12138-12142, Sep. 2002.
Hagihara et al., "Vinylogous Polypeptides: An Alternative Peptide Backbone," *J. Am. Chem. Soc.* 114(16):6568-6570, 1992.
Hardy et al., "Discovery of an allosteric site in the caspases,"*PNAS* 101(34):12461-12466, Aug. 2004.
Hattori et al., "Neutralizing monoclonal antibody against ras oncogene product p21 which impairs guanine nucleotide exchange," *Mol. Cell. Biol.* 7(5):1999-2002, May 1987.
Ito et al., "Regional Polysterism in the GTP-Bound Form of the Human c-Ha-Ras Protein," *Biochemistry* 36(30):9109-1919, Jul. 1997.
Johnson et al., "The Chemistry of β-Bromopropionyl Isocyanate. I. Synthesis of 1-Aryldihydrouracils," *The Journal of Organic Chemistry* 24(9):1391-1392, Sep. 1959.
Jones et al., "Increased frequency of the k-ras G12C mutation in MYH polyposis colorectal adenomas," *British Journal of Cancer* 90:1591-1593, 2004.
Jordan, "Tamoxifen: A most unlikely pioneering medicine," *Nature Reviews* 2:205-213, Mar. 2003.
Kelly et al., "Synthesis of Isomeric 3-Piperidinyl and 3-Pyrrolidinyl Benzo[5,6]cyclohepta[1,2-b]pyridines: Sulfonamido Derivatives as Inhibitors of Ras Prenylation," *Bioorganic & Medicinal Chemistry* 6(6):673-686, Jun. 1998.
Knochel et al., "Functionalization of heterocyclic compounds using polyfunctional magnesium and zinc reagents," *Beilstein Journal of Organic Chemistry* 7:1261-1277, 2011.
Kumar et al., "Synthesis of 3-Sulfonylamino Quinolines form 1-(2-Aminophenyl) Propargyl Alcohols through a Ag(I)-Catalyzed Hydroamination, (2 + 3) Cycloaddition, and an Unusual Strain-Driven Ring Expansion," *Organic Letters* 17(9):2226-2229, Apr. 2015.
Kraulis et al., "Solution Structure and Dynamics of Ras p21-GDP Determined by Heteronuclear Three- amd Four-Dimensional NMR Spectroscopy," *Biochemistry* 33:3515-3531, 1994.
Kurgyanagi et al., "Structure-Activity Relationships of 1,3-Benzoxazole-4-carbonitriles as Novel Antifungal Agents with Potent in Vivo Efficacy," *Chem. Pharm. Bull.* 59(3):341-352, 2011.
Le Picard et al., "Design and Synthesis of Naphthalenic Derivatives as Potential Inhibitors of Hydroxyindole-0-methyltransferase," *Pharm. Pharmacol. Commun.* 5:183-188, 1999.
Lee et al., "The mutation spectrum revealed by paired genome sequences from a lung cancer patient," *Nature* 465:473-477, May 2010.
Lenzen et al., "[10] Analysis of Intrinsic and CDC25-Stimulated Guanine Nucleotide Exchange of $p21^{ras}$—Nucleotide Complexes by Fluorescence Measurements," *Methods in Enzymology* 255:95-109, 1995.
Liang et al., "Parallel Synthesis and Screening of a Solid Phase Carbohydrate Library," *Science* 274:1520-1522, Nov. 1996.
Liu et al.,"*Polygonatum cyrtonema* lectin induces murine fibrosarcoma L929 cell apoptosis and autophagy via blocking Ras-Raf and PI3K-Akt signaling pathways," *Biochimie* 92:1934-1938, 2010.
Loboda et al., "A gene expression signature of RAS pathway dependence predicts response to PI3K and RAS pathway inhibitors and expands the population of Ras pathway activated tumors," *BMC Medical Genomics* 3(26):1-11, 2010.
Lone et al., "A substrate-free activity-based protein profiling screen for the discovery of selective PREPL inhibitors," *J. Am Chem Soc.* 133(30):11665-11674, Aug. 2011, 20 pages.
Long, "Taxol: An important compound with an impressive structure," Organic and General Chemistry at Flathead Valley Community College, Sep. 10, 2011, retrieved from https://longscience.com/2011/09/10/taxol-an-organic-compound-you-should-know-about/ on Feb. 22, 2017, 4 pages.
Malani et al., "Synthesis, characterization and in vitro screening on bacterial, fungal and malarial strain of piprazinyl cyano biphenyl based compounds," *Bioorganic Chemistry* 51:16-23, 2013.
Margarit et al., "Structural Evidence for Feedback Activation by Ras•GTP of the Ras-Specific Nucleotide Exchange Factor SOS," *Cell* 112:685-695, Mar. 2003.
Mattos et al., "Multiple Binding Modes," in Kubinyi (ed.), *3D QSAR in Drug Design—Theory Methods and Applications*, vol. 2-3, Springer, Boston, Massachusetts, USA, 1998, pp. 243-244. (6 Pages).
Maurer et al., "Small-molecule ligands bind to a distinct pocket in Ras and inhibit SOS-mediated nucleotide exchange activity," *PNAS* 109(14):5299-5304, Apr. 2012.
McMahon, "VEGF Receptor Signaling in Tumor Angiogenesis," *The Oncologist* 5(suppl. 1):3-10, 2000.
Milburn et al., "Molecular switch for signal transduction: structural differences between active and inactive forms of protooncogenic ras proteins," *Science* 247(4945):939-945, Feb. 1990.
Minto et al., "Pharmacokinetics and Pharmacodynamics of Nandrolone Esters in Oil Vehicle: Effects of Ester, Injection Site and Injection Volume," *The Journal of Pharmacology and Experimental Therapeutics* 281(1):93-102, 1997.
Noe et al., "Selective Inhibition of Aggrecanase in Osteoarthritis Treatment," U.S. Appl. No. 60/148,464, filed Aug. 12, 1999, 92 pages.
Ohnmacht, Jr. et al., "Antimalarials. 5. α-Dibutylaminomethyl- and α-(2-Piperidyl)-3-quinolinemethanols," *Journal of Medicinal Chemistry* 14(1):17-24, 197.
Ostrem et al., "K-Ras(G12C) inhibitors allosterically control GTP affinity and effector interactions," *Nature* 000, 2013, 14 pages.
Pacold et al., "Crystal structure and functional analysis of Ras binding to its effector phosphoinositide 3-kinase gamma," *Cell* 103(6):931-943, Dec. 2000.
Palmioli et al., "Selective cytotoxicity of a bicyclic Ras inhibitor in cancer cells expressing K-Ras$^{G13D}$," *Biochemical and Biophysical Research Communications* 386(4):593-597, Sep. 2009.
Palmioli et al., "First experimental identification of Ras-inhibitor binding interface using a water-soluble Ras ligand," *Bioorganic and Medicinal Chemistry* 19:4217-4222, 2009.
Pardin et al., "Synthesis and evaluation of peptidic irreversible inhibitors of tissue transglutaminase," *Bioorg Med Chem* 15(24):8379-8385, 2006.
Pathan et al., "Lead identification for the K-Ras protein: virtual screening and combinatorial fragment-based approaches," *OncoTargets and Therapy* 9:2575-2584, 2016.
Patricelli et al., "Selective Inhibition of Oncogenic KRAS Output with Small Molecules Targeting the Inactive State," *Cancer Discovery* 6(3)316-329, 2016.
Pautsch et al., "Crystal structure of the C3bot-RaIA complex reveals a novel type of action of a bacterial exoenzyme," *The EMBO Journal* 24:3670-3680, 2005.
Pédeboscq et al., "Synthesis and evaluation of apoptosis induction of thienopyrimidine compounds on KRAS and BRAF mutated colorectal cancer cell lines," *Bioorganic & Medicinal Chemistry* 20:6724-6731, 2012.
Peri et al., "Arabinose-derived bicyclic amino acids: synthesis, conformational analysis and construction of an $\alpha_v\beta_3$-selective RGD peptide," *J. Am. Chem. Soc., Perkins Trans* 1(5):638-644, Feb. 2002.
Peri et al., "Sugar-Derived Ras Inhibitors: Group Epitope Mapping by NMR Spectroscopy and Biological Evaluation," *Eur. J. Org. Chem.* 2006(16):3707-3720, Aug. 2006.
Peri et al., "Synthesis of bicyclic sugar azido acids and their incorporation in cyclic peptides," *Chem. Commun.* 23:2303-2304, Jan. 2000.
Pinedo et al., "Aggressive combination therapy to cure patients with metastatic cancer," *The Lancet Oncology* 1:72-73, Oct. 2000.
Pinedo et al., "Translational Research: The Role of VEGF in Tumor Angiogenesis," *The Oncologist* 5(suppl. 1):1-2, 2000.

(56) References Cited

OTHER PUBLICATIONS

Polinsky, "High-Speed Chemistry Libraries: Assessment of Drug-Likeness," in Wermuth (ed.), The Practice of Medicinal Chemistry, 2nd Ed., Academic Press, Cambridge, Massachusetts, USA, 2003, pp. 147-157.
PubChem Compound, "(2S,6R)-hexahydrofuro[3,2-b]furan-2,6-diyl dicarbonochloridate:Compound Summary CID 53396983," Oct. 30, 2011, retrieved from http://pubchem.ncbi.nlm.nih.gov/compound/53396983, 6 pages.
PubChem Compound, "(4-hydroxypiperidin-1-yl)-pyridin-4-ylmethanone: AC1LGBNJ," retrieved on Feb. 17, 2014, from http://pubchem.ncbi.nlm.nih.gov/summary/summary.cgi?cid=76837, Jul. 8, 2005, 5 pages.
PubChem Compound, "AKOS024742141," retrieved from http://pubchem.ncbi.nih.gov/compound/49702158#x304 on Nov. 20, 2015, 12 pages.
PubChem Compound, "Compound Summary for CID 21765509: Molecular Formula C18H21N5O8," Dec. 5, 2007, retrieved from http://pubchem.ncbi.nlm.nih.gov/compound/21765509, 4 pages.
PubChem Compound, "Compound Summary for CID 21765511: Molecular Formula C18H21N5O8," Dec. 5, 2007, retrieved from http://pubchem.ncbi.nlm.nih.gov/compound/21765511, 4 pages.
PubChem Compound, "Compound Summary for CID 60018735: Molecular Formula C30H30O13," Aug. 20, 2012, retrieved from http://pubchem.ncbi.nlm.nih.gov/compound/60018735#section=Top, 1 page.
PubChem Compound, "Compound Summary for CID 72623693: AGN-PC-0D83J7," Jan. 9, 2014, retrieved from http://pubchem.ncbi.nlm.nih.gov/compound/72623693, 6 pages.
PubChem Compound, "Compound Summary for CID 9897840: Molecular Formula C50H46O20," Oct. 25, 2006, retrieved from http://pubchem.ncbi.nlm.nih.gov/compound/9897840, 6 pages.
PubChem Compound, "SCHEMBL6797439," Dec. 1, 2012, retrieved from http://pubchem.ncbi.nim.nih.gov/compound/69898605#x304, CID 69898605, 12 pages.
PubChem Compound, "SCHEMBL6674271," Dec. 1, 2012, retrieved from http://pubchem.ncbi.nim.nih.gov/compound/69861127#x304, CID 69861127, 12 pages.
PubChem Substance Record for SID 22405303, Mar. 5, 2007, CID 2579941 (MLS000416491), retreived from https://pubchem.ncbi.nlm.nih.gov/substance/22405303, on May 15, 2017, 7 pages.
PubChem Substance Record for SID 44253980, Dec. 5, 2007, CID 966800 (1-Benzoylpyrrolidine), retrieved from https://pubchem.ncbi.nlm.nih.gov/substance/44253980#section=Top on May 11, 2017, 5 pages.
PubChem CID 10375614, Create Date: Oct. 25, 2006, date accessed Aug. 8, 2017.
PubChem, Compound Summary for CID 53064614: Molecular Formula C21H22N4O3, Jun. 21, 2011, retrieved from https://pubchem.ncbi.nim.nih.gov/compound/53064614, 11 pages.
PubChem, Compound Summary for CID 72080937: Molecular Formula C20H2ON4O3, Dec. 2, 2013, retrieved from https://pubchem.ncbi.nlm.nih.gov/compound/72080937, 10 pages.
PubChem, Compound Summary for CID 72080924: Molecular Formula C21H22N4O3, Dec. 2, 2013, retrieved from https://pubchem.ncbi.nlm.nih.gov/compound/72080924, 10 pages.
PubChem, Compound Summary for CID 72080923: Molecular Formula C21H22N4O2S, Dec. 2, 2013, retrieved from https://pubchem.ncbi.nlm.nih.gov/compound/72080923, 10 pages.
PubChem, Compound Summary for CID 53064615: Molecular Formula C21H22N4O2S, Jun. 21, 2011, retrieved from https://pubchem.ncbi.nlm.nih.gov/compound/53064615, 11 pages.
Rensland et al., "Substrate and Product Structural Requirements for Binding of Nucleotides to H-ras p21: The Mechanism of Discrimination between Guanosine and Adenosine Nucleotides," Biochemistry 34(2):593-599, 1995.
Sasaki et al., "Selective Formation of Stable Triplexes Including a TA or a CG Interrupting Site with New Bicyclic Nucleoside Analogues (WNA)," J. Am. Chem. Soc. 126(2):516-528, Jan. 2004.

Schubbert et al., "Biochemical and Functional Characterization of Germ Line KRAS Mutations," Molecular and Cellular Biology 27(22):7765-7770, Nov. 2007.
Shima et al., "Discovery of small molecule Ras inhibitors that display antitumor activity by interfering with Ras, GTP-effector interaction," Enzymes 34(pt. b):1-23, 2013.
Singh et al., "A Gene Expression Signature Associated with "K-Ras Addiction" Reveals Regulators of EMT and Tumor Cell Survival," Cancer Cell 15:489-500, Jun. 2009.
Spiegel et al., "Small-molecule modulation of Ras signaling," Nature Chemical Biology 10:613-622, Aug. 2014.
Stefanachi et al., "1-, 3-, and 8-substituted-9-deazaxanthines as potent and selective antagonists the human A2B adenosine receptor," Bioorg Med Chem 16(6):2852-2869, 2008.
STN Registry No. 1309145-12-7, "Methanone, 1-cyclopenten-1-yl [(3R,4R)-3-hydroxy-4-[4-(2-phenylethyl)-1-piperazinyl]-1-piperidinyl]-, rel-," Jun. 13, 2011, 1 page.
STN Registry No. 1212098-43-5, "Methanone, 1-cyclohexen-1-yl [(3R,4R)-3-hydroxy-4-[4-(2-phenylethyl)-1-piperazinyl]-1-piperidinyl]-, rel-," Mar. 21, 2010, 1 page.
STN Registry No. 1069909-93-8, "[1,4'-Bipiperidine]-4-carboxamide, 1'-(1-cyclopenten-1-ylcarbonyl]-N-(2-phenylethyl)-," Nov. 2, 2008, 1 page.
STN Registry No. 1069736-48-6, "[1,4'-Bipiperidine]-4-carboxamide, 1'-(1-cyclopenten-1-ylcarbonyl]-N-(3-pyridinylmethyl)-," Nov. 2, 2008, 1 page.
STN Registry No. 1069530-02-4, "[1,4'-Bipiperidine]-4-carboxamide, 1'-(1-cyclopenten-1-ylcarbonyl]-N-(2-pyridinylmethyl)-," Nov. 2, 2008, 1 page.
STN Registry No. 1069510-87-7, "[1,4'-Bipiperidine]-4-carboxadmide, 1'-(1-cyclohexen-1-ylcarbonyl]-N-(2-pyridinylmethyl)-," Nov. 2, 2008, 1 page.
STN Registry No. 1066915-72-7, "[3-[4-4-(1,3-benzodioxol-5-ylmethyl)-1-piperazinyl]-1-piperidinyl]-1-cyclohexen-l-yl-," Oct. 27, 2008, 1 page.
STN Registry No. 1066896-20-5, "Methanone, [3-[4-(1,3-benzodioxol-5-ylmethyl)-1-piperazinyl)-1-piperidinyl]-1-cyclopenten-l-yl-," Oct. 27, 2008, 1 page.
STN Registry No. 1066881-73-9, "[1,4'-Bipiperidine]-4-carboxamide, 1'-(1-cyclohexen-1-ylcarbonyl)-N-(3-pyridinylmethyl)-," Oct. 27, 2008, 1 page.
Streuff et al., "First asymmetric aminohydroxylation of acrylamides," Tetrahedron: Asymmetry 16(21):3492-3496, Oct. 2005.
Sun et al., "Discovery of small molecules that bind to K-Ras and inhibit Sos-mediated activation," Angew Chem Int Ed Engl. 51(25):6140-6143, 2012.
Sunaga et al., "Knockdown of Oncogenic KRAS in Non-Small Cell Lung Cancers Suppresses Tumor Growth and Sensitizes Tumor Cells to Targeted Therapy," Molecular Cancer Therapeutics 10(2):336-346, Feb. 2011.
Sundberg et al., "The O-Styrylnitrene Route to 2-Substituted Indoles. Pyrolysis of O-Azidostyrenes," Journal of Organic Chemistry 37(5):719-724, 1972.
Sydor et al., "Transient Kinetic Studies on the Interaction of Ras and the Ras-Binding Domain of c-Raf-1 Reveal Rapid Equilibration of the Complex," Biochemistry 37:14292-14299, 1998.
Taveras et al., "Ras Oncoprotein Inhibitors: The Discovery of Potent, Ras Nucleotide Exchange Inhibitors and the Structural Determination of a Drug-Protein Complex," Bioorganic and Medicinal Chemistry 5(1):125-133, 1997.
Terfloth et al., "Electronic Screening: Lead Finding from Database Mining," in Wermuth (ed.), The Practice of Medicinal Chemistry, 2nd Ed., Academic Press, Cambridge, Massachusetts, USA, 2003, pp. 131-145.
Tsubaki et al., "Reduction of metastasis, cell invasion, and adhesion in mouse osteosarcoma by YM529/ONO-5920-induced blockade of the Ras/MEK/ERK and Ras/PI3K/Akt pathway," Toxicology and Applied Pharmacology 259(3):402-410, Jan. 2012.
Tulshian et al., "Synthesis and Phosphodiesterase Activity of Carboxylic Acid Mimetics of Cyclic Guanosine 3',5'-Monophosphate," J. Med. Chem. 36(9):1210-1220, Jan. 1993.
Vetter et al., "The Guanine Nucleotide-Binding Switch in Three Dimensions," Science 294(5545): 1299-1304, Nov. 2001.

(56) References Cited

OTHER PUBLICATIONS

Vippagunta et al., "Crystalline solids," *Advanced Drug Delivery Reviews* 48:3-26, 2001.
Wolff, (ed.), *Burger's Medicinal Chemistry and Drug Discovery, Fifth Edition, vol. 1: Principles and Practice*, San Diego, California, John Wiley & Sons, 1994, pp. 975-977.
Wu et al., "Stereoselective synthesis of dioxabicycles from 1-C-allyl-2-O-benzyl-glycosides—An intramolecular cyclization between 2-O-benzyl oxygen and the allyl double bond," *Can. J. Chem.* 84(1):597-602, Jan. 2006.
Xu et al., "Design, Synthesis, and Biological Evaluation of 2-Oxo-3,4-dihydropyrimido[4,5-d]pyrimidinyl Derivatives as New Irreversible Epidermal Growth Factor Receptor Inhibitors with Improved Pharmacokinetic Properties," *Journal of Medicinal Chemistry* 56:8803-8813, 2013.
Yan et al., "Discovery and characterization of small molecules that target the GRPase Ral," *Nature* 515:443-447, Nov. 2014, 15 pages.
Yang et al., "Fragment-Based Discovery of Nonpeptidic BACE-1 Inhibitors Using Tethering," *Biochemistry* 48:4488-4496, 2009.
Young et al., "Oncogenic and Wild-type Ras Play Divergent Roles in the Regulation of Mitogen-Activated Protein Kinase Signaling," *Cancer Discovery* 3(1): 112-123, Jan. 2013.
Zenkl et al., "Sugar-Responsive Fluorescent Nanospheres," *Macromol. Biosci.* 8:146-152, 2008.
U.S. Appl. No. 16/374,356, filed Apr. 3, 2019.
U.S. Appl. No. 16/421,186, filed May 23, 2019.
U.S. Appl. No. 16/445,683, filed Jun. 19, 2019.
U.S. Appl. No. 16/449,967, filed Jun. 24, 2019.
U.S. Appl. No. 16/480,195.
U.S. Appl. No. 16/480,205.
U.S. Appl. No. 16/480,211.
U.S. Appl. No. 16/480,849.
U.S. Appl. No. 16/480,861.
U.S. Appl. No. 16/480,874.
U.S. Appl. No. 16/514,675, filed Jul. 17, 2019.
U.S. Appl. No. 16/535,999.
Registry: 2-Propen-l-one, 1-[-4-[4-4-(4-ethoxyphenyl)-2-pyrimidinyl]-1-piperazinyl]-(CA Index Name), 1 page, 2019.
Mirguet et al., "From ApoA1 upregulation to BET family bromodomain inhibition: Discovery of I-BET151," *Bioorganic & Medicinal Chemistry Letters* 22:2963-2967, 2012.

\* cited by examiner

COVALENT INHIBITORS OF KRAS

BACKGROUND

Technical Field

Embodiments of the present invention are generally directed to novel compounds and methods for their preparation and use as therapeutic or prophylactic agents, for example for treatment of cancer.

Description of the Related Art

RAS represents a group of closely related monomeric globular proteins of 189 amino acids (21 kDa molecular mass) which are associated with the plasma membrane and which bind either GDP or GTP. RAS acts as a molecular switch. When RAS contains bound GDP, it is in the resting or off position and is "inactive". In response to exposure of the cell to certain growth promoting stimuli, RAS is induced to exchange its bound GDP for a GTP. With GTP bound, RAS is "switched on" and is able to interact with and activate other proteins (its "downstream targets"). The RAS protein itself has a very low intrinsic ability to hydrolyze GTP back to GDP, thus turning itself into the off state. Switching RAS off requires extrinsic proteins termed GTPase-activating proteins (GAPs) that interact with RAS and greatly accelerate the conversion of GTP to GDP. Any mutation in RAS which affects its ability to interact with GAP or to convert GTP back to GDP will result in a prolonged activation of the protein and consequently a prolonged signal to the cell telling it to continue to grow and divide. Because these signals result in cell growth and division, overactive RAS signaling may ultimately lead to cancer.

Structurally, RAS proteins contain a G domain which is responsible for the enzymatic activity of RAS—the guanine nucleotide binding and the hydrolysis (GTPase reaction). It also contains a C-terminal extension, known as the CAAX box, which may be post-translationally modified and is responsible for targeting the protein to the membrane. The G domain is approximately 21-25 kDa in size and it contains a phosphate binding loop (P-loop). The P-loop represents the pocket where the nucleotides are bound in the protein, and this is the rigid part of the domain with conserved amino acid residues which are essential for nucleotide binding and hydrolysis (Glycine 12, Threonine 26 and Lysine 16). The G domain also contains the so called Switch I (residues 30-40) and Switch II (residues 60-76) regions, both of which are the dynamic parts of the protein which are often represented as the "spring-loaded" mechanism because of their ability to switch between the resting and loaded state. The key interaction is the hydrogen bonds formed by Threonine-35 and glycine-60 with the γ-phosphate of GTP which maintain Switch 1 and Switch 2 regions respectively in their active conformation. After hydrolysis of GTP and release of phosphate, these two relax into the inactive GDP conformation.

The most notable members of the RAS subfamily are HRAS, KRAS and NRAS, mainly for being implicated in many types of cancer. However, there are many other members including DIRAS1; DIRAS2; DIRAS3; ERAS; GEM; MRAS; NKIRAS1; NKIRAS2; NRAS; RALA; RALB; RAP1A; RAP1B; RAP2A; RAP2B; RAP2C; RASD1; RASD2; RASL10A; RASL10B; RASL11A; RASL11B; RASL12; REM1; REM2; RERG; RERGL; RRAD; RRAS and RRAS2.

Mutations in any one of the three main isoforms of RAS (HRAS, NRAS, or KRAS) genes are among the most common events in human tumorigenesis. About 30% of all human tumors are found to carry some mutation in RAS genes. Remarkably, KRAS mutations are detected in 25-30% of tumors. By comparison, the rates of oncogenic mutation occurring in the NRAS and HRAS family members are much lower (8% and 3% respectively). The most common KRAS mutations are found at residue G12 and G13 in the P-loop and at residue Q61.

G12C is a frequent mutation of KRAS gene (glycine-12 to cysteine). This mutation had been found in about 13% of cancer occurrences, about 43% of lung cancer occurrences, and in almost 100% of MYH-associates polyposis (familial colon cancer syndrome). However targeting this gene with small molecules is a challenge.

Accordingly, while progress has been made in this field, there remains a need in the art for improved compounds and methods for treatment of cancer, for example by inhibition of KRAS, HRAS or NRAS. The present invention fulfills this need and provides further related advantages.

BRIEF SUMMARY

In brief, embodiments of the present invention provide compounds, including pharmaceutically acceptable salt, isotopic form, stereoisomer or prodrug thereof, which are capable of modulating G12C mutant KRAS, HRAS and/or NRAS proteins. In some instances, the compounds act as electrophiles which are capable of forming a covalent bond with the cysteine residue at position 12 of a KRAS, HRAS or NRAS G12C mutant protein. Methods for use of such compounds for treatment of various diseases or conditions, such as cancer, are also provided.

In one embodiment, compounds having the following structure (I) are provided:

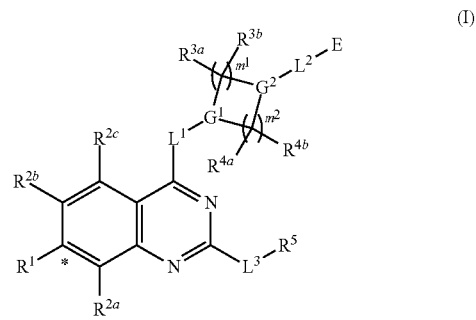

or a pharmaceutically acceptable salt, stereoisomer, isotopic form or prodrug thereof, wherein $R^1$, $R^{2a}$, $R^{2b}$, $R^{2c}$, $R^{3a}$, $R^{3b}$, $R^{4a}$, $R^{4b}$, $R^5$, $G^1$, $G^2$, $L^1$, $L^2$, $L^3$, E, $m^1$, $m^2$ and * are as defined herein. Pharmaceutical compositions comprising one or more compounds of structure (I) and a pharmaceutically acceptable carrier are also provided in various other embodiments.

In other embodiments, the present invention provides a method for treatment of cancer, the method comprising administering an effective amount of a pharmaceutical composition comprising any one or more of the compounds of structure (I) to a subject in need thereof.

Other provided methods include a method for regulating activity of a KRAS, HRAS or NRAS G12C mutant protein, the method comprising reacting the KRAS, HRAS or NRAS G12C mutant protein with any one of the compounds of structure (I). In other embodiments, a method for inhibiting proliferation of a cell population, the method comprising contacting the cell population with any one of the compounds of structure (I) is also provided.

In other embodiments, the invention is directed to a method for treating a disorder mediated by a KRAS, HRAS or NRAS G12C mutation in a subject in need thereof, the method comprising:

determining if the subject has a KRAS, HRAS or NRAS G12C mutation; and if the subject is determined to have the KRAS, HRAS or NRAS G12C mutation, then administering to the subject a therapeutically effective amount of a pharmaceutical composition comprising any one or more compounds of structure (I).

In still more embodiments, the invention is directed to a method for preparing a labeled KRAS, HRAS or NRAS G12C mutant protein, the method comprising reacting the KRAS, HRAS or NRAS G12C mutant with a compound of structure (I), to result in the labeled KRAS, HRAS or NRAS G12C protein.

These and other aspects of the invention will be apparent upon reference to the following detailed description.

DETAILED DESCRIPTION

In the following description, certain specific details are set forth in order to provide a thorough understanding of various embodiments of the invention. However, one skilled in the art will understand that the invention may be practiced without these details.

Unless the context requires otherwise, throughout the present specification and claims, the word "comprise" and variations thereof, such as, "comprises" and "comprising" are to be construed in an open, inclusive sense, that is, as "including, but not limited to".

Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Unless defined otherwise, all technical and scientific terms used herein have the same meaning as is commonly understood by one of skill in the art to which this invention belongs. As used in the specification and claims, the singular form "a", "an" and "the" include plural references unless the context clearly dictates otherwise.

"Amidinyl" refers to a radical of the form —(C=$NR_a$) $NR_bR_c$, wherein $R_a$, $R_b$ and $R_c$ are each independently H or $C_1$-$C_6$ alkyl.

"Amino" refers to the —$NH_2$ radical.

"Aminylsulfone" refers to the —$S(O)_2NH_2$ radical.

"Carboxy" or "carboxyl" refers to the —$CO_2H$ radical.

"Cyano" refers to the —CN radical.

"Guanidinyl" refers to a radical of the form —$NR_d$ (C=$NR_a$)$NR_bR_c$, wherein $R_a$, $R_b$, $R_c$ and $R_d$ are each independently H or $C_1$-$C_6$ alkyl.

"Hydroxy" or "hydroxyl" refers to the —OH radical.

"Imino" refers to the =NH substituent.

"Nitro" refers to the —$NO_2$ radical.

"Oxo" refers to the =O substituent.

"Thioxo" refers to the =S substituent.

"Alkyl" refers to a saturated, straight or branched hydrocarbon chain radical consisting solely of carbon and hydrogen atoms, having from one to twelve carbon atoms ($C_1$-$C_{12}$ alkyl), preferably one to eight carbon atoms ($C_1$-$C_8$ alkyl) or one to six carbon atoms ($C_1$-$C_6$ alkyl), and which is attached to the rest of the molecule by a single bond, e.g., methyl, ethyl, n-propyl, 1-methylethyl (iso-propyl), n-butyl, n-pentyl, 1,1-dimethylethyl (t-butyl), 3-methylhexyl, 2-methylhexyl and the like. "Amidinylalkyl" refers to an alkyl group comprising at least one amidinyl substituent. "Guanidinylalkyl" refers to an alkyl group comprising at least one guanidinyl substituent. Unless stated otherwise specifically in the specification, an alkyl, amidinylalkyl and/or guanidinylalkyl group is optionally substituted.

"Alkenyl" refers to an unsaturated, straight or branched hydrocarbon chain radical consisting solely of carbon and hydrogen atoms, which contains one or more carbon-carbon double bonds), having from two to twelve carbon atoms ($C_2$-$C_{12}$ alkenyl), preferably one to two carbon atoms ($C_2$—C alkenyl) or two to six carbon atoms ($C_2$-$C_6$ alkenyl), and which is attached to the rest of the molecule by a single bond, e.g., ethenyl, prop-1-enyl, but-1-enyl, pent-1-enyl, penta-1,4-dienyl, and the like. Unless stated otherwise specifically in the specification, an alkenyl group is optionally substituted.

"Alkynyl" refers to an unsaturated, straight or branched hydrocarbon chain radical consisting solely of carbon and hydrogen atoms, which contains one or more carbon-carbon triple bonds), having from two to twelve carbon atoms ($C_2$-$C_{12}$ alkynyl), preferably one to two carbon atoms ($C_2$-$C_8$ alkynyl) or two to six carbon atoms ($C_2$-$C_6$ alkynyl), and which is attached to the rest of the molecule by a single bond, e.g., ethynyl, propynyl, butynyl, pentynyl, hexynyl, and the like. Unless stated otherwise specifically in the specification, an alkynyl group is optionally substituted.

"Alkylene" or "alkylene chain" refers to a straight or branched divalent hydrocarbon chain linking the rest of the molecule to a radical group, consisting solely of carbon and hydrogen, which is saturated or unsaturated (i.e., contains one or more double and/or triple bonds), and having from one to twelve carbon atoms, e.g., methylene, ethylene, propylene, n-butylene, ethenylene, propenylene, n-butenylene, propynylene, n-butynylene, and the like. The alkylene chain is attached to the rest of the molecule through a single or double bond and to the radical group through a single or double bond. The points of attachment of the alkylene chain to the rest of the molecule and to the radical group can be through one carbon or any two carbons within the chain. Unless stated otherwise specifically in the specification, an alkylene chain is optionally substituted.

"Alkylcycloalkyl" refers to a radical of the formula —$R_bR_d$ where $R_b$ is cycloalkyl as defined herein and $R_d$ is an alkyl radical as defined above. Unless stated otherwise specifically in the specification, an alkylcycloalkyl group is optionally substituted.

"Alkoxy" refers to a radical of the formula —$OR_a$ where $R_a$ is an alkyl radical as defined above containing one to twelve carbon atoms. "Amidinylalkyloxy" refers to an alkoxy group comprising at least one amidinyl substituent on the alkyl group. "Guanidinylalkyloxy" refers to an alkoxy group comprising at least one guanidinyl substituent on the alkyl group. "Alkylcarbonylaminylalkyloxy" refers to an alkoxy group comprising at least one alkylcarbonylaminyl substituent on the alkyl group. "Heterocyclylalkyloxy" refers to an alkoxy group comprising at least one heterocyclyl substituent on the alkyl group. "Heteroarylalkyloxy"

refers to an alkoxy group comprising at least one heteroaryl substituent on the alkyl group. "Aminylalkyloxy" refers to an alkoxy group comprising at least one substituent of the form —$NR_aR_b$, where $R_a$ and $R_b$ are each independently H or $C_1$-$C_6$ alkyl, on the alkyl group. Unless stated otherwise specifically in the specification, an alkoxy, amidinylalkyloxy, guanidinylalkyloxy, alkylcarbonylaminylalkyloxy, heterocyclylalkyloxy, heteroarlyalkyloxy and/or aminylalkyloxy group is optionally substituted.

"Alkoxyalkyl" refers to a radical of the formula —$R_bOR_a$ where $R_a$ is an alkyl radical as defined above containing one to twelve carbon atoms and $R_b$ is an alkylene radical as defined above containing one to twelve carbon atoms. Unless stated otherwise specifically in the specification, an alkoxyalkyl group is optionally substituted.

"Alkoxyalkynyl" refers to a radical of the formula —$R_bOR_a$ where $R_a$ is an alkyl radical as defined above containing one to twelve carbon atoms and $R_b$ is an alkynylene radical as defined above containing one to twelve carbon atoms. Unless stated otherwise specifically in the specification, an alkoxyalkynyl group is optionally substituted.

"Alkoxycarbonyl" refers to a radical of the formula —$C(=O)OR_a$ where $R_a$ is an alkyl radical as defined above containing one to twelve carbon atoms. Unless stated otherwise specifically in the specification, an alkoxycarbonyl group is optionally substituted.

"Alkylphosphoryl" refers to a radical of the formula —$P(=O)(R_a)$ where each $R_a$ is independently an alkyl radical as defined above. Unless stated otherwise specifically in the specification, an alkylphosphoryl group is optionally substituted.

"Alkylphosphorylaminyl" refers to a radical of the formula —$NR_bP(=O)(R_a)$ where each $R_a$ is independently an alkyl radical as defined above and $R_b$ is H or an alkyl radical as defined above. Unless stated otherwise specifically in the specification, an alkylphosphorylaminyl group is optionally substituted.

"Aryloxy" refers to a radical of the formula —$OR_a$ where $R_a$ is an aryl radical as defined herein. Unless stated otherwise specifically in the specification, an aryloxy group is optionally substituted.

"Alkylaminyl" refers to a radical of the formula —$NHR_a$ or —$NR_aR_a$ where each $R_a$ is, independently, an alkyl radical as defined above containing one to twelve carbon atoms. A "haloalkylaminyl" group is an alkylaminyl group comprising at least one halo substituent on the alkyl group. A "hydroxylalkylaminyl" group is an alkylaminyl group comprising at least one hydroxyl substituent on the alkyl group. An "amidinylalkylaminyl" group is an alkylaminyl group comprising at least one amidinyl substituent on the alkyl group. A "guanidinylalkylaminyl" group is an alkylaminyl group comprising at least one guanidinyl substituent on the alkyl group. Unless stated otherwise specifically in the specification, an alkylaminyl, haloalkylaminyl, hydroxylalkylaminyl, amidinylalkylaminyl and/or guanidinylalkylaminyl group is optionally substituted.

"Aminylalkyl" refers to an alkyl group comprising at least one aminyl substituent (—$NR_aR_b$ wherein $R_a$ and $R_b$ are each independently H or $C_1$-$C_6$ alkyl). The aminyl substituent can be on a tertiary, secondary or primary carbon. Unless stated otherwise specifically in the specification, an aminylalkyl group is optionally substituted.

"Aminylalkynyl" refers to an alkynyl group comprising at least one aminyl substituent (—$NR_aR_b$ wherein $R_a$ and $R_b$ are each independently H or $C_1$-$C_6$ alkyl). The aminyl substituent can be on a tertiary, secondary or primary carbon. Unless stated otherwise specifically in the specification, an aminylalkynyl group is optionally substituted.

"Aminylalkylaminyl" refers to a radical of the formula —$NR_aR_b$ wherein $R_a$ is H or $C_1$-$C_6$ alkyl and $R_b$ is aminylalkyl. Unless stated otherwise specifically in the specification, an aminylalkylaminyl group is optionally substituted.

"Aminylalkoxy" refers to a radical of the formula —$OR_aNH_2$ wherein $R_a$ is alkylene. Unless stated otherwise specifically in the specification, an aminylalkoxy group is optionally substituted.

"Alkylaminylalkoxy" refers to a radical of the formula —$OR_aNR_bR_c$ wherein $R_a$ is alkylene and $R_b$ and $R_c$ are each independently H or $C_1$-$C_6$ alkyl, provided one of $R_b$ or $R_c$ is $C_1$-$C_6$ alkyl. Unless stated otherwise specifically in the specification, an alkylaminylalkoxy group is optionally substituted.

"Alkylcarbonylaminyl" refers to a radical of the formula —$NH(C=O)R_a$ where $R_a$ is an alkyl radical as defined above containing one to twelve carbon atoms. Unless stated otherwise specifically in the specification, an alkylcarbonylaminyl group is optionally substituted, for example optionally substituted with aminyl to form an "aminylalkylcarbonylaminyl" group. An alkenylcarbonylaminyl is an alkylcarbonylaminyl containing at least one carbon-carbon double bond. An alkylcarbonylaminyl and alkenylcarbonylaminyl group is optionally substituted.

"Alkylcarbonylaminylalkoxy" refers to a radical of the formula —$OR_bNH(C=O)R_a$ where $R_a$ is an alkyl radical as defined above containing one to twelve carbon atoms and $R_b$ is alkylene. Unless stated otherwise specifically in the specification, an alkylcarbonylaminylalkoxy group is optionally substituted.

"Alkylaminylalkyl" refers to an alkyl group comprising at least one alkylaminyl substituent. The alkylaminyl substituent can be on a tertiary, secondary or primary carbon. Unless stated otherwise specifically in the specification, an alkylaminylalkyl group is optionally substituted.

"Aminylcarbonyl" refers to a radical of the formula —$C(=O)NR_aR_b$ where $R_a$ and $R_b$ are each independently H or alkyl. Unless stated otherwise specifically in the specification, an aminylcarbonyl group is optionally substituted.

"Alkylaminylcarbonyl" refers to a radical of the formula —$C(=O)NR_aR_b$, where $R_a$ and $R_b$ are each independently H or alkyl, provided at least one of $R_a$ or $R_b$ is alkyl. Unless stated otherwise specifically in the specification, an alkylaminylcarbonyl group is optionally substituted.

"Aminylcarbonylalkyl" refers to a radical of the formula —$R_cC(=O)NR_aR_b$, where $R_a$ and $R_b$ are each independently H or alkyl and $R_c$ is alkylene. Unless stated otherwise specifically in the specification, an aminylcarbonylalkyl group is optionally substituted.

"Aminylcarbonycycloalkyl" refers to a radical of the formula —$R_cC(=O)NR_aR_b$, where $R_a$ and $R_b$ are each independently H or alkyl and $R_c$ is cycloalkyl. Unless stated otherwise specifically in the specification, an aminylcarbonylcycloalkyl group is optionally substituted.

"Aromatic ring" refers to a cyclic planar portion of a molecule (i.e., a radical) with a ring of resonance bonds that exhibits increased stability relative to other connective arrangements with the same sets of atoms. Generally, aromatic rings contains a set of covalently bound co-planar atoms and comprises a number of π-electrons (for example, alternating double and single bonds) that is even but not a multiple of 4 (i.e., 4n+2 π-electrons, where n=0, 1, 2, 3, etc.). Aromatic rings include, but are not limited to, phenyl, naphthenyl, imidazolyl, pyrrolyl, pyridinyl, pyrimidinyl, pyrazinyl, pyridonyl, pyridazinyl, pyrimidonyl. Unless stated otherwise specifically in the specification, an "aromatic ring" includes all radicals that are optionally substituted.

"Aryl" refers to a carbocyclic ring system radical comprising 6 to 18 carbon atoms and at least one aromatic ring. For purposes of embodiments of this invention, the aryl radical is a monocyclic, bicyclic, tricyclic or tetracyclic ring system, which may include fused or bridged ring systems. Aryl radicals include, but are not limited to, aryl radicals derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, the term "aryl" or the prefix "ar-" (such as in "aralkyl") is meant to include aryl radicals that are optionally substituted.

"Aralkyl" refers to a radical of the formula —$R_b$—$R_c$ where $R_b$ is an alkylene chain as defined above and $R_c$ is one or more aryl radicals as defined above, for example, benzyl, diphenylmethyl and the like. Unless stated otherwise specifically in the specification, an aralkyl group is optionally substituted.

"Arylalkyloxy" refers to a radical of the formula —$OR_b$—$R_c$ where $R_b$ is an alkylene chain as defined above and $R_c$ is one or more aryl radicals as defined above, for example, benzyl, diphenylmethyl and the like. Unless stated otherwise specifically in the specification, an arylalkyloxy group is optionally substituted.

"Arylalkylaminyl" refers to a radical of the formula —N($R_a$)$R_b$—$R_c$ where $R_a$ is H or $C_1$-$C_6$ alkyl, $R_b$ is an alkylene chain as defined above and $R_c$ is one or more aryl radicals as defined above, for example, benzyl, diphenylmethyl and the like. Unless stated otherwise specifically in the specification, an arylalkylaminyl group is optionally substituted.

"Carboxyalkyl" refers to a radical of the formula —$R_b$—$R_c$ where $R_b$ is an alkylene chain as defined above and $R_c$ is a carboxyl group as defined above. Unless stated otherwise specifically in the specification, carboxyalkyl group is optionally substituted.

"Cyanoalkyl" refers to a radical of the formula —$R_b$—$R_c$ where $R_b$ is an alkylene chain as defined above and $R_c$ is a cyano group as defined above. Unless stated otherwise specifically in the specification, a cyanoalkyl group is optionally substituted.

"Carbocyclic" or "carbocycle" refers to a ring system, wherein each of the ring atoms are carbon.

"Cycloalkyl" refers to a stable non-aromatic monocyclic or polycyclic carbocyclic radical consisting solely of carbon and hydrogen atoms, which may include fused or bridged ring systems, having from three to fifteen carbon atoms, preferably having from three to ten carbon atoms, and which is saturated or unsaturated and attached to the rest of the molecule by a single bond. Monocyclic radicals include, for example, cyclopropyl, cyclobutyl, cyclopentyl, cyclohexyl, cycloheptyl, and cyclooctyl. Polycyclic radicals include, for example, adamantyl, norbornyl, decalinyl, 7,7-dimethyl-bicyclo[2.2.1]heptanyl, and the like. A "cycloalkenyl" is a cycloalkyl comprising one or more carbon-carbon double bonds within the ring. Unless otherwise stated specifically in the specification, a cycloalkyl (or cycloalkenyl) group is optionally substituted.

"Cyanocycloalkyl" refers to a radical of the formula —$R_b$—$R_c$ where $R_b$ is cycloalkyl and $R_c$ is a cyano group as defined above. Unless stated otherwise specifically in the specification, a cyanocycloalkyl group is optionally substituted.

"Cycloalkylaminylcarbonyl" refers to a radical of the formula —C(=O)N$R_a R_b$, where $R_a$ and $R_b$ are each independently H or cycloalkyl, provided at least one of $R_a$ or $R_b$ is cycloalkyl. Unless stated otherwise specifically in the specification, n-cycloalkylaminylcarbonyl group is optionally substituted.

"Cycloalkylalkyl" refers to a radical of the formula —$R_b R_d$ where $R_b$ is an alkylene chain as defined above and $R_d$ is a cycloalkyl radical as defined above. Unless stated otherwise specifically in the specification, a cycloalkylalkyl group is optionally substituted.

"Fused" refers to any ring structure described herein which is fused to an existing ring structure in the compounds of the invention. When the fused ring is a heterocyclyl ring or a heteroaryl ring, any carbon atom on the existing ring structure which becomes part of the fused heterocyclyl ring or the fused heteroaryl ring is replaced with a nitrogen atom.

"Halo" or "halogen" refers to bromo, chloro, fluoro or iodo.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1,2-difluoroethyl, 3-bromo-2-fluoropropyl, 1,2-dibromoethyl, and the like. A "perhaloalkyl" is an alkyl radical, as defined above, wherein each H atom is replaced with a halogen. Unless stated otherwise specifically in the specification, a haloalkyl group is optionally substituted.

"Haloalkoxy" refers to a radical of the formula —$OR_a$ where $R_a$ is a haloalkyl radical as defined herein containing one to twelve carbon atoms. Unless stated otherwise specifically in the specification, a haloalkoxy group is optionally substituted.

"Heterocyclyl" or "heterocyclic ring" refers to a stable 3- to 18-membered non-aromatic ring radical having one to twelve ring carbon atoms (e.g., two to twelve) and from one to six ring heteroatoms selected from the group consisting of nitrogen, oxygen and sulfur. Unless stated otherwise specifically in the specification, the heterocyclyl radical is a monocyclic, bicyclic, tricyclic or tetracyclic ring system, which may include fused, spirocyclic ("spiro-heterocyclyl") and/or bridged ring systems; and the nitrogen, carbon or sulfur atoms in the heterocyclyl radical is optionally oxidized; the nitrogen atom is optionally quaternized; and the heterocyclyl radical is partially or fully saturated. Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. "Heterocyclyloxy" refers to a heterocyclyl group bound to the remainder of the molecule via an oxygen bond (—O—). "Heterocyclylaminyl" refers to a heterocyclyl group bound to the remainder of the molecule via a nitrogen bond (—$NR_a$—, where $R_a$ is H or $C_1$-$C_6$ alkyl). Unless stated otherwise specifically in the specification, a heterocyclyl, heterocyclyloxy and/or heterocyclylaminyl group is optionally substituted.

"N-heterocyclyl" refers to a heterocyclyl radical as defined above containing at least one nitrogen and where the point of attachment of the heterocyclyl radical to the rest of the molecule is through a nitrogen atom in the heterocyclyl radical. Unless stated otherwise specifically in the specification, an N-heterocyclyl group is optionally substituted.

"Heterocyclylene" refers to a divalent heterocyclyl group as defined above. Unless stated otherwise specifically in the specification, a heterocyclylene group is optionally substituted.

"Aminylheterocyclylene" refers to a divalent radical of the formula —N($R_a$)$R_b$— where $R_a$ is H or $C_1$-$C_6$ alkyl and $R_b$ is heterocyclylene as defined above. Unless stated otherwise specifically in the specification, an aminylheterocyclylene group is optionally substituted.

"Alkylheterocyclylene" refers to a divalent radical of the formula —$R_a R_b$— where $R_a$ is alkylene and $R_b$ is heterocyclylene as defined above. Unless stated otherwise specifically in the specification, an alkylheterocyclylene group is optionally substituted.

"Heteroalkylheterocyclylene" refers to a divalent radical of the formula —$R_a R_b$— where $R_a$ is heteroalkylene and $R_b$ is heterocyclylene as defined above. Unless stated otherwise specifically in the specification, an heteroalkylheterocyclylene group is optionally substituted.

"Heterocyclylalkyl" refers to a radical of the formula —$R_b R_e$ where $R_b$ is an alkylene chain as defined above and $R_e$ is a heterocyclyl radical as defined above, and if the heterocyclyl is a nitrogen-containing heterocyclyl, the heterocyclyl is optionally attached to the alkyl radical at the nitrogen atom. Unless stated otherwise specifically in the specification, a heterocyclylalkyl group is optionally substituted.

"Heterocyclylalkyloxy" refers to a radical of the formula —O$R_b R_e$ where $R_b$ is an alkylene chain as defined above and $R_e$ is a heterocyclyl radical as defined above, and if the heterocyclyl is a nitrogen-containing heterocyclyl, the heterocyclyl is optionally attached to the alkyl radical at the nitrogen atom. Unless stated otherwise specifically in the specification, a heterocyclylalkyloxy group is optionally substituted.

"Heterocyclylalkylaminyl" refers to a radical of the formula —N($R_c$)$R_b R_e$ where $R_b$ is an alkylene chain as defined above and $R_e$ is a heterocyclyl radical as defined above, and if the heterocyclyl is a nitrogen-containing heterocyclyl, the heterocyclyl is optionally attached to the alkyl radical at the nitrogen atom, $R_c$ is H or $C_1$-$C_6$ alkyl. Unless stated otherwise specifically in the specification, a heterocyclylalkylaminyl group is optionally substituted.

"Heteroaryl" refers to a 5- to 14-membered ring system radical comprising hydrogen atoms, one to thirteen ring carbon atoms, one to six ring heteroatoms selected from the group consisting of nitrogen, oxygen and sulfur, and at least one aromatic ring comprising a heteroatom. For purposes of embodiments of this invention, the heteroaryl radical may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e., thienyl). "Heteroaryloxy" refers to a heteroaryl group bound to the remainder of the molecule via an oxygen bond (—O—). "Heteroarylaminyl" refers to a heteroaryl group bound to the remainder of the molecule via a nitrogen bond (—N$R_a$—, where $R_a$ is H or $C_1$-$C_6$ alkyl). Unless stated otherwise specifically in the specification, a heteroaryl, heteroaryloxy and/or heteroarylaminyl group is optionally substituted.

"N-heteroaryl" refers to a heteroaryl radical as defined above containing at least one nitrogen and where the point of attachment of the heteroaryl radical to the rest of the molecule is through a nitrogen atom in the heteroaryl radical. Unless stated otherwise specifically in the specification, an N-heteroaryl group is optionally substituted.

"Heteroarylalkyl" refers to a radical of the formula —$R_b R_f$ where $R_b$ is an alkylene chain as defined above and $R_f$ is a heteroaryl radical as defined above. Unless stated otherwise specifically in the specification, a heteroarylalkyl group is optionally substituted.

"Heteroarylalkyloxy" refers to a radical of the formula —O$R_b R_f$ where $R_b$ is an alkylene chain as defined above and $R_f$ is a heteroaryl radical as defined above, and if the heteroaryl is a nitrogen-containing heterocyclyl, the heterocyclyl is optionally attached to the alkyl radical at the nitrogen atom. Unless stated otherwise specifically in the specification, a heteroarylalkyloxy group is optionally substituted.

"Heteroarylalkylaminyl" refers to a radical of the formula —N$R_c R_b R_f$ where $R_b$ is an alkylene chain as defined above and $R_f$ is a heteroaryl radical as defined above, and if the heteroaryl is a nitrogen-containing heterocyclyl, the heterocyclyl is optionally attached to the alkyl radical at the nitrogen atom, and $R_c$ is H or $C_1$-$C_6$ alkyl. Unless stated otherwise specifically in the specification, a heteroarylalkylaminyl group is optionally substituted. "Hydroxylalkyl" refers to an alkyl group comprising at least one hydroxyl substituent. The —OH substituent may be on a primary, secondary or tertiary carbon. Unless stated otherwise specifically in the specification, a hydroxylalkyl group is optionally substituted. "Hydroxylalkylaminyl" is an alkylaminyl groups comprising at least one —OH substituent, which is on a primary, secondary or tertiary carbon. Unless stated otherwise specifically in the specification, a hydroxylalkylaminyl group is optionally substituted.

"Phosphate" refers to the —OP(=O)($R_a$)$R_b$ group, where $R_a$ is OH, O— or O$R_c$ and $R_b$ is OH, O—, O$R_c$, or a further phosphate group (e.g., to form a di- or triphosphate), wherein $R_c$ is a counter ion (e.g., Na+ and the like).

"Phosphoalkoxy" refers to an alkoxy group, as defined herein, which is substituted with at least one phosphate group, as defined herein. Unless stated otherwise specifically in the specification, a phosphoalkoxy group is optionally substituted.

"Thioalkyl" refers to a radical of the formula —S$R_a$ where $R_a$ is an alkyl radical as defined above containing one to twelve carbon atoms. Unless stated otherwise specifically in the specification, a thioalkyl group is optionally substituted.

The term "substituted" as used herein means any of the above groups (e.g., alkyl, alkylene, alkylcycloalkyl, alkoxy, alkylphosphoryl, alkylphosphorylaminyl, amidinylalkyloxy, guanidinylalkyloxy, alkylcarbonylaminylalkyloxy, heterocyclylalkyloxy, heteroarylalkyloxy, aminylalkyloxy, alkoxyalkyl, alkoxycarbonyl, haloalkylaminyl, hydroxylalkylaminyl, amidinylalkylaminyl, guanidinylalkylaminyl, aminylalkyl, aminylalkylaminyl, aminylalkoxy, alkylaminylalkoxy aryloxy, alkylaminyl, alkylcarbonylaminyl, alkylaminylalkyl, aminylcarbonyl, alkylaminylcarbonyl, alkylcarbonylaminylalkoxy, aminylcarbonylalkyl, aminylcarbonycycloalkylalkyl, thioalkyl, aryl, aralkyl, arylalkyloxy, arylalkylaminyl, carboxyalkyl, cyanoalkyl, cycloalkyl, cycloalkyloxy, cycloalkylaminyl, cyanocycloalkyl, cycloalkylaminylcarbonyl, cycloalkylalkyl, haloalkyl, haloalkoxy, heterocyclyl, heterocyclyloxy, heterocyclylaminyl, N-heterocyclyl, heterocyclylalkyl, heterocyclylalkyloxy, heterocyclylalkylaminyl, heteroaryl, N-heteroaryl, heteroarylalkyl, heteroarylalkyloxy, heteroarylalkylaminyl, hydroxylalkylaminyl, phosphoalkoxy and/or hydroxylalkyl) wherein at least one hydrogen atom (e.g., 1, 2, 3 or all hydrogen atoms) is replaced by a bond to a non-hydrogen atom such as, but not limited to: a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with $-NR_gR_h$, $-NR_gC(=O)R_h$, $-NR_gC(=O)NR_gR_h$, $-NR_gC(=O)OR_h$, $-NR_gSO_2R_h$, $-OC(=O)NR_gR_h$, $-OR_g$, $-SR_g$, $-SOR_g$, $-SO_2R_g$, $-OSO_2R_g$, $-SO_2OR_g$, $=NSO_2R_g$, and $-SO_2NR_gR_h$. "Substituted" also means any of the above groups in which one or more hydrogen atoms are replaced with $-C(=O)R_g$, $-C(=O)OR_g$, $-C(=O)NR_gR_h$, $-CH_2SO_2R_g$, $-CH_2SO_2NR_gR_h$. In the foregoing, $R_g$ and $R_h$ are the same or different and independently hydrogen, alkyl, alkoxy, alkylaminyl, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl. "Substituted" further means any of the above groups in which one or more hydrogen atoms are replaced by a bond to an aminyl, cyano, hydroxyl, imino, nitro, oxo, thioxo, halo, alkyl, alkoxy, alkylaminyl, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl group. In addition, each of the foregoing substituents may also be optionally substituted with one or more of the above substituents.

It is understood that each choice for $R^1$, $R^{2a}$, $R^{2b}$, $R^{2c}$, $R^{3a}$, $R^{3b}$, $R^{4a}$, $R^{4b}$, $R^5$, $L^1$, $L^2$ and E is optionally substituted as described above unless specifically stated otherwise, and provided that all valences are satisfied by the substitution. Specifically, each choice for $R^1$, $R^{2a}$, $R^{2b}$, $R^{2c}$, $R^{3a}$, $R^{3b}$, $R^{4a}$, $R^{4b}$, $R^5$, $L^1$, $L^2$ and E is optionally substituted unless specifically stated otherwise, and provided such substitution results in a stable molecule (e.g., groups such as H and halo are not optionally substituted).

"Electrophile" or "electrophilic moiety" is any moiety capable of reacting with a nucleophile (e.g., a moiety having a lone pair of electrons, a negative charge, a partial negative charge and/or an excess of electrons, for example a —SH group). Electrophiles typically are electron poor or comprise atoms which are electron poor. In certain embodiments an electrophile contains a positive charge or partial positive charge, has a resonance structure which contains a positive charge or partial positive charge or is a moiety in which delocalization or polarization of electrons results in one or more atom which contains a positive charge or partial positive charge. In some embodiments, the electrophiles comprise conjugated double bonds, for example an α,β-unsaturated carbonyl or α,β-unsaturated thiocarbonyl compound.

The term "effective amount" or "therapeutically effective amount" refers to that amount of a compound described herein that is sufficient to effect the intended application including but not limited to disease treatment, as defined below. The therapeutically effective amount may vary depending upon the intended treatment application (in vivo), or the subject and disease condition being treated, e.g., the weight and age of the subject, the severity of the disease condition, the manner of administration and the like, which can readily be determined by one of ordinary skill in the art. The term also applies to a dose that will induce a particular response in target cells, e.g., reduction of platelet adhesion and/or cell migration. The specific dose will vary depending on the particular compounds chosen, the dosing regimen to be followed, whether it is administered in combination with other compounds, timing of administration, the tissue to which it is administered, and the physical delivery system in which it is carried.

As used herein, "treatment" or "treating" refer to an approach for obtaining beneficial or desired results with respect to a disease, disorder or medical condition including but not limited to a therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the subject, notwithstanding that the subject may still be afflicted with the underlying disorder. In certain embodiments, for prophylactic benefit, the compositions are administered to a subject at risk of developing a particular disease, or to a subject reporting one or more of the physiological symptoms of a disease, even though a diagnosis of this disease may not have been made.

A "therapeutic effect," as that term is used herein, encompasses a therapeutic benefit and/or a prophylactic benefit as described above. A prophylactic effect includes delaying or eliminating the appearance of a disease or condition, delaying or eliminating the onset of symptoms of a disease or condition, slowing, halting, or reversing the progression of a disease or condition, or any combination thereof.

The term "co-administration," "administered in combination with," and their grammatical equivalents, as used herein, encompass administration of two or more agents to an animal, including humans, so that both agents and/or their metabolites are present in the subject at the same time. Co-administration includes simultaneous administration in separate compositions, administration at different times in separate compositions, or administration in a composition in which both agents are present.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

In some embodiments, pharmaceutically acceptable salts include quaternary ammonium salts such as quaternary amine alkyl halide salts (e.g., methyl bromide).

The terms "antagonist" and "inhibitor" are used interchangeably, and they refer to a compound having the ability to inhibit a biological function of a target protein, whether by inhibiting the activity or expression of the protein, such as KRAS, HRAS or NRAS G12C. Accordingly, the terms "antagonist" and "inhibitors" are defined in the context of the biological role of the target protein. While preferred antagonists herein specifically interact with (e.g., bind to) the target, compounds that inhibit a biological activity of the target protein by interacting with other members of the signal transduction pathway of which the target protein is a member are also specifically included within this definition. A preferred biological activity inhibited by an antagonist is associated with the development, growth, or spread of a tumor.

The term "agonist" as used herein refers to a compound having the ability to initiate or enhance a biological function of a target protein, whether by inhibiting the activity or expression of the target protein. Accordingly, the term "agonist" is defined in the context of the biological role of the target polypeptide. While preferred agonists herein specifically interact with (e.g., bind to) the target, compounds that initiate or enhance a biological activity of the target polypeptide by interacting with other members of the signal transduction pathway of which the target polypeptide is a member are also specifically included within this definition.

As used herein, "agent" or "biologically active agent" refers to a biological, pharmaceutical, or chemical compound or other moiety. Non-limiting examples include a simple or complex organic or inorganic molecule, a peptide, a protein, an oligonucleotide, an antibody, an antibody derivative, antibody fragment, a vitamin derivative, a carbohydrate, a toxin, or a chemotherapeutic compound. Various compounds can be synthesized, for example, small molecules and oligomers (e.g., oligopeptides and oligonucleotides), and synthetic organic compounds based on various core structures. In addition, various natural sources can provide compounds for screening, such as plant or animal extracts, and the like.

"Signal transduction" is a process during which stimulatory or inhibitory signals are transmitted into and within a cell to elicit an intracellular response. A modulator of a signal transduction pathway refers to a compound which modulates the activity of one or more cellular proteins mapped to the same specific signal transduction pathway. A modulator may augment (agonist) or suppress (antagonist) the activity of a signaling molecule.

An "anti-cancer agent", "anti-tumor agent" or "chemotherapeutic agent" refers to any agent useful in the treatment of a neoplastic condition. One class of anti-cancer agents comprises chemotherapeutic agents. "Chemotherapy" means the administration of one or more chemotherapeutic drugs and/or other agents to a cancer patient by various methods, including intravenous, oral, intramuscular, intraperitoneal, intravesical, subcutaneous, transdermal, buccal, or inhalation or in the form of a suppository.

The term "cell proliferation" refers to a phenomenon by which the cell number has changed as a result of division. This term also encompasses cell growth by which the cell morphology has changed (e.g., increased in size) consistent with a proliferative signal.

The term "selective inhibition" or "selectively inhibit" refers to a biologically active agent refers to the agent's ability to preferentially reduce the target signaling activity as compared to off-target signaling activity, via direct or indirect interaction with the target.

"Subject" refers to an animal, such as a mammal, for example a human. The methods described herein can be useful in both human therapeutics and veterinary applications. In some embodiments, the subject is a mammal, and in some embodiments, the subject is human.

"Mammal" includes humans and both domestic animals such as laboratory animals and household pets (e.g., cats, dogs, swine, cattle, sheep, goats, horses, rabbits), and non-domestic animals such as wildlife and the like.

"Radiation therapy" means exposing a subject, using routine methods and compositions known to the practitioner, to radiation emitters such as alpha-particle emitting radionuclides (e.g., actinium and thorium radionuclides), low linear energy transfer (LET) radiation emitters (i.e., beta emitters), conversion electron emitters (e.g., strontium-89 and samarium-153-EDTMP, or high-energy radiation, including without limitation x-rays, gamma rays, and neutrons.

An "anti-cancer agent", "anti-tumor agent" or "chemotherapeutic agent" refers to any agent useful in the treatment of a neoplastic condition. One class of anti-cancer agents comprises chemotherapeutic agents. "Chemotherapy"

means the administration of one or more chemotherapeutic drugs and/or other agents to a cancer patient by various methods, including intravenous, oral, intramuscular, intraperitoneal, intravesical, subcutaneous, transdermal, buccal, or inhalation or in the form of a suppository.

"Prodrug" is meant to indicate a compound that may be converted under physiological conditions or by solvolysis to a biologically active compound described herein (e.g., compound of structure (I)). Thus, the term "prodrug" refers to a precursor of a biologically active compound that is pharmaceutically acceptable. In some aspects, a prodrug is inactive when administered to a subject, but is converted in vivo to an active compound, for example, by hydrolysis. The prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam). A discussion of prodrugs is provided in Higuchi, T., et al., "Pro-drugs as Novel Delivery Systems," A.C.S. Symposium Series, Vol. 14, and in Biorevisible Carriers in Drug Design, ed. Edward B. Roche, American Pharmaceutical Association and Pergamon Press, 1987, both of which are incorporated in full by reference herein. The term "prodrug" is also meant to include any covalently bonded carriers, which release the active compound in vivo when such prodrug is administered to a mammalian subject. Prodrugs of an active compound, as described herein, are typically prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a mammalian subject, cleaves to form a free hydroxy, free amino or free mercapto group, respectively. Examples of prodrugs include, but are not limited to, acetate, formate and benzoate derivatives of a hydroxy functional group, or acetamide, formamide and benzamide derivatives of an amine functional group in the active compound and the like.

In some embodiments, prodrugs include compounds of structure (I) having a phosphate, phosphoalkoxy, ester or boronic ester substituent. Without being bound by theory, it is believed that such substituents are converted to a hydroxyl group under physiological conditions. Accordingly, embodiments include any of the compounds disclosed herein, wherein a hydroxyl group has been replaced with a phosphate, phosphoalkoxy, ester or boronic ester group, for example a phosphate or phosphoalkoxy group. For example, in some embodiments a hydroxyl group on the $R^1$ moiety is replaced with a phosphate, phosphoalkoxy, ester or boronic ester group, for example a phosphate or alkoxy phosphate group. Exemplary prodrugs of certain embodiments thus include $R^1$ moieties substituted with one of the following substituents:

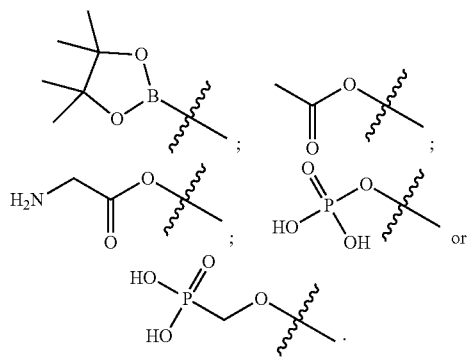

The term "in vivo" refers to an event that takes place in a subject's body.

Embodiments of the invention disclosed herein are also meant to encompass all pharmaceutically acceptable compounds of structure (I) being isotopically-labelled by having one or more atoms replaced by an atom having a different atomic mass or mass number (i.e., an "isotopic form" of a compound of structure (I)). Examples of isotopes that can be incorporated into the disclosed compounds include isotopes of hydrogen, carbon, nitrogen, oxygen, phosphorous, fluorine, chlorine, and iodine, such as $^2$H, $^3$H, $^{11}$C, $^{13}$C, $^{14}$C, $^{13}$N, $^{15}$N, $^{15}$O, $^{17}$O, $^{18}$O, $^{31}$P, $^{32}$P, $^{35}$S, $^{18}$F, $^{36}$Cl, $^{123}$I, and $^{125}$I, respectively. These radiolabeled compounds could be useful to help determine or measure the effectiveness of the compounds, by characterizing, for example, the site or mode of action, or binding affinity to pharmacologically important site of action. Certain isotopically-labeled compounds of structure (I), for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection.

Substitution with heavier isotopes such as deuterium, i.e., $^2$H, may afford certain therapeutic advantages resulting from greater metabolic stability, for example, increased in vivo half-life or reduced dosage requirements, and hence are preferred in some circumstances.

Substitution with positron emitting isotopes, such as $^{11}$C, $^{18}$F, $^{15}$O and $^{13}$N, can be useful in Positron Emission Topography (PET) studies for examining substrate receptor occupancy. Isotopically-labeled compounds of structure (I) can generally be prepared by conventional techniques known to those skilled in the art or by processes analogous to those described in the Examples as set out below using an appropriate isotopically-labeled reagent in place of the non-labeled reagent previously employed.

Certain embodiments are also meant to encompass the in vivo metabolic products of the disclosed compounds. Such products may result from, for example, the oxidation, reduction, hydrolysis, amidation, esterification, and the like of the administered compound, primarily due to enzymatic processes. Accordingly, the embodiments include compounds produced by a process comprising administering a compound of this invention to a mammal for a period of time sufficient to yield a metabolic product thereof. Such products are typically identified by administering a radiolabeled compound of the invention in a detectable dose to an animal, such as rat, mouse, guinea pig, monkey, or to human, allowing sufficient time for metabolism to occur, and isolating its conversion products from the urine, blood or other biological samples.

"Stable compound" and "stable structure" are meant to indicate a compound that is sufficiently robust to survive isolation to a useful degree of purity from a reaction mixture, and formulation into an efficacious therapeutic agent.

Often crystallizations produce a solvate of the compound of the invention. As used herein, the term "solvate" refers to an aggregate that comprises one or more molecules of a compound of the invention with one or more molecules of solvent. In some embodiments, the solvent is water, in which case the solvate is a hydrate. Alternatively, in other embodiments, the solvent is an organic solvent. Thus, the compounds of the present invention may exist as a hydrate, including a monohydrate, dihydrate, hemihydrate, sesquihydrate, trihydrate, tetrahydrate and the like, as well as the corresponding solvated forms. In some aspects, the compound of the invention is a true solvate, while in other cases, the compound of the invention merely retains adventitious water or is a mixture of water plus some adventitious solvent.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution.

A "pharmaceutical composition" refers to a formulation of a compound of the invention and a medium generally accepted in the art for the delivery of the biologically active compound to mammals, e.g., humans. Such a medium includes all pharmaceutically acceptable carriers, diluents or excipients therefor.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

The compounds of the invention (i.e., compounds of structure (I) and embodiments thereof), or their pharmaceutically acceptable salts may contain one or more centers of geometric asymmetry and may thus give rise to enantiomers, diastereomers, and other stereoisomeric forms that are defined, in terms of absolute stereochemistry, as (R)- or (S)- or, as (D)- or (L)- for amino acids. Embodiments thus include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centers of geometric asymmetry, and unless specified otherwise, it is intended that the compounds include both E and Z geometric isomers. Likewise, all tautomeric forms are also intended to be included.

Embodiments of the present invention include all manner of rotamers and conformationally restricted states of a compound of the invention. Atropisomers, which are stereoisomers arising because of hindered rotation about a single bond, where energy differences due to steric strain or other contributors create a barrier to rotation that is high enough to allow for isolation of individual conformers, are also included. As an example, certain compounds of the invention may exist as mixtures of atropisomers or purified or enriched for the presence of one atropisomer. Non-limiting examples of compounds which exist as atropisomers include the following compounds:

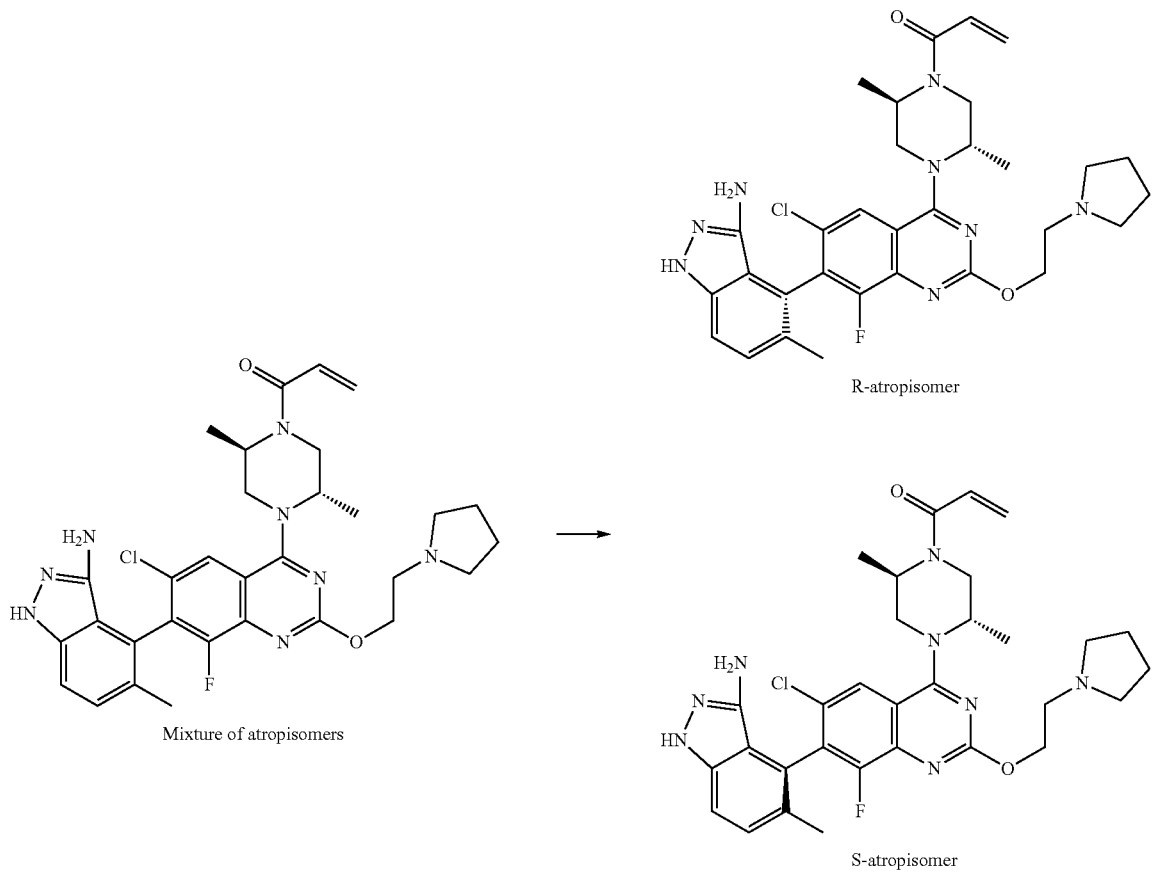

and

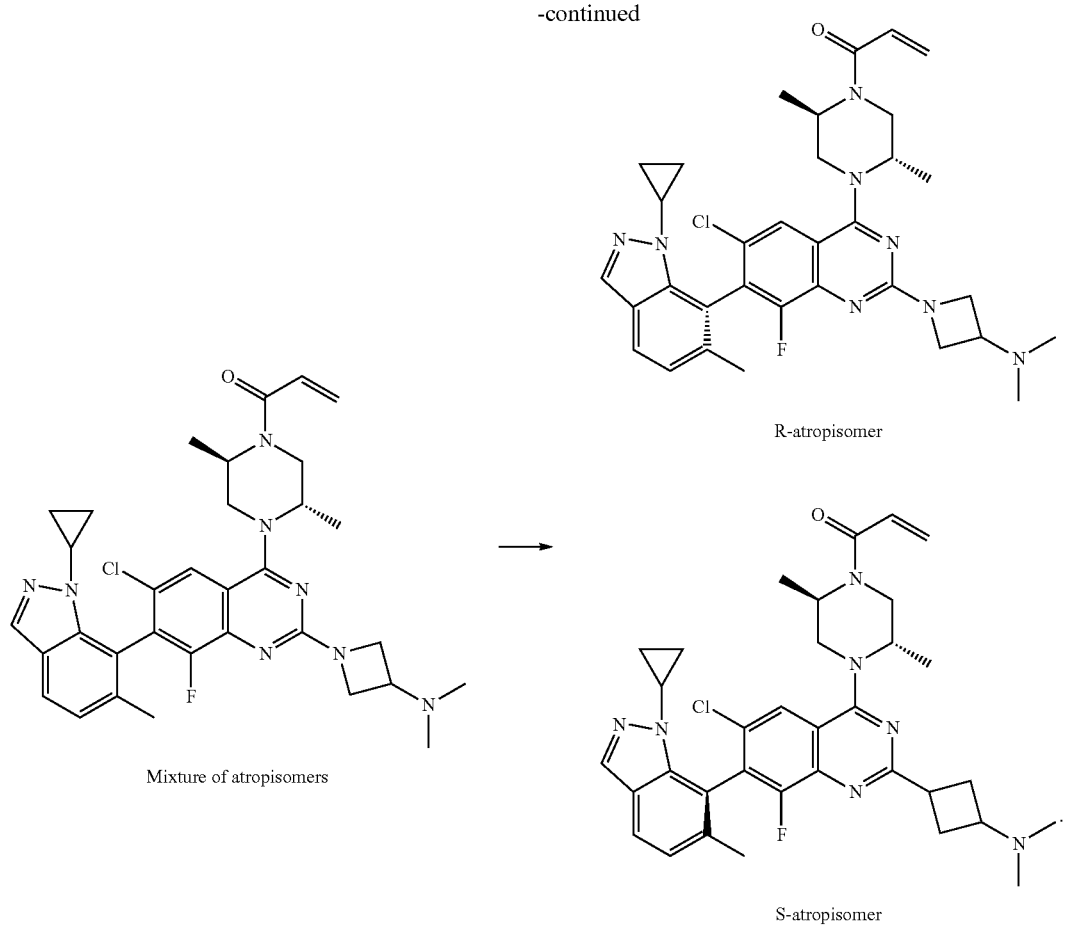

Mixture of atropisomers

R-atropisomer

S-atropisomer

In some embodiments, the compound of structure (I) is a mixture of atropisomers. In other embodiments, the compound of structure (I) is a substantially purified atropisomer. In some embodiments, the compound of structure (I) is a substantially purified R-atropisomer. In some other embodiments, the compound of structure (I) is a substantially purified S-atropisomer.

A "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are non-superimposable mirror images of one another.

A "tautomer" refers to a proton shift from one atom of a molecule to another atom of the same molecule. Embodiments thus include tautomers of the disclosed compounds.

The chemical naming protocol and structure diagrams used herein are a modified form of the I.U.P.A.C. nomenclature system, using the ACD/Name Version 9.07 software program and/or ChemDraw Ultra Version 11.0.1 software naming program (CambridgeSoft). For complex chemical names employed herein, a substituent group is typically named before the group to which it attaches. For example, cyclopropylethyl comprises an ethyl backbone with a cyclopropyl substituent. Except as described below, all bonds are identified in the chemical structure diagrams herein, except for all bonds on some carbon atoms, which are assumed to be bonded to sufficient hydrogen atoms to complete the valency.

Compounds

In an aspect, the invention provides compounds which are capable of selectively binding to and/or modulating a G12C mutant KRAS, HRAS or NRAS protein. The compounds may modulate the G12C mutant KRAS, HRAS or NRAS protein by reaction with an amino acid. While not wishing to be bound by theory, the present applicants believe that, in some embodiments, the compounds of the invention selectively react with the G12C mutant KRAS, HRAS or NRAS proteins by forming a covalent bond with the cysteine at the 12 position of a G12C mutant KRAS, HRAS or NRAS protein. By binding to the Cysteine 12, the compounds of the invention may lock the switch II of the G12C mutant KRAS, HRAS or NRAS into an inactive stage. This inactive stage may be distinct from those observed for GTP and GDP bound KRAS, HRAS or NRAS. Some compounds of the invention may also be able to perturb the switch I conformation. Some compounds of the invention may favor the binding of the bound KRAS, HRAS or NRAS to GDP rather than GTP and therefore sequester the KRAS, HRAS or NRAS into an inactive KRAS, HRAS or NRAS GDP state. Because effector binding to KRAS, HRAS or NRAS is highly sensitive to the conformation of switch I and II, the irreversible binding of these compounds may disrupt KRAS, HRAS or NRAS downstream signaling.

As noted above, in one embodiment of the present invention, compounds having activity as modulators of a G12C mutant KRAS, HRAS or NRAS protein are provided, the compounds have the following structure (I):

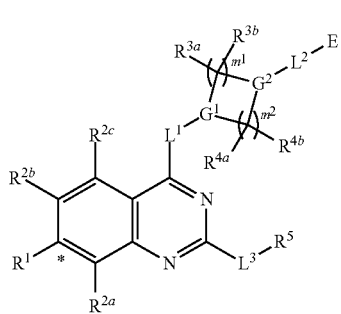

(I)

or a pharmaceutically acceptable salt, isotopic form, stereoisomer or prodrug thereof,
wherein:
$G^1$ and $G^2$ are each independently N or CH;
L is a bond or —$NR^6$—;
$L^2$ is a bond or alkylene;
$L^3$ is a bond, —O—, —$NR^6$—, —S—, —S(=O)— or —S(=O)$_2$—;
$R^1$ is unsubstituted naphthyl or optionally substituted quinolinyl when at least one or $R^{3a}$, $R^{3b}$, $R^{4a}$ and $R^{4b}$ is not H; or $R^1$ has the following structure (R'):

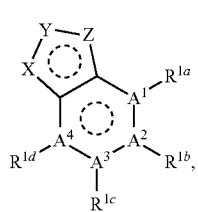

(R1')

wherein:
each

represents an aromatic ring;
$A^1$, $A^2$, $A^3$ and $A^4$ are each independently C or N;
X is O, S, N, NH, C(=O), $CR^{1e}$ or $NR^{1e'}$;
Y is O, S, N, NH, C(=O), $CR^{1f}$ or $NR^{1f'}$;
Z is O, S, N, NH, C(=O), $CR^{1g}$ or $NR^{1g'}$;
one of $R^{1a}$, $R^{1b}$, $R^{1c}$ and $R^{1d}$ is a covalent bond to the carbon marked with *, and the other of $R^{1a}$, $R^{1b}$, $R^{1c}$ and $R^{1d}$ are each independently H, amino, cyano, halo, hydroxyl, $C_1$-$C_6$ alkyl, $C_2$-$C_6$ alkenyl, $C_2$-$C_6$ alkynyl, alkylaminyl, $C_1$-$C_6$ haloalkyl, $C_1$-$C_6$ alkoxy, $C_1$-$C_6$ haloalkoxy; cycloalkyl, heterocyclyl, aminylalkyl, $C_1$-$C_6$ cyanoalkyl, $C_1$-$C_6$ carboxyalkyl, aminylcarbonylalkyl or aminylcarbonyl;
$R^{1e}$, $R^{1f}$ and $R^{1g}$ are each independently H, amino, cyano, halo, hydroxyl, $C_1$-$C_6$ alkyl, $C_2$-$C_6$ alkenyl, $C_2$-$C_6$ alkynyl, alkylaminyl, $C_1$-$C_6$ haloalkyl, $C_1$-$C_6$ alkoxy, $C_1$-$C_6$ haloalkoxy, cycloalkyl, cycloalkylalkyl, cycloalkylalkylaminyl, cycloalkylaminyl, alkylcarbonylaminyl, heterocyclyl, aminylalkyl, $C_1$-$C_6$ cyanoalkyl, $C_1$-$C_6$ carboxyalkyl, aminylcarbonylalkyl or aminylcarbonyl; and
$R^{1e'}$, $R^{1f'}$ and $R^{1g'}$ are each independently $C_1$-$C_6$ alkyl, $C_2$-$C_6$ alkenyl, $C_2$-$C_6$ alkynyl, cycloalkyl, cycloalkylalkyl, heterocyclyl or heterocyclylalkyl, provided that when each of $A^1$, $A^2$, $A^3$ and $A^4$ are C, $R^{1a}$ is a covalent bond to the carbon marked with *, one of $R^{1b}$, $R^{1c}$ and $R^{1d}$ is methyl and: i) X is NH, Y is N and Z is $CR^{1g}$; ii) Y is N and Z is NH; iii) X is NH, Y is $CR^{1f}$ and Z is $CR^{1g}$; or iv) X is NH, Y is $CR^{1f}$ and Z is N, then at least one of $R^{1b}$, $R^{1c}$, $R^{1d}$, $R^{1e}$, $R^{1f}$ and $R^{1g}$ is not H, or at least one of $R^{3a}$, $R^{3b}$, $R^{4a}$ and $R^{4b}$ is $C_1$-$C_6$ cyanoalkyl, and provided that at least one of X, Y and Z is O, N or NH;

$R^{2a}$, $R^{2b}$ and $R^{2c}$ are each independently H, amino, cyano, halo, hydroxyl, $C_1$-$C_6$ alkyl, $C_2$-$C_6$ alkenyl, $C_2$-$C_6$ alkynyl, $C_1$-$C_6$ alkylaminyl, $C_1$-$C_6$ haloalkyl, $C_1$-$C_6$ alkoxy, $C_1$-$C_6$ haloalkoxy; cycloalkyl, cycloalkylalkyl, heterocyclyl, heterocyclylalkyl, aminylalkyl, alkylaminylalkyl, cyanoalkyl, carboxyalkyl, aminylcarbonylalkyl, aminylcarbonyl, heteroaryl or aryl;

$R^{3a}$ and $R^{3b}$ are, at each occurrence, independently H, —OH, —$NH_2$, —$CO_2H$, halo, cyano, $C_1$-$C_6$ alkyl, $C_2$-$C_6$ alkenyl, $C_2$-$C_6$ alkynyl, $C_1$-$C_6$ haloalkyl, $C_1$-$C_6$ haloalkoxy, $C_1$-$C_6$ hydroxyalkyl, alkoxyalkyl, aminylalkyl, alkylaminylalkyl, $C_1$-$C_6$ cyanoalkyl, $C_1$-$C_6$ carboxyalkyl, aminylcarbonylalkyl or aminylcarbonyl; or $R^{3a}$ and $R^{3b}$ join to form oxo, a carbocyclic or heterocyclic ring; or $R^{3a}$ is H, —OH, —$NH_2$, —$CO_2H$, halo, cyano, $C_1$-$C_6$ alkyl, $C_2$-$C_6$ alkenyl, $C_2$-$C_6$ alkynyl, $C_1$-$C_6$ haloalkyl, $C_1$-$C_6$ haloalkoxy, $C_1$-$C_6$ hydroxyalkyl, alkoxyalkyl, aminylalkyl, alkylaminylalkyl, $C_1$-$C_6$ cyanoalkyl, $C_1$-$C_6$ carboxyalkyl, aminylcarbonylalkyl or aminylcarbonyl, and $R^{3b}$ joins with $R^{4b}$ to form a carbocyclic or heterocyclic ring;

$R^{4a}$ and $R^{4b}$ are, at each occurrence, independently H, —OH, —$NH_2$, —$CO_2H$, halo, cyano, $C_1$-$C_6$ alkyl, $C_2$-$C_6$ alkenyl, $C_2$-$C_6$ alkynyl, $C_1$-$C_6$ haloalkyl, $C_1$-$C_6$ haloalkoxy, $C_1$-$C_6$ hydroxyalkyl, alkoxyalkyl, aminylalkyl, alkylaminylalkyl, $C_1$-$C_6$ cyanoalkyl, $C_1$-$C_6$ carboxyalkyl, aminylcarbonylalkyl or aminylcarbonyl; or $R^{4a}$ and $R^{4b}$ join to form oxo, a carbocyclic or heterocyclic ring; or $R^{4a}$ is H, —OH, —$NH_2$, —$CO_2H$, halo, cyano, $C_1$-$C_6$ alkyl, $C_2$-$C_6$ alkenyl, $C_2$-$C_6$ alkynyl, $C_1$-$C_6$ haloalkyl, $C_1$-$C_6$ haloalkoxy, $C_1$-$C_6$ hydroxyalkyl, alkoxyalkyl, aminylalkyl, alkylaminylalkyl, $C_1$-$C_6$ cyanoalkyl, $C_1$-$C_6$ carboxyalkyl, aminylcarbonylalkyl or aminylcarbonyl, and $R^{4b}$ joins with $R^{3b}$ to form a carbocyclic or heterocyclic ring;

$R^5$ is amino, cyano, hydroxyl, $C_1$-$C_6$ alkyl, $C_2$-$C_6$ alkynyl; $C_1$-$C_6$ haloalkyl, $C_1$-$C_6$ hydroxyalkyl, $C_1$-$C_6$ cyanoalkyl, alkoxy, aminylalkyl, aminylalkynyl, alkoxyalkyl, alkoxyalkynyl, alkylcarbonylaminyl, aminylalkylcarbonylaminyl, aminylcarbonylalkyl, cycloalkyl, cycloalkylalkyl, heterocyclyl, heterocyclylalkyl, heterocyclylcarbonylalkyl, aryl, aralkyl, heteroaryl, heteroarylalkyl; —$NR^aR^b$, $C_1$-$C_6$ alkylphosphoryl, $C_1$-$C_6$ alkylphosphorylaminyl, heteroarylalkyloxy or heteroarylalkylaminyl, wherein $R^a$ is H or $C_1$-$C_6$ alkyl, and $R^b$ is $C_1$-$C_6$ alkyl;

$R^6$ is, at each occurrence, independently H or $C_1$-$C_6$ alkyl;
$m^1$ and $m^2$ are each independently 1, 2 or 3; and
E is an electrophilic moiety capable of forming a covalent bond with the cysteine residue at position 12 of a KRAS, HRAS or NRAS G12C mutant protein, wherein each occurrence of alkyl, alkynyl, alkenyl, alkylene, aryl, aralkyl, heteroaryl, heteroarylalkyl, cycloalkyl, cycloalkylalkyl, heterocyclyl, heterocyclylalkyl, alkylaminyl, haloalkyl, hydroxylalkyl, alkoxy, alkoxyalkyl, haloalkoxy, heterocyclylalkyl, aminylalkyl, alkylaminylalkyl, cyanoalkyl, carboxyalkyl, aminylcarbonyl, aminylcarbonylalkyl, and carbocyclic and heterocyclic rings is optionally substituted with one or more substituents unless otherwise specified; and provided the compound is not a compound in Table 2.

In some different embodiments of structure (I):
$G^1$ and $G^2$ are each independently N or CH;
$L^1$ is a bond or —$NR^6$—;
$L^2$ is a bond or alkylene;
$L^3$ is a bond, —O—, —$NR^6$—, —S—, —S(=O)— or —S(=O)$_2$—;
$R^1$ is unsubstituted naphthyl or optionally substituted quinolinyl when at least one or $R^{3a}$, $R^{3b}$, $R^{4a}$ and $R^{4b}$ is not H; or $R^1$ has the following structure ($R^{1''}$):

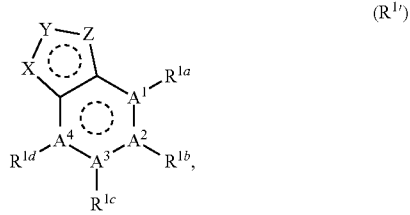

wherein:
each

represents an aromatic ring;
$A^1$, $A^2$, $A^3$ and $A^4$ are each independently C or N;
X is O, S, N, NH, C(=O), $CR^{1e}$ or $NR^{1e'}$;
Y is O, S, N, NH, C(=O), $CR^{1f}$ or $NR^{1f'}$;
Z is O, S, N, NH, C(=O), $CR^{1g}$ or $NR^{1g'}$;
one of $R^{1a}$, $R^{1b}$, $R^{1c}$ and $R^{1d}$ is a covalent bond to the carbon marked with *, and the other of $R^{1a}$, $R^{1b}$, $R^{1c}$ and $R^{1d}$ are each independently H, amino, cyano, halo, hydroxyl, $C_1$-$C_6$ alkyl, $C_2$-$C_6$ alkenyl, $C_2$-$C_6$ alkynyl, alkylaminyl, $C_1$-$C_6$ haloalkyl, $C_1$-$C_6$ alkoxy, $C_1$-$C_6$ haloalkoxy; cycloalkyl, heterocyclyl, aminylalkyl, $C_1$-$C_6$ cyanoalkyl, $C_1$-$C_6$ carboxyalkyl, aminylcarbonylalkyl or aminylcarbonyl;
$R^{1e}$, $R^{1f}$ and $R^{1g}$ are each independently H, amino, cyano, halo, hydroxyl, $C_1$-$C_6$ alkyl, $C_2$-$C_6$ alkenyl, $C_2$-$C_6$ alkynyl, alkylaminyl, $C_1$-$C_6$ haloalkyl, $C_1$-$C_6$ alkoxy, $C_1$-$C_6$ haloalkoxy, cycloalkyl, cycloalkylalkyl, cycloalkylalkylaminyl, cycloalkylaminyl, alkylcarbonylaminyl, heterocyclyl, aminylalkyl, $C_1$-$C_6$ cyanoalkyl, $C_1$-$C_6$ carboxyalkyl, aminylcarbonylalkyl or aminylcarbonyl, and
$R^{1e'}$, $R^{1f'}$ and $R^{1g'}$ are each independently $C_1$-$C_6$ alkyl, $C_2$-$C_6$ alkenyl, $C_2$-$C_6$ alkynyl, cycloalkyl, cycloalkylalkyl, heterocyclyl or heterocyclylalkyl,
provided that when each of $A^1$, $A^2$, $A^3$ and $A^4$ are C, $R^{1a}$ is a covalent bond to the carbon marked with *, one of $R^{1b}$, $R^{1c}$ and $R^{1d}$ is methyl and: i) X is NH, Y is N and Z is $CR^{1g}$; ii) Y is N and Z is NH; iii) X is NH, Y is $CR^{1f}$ and Z is $CR^{1g}$; or iv) X is NH, Y is $CR^{1f}$ and Z is N, then at least one of $R^{1b}$, $R^{1c}$, $R^{1d}$, $R^{1e}$, $R^{1f}$ and $R^{1g}$ is not H, and provided that at least one of X, Y and Z is O, N or NH;
$R^{2a}$, $R^{2b}$ and $R^{2c}$ are each independently H, amino, cyano, halo, hydroxyl, $C_1$-$C_6$ alkyl, $C_2$-$C_6$ alkenyl, $C_2$-$C_6$ alkynyl, $C_1$-$C_6$ alkylaminyl, $C_1$-$C_6$ haloalkyl, $C_1$-$C_6$ alkoxy, $C_1$-$C_6$ haloalkoxy; cycloalkyl, cycloalkylalkyl, heterocyclyl, heterocyclylalkyl, aminylalkyl, alkylaminylalkyl, cyanoalkyl, carboxyalkyl, aminylcarbonylalkyl, aminylcarbonyl, heteroaryl or aryl;

$R^{3a}$ and $R^{3b}$ are, at each occurrence, independently H, —OH, —$NH_2$, —$CO_2H$, halo, cyano, $C_1$-$C_6$ alkyl, $C_2$-$C_6$ alkenyl, $C_2$-$C_6$ alkynyl, $C_1$-$C_6$ haloalkyl, $C_1$-$C_6$ haloalkoxy, $C_1$-$C_6$ hydroxylalkyl, alkoxyalkyl, aminylalkyl, alkylaminylalkyl, $C_1$-$C_6$ cyanoalkyl, $C_1$-$C_6$ carboxyalkyl, aminylcarbonylalkyl or aminylcarbonyl; or $R^{3a}$ and $R^{3b}$ join to form oxo, a carbocyclic or heterocyclic ring; or $R^{3a}$ is H, —OH, —$NH_2$, —$CO_2H$, halo, cyano, $C_1$-$C_6$ alkyl, $C_2$-$C_6$ alkenyl, $C_2$-$C_6$ alkynyl, $C_1$-$C_6$ haloalkyl, $C_1$-$C_6$ haloalkoxy, $C_1$-$C_6$ hydroxylalkyl, alkoxyalkyl, aminylalkyl, alkylaminylalkyl, $C_1$-$C_6$ cyanoalkyl, $C_1$-$C_6$ carboxyalkyl, aminylcarbonylalkyl or aminylcarbonyl, and $R^{3b}$ joins with $R^{4b}$ to form a carbocyclic or heterocyclic ring;
$R^{4a}$ and $R^{4b}$ are, at each occurrence, independently H, —OH, —$NH_2$, —$CO_2H$, halo, cyano, $C_1$-$C_6$ alkyl, $C_2$-$C_6$ alkenyl, $C_2$-$C_6$ alkynyl, $C_1$-$C_6$ haloalkyl, $C_1$-$C_6$ haloalkoxy, $C_1$-$C_6$ hydroxylalkyl, alkoxyalkyl, aminylalkyl, alkylaminylalkyl, $C_1$-$C_6$ cyanoalkyl, $C_1$-$C_6$ carboxyalkyl, aminylcarbonylalkyl or aminylcarbonyl; or $R^{4a}$ and $R^{4b}$ join to form oxo, a carbocyclic or heterocyclic ring; or $R^{4a}$ is H, —OH, —$NH_2$, —$CO_2H$, halo, cyano, $C_1$-$C_6$ alkyl, $C_2$-$C_6$ alkenyl, $C_2$-$C_6$ alkynyl, $C_1$-$C_6$ haloalkyl, $C_1$-$C_6$ haloalkoxy, $C_1$-$C_6$ hydroxylalkyl, alkoxyalkyl, aminylalkyl, alkylaminylalkyl, $C_1$-$C_6$ cyanoalkyl, $C_1$-$C_6$ carboxyalkyl, aminylcarbonylalkyl or aminylcarbonyl, and $R^{4b}$ joins with $R^{3b}$ to form a carbocyclic or heterocyclic ring;
$R^5$ is amino, cyano, hydroxyl, $C_1$-$C_6$ alkyl, $C_1$-$C_6$ haloalkyl, $C_1$-$C_6$ hydroxylalkyl, —$C_1$-$C_6$ cyanoalkyl, aminylalkyl, aminylcarbonylalkyl, cycloalkyl, cycloalkylalkyl, heterocyclyl, heterocyclylalkyl, heterocyclylcarbonylalkyl, aryl, aralkyl, heteroaryl or heteroarylalkyl,
$R^6$ is, at each occurrence, independently H or $C_1$-$C_6$ alkyl;
$m^1$ and $m^2$ are each independently 1, 2 or 3; and
E is an electrophilic moiety capable of forming a covalent bond with the cysteine residue at position 12 of a KRAS, HRAS or NRAS G12C mutant protein,
wherein each occurrence of alkyl, alkynyl, alkenyl, alkylene, aryl, aralkyl, heteroaryl, heteroarylalkyl, cycloalkyl, cycloalkylalkyl, heterocyclyl, heterocyclylalkyl, alkylaminyl, haloalkyl, hydroxylalkyl, alkoxy, alkoxyalkyl, haloalkoxy, heterocyclylalkyl, aminylalkyl, alkylaminylalkyl, cyanoalkyl, carboxyalkyl, aminylcarbonyl, aminylcarbonylalkyl, and carbocyclic and heterocyclic rings is optionally substituted with one or more substituents unless otherwise specified; and
provided the compound is not a compound in Table 2.
In other embodiments of compounds of structure (I):
$G^1$ and $G^2$ are each independently N or CH;
$L^1$ is a bond or —$NR^6$—;
$L^2$ is a bond or alkylene;
$L^3$ is a bond, —O—, —$NR^6$—, —S—, —S(=O)— or —S(=O)$_2$—;
$R^1$ is unsubstituted naphthyl or optionally substituted quinolinyl when at least one or $R^{3a}$, $R^{3b}$, $R^{4a}$ and $R^{4b}$ is not H; or $R^1$ has the following structure ($R^{1'''}$):

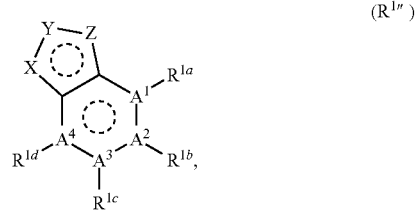

wherein:
each

represents an aromatic ring;
$A^1$, $A^2$, $A^3$ and $A^4$ are each independently C or N;
X is N, NH or $CR^{1e}$;
Y is N, NH or $CR^{1f}$;
Z is N, NH or $CR^{1g}$;
one of $R^{1a}$, $R^{1b}$, $R^{1c}$ and $R^{1d}$ is a covalent bond to the carbon marked with *, and the other of $R^{1a}$, $R^{1b}$, $R^{1c}$ and $R^{1d}$ are each independently H, amino, cyano, halo, hydroxyl, $C_1$-$C_6$ alkyl, $C_2$-$C_6$ alkenyl, $C_2$-$C_6$ alkynyl, alkylaminyl, $C_1$-$C_6$ haloalkyl, $C_1$-$C_6$ alkoxy, $C_1$-$C_6$ haloalkoxy; cycloalkyl, heterocyclyl, aminylalkyl, $C_1$-$C_6$ cyanoalkyl, $C_1$-$C_6$ carboxyalkyl, aminylcarbonylalkyl or aminylcarbonyl;
$R^{1e}$, $R^{1f}$ and $R^{1g}$ are each independently H, amino, cyano, halo, hydroxyl, $C_1$-$C_6$ alkyl, $C_2$-$C_6$ alkenyl, $C_2$-$C_6$ alkynyl, alkylaminyl, $C_1$-$C_6$ haloalkyl, $C_1$-$C_6$ alkoxy, $C_1$-$C_6$ haloalkoxy; cycloalkyl, heterocyclyl, aminylalkyl, $C_1$-$C_6$ cyanoalkyl, $C_1$-$C_6$ carboxyalkyl, aminylcarbonylalkyl or aminylcarbonyl, and
provided that when each of $A^1$, $A^2$, $A^3$ and $A^4$ are C, X is NH, Y is N and one of the other of $R^{1a}$, $R^{1b}$, $R^{1c}$ and $R^{1d}$ is methyl, then at least one other of $R^{1a}$, $R^{1b}$, $R^{1c}$, $R^{1d}$, $R^{1e}$, $R^{1f}$ and $R^{1g}$ is not H, and provided that at least one of X, Y and Z is N or NH;
$R^{2a}$, $R^{2b}$ and $R^{2c}$ are each independently H, amino, cyano, halo, hydroxyl, $C_1$-$C_6$ alkyl, $C_2$-$C_6$ alkenyl, $C_2$-$C_6$ alkynyl, $C_1$-$C_6$ alkylaminyl, $C_1$-$C_6$ haloalkyl, $C_1$-$C_6$ alkoxy, $C_1$-$C_6$ haloalkoxy; cycloalkyl, cycloalkylalkyl, heterocyclyl, heterocyclylalkyl, aminylalkyl, alkylaminylalkyl, cyanoalkyl, carboxyalkyl, aminylcarbonylalkyl, aminylcarbonyl, heteroaryl or aryl;
$R^{3a}$ and $R^{3b}$ are, at each occurrence, independently H, —OH, —NH$_2$, —CO$_2$H, halo, cyano, $C_1$-$C_6$ alkyl, $C_2$-$C_6$ alkenyl, $C_2$-$C_6$ alkynyl, $C_1$-$C_6$ haloalkyl, $C_1$-$C_6$ haloalkoxy, $C_1$-$C_6$ hydroxylalkyl, alkoxyalkyl, aminylalkyl, alkylaminylalkyl, $C_1$-$C_6$ cyanoalkyl, $C_1$-$C_6$ carboxyalkyl, aminylcarbonylalkyl or aminylcarbonyl; or $R^{3a}$ and $R^{3b}$ join to form oxo, a carbocyclic or heterocyclic ring; or $R^{3a}$ is H, —OH, —NH$_2$, —CO$_2$H, halo, cyano, $C_1$-$C_6$ alkyl, $C_2$-$C_6$ alkenyl, $C_2$-$C_6$ alkynyl, $C_1$-$C_6$ haloalkyl, $C_1$-$C_6$ haloalkoxy, $C_1$-$C_6$ hydroxylalkyl, alkoxyalkyl, aminylalkyl, alkylaminylalkyl, $C_1$-$C_6$ cyanoalkyl, $C_1$-$C_6$ carboxyalkyl, aminylcarbonylalkyl or aminylcarbonyl, and $R^{3b}$ joins with $R^{4b}$ to form a carbocyclic or heterocyclic ring;
$R^{4a}$ and $R^{4b}$ are, at each occurrence, independently H, —OH, —NH$_2$, —CO$_2$H, halo, cyano, $C_1$-$C_6$ alkyl, $C_2$-$C_6$ alkenyl, $C_2$-$C_6$ alkynyl, $C_1$-$C_6$ haloalkyl, $C_1$-$C_6$ haloalkoxy, $C_1$-$C_6$ hydroxylalkyl, alkoxyalkyl, aminylalkyl, alkylaminylalkyl, $C_1$-$C_6$ cyanoalkyl, $C_1$-$C_6$ carboxyalkyl, aminylcarbonylalkyl or aminylcarbonyl; or $R^{4a}$ and $R^{4b}$ join to form oxo, a carbocyclic or heterocyclic ring; or $R^{4a}$ is H, —OH, —NH$_2$, —CO$_2$H, halo, cyano, $C_1$-$C_6$ alkyl, $C_2$-$C_6$ alkenyl, $C_2$-$C_6$ alkynyl, $C_1$-$C_6$ haloalkyl, $C_1$-$C_6$ haloalkoxy, $C_1$-$C_6$ hydroxylalkyl, alkoxyalkyl, aminylalkyl, alkylaminylalkyl, $C_1$-$C_6$ cyanoalkyl, $C_1$-$C_6$ carboxyalkyl, aminylcarbonylalkyl or aminylcarbonyl, and $R^{4b}$ joins with $R^{3b}$ to form a carbocyclic or heterocyclic ring;
$R^5$ is amino, cyano, hydroxyl, $C_1$-$C_6$ alkyl, $C_1$-$C_6$ haloalkyl, $C_1$-$C_6$ hydroxylalkyl, $C_1$-$C_6$ cyanoalkyl, aminylalkyl, cycloalkyl, cycloalkylalkyl, heterocyclyl, heterocyclylalkyl, aryl, aralkyl, heteroaryl or heteroarylalkyl,
$R^6$ is, at each occurrence, independently H or $C_1$-$C_6$ alkyl;
$m^1$ and $m^2$ are each independently 1, 2 or 3; and
E is an electrophilic moiety capable of forming a covalent bond with the cysteine residue at position 12 of a KRAS, HRAS or NRAS G12C mutant protein,
wherein each occurrence of alkyl, alkynyl, alkenyl, alkylene, aryl, aralkyl, heteroaryl, heteroarylalkyl, cycloalkyl, cycloalkylalkyl, heterocyclyl, heterocyclylalkyl, alkylaminyl, haloalkyl, hydroxylalkyl, alkoxy, alkoxyalkyl, haloalkoxy, heterocyclylalkyl, aminylalkyl, alkylaminylalkyl, cyanoalkyl, carboxyalkyl, aminylcarbonyl, aminylcarbonylalkyl, and carbocyclic and heterocyclic rings is optionally substituted with one or more substituents unless otherwise specified.

Each of $R^1$, $R^{2a}$, $R^{2b}$, $R^{2c}$, $R^{3a}$, $R^{3b}$, $R^{4a}$, $R^{4b}$, $R^5$, $L^1$, $L^2$, $L^3$ and E in the compound of structure (I) is optionally substituted unless specifically stated otherwise or such substitution would result in an unstable structure or improper valence. For example, in some embodiments each occurrence of alkyl, alkynyl, alkenyl, alkylene, aryl, aralkyl, heteroaryl, heteroarylalkyl, cycloalkyl, cycloalkylalkyl, heterocyclyl, heterocyclylalkyl, alkylaminyl, haloalkyl, hydroxylalkyl, alkoxy, alkoxyalkyl, haloalkoxy, heterocyclylalkyl, aminylalkyl, alkylaminylalkyl, cyanoalkyl, carboxyalkyl, aminylcarbonyl, aminylcarbonylalkyl, and carbocyclic and heterocyclic rings is optionally substituted with in the compound of structure (I) is optionally substituted with one or more substituents.

In some of the foregoing embodiments, the compound is not a compound in Table 2. In some embodiments, for example, the compound is not one of the following compounds:
1-((2R,5S)-4-(6-chloro-7-(3,6-dimethyl-1H-indazol-7-yl)-2-(3-(dimethylamino)azetidin-1-yl)-8-fluoroquinazolin-4-yl)-2,5-dimethylpiperazin-1-yl)prop-2-en-1-one; 1-((2R,5S)-4-(6-chloro-7-(3,5-dimethyl-1H-indazol-4-yl)-2-(3-(dimethylamino)azetidin-1-yl)-8-fluoroquinazolin-4-yl)-2,5-dimethylpiperazin-1-yl)prop-2-en-1-one; 1-((2R,5S)-4-(6-chloro-2-(3-(dimethylamino)azetidin-1-yl)-8-fluoro-7-(6-fluoro-1H-indazol-7-yl)quinazolin-4-yl)-2,5-dimethylpiperazin-1-yl)prop-2-en-1-one; 1-((2R,5S)-4-(6-chloro-2-(3-(dimethylamino)azetidin-1-yl)-8-fluoro-7-(3-iodo-5-methyl-1H-indazol-4-yl)quinazolin-4-yl)-2,5-dimethylpiperazin-1-yl)prop-2-en-1-one; 4-(4-((2S,5R)-4-acryloyl-2,5-dimethylpiperazin-1-yl)-6-chloro-2-(3-(dimethylamino)azetidin-1-yl)-8-fluoroquinazolin-7-yl)-5-methyl-1H-indazole-3-carbonitrile; 4-(4-((2S,5R)-4-acryloyl-2,5-dimethylpiperazin-1-yl)-6-chloro-2-(3-(dimethylamino)azetidin-1-yl)-8-fluoroquinazolin-7-yl)-5-methyl-1H-indazole-3-carboxamide; 1-((2R,5S)-4-(7-(3-amino-5-methyl-1H-indazol-4-yl)-6-chloro-2-(3-(dimethylamino)azetidin-1-yl)-8-fluoroquinazolin-4-yl)-2,5-dimethylpiperazin-1-yl)prop-2-en-1-one; 1-((2R,5S)-4-(6-chloro-2-(3-(dimethylamino)azetidin-1-yl)-8-fluoro-7-(3-(hydroxymethyl)-5-methyl-1H-indazol-4-yl)quinazolin-4-yl)-2,5-dimethylpiperazin-1-yl)prop-2-en-1-one; 1-((2R,5S)-4-(6-chloro-2-(3-(dimethylamino)azetidin-1-yl)-8-fluoro-7-(5-methyl-1H-benzo[d]imidazol-4-yl)quinazolin-4-yl)-2,5-dimethylpiperazin-1-yl)prop-2-en-1-one or 1-((2R,5S)-4-(6-chloro-2-(3-(dimethylamino)azetidin-1-yl)-8-fluoro-7-(5-methyl-1H-indol-4-yl)quinazolin-4-yl)-2,5-dimethylpiperazin-1-yl)prop-2-en-1-one, which compounds are disclosed in U.S. application Ser. No. 15/353,402.

In some embodiments, the compound has the following structure (I'a):

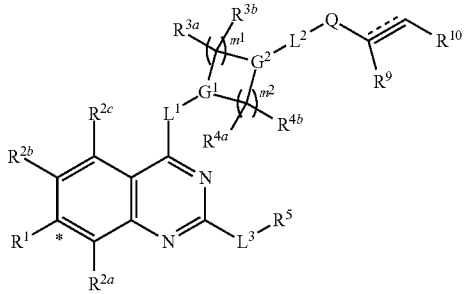

(I'a)

wherein:

≡ represents a double or triple bond;

Q is —C(=O)—, —C(=NR$^{8'}$)—, —NR$^8$C(=O)—, —S(=O)$_2$— or —NR$^8$S(=O)$_2$—;

R$^8$ is H, C$_1$-C$_6$ alkyl, hydroxylalkyl, aminoalkyl, alkoxyalkyl, aminylalkyl, alkylaminylalkyl, cyanoalkyl, carboxyalkyl, aminylcarbonylalkyl, C$_3$-C$_8$ cycloalkyl or heterocyclylalkyl;

R$^{8'}$ is H, —OH, —CN or C$_1$-C$_6$ alkyl;

when ≡ is a double bond then R$^9$ and R$^{10}$ are each independently H, halo, cyano, carboxyl, C$_1$-C$_6$ alkyl, alkoxycarbonyl, aminylalkyl, alkylaminylalkyl, aryl, heterocyclyl, heterocyclylalkyl, heteroaryl or hydroxylalkyl, or R$^9$ and R$^{10}$ join to form a carbocyclic, heterocyclic or heteroaryl ring; and when ≡ is a triple bond then R$^9$ is absent and R$^{10}$ is H, C$_1$-C$_6$ alkyl, aminylalkyl, alkylaminylalkyl or hydroxylalkyl, wherein each occurrence of alkyl, hydroxylalkyl, aminoalkyl, alkoxyalkyl, aminylalkyl, alkylaminylalkyl, cyanoalkyl, carboxyalkyl, aminylcarbonylalkyl, cycloalkyl, heterocyclylalkyl, alkoxycarbonyl, heteroaryl, and carbocyclic, heterocyclic and heteroaryl rings is optionally substituted with one or more substituents unless otherwise specified.

In different embodiments, the compound has one of the following structures (I'b) (I'c) (I'd) or (I'e):

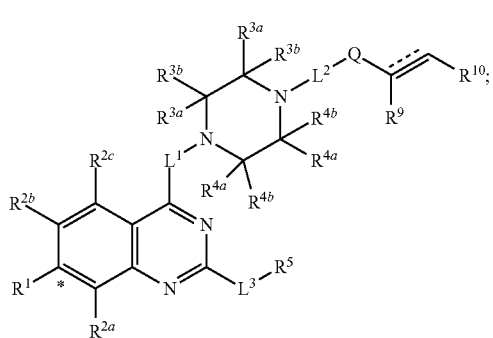

(I'b)

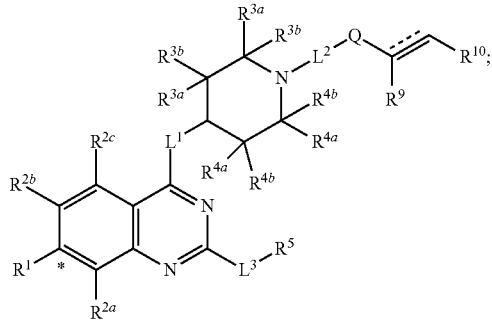

(I'c)

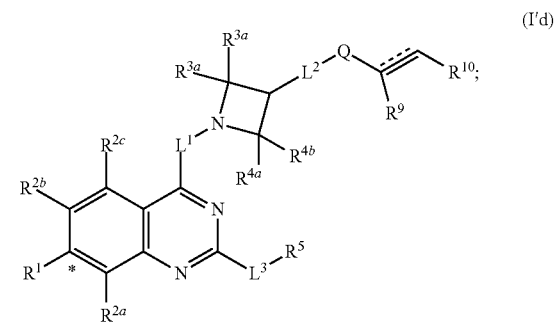

(I'd)

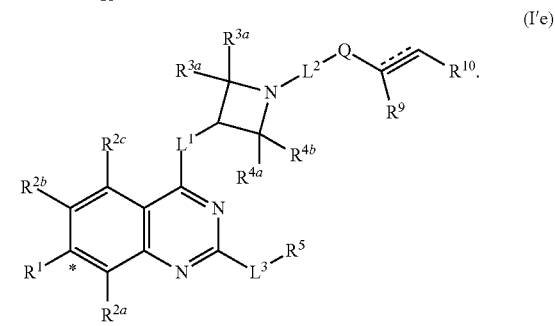

(I'e)

Without wishing to be bound by theory, Applicants believe correct selection of the R$^1$ substituent may play a part in the compounds' inhibitory activity (e.g., against KRAS, HRAS or NRAS G12C). In some embodiments, R$^1$ is capable of reversible interaction with KRAS, HRAS or NRAS G12C mutant protein. In some embodiments R$^1$ has high affinity towards KRAS, HRAS or NRAS and is highly specific towards G12C KRAS, HRAS or NRAS. In some embodiments R$^1$ is capable of hydrophobic interaction with KRAS, HRAS or NRAS G12C. In some embodiments R$^1$ is able to form hydrogen bonds with various residues of G12C KRAS, HRAS or NRAS protein. In some embodiments, R$^1$ is unsubstituted naphthyl. In other embodiments, R$^1$ is optionally substituted quinolinyl, such as optionally substituted 1,2,3,4-tetrahydroquinolinyl. In some embodiments, R$^1$ is R$^{1'}$. In some other embodiments, R$^1$ is R$^{1'}$. In different embodiments, R$^1$ has the following structure:

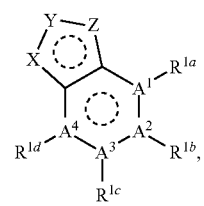

wherein:

each 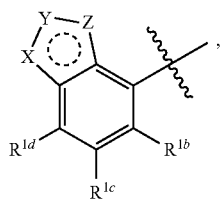 represents an aromatic ring;

$A^1$, $A^2$, $A^3$ and $A^4$ are each independently C or N;

X is N, NH or $CR^{1e}$;

Y is N, NH or $CR^{1f}$;

Z is N, NH or $CR^{1g}$;

one of $R^{1a}$, $R^{1b}$, $R^{1c}$ and $R^{1d}$ is a covalent bond to the carbon marked with *, and the other of $R^{1a}$, $R^{1b}$, $R^{1c}$ and $R^{1d}$ are each independently H, amino, cyano, halo, hydroxyl, $C_1$-$C_6$ alkyl, $C_2$-$C_6$ alkenyl, $C_2$-$C_6$ alkynyl, alkylaminyl, $C_1$-$C_6$ haloalkyl, $C_1$-$C_6$ alkoxy, $C_1$-$C_6$ haloalkoxy; cycloalkyl, heterocyclyl, aminylalkyl, $C_1$-$C_6$ cyanoalkyl, $C_1$-$C_6$ carboxyalkyl, aminylcarbonylalkyl or aminylcarbonyl;

$R^{1e}$, $R^{1f}$ and $R^{1g}$ are each independently H, amino, cyano, halo, hydroxyl, $C_1$-$C_6$ alkyl, $C_2$-$C_6$ alkenyl, $C_2$-$C_6$ alkynyl, alkylaminyl, $C_1$-$C_6$ haloalkyl, $C_1$-$C_6$ alkoxy, $C_1$-$C_6$ haloalkoxy; cycloalkyl, heterocyclyl, aminylalkyl, $C_1$-$C_6$ cyanoalkyl, $C_1$-$C_6$ carboxyalkyl, aminylcarbonylalkyl or aminylcarbonyl, and provided that when each of $A^1$, $A^2$, $A^3$ and $A^4$ are C, X is NH, Y is N and one of the other of $R^{1a}$, $R^{1b}$, $R^{1c}$ and $R^{1d}$ is methyl, then at least one other of $R^{1a}$, $R^{1b}$, $R^{1c}$, $R^{1d}$, $R^{1e}$, $R^{1f}$ and $R^{1g}$ is not H, and provided that at least one of X, Y and Z is N or NH.

In some embodiments, each $A^1$, $A^2$, $A^3$ and $A^4$ is C. In other embodiments, one of $A^1$, $A^2$, $A^3$ and $A^4$ is N, and each remaining $A^1$, $A^2$, $A^3$ and $A^4$ is C.

In any of the foregoing embodiments, $R^1$ has the following structure:

provided that when $R^{1b}$ is methyl, then at least one of $R^{1c}$, $R^{1d}$, $R^{1e}$, $R^{1f}$ and $R^{1g}$ is not H. For example, in some embodiments, X is NH, Y is N and Z is $CR^{1g}$. In some embodiments, X is NH, Y is $CR^{1f}$ and Z is $CR^{1g}$. In certain embodiments, X is $CR^{1e}$, Y is $CR^{1f}$ and Z is NH. In other embodiments, X is $CR^{1e}$, Y is N and Z is NH. In some specific embodiments, X is N, Y is $CR^{1f}$ and Z is NH.

In some of the foregoing embodiments, the other of $R^{1a}$, $R^{1b}$, $R^{1c}$ and $R^{1d}$, and each of $R^{1e}$, $R^{1f}$ and $R^{1g}$ are each independently H, amino, halo, hydroxyl, $C_1$-$C_6$ alkyl, $C_2$-$C_6$ alkenyl, $C_2$-$C_6$ alkynyl, alkylaminyl or cycloalkyl. In other embodiments, the other of $R^{1a}$, $R^{1b}$, $R^{1c}$ and $R^{1d}$, and each of $R^{1e}$, $R^{1f}$ and $R^{1g}$ are each independently H, amino, fluoro, chloro, hydroxyl, methyl, methylaminyl or cyclopropyl.

In certain embodiments, $R^1$ has one of the following structures:

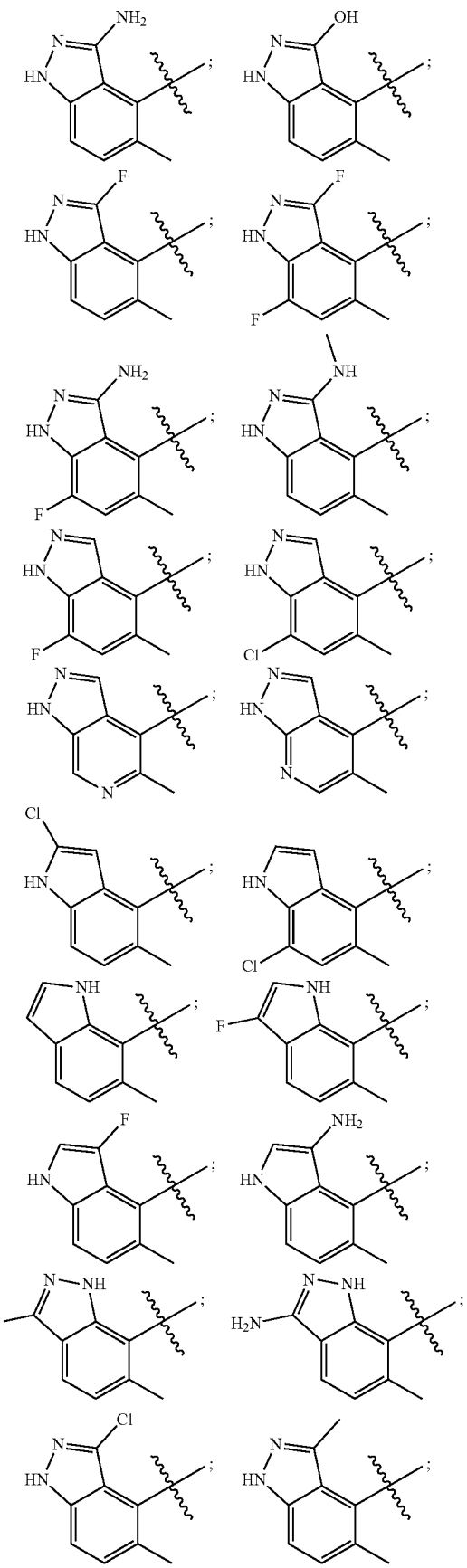

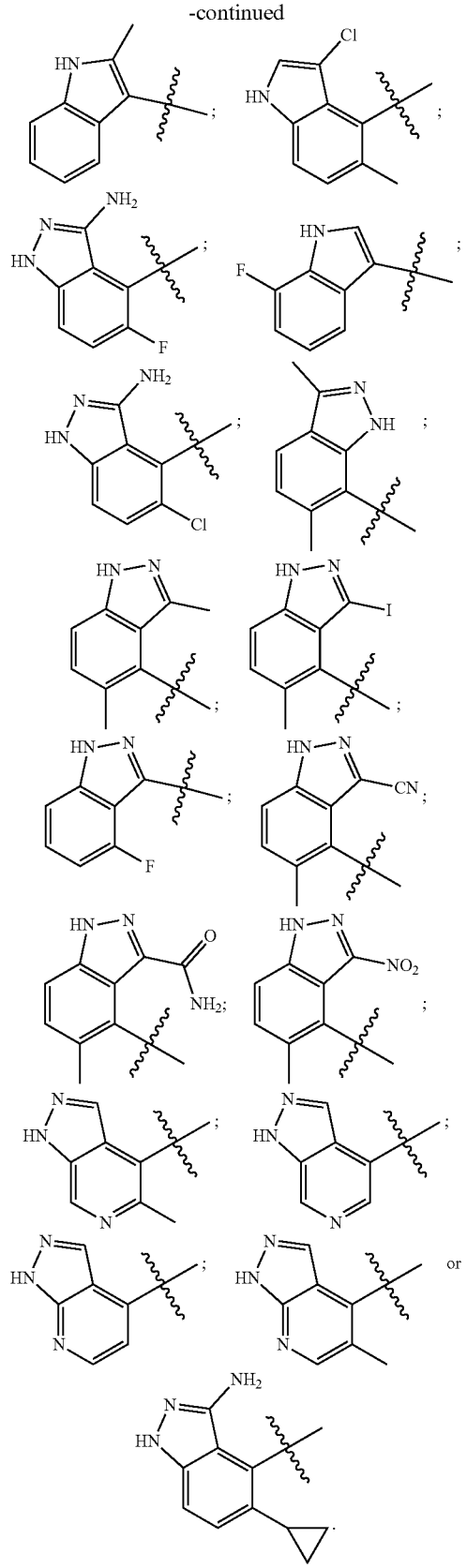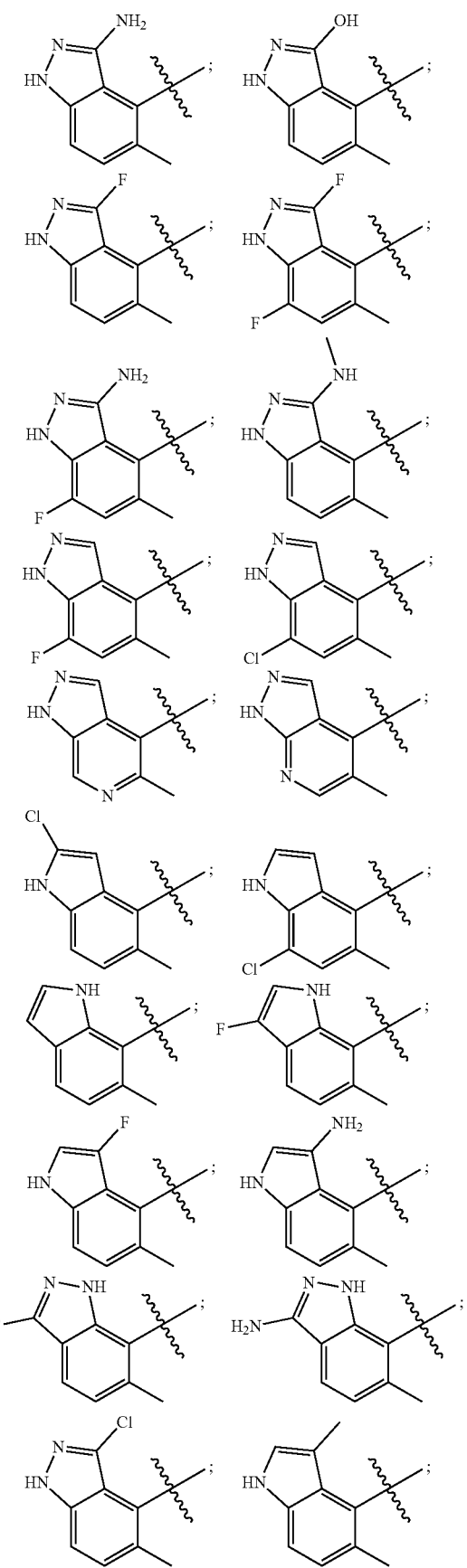
In certain other embodiments, $R^1$ has one of the following structures:

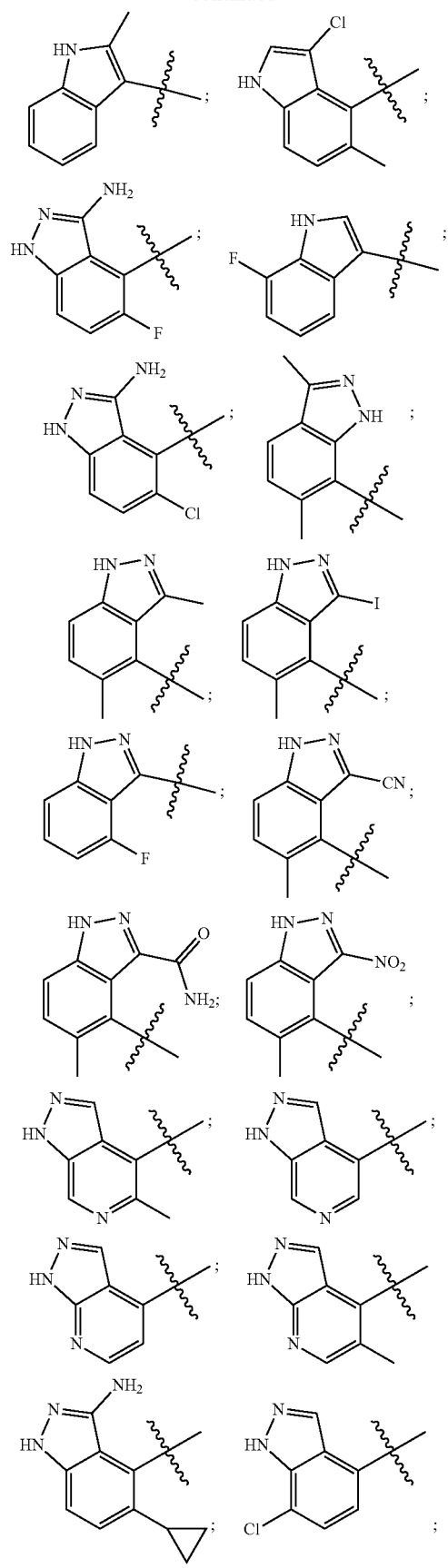
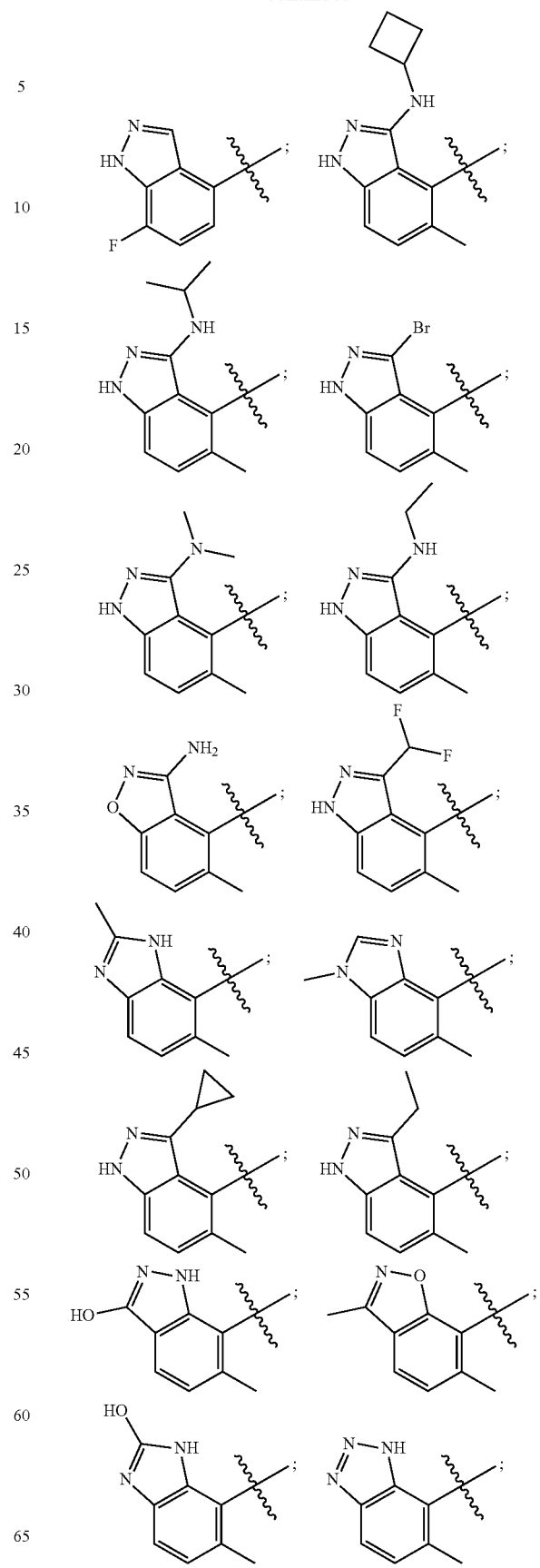

35
-continued
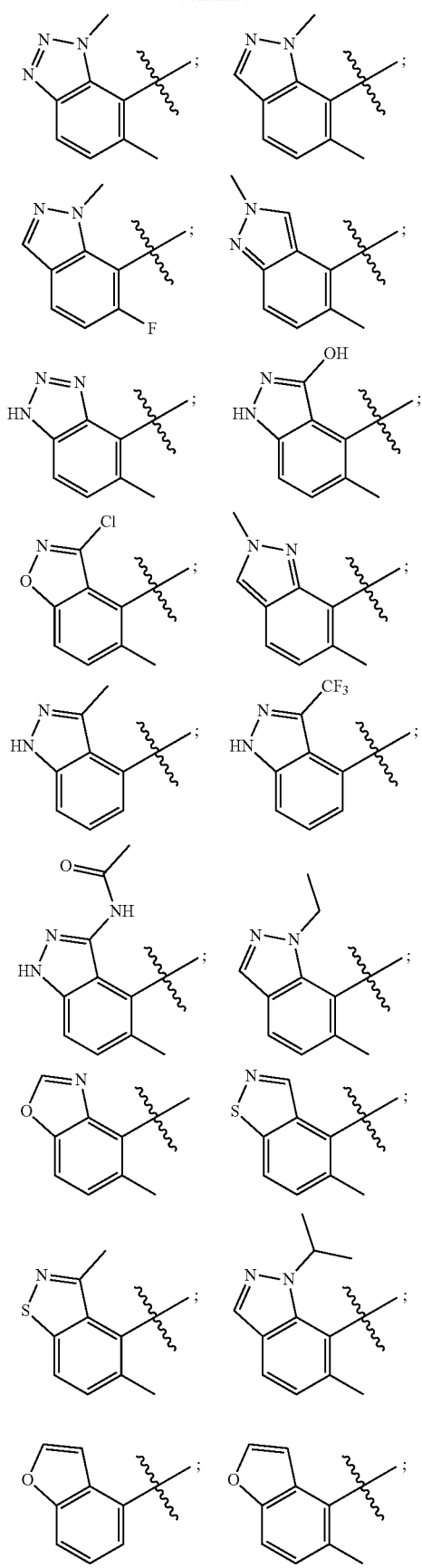
36
-continued
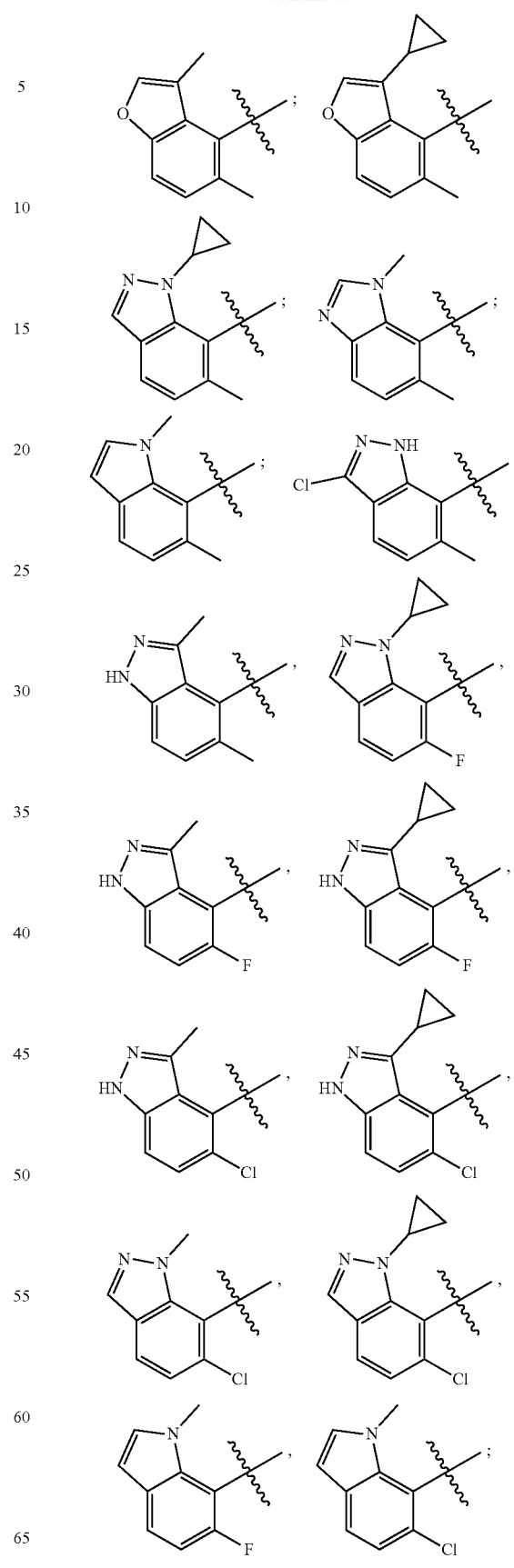

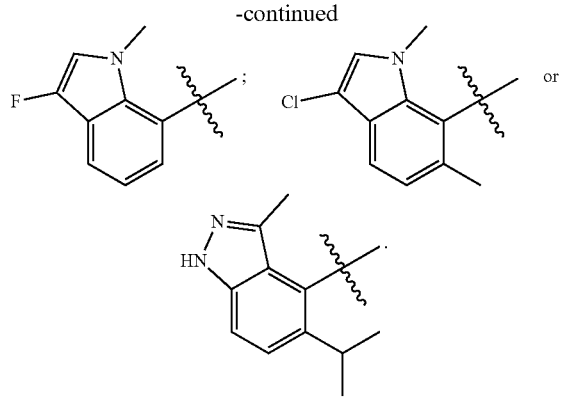
In some other different embodiments, R¹ has one of the following structures:
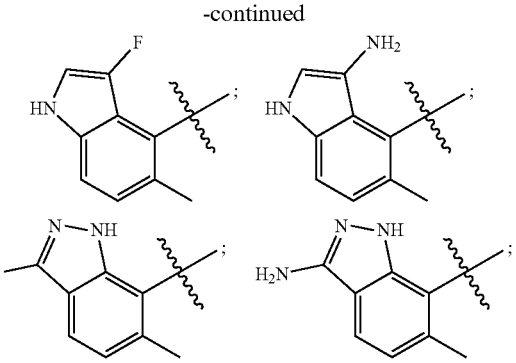
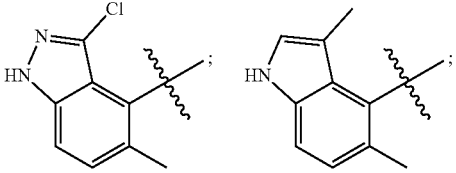
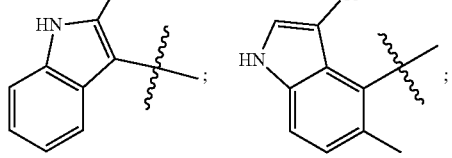
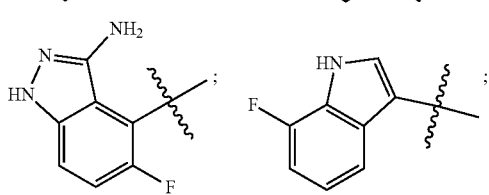
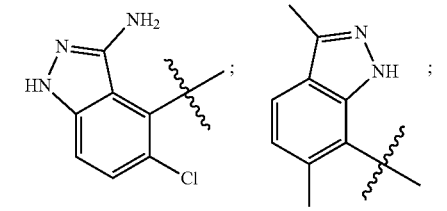
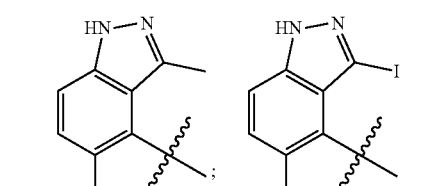
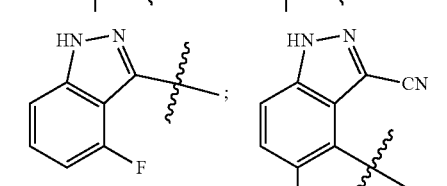
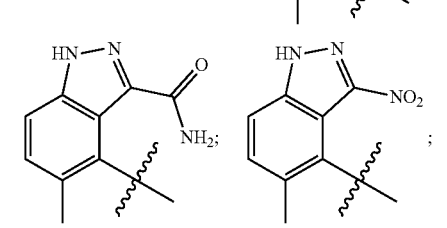

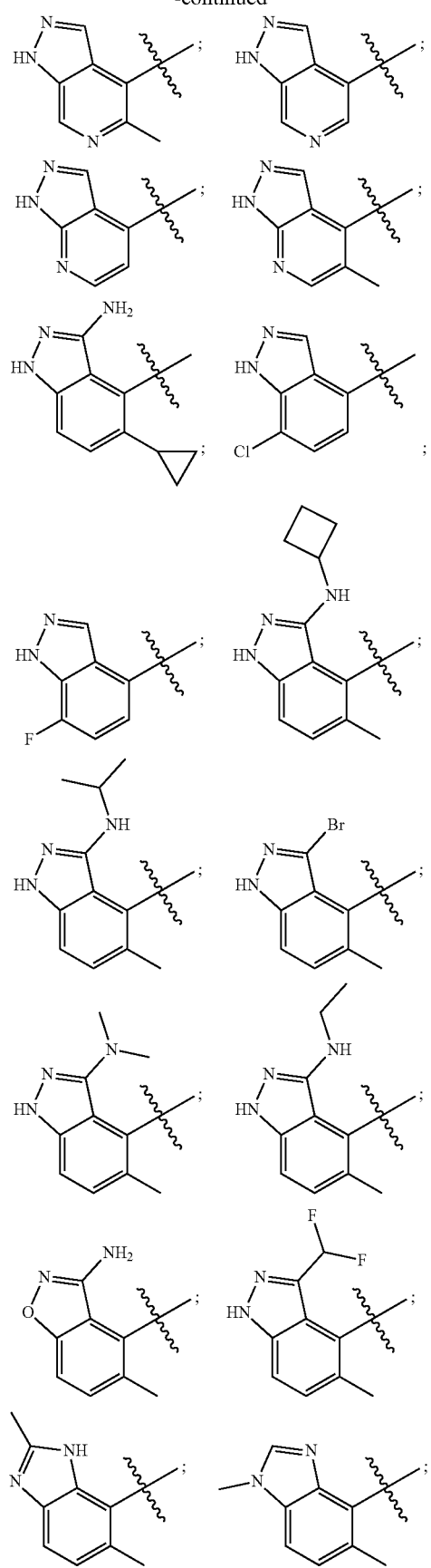
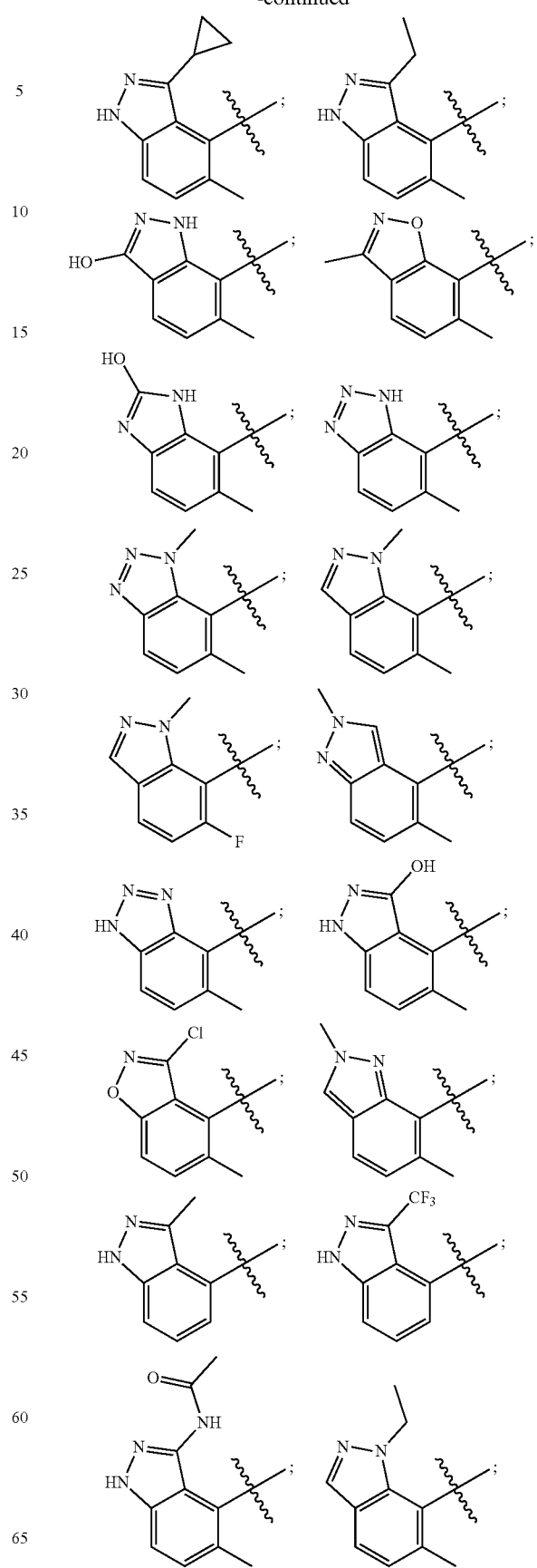

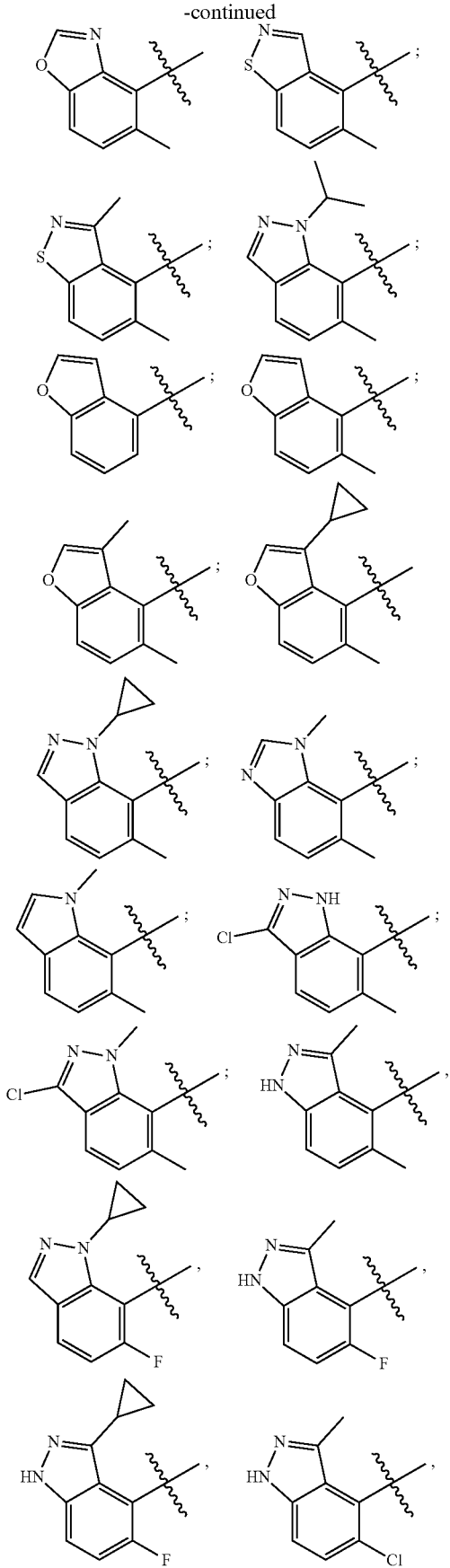
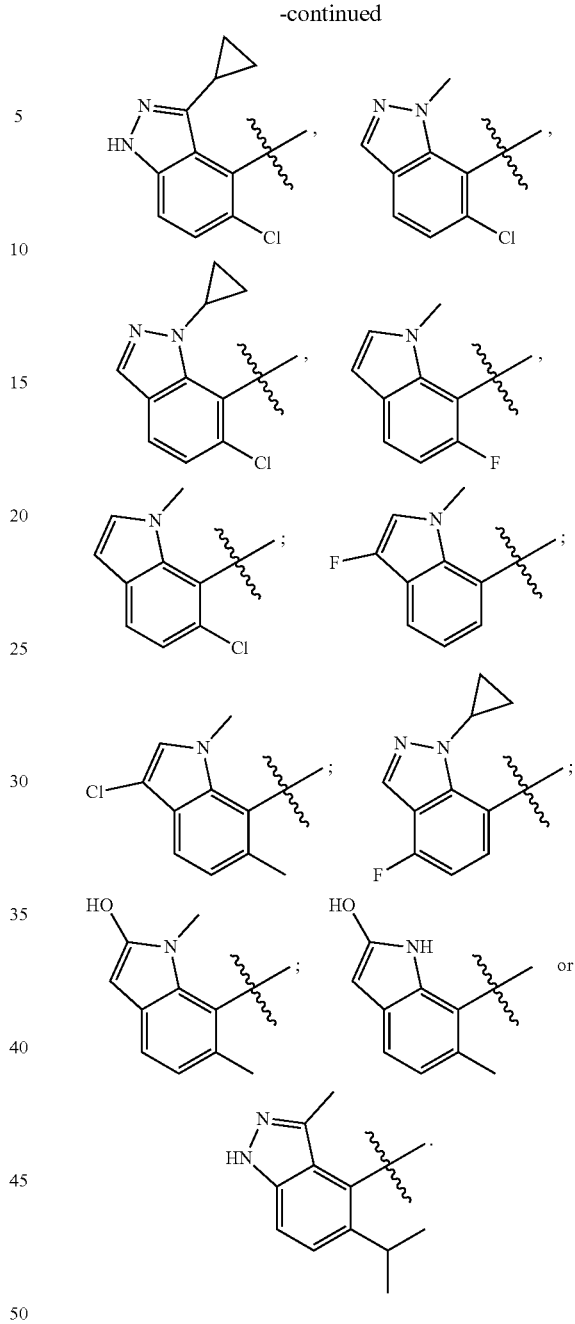
It should be noted that in some instances, tautomeric forms are possible, and either tautomer may be depicted, but all tautomer are included in various embodiments. For example, the following structures are considered tautomers, and both are included in the scope of certain embodiments, although only one of them may be depicted:
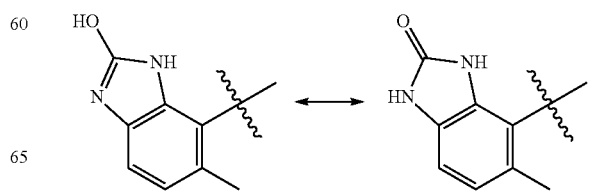

-continued

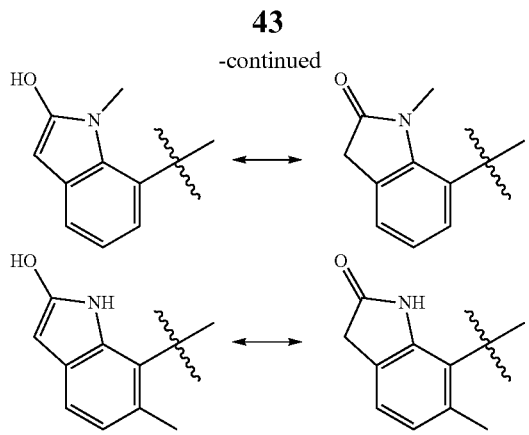

In different embodiments, $R^1$ has the following structure:

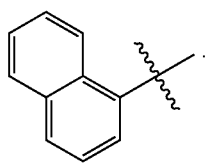 [SMILES: *c1cccc2ccccc12]

In different embodiments, $R^1$ has one of the following structures:

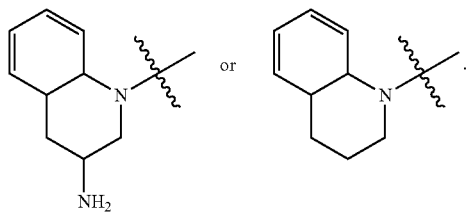 [SMILES: *N1CC(N)CC2C=CC=CC21 ; *N1CCCC2C=CC=CC21]

In some of the foregoing embodiments $R^{2c}$ is H. In some of the foregoing embodiments, $R^{2a}$ and $R^{2b}$ are each independently halo, haloalkyl, alkyl, or alkoxy. In other of any of the foregoing embodiments, $R^{2a}$ and $R^{2b}$ are each halo. In some embodiments, $R^{2a}$ is fluoro, chloro or methoxy. In other embodiments, $R^{2b}$ is chloro, fluoro or $CF_3$. For example, in some embodiments $R^{2a}$ is fluoro, and in other embodiments, $R^{2b}$ is chloro. In some other embodiments $R^{2a}$ is fluoro, and $R^{2b}$ is chloro.

In some embodiments, $L^3$ is —O—, —$NR^6$— or a bond. In some embodiments, $L^3$ is —O—. In some other embodiments, $L^3$ is —$NR^6$—. In some of these embodiments $R^6$ is H. In other of these embodiments, $R^6$ is $C_1$-$C_6$ alkyl. In still other embodiments, $L^3$ is a bond.

In certain embodiments, $R^5$ is amino, cyano, hydroxyl, $C_1$-$C_6$ alkyl, $C_2$-$C_6$ alkynyl; $C_1$-$C_6$ haloalkyl, $C_1$-$C_6$ hydroxylalkyl, $C_1$-$C_6$ cyanoalkyl, aminylalkyl, aminylalkynyl, alkoxyalkyl, alkoxyalkynyl, alkylcarbonylaminyl, aminylalkylcarbonylaminyl, aminylcarbonylalkyl, cycloalkyl, cycloalkylalkyl, heterocyclyl, heterocyclylalkyl, heterocyclylcarbonylalkyl, aryl, aralkyl, heteroaryl or heteroarylalkyl, In any of the foregoing embodiments, $R^5$ is aminylalkyl, heterocyclyl, heterocyclylalkyl, heteroaryl or heteroarylalkyl.

In some of the foregoing embodiments, -$L^3$-$R^5$ has one of the following structures:

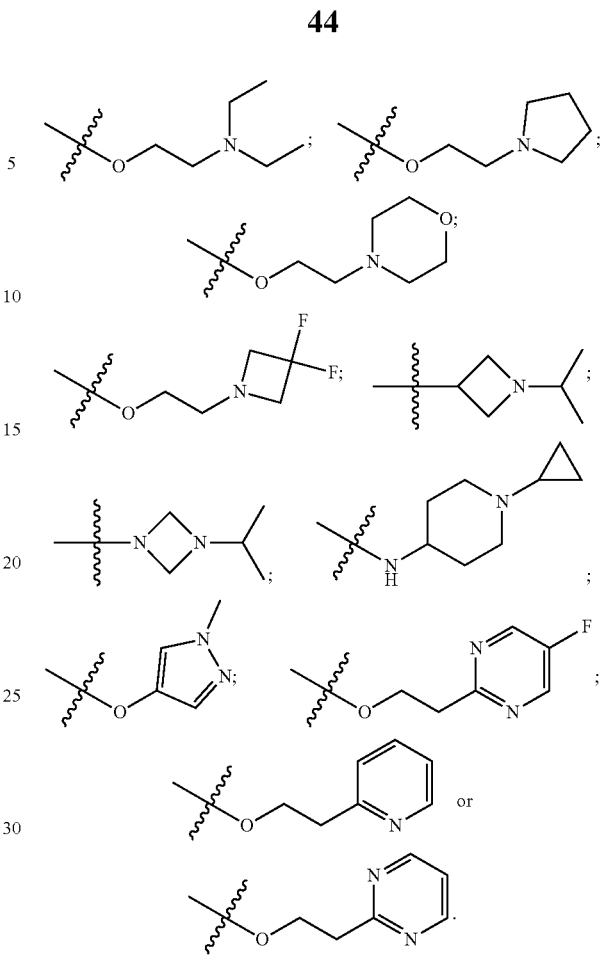

In some other of the foregoing embodiments, -$L^3$-$R^5$ has one of the following structures:

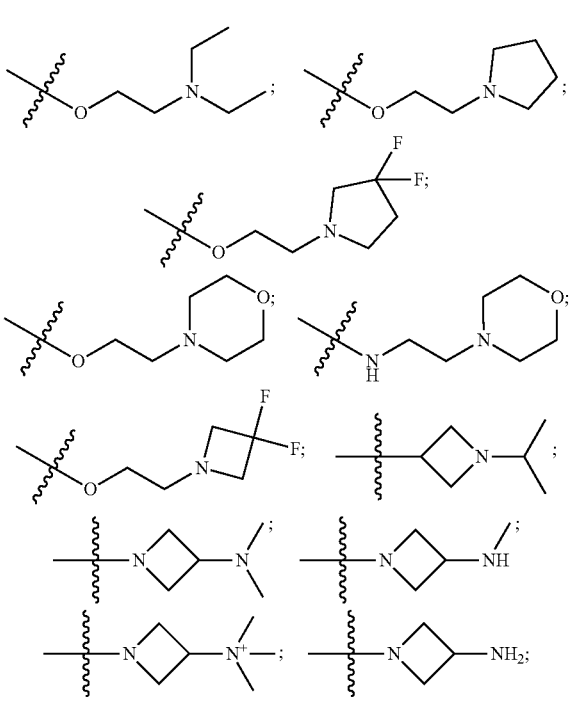

-continued
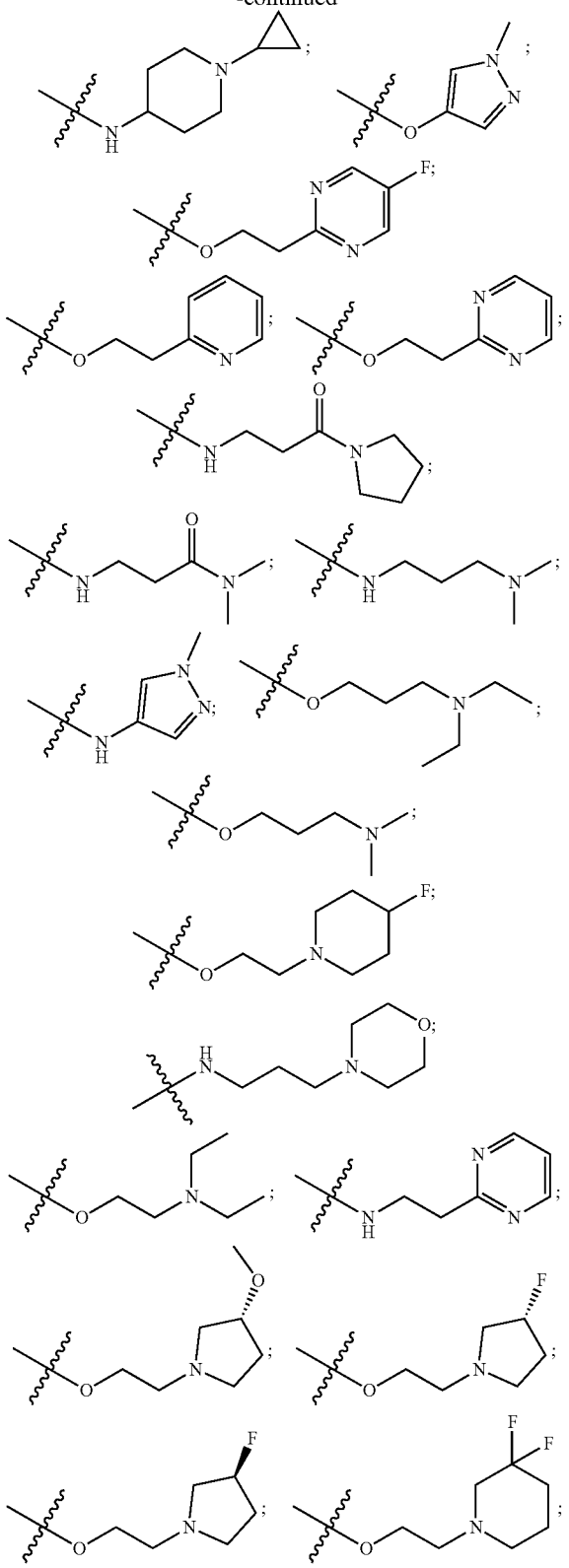
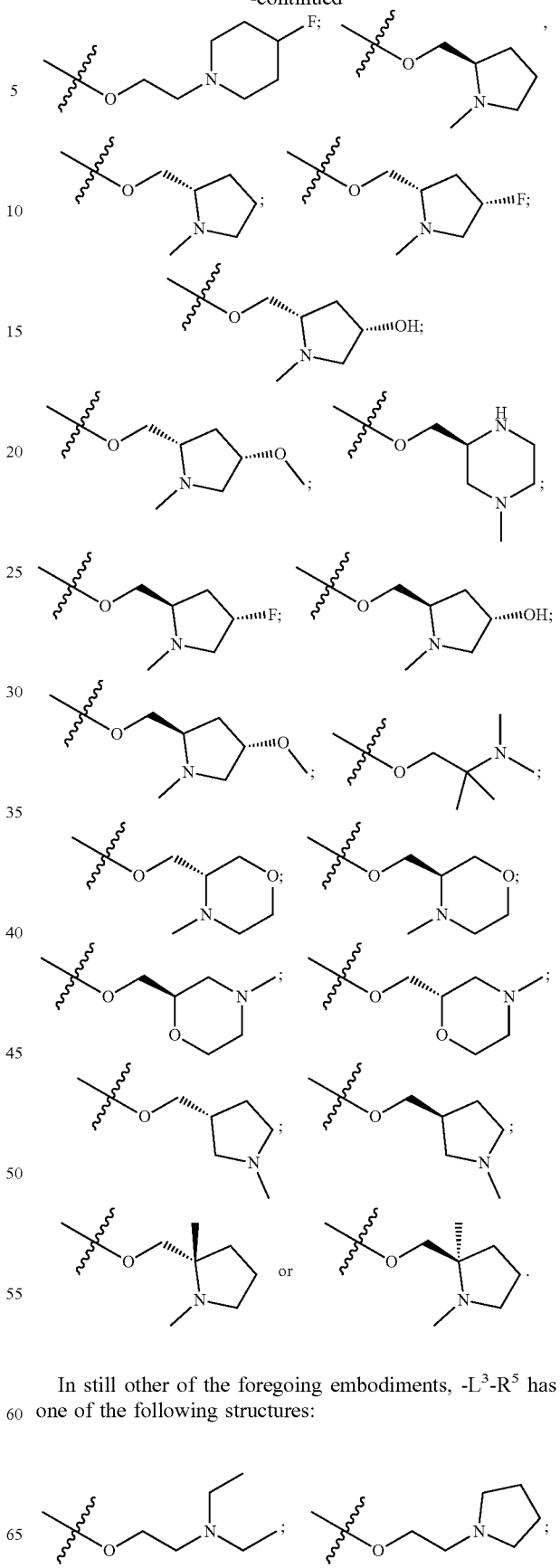
In still other of the foregoing embodiments, -L³-R⁵ has one of the following structures:

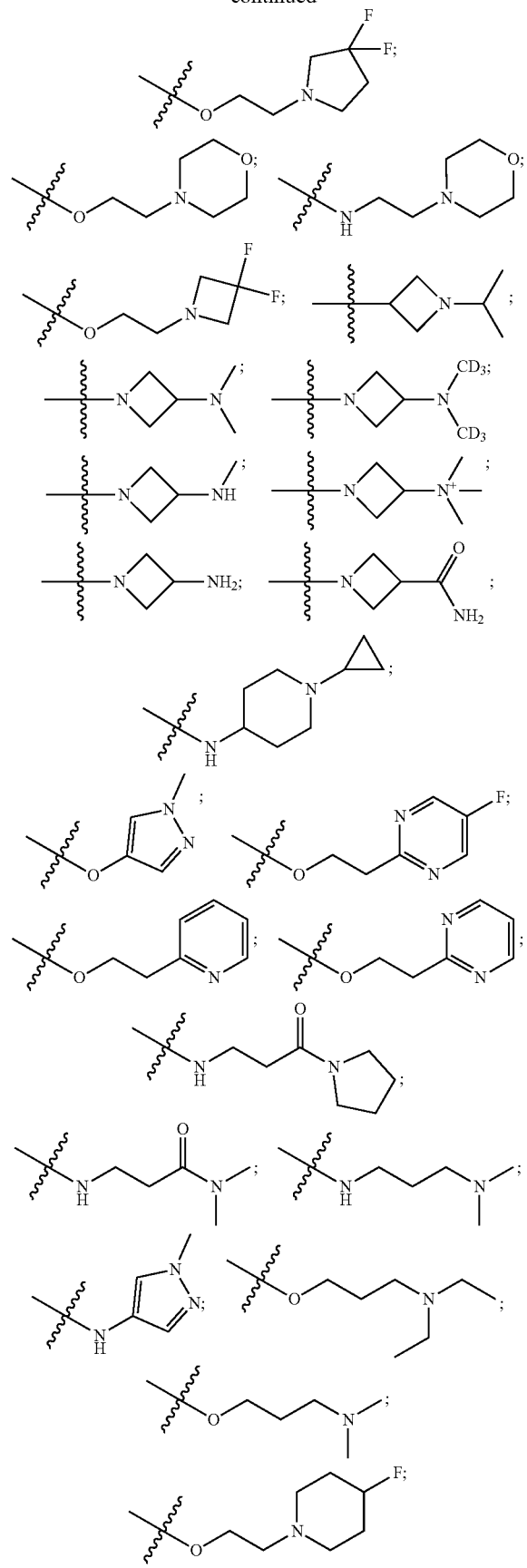
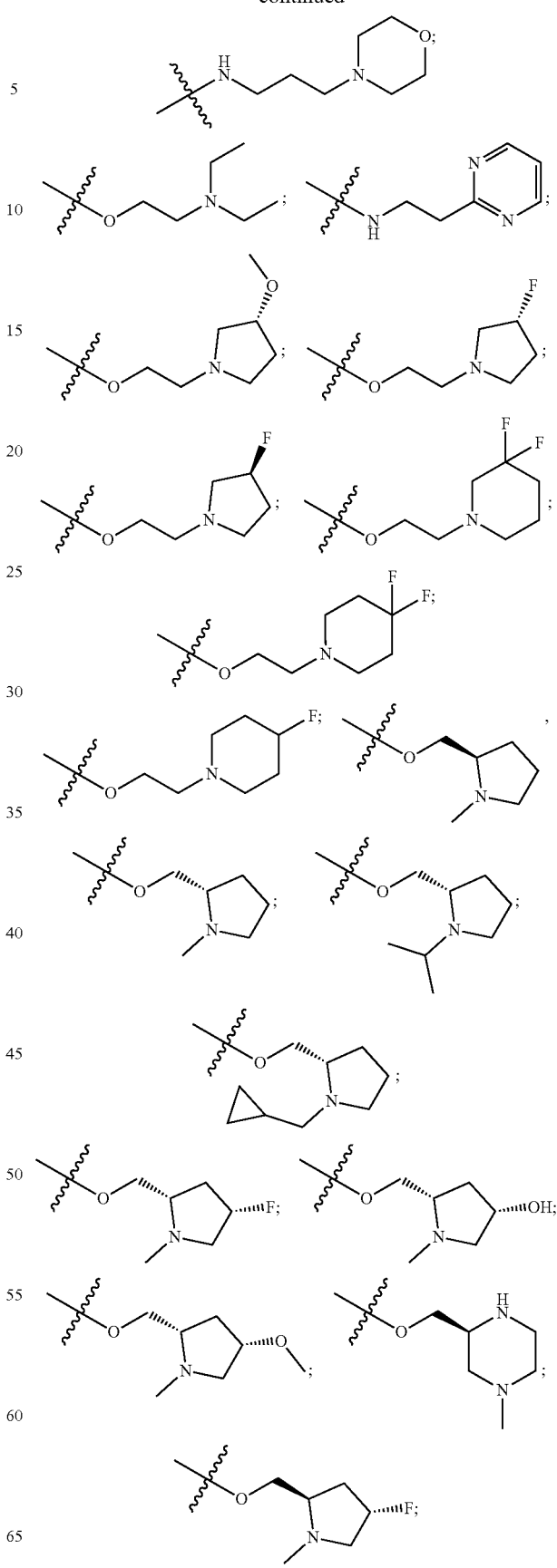

$R^{4a}$ and $R^{4b}$ are $C_1$-$C_6$ alkyl. For example in some of the foregoing embodiments, $C_1$-$C_6$ alkyl is methyl.

In different embodiments, at least one of $R^{3a}$ and $R^{4a}$ is $C_1$-$C_6$ cyanoalkyl, such as cyanomethyl.

In certain embodiments, $R^{3a}$ and $R^{3b}$ are, at each occurrence, independently H, —OH, —NH$_2$, —CO$_2$H, halo, cyano, hydroxylalkyl, aminylalkyl, cyanoalkyl, carboxyalkyl or aminylcarbonyl, and $R^{4a}$ and $R^{4b}$ are, at each occurrence, independently H, —OH, —NH$_2$, —CO$_2$H, halo, cyano, hydroxylalkyl, aminylalkyl, cyanoalkyl, carboxyalkyl or aminylcarbonyl.

In other of the foregoing embodiments, $R^{3a}$ and $R^{4a}$ are, at each occurrence, independently H, —OH, hydroxylalkyl, cyano, or aminylcarbonyl and $R^{3b}$ and $R^{4b}$ are, at each occurrence, H.

In certain other embodiments, $R^{3a}$ and $R^{4a}$ are, at each occurrence, H and $R^{3b}$ and $R^{4b}$ are, at each occurrence, independently H, —OH, —NH$_2$, —CO$_2$H, halo, cyano, hydroxylalkyl, aminylalkyl, cyanoalkyl, carboxyalkyl or aminylcarbonyl.

In any of the foregoing embodiments, at least one occurrence of $R^{3a}$, $R^{3b}$ $R^{4a}$ or $R^{4b}$ is H, and at least one occurrence of $R^{3a}$, $R^{3b}$, $R^{4a}$ or $R^{4b}$ is not H.

In some embodiments, at least one occurrence of $R^{3a}$ is —OH, —NH$_2$, —CO$_2$H, halo, cyano, hydroxylalkyl, aminylalkyl, cyanoalkyl, carboxyalkyl or aminylcarbonyl, and $R^{3b}$, $R^{4a}$ and $R^{4b}$ are, at each occurrence, H.

In other of the foregoing embodiments, $R^{3a}$ and $R^{4a}$ are, at each occurrence, independently H or $C_1$-$C_6$ alkyl. In some embodiments, at least one occurrence of $R^{3a}$, $R^{4a}$, $R^{3b}$ or $R^{4b}$ is independently $C_1$-$C_6$ alkyl, such as methyl. In some embodiments, one occurrence of $R^{3a}$ is $C_1$-$C_6$ alkyl, such as methyl, and the remaining $R^{3a}$ and each $R^{4a}$ is H. In some other embodiments, two occurrences of $R^{3a}$ are $C_1$-$C_6$ alkyl, such as methyl, and the remaining $R^{3a}$ and each $R^{4a}$ is H. In some other embodiments, one occurrence of $R^{3a}$ and one occurrence of $R^{4a}$ is independently $C_1$-$C_6$ alkyl, such as methyl, and the remaining $R^{3a}$ and $R^{4a}$ are each H.

In other embodiments, at least one occurrence of $R^{4a}$ is —OH, —NH$_2$, —CO$_2$H, halo, cyano, hydroxylalkyl, aminylalkyl, cyanoalkyl, carboxyalkyl or aminylcarbonyl, and $R^{3a}$, $R^{3b}$ and $R^{4b}$ are, at each occurrence, H.

In other embodiments, at least one occurrence of $R^{3a}$ is H, —OH, —NH$_2$, —CO$_2$H, halo, cyano, hydroxylalkyl, aminylalkyl, cyanoalkyl, carboxyalkyl or aminylcarbonyl, and at least one occurrence of $R^{3b}$ joins with an $R^{4b}$ to form a carbocyclic or heterocyclic ring.

In still more embodiments, at least one occurrence of $R^{4a}$ is H, —OH, —NH$_2$, —CO$_2$H, halo, cyano, hydroxylalkyl, aminylalkyl, cyanoalkyl, carboxyalkyl or aminylcarbonyl, and at least one occurrence of $R^{4b}$ joins with an $R^{3b}$ to form a carbocyclic or heterocyclic ring.

In other embodiments, at least one occurrence of $R^{3a}$ and $R^{3b}$ join to form a carbocyclic or heterocyclic ring. In other embodiments, at least one occurrence of $R^{4a}$ and $R^{4b}$ join to form a carbocyclic or heterocyclic ring.

In still other embodiments, at least one occurrence of $R^{3a}$ or $R^{4a}$ s aminylcarbonyl. For example, in certain embodiments, the aminylcarbonyl is

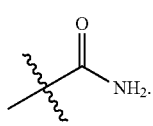

In more embodiments of any of the foregoing compounds of structures (I), and sub-embodiments thereof, $R^{3a}$, $R^{3b}$, $R^{4a}$ and $R^{4b}$ are H at each occurrence. In other embodiments, at least one occurrence of $R^{3a}$, $R^{3b}$, $R^{4a}$ or $R^{4b}$ is not H. In some embodiments, at least two of $R^{3a}$, $R^{3b}$, $R^{4a}$ or $R^{4b}$ is not H.

In some embodiments, one of occurrence $R^{3a}$, $R^{3b}$, $R^{4a}$ or $R^{4b}$ is $C_1$-$C_6$ alkyl. In certain embodiments, two of $R^{3a}$, $R^{3b}$, In other embodiments, at least one occurrence of $R^{3a}$ or $R^{4a}$ is cyano. In other embodiments, at least one occurrence of $R^{3a}$ or $R^{4a}$ is —OH. In other embodiments, at least one occurrence of $R^{3a}$ or $R^{4a}$ is hydroxylalkyl, for example hydroxylmethyl.
In any of the foregoing embodiments, the compound has one of the following structures:
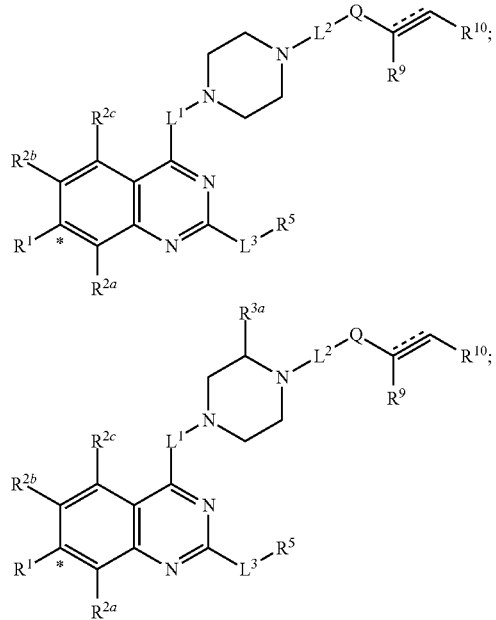
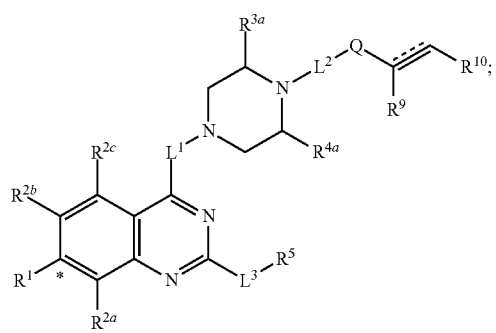
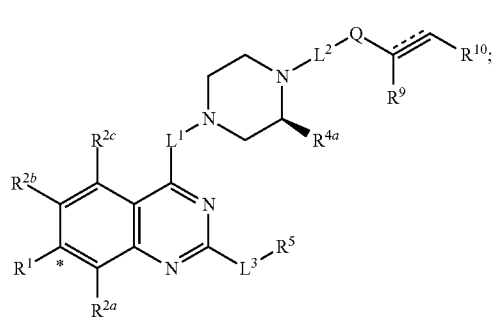
-continued
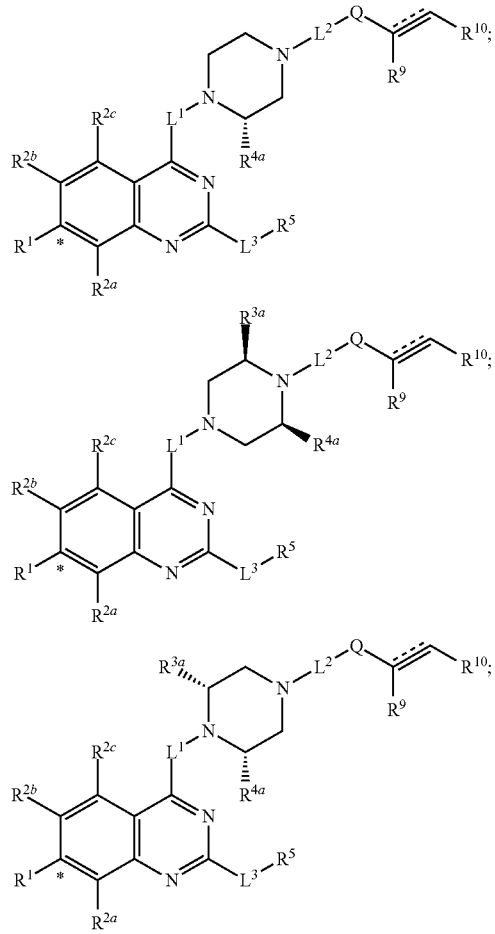
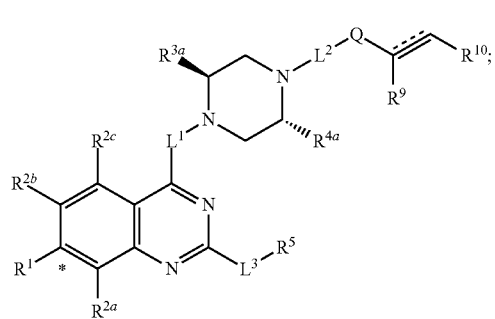

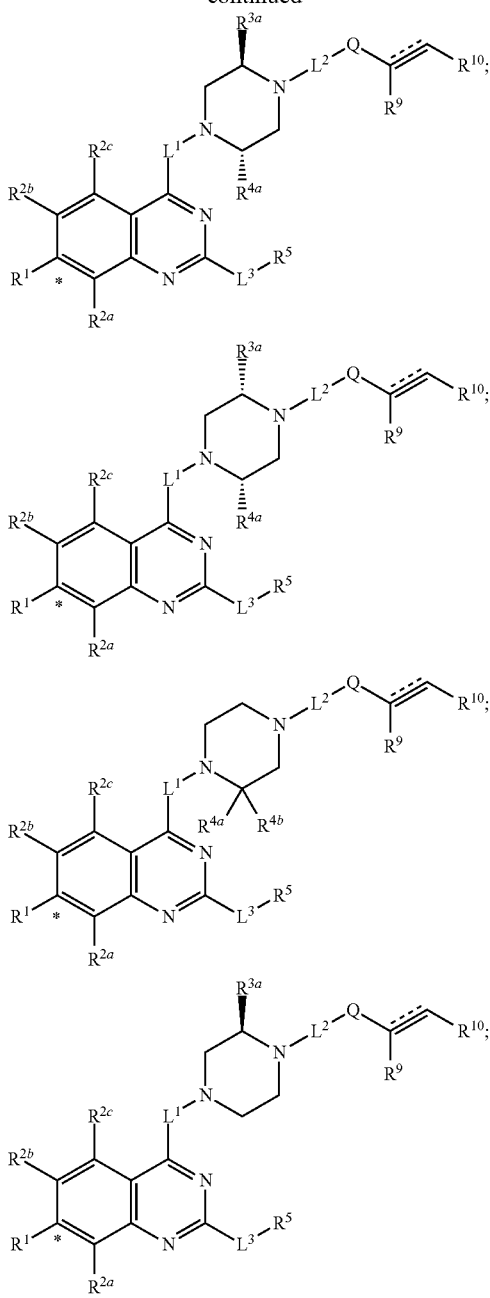

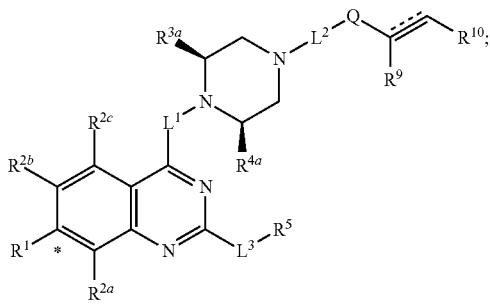

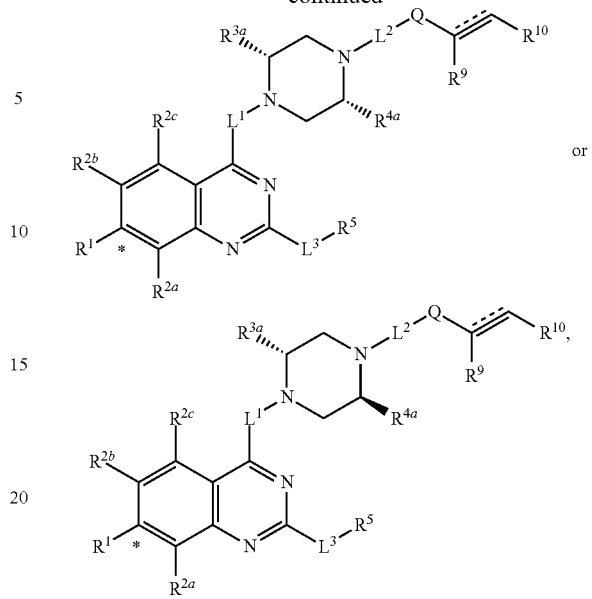

wherein $R^{3a}$ and $R^{4a}$ are independently —OH, —NH$_2$, —CO$_2$H, halo, cyano, C$_1$-C$_6$ alkyl, C$_1$-C$_6$ haloalkyl, C$_1$-C$_6$ haloalkoxy, C$_1$-C$_6$ alkynyl, hydroxylalkyl, alkoxyalkyl, aminylalkyl, alkylaminylalkyl, cyanoalkyl, carboxyalkyl, aminylcarbonylalkyl or aminylcarbonyl.

In yet more of any of the foregoing embodiments, E has the following structure:

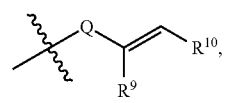

wherein:
Q is —C(=O)—, —C(=NR$^{8'}$)—, —NR$^8$C(=O)—, —S(=O)$_2$— or —NR$^8$S(=O)$_2$—;
R$^8$ is H, C$_1$-C$_6$alkyl or hydroxylalkyl;
R$^{8'}$ is H, —OH, —CN or C$_1$-C$_6$alkyl; and
R$^9$ and R$^{10}$ are each independently H, halo, cyano, carboxyl, C$_1$-C$_6$ alkyl, alkoxycarbonyl, aminylalkyl, alkylaminylalkyl, aryl, heterocyclyl, heterocyclylalkyl, heteroaryl or hydroxylalkyl, or R$^9$ and R$^{10}$ join to form a carbocyclic, heterocyclic or heteroaryl ring.

In still other of any of the foregoing embodiments, E has the following structure:

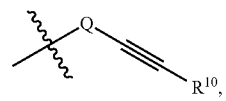

wherein:
Q is —C(=O)—, —NR$^8$C(=O)—, —S(=O)$_2$— or —NR$^8$S(=O)$_2$—;
R$^8$ is H, C$_1$-C$_6$alkyl or hydroxylalkyl; and
R$^{10}$ is H, C$_1$-C$_6$alkyl, aminylalkyl, alkylaminylalkyl or hydroxylalkyl.

The Q moiety is typically selected to optimize the reactivity (i.e., electrophilicity) of E. In some of the foregoing embodiments Q is —C(=O)—, —NR$^8$C(=O)—, —S(=O)₂— or —NR⁸S(=O)₂—. In certain of the foregoing embodiments, Q is —C(=O)—. In other embodiments, Q is —S(=O)₂—. In still more embodiments, Q is —NR⁸C(=O)—. In still more different embodiments, Q is —NR⁸S(=O)₂—.

In some embodiments Q is —C(=O)—. In some other of the foregoing embodiments, Q is —C(=NR⁸')—, wherein R⁸' is H, —OH, —CN or C₁-C₆alkyl. For example, in some embodiments R⁸' is H. In other embodiments, R⁸' is —CN. In other embodiments, R⁸' is —OH.

In some of the foregoing embodiments, R⁸ is H. In other of these embodiments, R⁸ is hydroxylalkyl, for example in some embodiments the hydroxylalkyl is 2-hydroxylalkyl.

In some of any one of the foregoing embodiments, at least one of R⁹ or R¹⁰ is H. For example, in some embodiments each of R⁹ and R¹⁰ are H.

In other of the foregoing embodiments, R¹⁰ is alkylaminylalkyl. In some of these embodiments, R¹⁰ has the following structure:

In other embodiments, R¹⁰ is hydroxylalkyl, such as 2-hydroxylalkyl.

In some other different embodiments of the foregoing embodiments, R⁹ and R¹⁰ join to form a carbocyclic ring. For example, in some of these embodiments the carbocyclic ring is a cyclopentene, cyclohexene or phenyl ring. In other embodiments, the carbocyclic ring is a cyclopentene or cyclohexene ring. In other embodiments, the carbocyclic ring is a phenyl ring, for example a phenyl ring having the following structure:

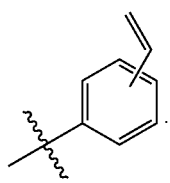

In some of any of the foregoing embodiments E is an electrophile capable of bonding with a KRAS, HRAS or NRAS protein comprising G12C mutation. In some embodiments, the electrophile E is capable of forming an irreversible covalent bond with a G12C mutant KRAS, HRAS or NRAS protein. In some cases, the electrophile E may bind with the cysteine residue at the position 12 of a G12C mutant KRAS, HRAS or NRAS protein. In various embodiments of any of the foregoing, E has one of the following structures:

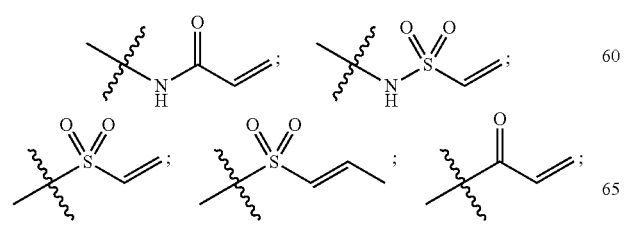

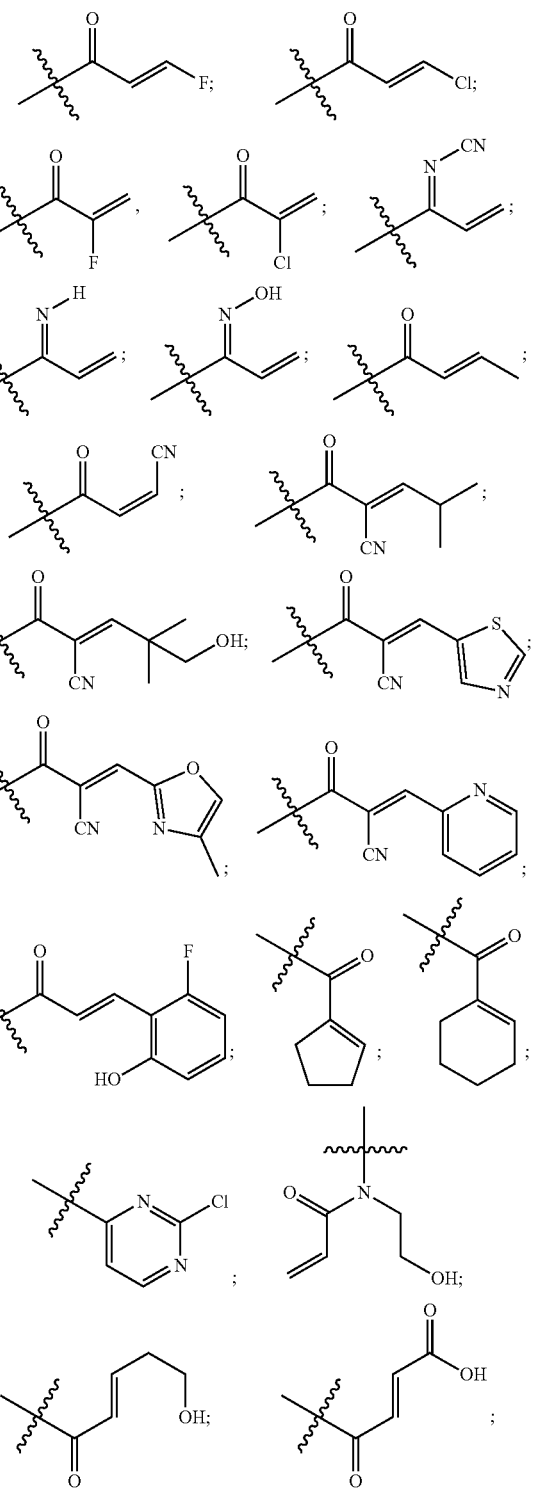

In some embodiments E is

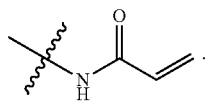 [SMILES: *NC(=O)C=C]

In some embodiments E is $L^2$ can be selected to provide proper spacing and/or orientation for the E group to form a bond with the KRAS, HRAS or NRAS protein. In some of the foregoing embodiments, $L^2$ is a bond. In other of the foregoing embodiments, $L^2$ is alkylene.

In any of the foregoing embodiments, $L^1$ is a bond. In other embodiments, $L^1$ is —$NR^6$—.

Some embodiments of the compounds include more than one stereoisomer. Other embodiments are directed to a single stereoisomer. In some embodiments the compounds are racemic (e.g., mixture of atropisomers), while in other embodiments the compounds are substantially a single isomer, for example a substantially purified atropisomer. In some embodiments, the compound is a substantially purified S-atropisomer. In some different embodiments, the compound is a substantially purified R-atropisomer.

In various different embodiments, the compound has one of the structures set forth in Table 1 below. Representative compounds in Table 1 were prepared and analyzed by mass spectrometry and/or $^1$H NMR. Other representative compounds may be prepared by the exemplary method indicated in Table 1 or by other methods known or derivable by one of ordinary skill in the art.

TABLE 1

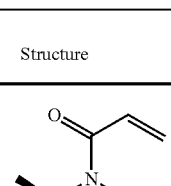

TABLE 1-continued

Representative Compounds

| No. | Structure | Name | Method | [M + H]+ |
|---|---|---|---|---|
| 2 | 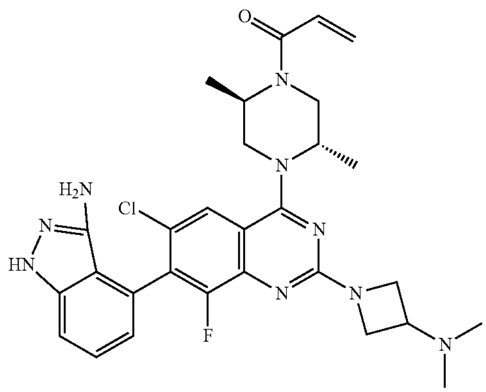 [SMILES: C=CC(=O)N1C[C@H](C)N(c2nc(N3CC(N(C)C)C3)nc3c(F)c(-c4cccc5[nH]nc(N)c45)c(Cl)cc23)C[C@H]1C] | 1-((2R,5S)-4-(7-(3-amino-1H-indazol-4-yl)-6-chloro-2-(3-(dimethylamino)-azetidin-1-yl)-8-fluoroquinazolin-4-yl)-2,5-dimethyl-piperazin-1-yl)prop-2-en-1-one | A | 578.2 |
| 3 | 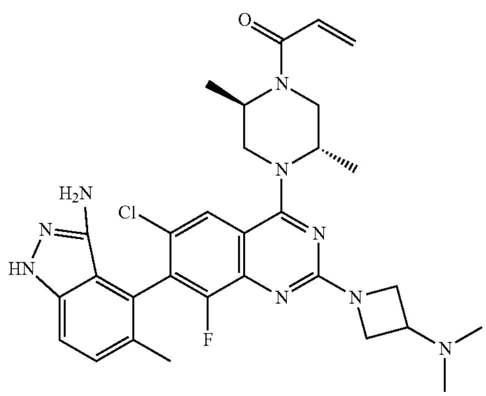 | 1-((2R,5S)-4-(7-(3-amino-5-methyl-1H-indazol-4-yl)-6-chloro-2-(3-(dimethylamino)-azetidin-1-yl)-8-fluoroquinazolin-4-yl)-2,5-dimethyl-piperazin-1-yl)prop-2-en-1-one | B | 592.2 |
| 4 | 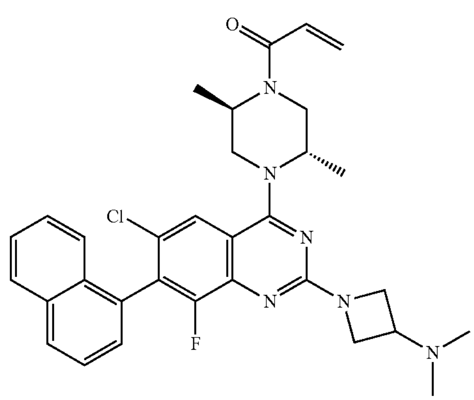 [SMILES: C=CC(=O)N1C[C@H](C)N(c2nc(N3CC(N(C)C)C3)nc3c(F)c(-c4cccc5ccccc45)c(Cl)cc23)C[C@H]1C] | 1-((2R,5S)-4-(6-chloro-2-(3-(dimethylamino)-azetidin-1-yl)-8-fluoro-7-(naphthalen-1-yl)-quinazolin-4-yl)-2,5-dimethylpiperazin-1-yl)prop-2-en-1-one | A | 574.6 |
| 5 | 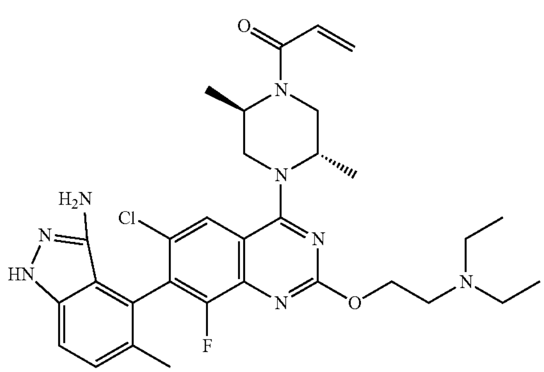 [SMILES: C=CC(=O)N1C[C@H](C)N(c2nc(OCCN(CC)CC)nc3c(F)c(-c4c(C)ccc5[nH]nc(N)c45)c(Cl)cc23)C[C@H]1C] | 1-((2R,5S)-4-(7-(3-amino-5-methyl-1H-indazol-4-yl)-6-chloro-2-(2-(diethylamino)-ethoxy)-8-fluoro-quinazolin-4-yl)-2,5-dimethylpiperazin-1-yl)prop-2-en-1-one | B | ND |

TABLE 1-continued

Representative Compounds

| No. | Structure | Name | Method | [M + H]+ |
|---|---|---|---|---|
| 6 | 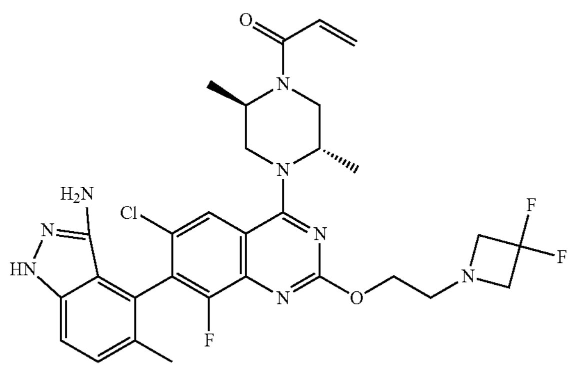 [SMILES: C=CC(=O)N1C[C@H](C)N(c2nc(OCCN3CC(F)(F)C3)nc3c(F)c(-c4c(C)ccc5[nH]nc(N)c45)c(Cl)cc23)C[C@H]1C] | 1-((2R,5S)-4-(7-(3-amino-5-methyl-1H-indazol-4-yl)-6-chloro-2-(2-(3,3-difluoroazetidin-1-yl)-ethoxy)-8-fluoro-quinazolin-4-yl)-2,5-dimethylpiperazin-1-yl)prop-2-en-1-one | B | 629.2 |
| 7 | 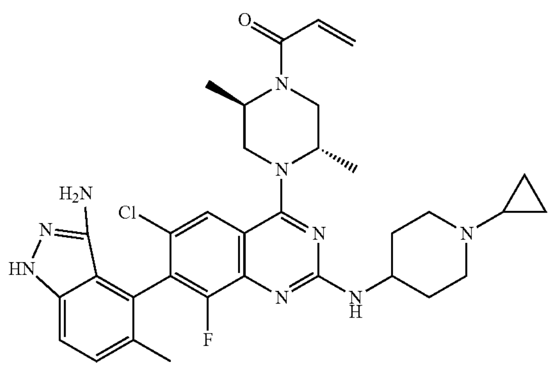 [SMILES: C=CC(=O)N1C[C@H](C)N(c2nc(NC3CCN(C4CC4)CC3)nc3c(F)c(-c4c(C)ccc5[nH]nc(N)c45)c(Cl)cc23)C[C@H]1C] | 1-((2R,5S)-4-(7-(3-amino-5-methyl-1H-indazol-4-yl)-6-chloro-2-(1-cyclopropyl-piperidin-4-ylamino)-8-fluoroquinazolin-4-yl)-2,5-dimethyl-piperazin-1-yl)prop-2-en-1-one | B | ND |
| 8 | 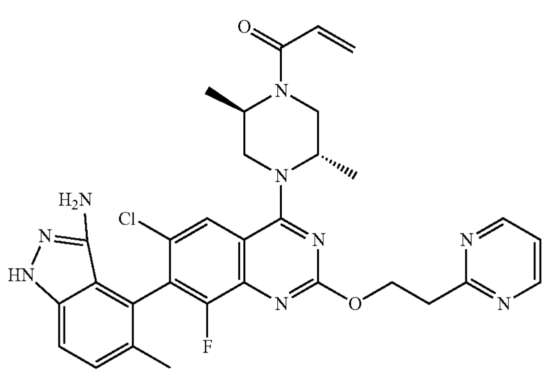 [SMILES: C=CC(=O)N1C[C@H](C)N(c2nc(OCCc3ncccn3)nc3c(F)c(-c4c(C)ccc5[nH]nc(N)c45)c(Cl)cc23)C[C@H]1C] | 1-((2R,5S)-4-(7-(3-amino-5-methyl-1H-indazol-4-yl)-6-chloro-8-fluoro-2-(2-(pyrimidin-2-yl)-ethoxy)quinazolin-4-yl)-2,5-dimethyl-piperazin-1-yl)-prop-2-en-1-one | B | ND |
| 9 | 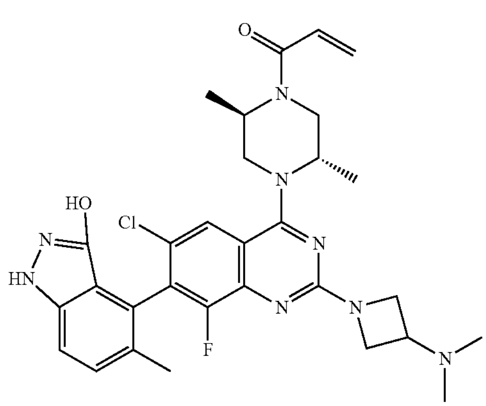 [SMILES: C=CC(=O)N1C[C@H](C)N(c2nc(N3CC(N(C)C)C3)nc3c(F)c(-c4c(C)ccc5[nH]nc(O)c45)c(Cl)cc23)C[C@H]1C] | 1-((2R,5S)-4-(6-chloro-2-(3-(dimethyl-amino)azetidin-1-yl)-8-fluoro-7-(3-hydroxy-5-methyl-1H-indazol-4-yl)quinazolin-4-yl)-2,5-dimethylpiperazin-1-yl)prop-2-en-1-one | B | ND |

TABLE 1-continued

Representative Compounds

| No. | Structure | Name | Method | [M + H]+ |
|---|---|---|---|---|
| 10 | 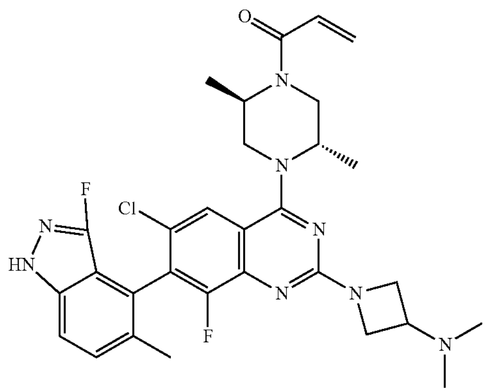 [SMILES: C=CC(=O)N1C[C@H](C)N(c2nc(N3CC(N(C)C)C3)nc3c(F)c(-c4c(C)ccc5[nH]nc(F)c45)c(Cl)cc23)C[C@H]1C] | 1-((2R,5S)-4-(6-chloro-2-(3-(dimethylamino-azetidin-1-yl)-8-fluoro-7-(3-fluoro-5-methyl-1H-indazol-4-yl)-quinazolin-4-yl)-2,5-dimethylpiperazin-1-yl)prop-2-en-1-one | B | ND |
| 11 | 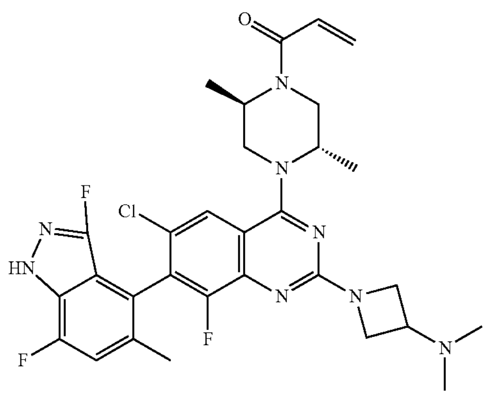 [SMILES: C=CC(=O)N1C[C@H](C)N(c2nc(N3CC(N(C)C)C3)nc3c(F)c(-c4c(C)cc(F)c5[nH]nc(F)c45)c(Cl)cc23)C[C@H]1C] | 1-((2R,5S)-4-(6-chloro-7-(3,7-difluoro-5-methyl-1H-indazol-4-yl)-2-(3-(dimethyl-amino)azetidin-1-yl)-8-fluoroquinazolin-4-yl)-2,5-dimethyl-piperazin-1-yl)prop-2-en-1-one | B | ND |
| 12 | 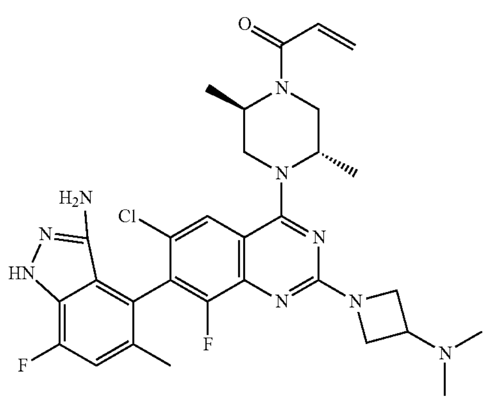 [SMILES: C=CC(=O)N1C[C@H](C)N(c2nc(N3CC(N(C)C)C3)nc3c(F)c(-c4c(C)cc(F)c5[nH]nc(N)c45)c(Cl)cc23)C[C@H]1C] | 1-((2R,5S)-4-(7-(3-amino-7-fluoro-5-methyl-1H-indazol-4-yl)-6-chloro-2-(3-(dimethylamino)-azetidin-1-yl)-8-fluoroquinazolin-4-yl)-2,5-dimethyl-piperazin-1-yl)prop-2-en-1-one | B | ND |
| 13 | 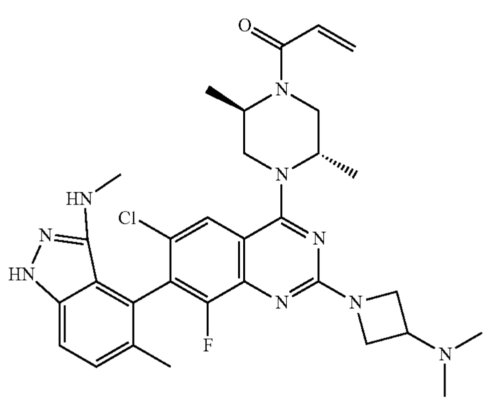 [SMILES: C=CC(=O)N1C[C@H](C)N(c2nc(N3CC(N(C)C)C3)nc3c(F)c(-c4c(C)ccc5[nH]nc(NC)c45)c(Cl)cc23)C[C@H]1C] | 1-((2R,5S)-4-(6-chloro-2-(3-(dimethyl-amino)azetidin-1-yl)-8-fluoro-7-(5-methyl-3-(methylamino)-1H-indazol-4-yl)-quinazolin-4-yl)-2,5-dimethylpiperazin-1-yl)prop-2-en-1-one | B | 606.0 |

TABLE 1-continued

Representative Compounds

| No. | Structure | Name | Method | [M + H]+ |
|-----|-----------|------|--------|----------|
| 14 | 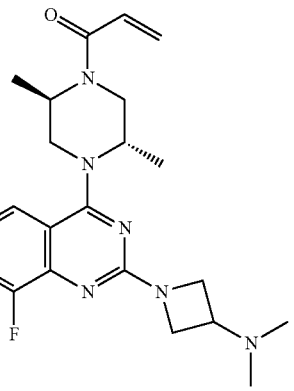 | 1-((2R,5S)-4-(6-chloro-2-(3-(dimethyl-amino)azetidin-1-yl)-8-fluoro-7-(7-fluoro-5-methyl-1H-indazol-4-yl)quinazolin-4-yl)-2,5-dimethylpiperazin-1-yl)prop-2-en-1-one | B | ND |
| 15 | 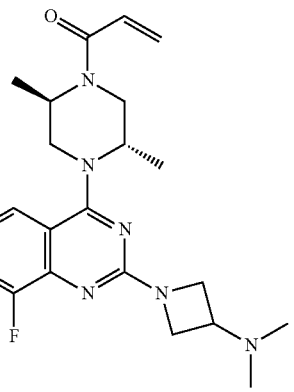 | 1-((2R,5S)-4-(6-chloro-7-(2-chloro-5-methyl-1H-indol-4-yl)-2-(3-(dimethyl-amino)azetidin-1-yl)-8-fluoroquinazolin-4-yl)-2,5-dimethyl-piperazin-1-yl)prop-2-en-1-one | B | ND |
| 16 | 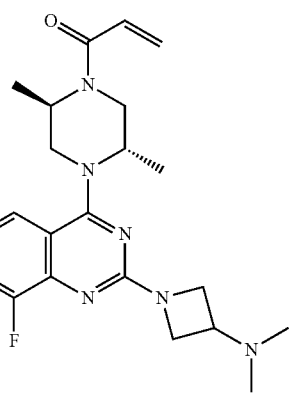 | 1-((2R,5S)-4-(6-chloro-7-(7-chloro-5-methyl-1H-indol-4-yl)-2-(3-(dimethyl-amino)azetidin-1-yl)-8-fluoroquinazolin-4-yl)-2,5-dimethyl-piperazin-1-yl)prop-2-en-1-one | B | ND |

TABLE 1-continued

Representative Compounds

| No. | Structure | Name | Method | [M + H]+ |
|---|---|---|---|---|
| 17 | 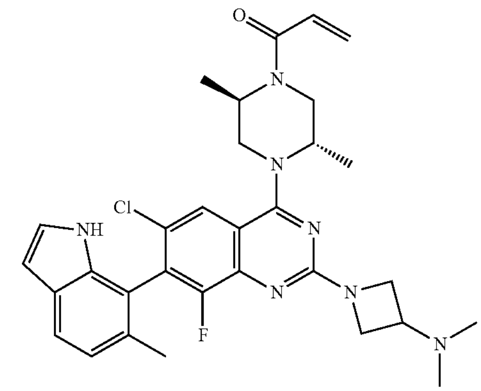 [SMILES: C=CC(=O)N1C[C@H](C)N(c2nc(N3CC(N(C)C)C3)nc3c(F)c(-c4c(C)ccc5cc[nH]c45)c(Cl)cc23)C[C@H]1C] | 1-((2R,5S)-4-(6-chloro-2-(3-(dimethylamino)azetidin-1-yl)-8-fluoro-7-(6-methyl-1H-indol-7-yl)-quinazolin-4-yl)-2,5-dimethylpiperazin-1-yl)prop-2-en-1-one | B | ND |
| 18 | 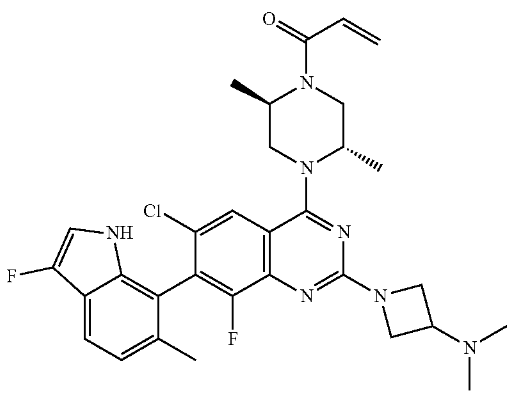 [SMILES: C=CC(=O)N1C[C@H](C)N(c2nc(N3CC(N(C)C)C3)nc3c(F)c(-c4c(C)ccc5c(F)c[nH]c45)c(Cl)cc23)C[C@H]1C] | 1-((2R,5S)-4-(6-chloro-2-(3-(dimethylamino)azetidin-1-yl)-8-fluoro-7-(3-fluoro-6-methyl-1H-indol-7-yl)quinazolin-4-yl)-2,5-dimethylpiperazin-1-yl)prop-2-en-1-one | B | ND |
| 19 | 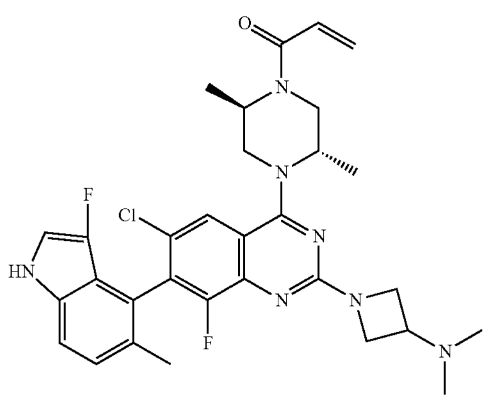 [SMILES: C=CC(=O)N1C[C@H](C)N(c2nc(N3CC(N(C)C)C3)nc3c(F)c(-c4c(C)ccc5[nH]cc(F)c45)c(Cl)cc23)C[C@H]1C] | 1-((2R,5S)-4-(6-chloro-2-(3-(dimethylamino)azetidin-1-yl)-8-fluoro-7-(3-fluoro-5-methyl-1H-indol-4-yl)quinazolin-4-yl)-2,5-dimethylpiperazin-1-yl)prop-2-en-1-one | B | ND |
| 20 | 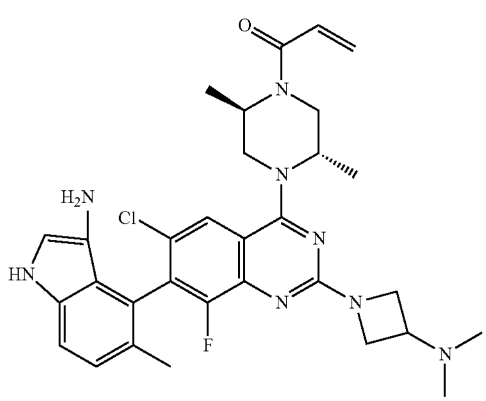 [SMILES: C=CC(=O)N1C[C@H](C)N(c2nc(N3CC(N(C)C)C3)nc3c(F)c(-c4c(C)ccc5[nH]cc(N)c45)c(Cl)cc23)C[C@H]1C] | 1-((2R,5S)-4-(7-(3-amino-5-methyl-1H-indol-4-yl)-6-chloro-2-(3-(dimethylamino)-azetidin-1-yl)-8-fluoroquinazolin-4-yl)-2,5-dimethyl-piperazin-1-yl)prop-2-en-1-one | B | ND |

TABLE 1-continued

Representative Compounds

| No. | Structure | Name | Method | [M + H]+ |
|---|---|---|---|---|
| 21 | 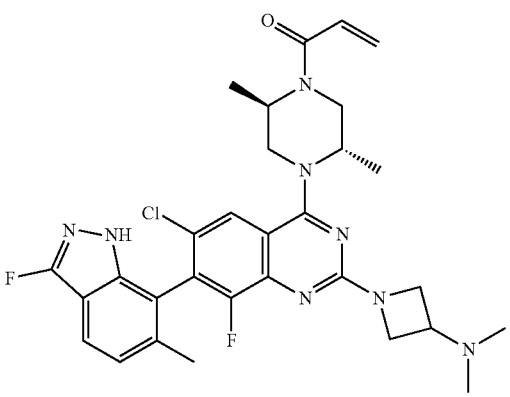 [SMILES: C=CC(=O)N1C[C@H](C)N(c2nc(N3CC(N(C)C)C3)nc3c(F)c(-c4c(C)ccc5c(F)n[nH]c45)c(Cl)cc23)C[C@H]1C] | 1-((2R,5S)-4-(6-chloro-2-(3-(dimethyl-amino)azetidin-1-yl)-8-fluoro-7-(3-fluoro-6-methyl-1H-indazol-7-yl)quinazolin-4-yl)-2,5-dimethylpiperazin-1-yl)prop-2-en-1-one | B | ND |
| 22 | 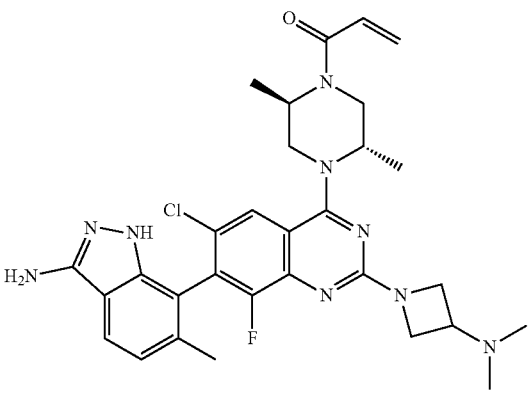 [SMILES: C=CC(=O)N1C[C@H](C)N(c2nc(N3CC(N(C)C)C3)nc3c(F)c(-c4c(C)ccc5c(N)n[nH]c45)c(Cl)cc23)C[C@H]1C] | 1-((2R,5S)-4-(7-(3-amino-6-methyl-1H-indazol-7-yl)-6-chloro-2-(3-(dimethylamino)-azetidin-1-yl)-8-fluoroquinazolin-4-yl)-2,5-dimethyl-piperazin-1-yl)prop-2-en-1-one | B | 592.2 |
| 23 | 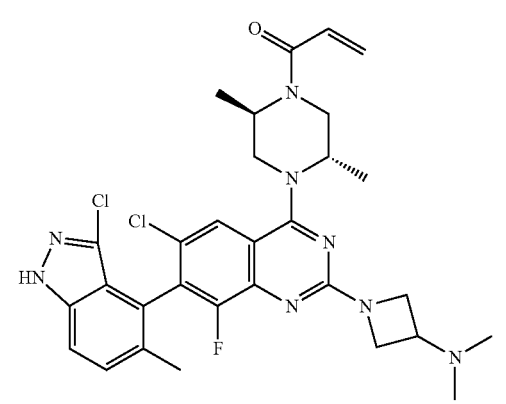 [SMILES: C=CC(=O)N1C[C@H](C)N(c2nc(N3CC(N(C)C)C3)nc3c(F)c(-c4c(C)ccc5[nH]nc(Cl)c45)c(Cl)cc23)C[C@H]1C] | 1-((2R,5S)-4-(6-chloro-7-(3-chloro-5-methyl-1H-indazol-4-yl)-2-(3-(dimethyl-amino)azetidin-1-yl)-8-fluoroquinazolin-4-yl)-2,5-dimethyl-piperazin-1-yl)prop-2-en-1-one | B | 611.2 |

TABLE 1-continued

Representative Compounds

| No. | Structure | Name | Method | [M + H]+ |
|---|---|---|---|---|
| 24 | 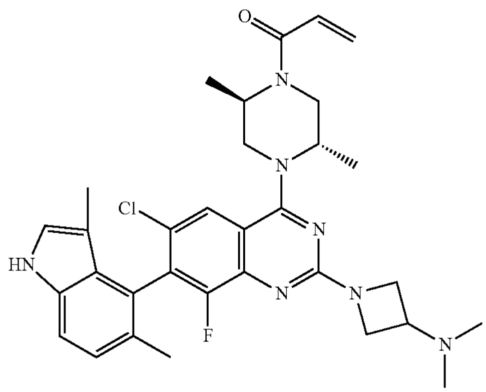 [SMILES: C=CC(=O)N1C[C@H](C)N(c2nc(N3CC(N(C)C)C3)nc3c(F)c(-c4c(C)ccc5[nH]cc(C)c45)c(Cl)cc23)C[C@H]1C] | 1-((2R,5S)-4-(6-chloro-7-(3,5-dimethyl-1H-indol-4-yl)-2-(3-(dimethylamino)-azetidin-1-yl)-8-fluoroquinazolin-4-yl)-2,5-dimethyl-piperazin-1-yl)prop-2-en-1-one | B | ND |
| 25 | 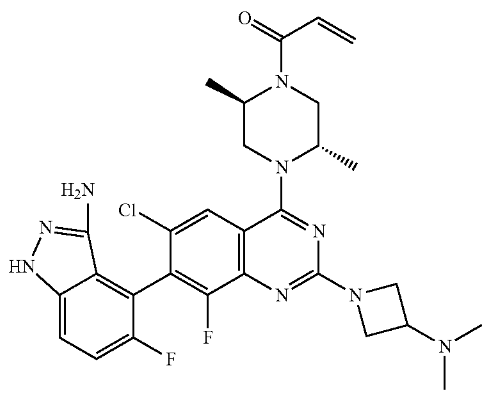 [SMILES: C=CC(=O)N1C[C@H](C)N(c2nc(N3CC(N(C)C)C3)nc3c(F)c(-c4c(F)ccc5[nH]nc(N)c45)c(Cl)cc23)C[C@H]1C] | 1-((2R,5S)-4-(7-(3-amino-5-fluoro-1H-indazol-4-yl)-6-chloro-2-(3-(dimethylamino)-azetidin-1-yl)-8-fluoroquinazolin-4-yl)-2,5-dimethyl-piperazin-1-yl)prop-2-en-1-one | B | ND |
| 26 | 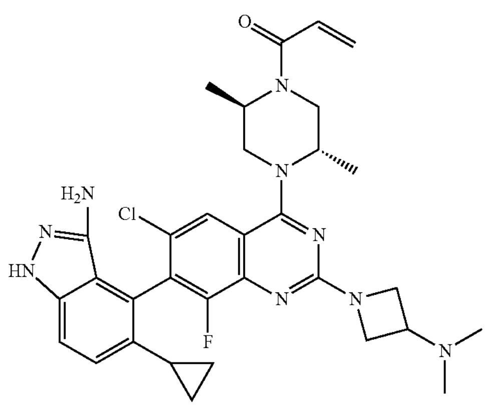 [SMILES: C=CC(=O)N1C[C@H](C)N(c2nc(N3CC(N(C)C)C3)nc3c(F)c(-c4c(C5CC5)ccc5[nH]nc(N)c45)c(Cl)cc23)C[C@H]1C] | 1-((2R,5S)-4-(7-(3-amino-5-cyclopropyl-1H-indazol-4-yl)-6-chloro-2-(3-(dimethyl-amino)azetidin-1-yl)-8-fluoroquinazolin-4-yl)-2,5-dimethyl-piperazin-1-yl)prop-2-en-1-one | B | ND |
| 27 | 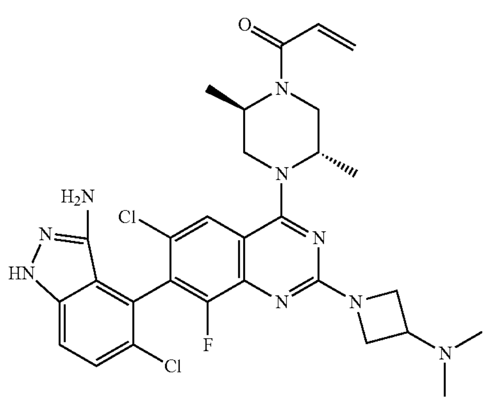 | 1-((2R,5S)-4-(7-(3-amino-5-chloro-1H-indazol-4-yl)-6-chloro-2-(3-(dimethylamino)-azetidin-1-yl)-8-fluoroquinazolin-4-yl)-2,5-dimethyl-piperazin-1-yl)prop-2-en-1-one | B | ND |

TABLE 1-continued

Representative Compounds

| No. | Structure | Name | Method | [M + H]+ |
|---|---|---|---|---|
| 28 | 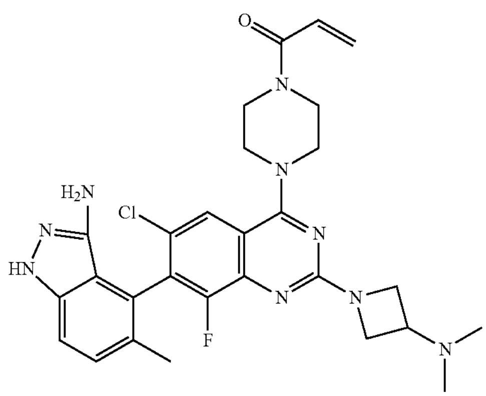 [SMILES: C=CC(=O)N1CCN(c2nc(N3CC(N(C)C)C3)nc3c(F)c(-c4c(C)ccc5[nH]nc(N)c45)c(Cl)cc23)CC1] | 1-(4-(7-(3-amino-5-methyl-1H-indazol-4-yl)-6-chloro-2-(3-(dimethylamino)-azetidin-1-yl)-8-fluoroquinazolin-4-yl)piperazin-1-yl)prop-2-en-1-one | B | 564.5 |
| 29 | 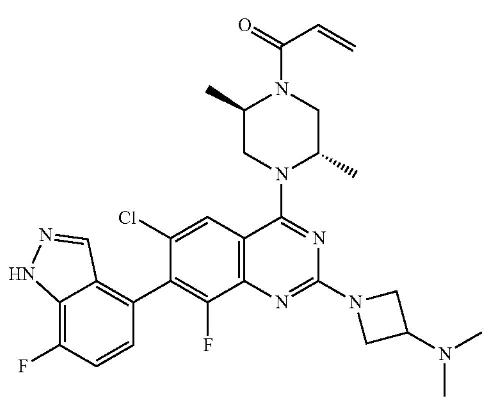 [SMILES: C=CC(=O)N1C[C@H](C)N(c2nc(N3CC(N(C)C)C3)nc3c(F)c(-c4ccc(F)c5[nH]ncc45)c(Cl)cc23)C[C@H]1C] | 1-((2R,5S)-4-(6-chloro-2-(3-(dimethyl-amino)azetidin-1-yl)-8-fluoro-7-(7-fluoro-1H-indazol-4-yl)-quinazolin-4-yl)-2,5-dimethylpiperazin-1-yl)prop-2-en-1-one | A | 581.2 |
| 30 | 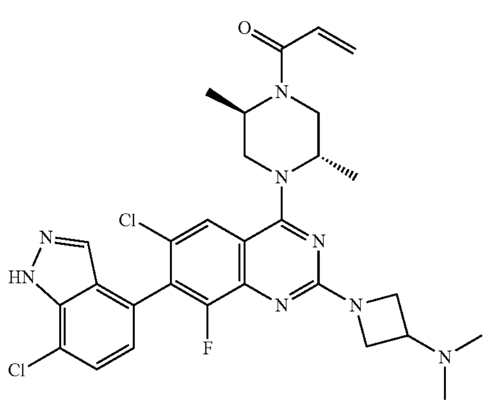 [SMILES: C=CC(=O)N1C[C@H](C)N(c2nc(N3CC(N(C)C)C3)nc3c(F)c(-c4ccc(Cl)c5[nH]ncc45)c(Cl)cc23)C[C@H]1C] | 1-((2R,5S)-4-(6-chloro-7-(7-chloro-1H-indazol-4-yl)-2-(3-(dimethylamino)-azetidin-1-yl)-8-fluoroquinazolin-4-yl)-2,5-dimethyl-piperazin-1-yl)prop-2-en-1-one | A | 597.2 |

TABLE 1-continued

Representative Compounds

| No. | Structure | Name | Method | [M + H]+ |
|---|---|---|---|---|
| 31 | 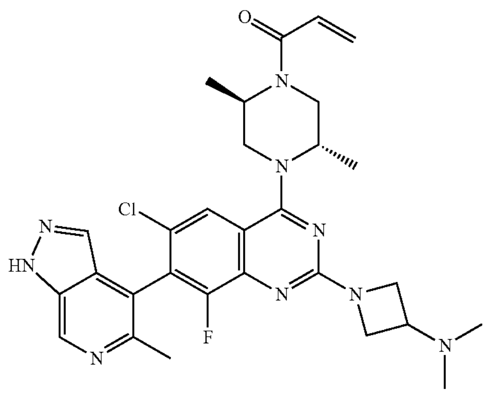 [SMILES: C=CC(=O)N1C[C@H](C)N(c2nc(N3CC(N(C)C)C3)nc3c(F)c(-c4c(C)ncc5[nH]ncc45)c(Cl)cc23)C[C@H]1C] | 1-((2R,5S)-4-(6-chloro-2-(3-(dimethyl-amino)azetidin-1-yl)-8-fluoro-7-(5-methyl-1H-pyrazolo[3,4-c]pyridin-4-yl)-quinazolin-4-yl)-2,5-dimethylpiperazin-1-yl)prop-2-en-1-one | A | ND |
| 32 | 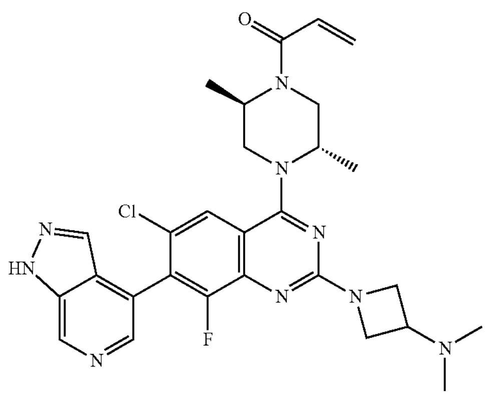 [SMILES: C=CC(=O)N1C[C@H](C)N(c2nc(N3CC(N(C)C)C3)nc3c(F)c(-c4cncc5[nH]ncc45)c(Cl)cc23)C[C@H]1C] | 1-((2R,5S)-4-(6-chloro-2-(3-(dimethyl-amino)azetidin-1-yl)-8-fluoro-7-(1H-pyrazolo[3,4-c]pyridin-4-yl)quinazolin-4-yl)-2,5-dimethylpiperazin-1-yl)prop-2-en-1-one | A | 564.2 |
| 33 | 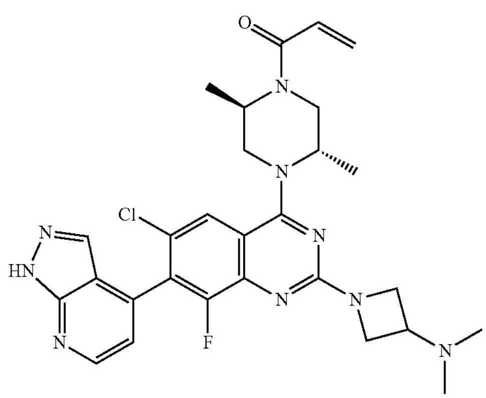 [SMILES: C=CC(=O)N1C[C@H](C)N(c2nc(N3CC(N(C)C)C3)nc3c(F)c(-c4ccnc5[nH]ncc45)c(Cl)cc23)C[C@H]1C] | 1-((2R,5S)-4-(6-chloro-2-(3-(dimethyl-amino)azetidin-1-yl)-8-fluoro-7-(1H-pyrazolo[3,4-b]-pyridin-4-yl)-quinazolin-4-yl)-2,5-dimethylpiperazin-1-yl)prop-2-en-1-one | A | 564.2 |
| 34 | 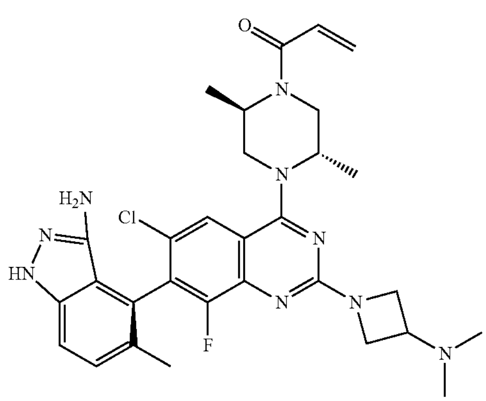 | 1-((2R,5S)-4-((S)-7-(3-amino-5-methyl-1H-indazol-4-yl)-6-chloro-2-(3-(dimethyl-amino)azetidin-1-yl)-8-fluoroquinazolin-4-yl)-2,5-dimethyl-piperazin-1-yl)prop-2-en-1-one | B | 592.4 |

TABLE 1-continued

Representative Compounds

| No. | Structure | Name | Method | [M + H]+ |
|---|---|---|---|---|
| 35 | 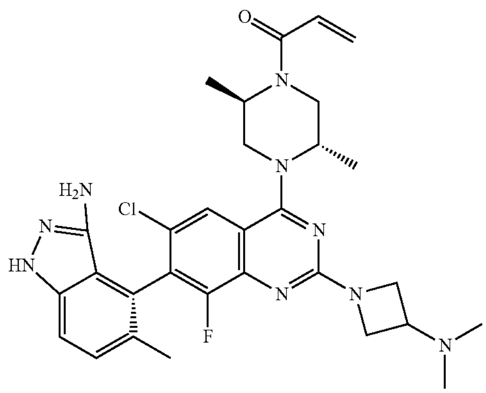 | 1-((2R,5S)-4-((R)-7-(3-amino-5-methyl-1H-indazol-4-yl)-6-chloro-2-(3-(dimethylamino)azetidin-1-yl)-8-fluoroquinazolin-4-yl)-2,5-dimethylpiperazin-1-yl)prop-2-en-1-one | B | 592.4 |
| 36 | 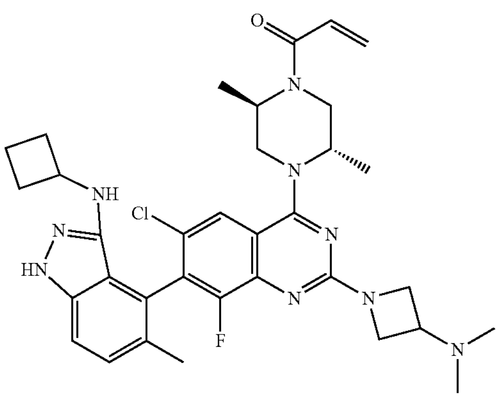 [SMILES: C=CC(=O)N1C[C@H](C)N(c2nc(N3CC(N(C)C)C3)nc3c(F)c(-c4c(C)ccc5[nH]nc(NC6CCC6)c45)c(Cl)cc23)C[C@H]1C] | 1-((2R,5S)-4-(6-chloro-7-(3-(cyclobutylamino)-5-methyl-1H-indazol-4-yl)-2-(3-(dimethylamino)azetidin-1-yl)-8-fluoroquinazolin-4-yl)-2,5-dimethylpiperazin-1-yl)prop-2-en-1-one | E | 646.5 |
| 37 | 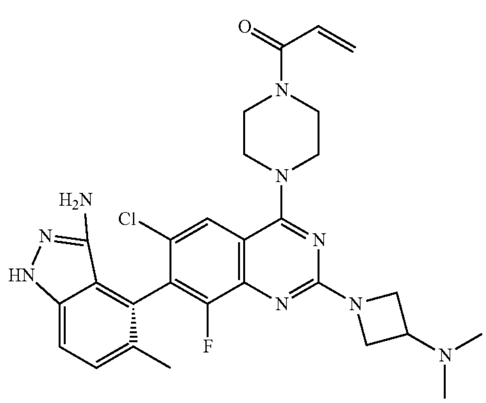 | (R)-1-(4-(7-(3-amino-5-methyl-1H-indazol-4-yl)-6-chloro-2-(3-(dimethylamino)azetidin-1-yl)-8-fluoroquinazolin-4-yl)piperazin-1-yl)-prop-2-en-1-one | B | 564.5 |

TABLE 1-continued

Representative Compounds

| No. | Structure | Name | Method | [M + H]+ |
|---|---|---|---|---|
| 38 | 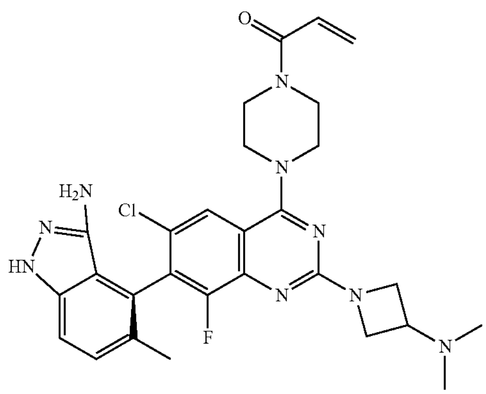 | (S)-1-(4-(7-(3-amino-5-methyl-1H-indazol-4-yl)-6-chloro-2-(3-(dimethylamino)azetidin-1-yl)-8-fluoroquinazolin-4-yl)piperazin-1-yl)-prop-2-en-1-one | B | 564.5 |
| 39 | 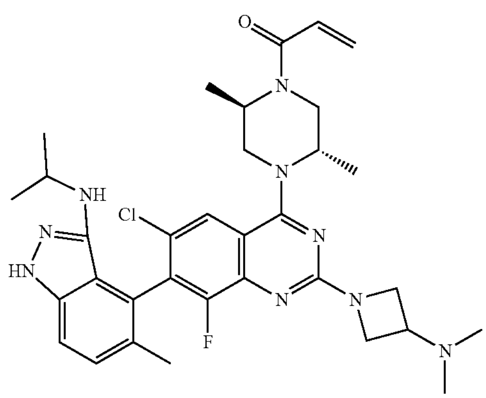 [SMILES: C=CC(=O)N1C[C@H](C)N(c2nc(N3CC(N(C)C)C3)nc3c(F)c(-c4c(C)ccc5[nH]nc(NC(C)C)c45)c(Cl)cc23)C[C@H]1C] | 1-((2R,5S)-4-(6-chloro-2-(3-(dimethylamino)azetidin-1-yl)-8-fluoro-7-(3-(isopropylamino)-5-methyl-1H-indazol-4-yl)quinazolin-4-yl)-2,5-dimethylpiperazin-1-yl)prop-2-en-1-one | E | 634.4 |
| 40 | 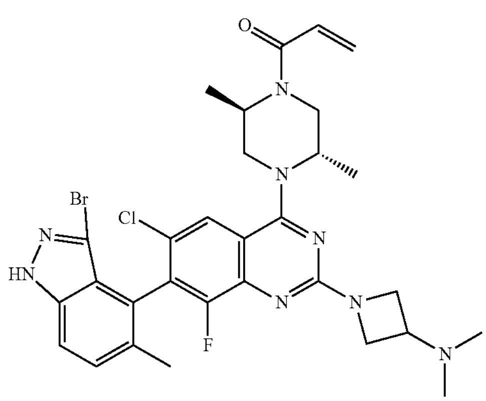 [SMILES: C=CC(=O)N1C[C@H](C)N(c2nc(N3CC(N(C)C)C3)nc3c(F)c(-c4c(C)ccc5[nH]nc(Br)c45)c(Cl)cc23)C[C@H]1C] | 1-((2R,5S)-4-(7-(3-bromo-5-methyl-1H-indazol-4-yl)-6-chloro-2-(3-(dimethylamino)azetidin-1-yl)-8-fluoroquinazolin-4-yl)-2,5-dimethylpiperazin-1-yl)prop-2-en-1-one | B | 655.1 |
| 41 | 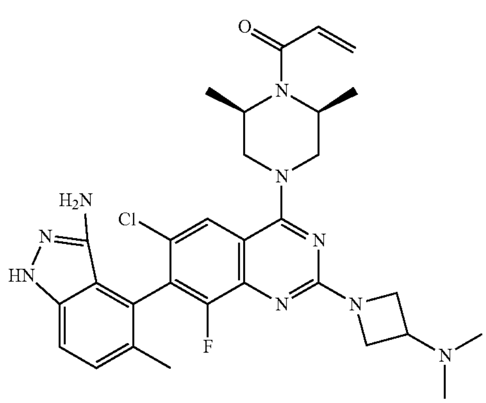 [SMILES: C=CC(=O)N1[C@H](C)CN(c2nc(N3CC(N(C)C)C3)nc3c(F)c(-c4c(C)ccc5[nH]nc(N)c45)c(Cl)cc23)C[C@@H]1C] | 1-((2S,6R)-4-(7-(3-amino-5-methyl-1H-indazol-4-yl)-6-chloro-2-(3-(dimethylamino)azetidin-1-yl)-8-fluoroquinazolin-4-yl)-2,6-dimethylpiperazin-1-yl)prop-2-en-1-one | B | 592.0 |

TABLE 1-continued

Representative Compounds

| No. | Structure | Name | Method | [M + H]+ |
|-----|-----------|------|--------|----------|
| 42 | 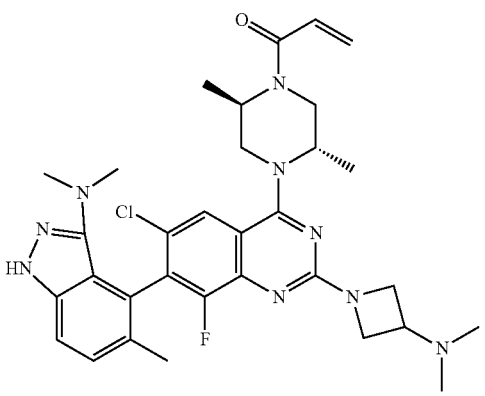 [SMILES: C=CC(=O)N1C[C@H](C)N(c2nc(N3CC(N(C)C)C3)nc3c(F)c(-c4c(C)ccc5[nH]nc(N(C)C)c45)c(Cl)cc23)C[C@H]1C] | 1-((2R,5S)-4-(6-chloro-7-(3-(dimethylamino)-5-methyl-1H-indazol-4-yl)-2-(3-(dimethylamino)azetidin-1-yl)-8-fluoroquinazolin-4-yl)-2,5-dimethylpiperazin-1-yl)prop-2-en-1-one | E | 620.0 |
| 43 | 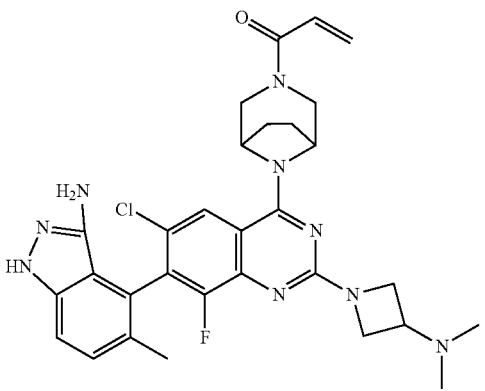 [SMILES: C=CC(=O)N1CC2CCC(C1)N2c1nc(N2CC(N(C)C)C2)nc2c(F)c(-c3c(C)ccc4[nH]nc(N)c34)c(Cl)cc12] | 1-((1R,5S)-8-(7-(3-amino-5-methyl-1H-indazol-4-yl)-6-chloro-2-(3-(dimethylamino)azetidin-1-yl)-8-fluoroquinazolin-4-yl)-3,8-diazabicyclo[3.2.1]octan-3-yl)prop-2-en-1-one | B | 590.0 |
| 44 | 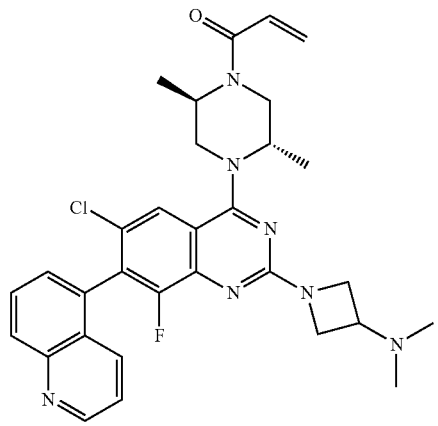 [SMILES: C=CC(=O)N1C[C@H](C)N(c2nc(N3CC(N(C)C)C3)nc3c(F)c(-c4cccc5ncccc45)c(Cl)cc23)C[C@H]1C] | 1-((2R,5S)-4-(6-chloro-2-(3-(dimethylamino)azetidin-1-yl)-8-fluoro-7-(quinolin-5-yl)quinazolin-4-yl)-2,5-dimethylpiperazin-1-yl)prop-2-en-1-one | A | 574.0 |

TABLE 1-continued

Representative Compounds

| No. | Structure | Name | Method | [M + H]+ |
|---|---|---|---|---|
| 45 | 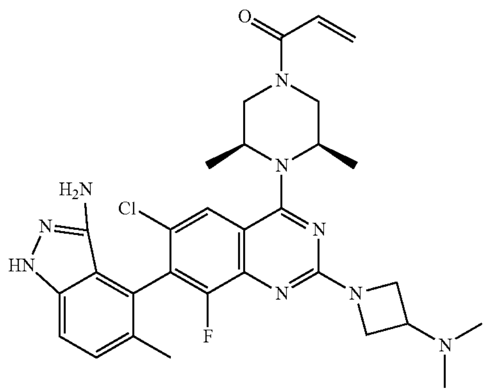 [SMILES: C=CC(=O)N1C[C@@H](C)N(c2nc(N3CC(N(C)C)C3)nc3c(F)c(-c4c(C)ccc5[nH]nc(N)c45)c(Cl)cc23)[C@@H](C)C1] | 1-((3R,5S)-4-(7-(3-amino-5-methyl-1H-indazol-4-yl)-6-chloro-2-(3-(dimethylamino)azetidin-1-yl)-8-fluoroquinazolin-4-yl)-3,5-dimethylpiperazin-1-yl)prop-2-en-1-one | B | 592.0 |
| 46 | 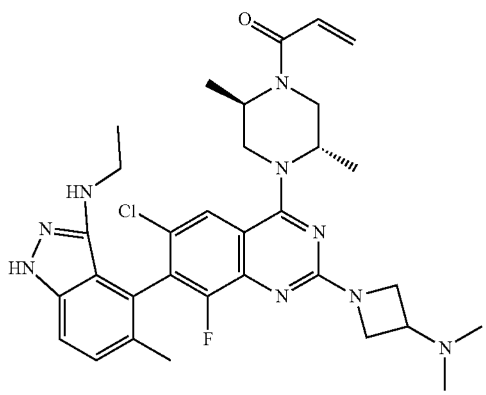 [SMILES: C=CC(=O)N1C[C@H](C)N(c2nc(N3CC(N(C)C)C3)nc3c(F)c(-c4c(C)ccc5[nH]nc(NCC)c45)c(Cl)cc23)C[C@H]1C] | 1-((2R,5S)-4-(6-chloro-2-(3-(dimethylamino)azetidin-1-yl)-7-(3-(ethylamino)-5-methyl-1H-indazol-4-yl)-8-fluoroquinazolin-4-yl)-2,5-dimethylpiperazin-1-yl)prop-2-en-1-one | E | 620.0 |
| 47 | 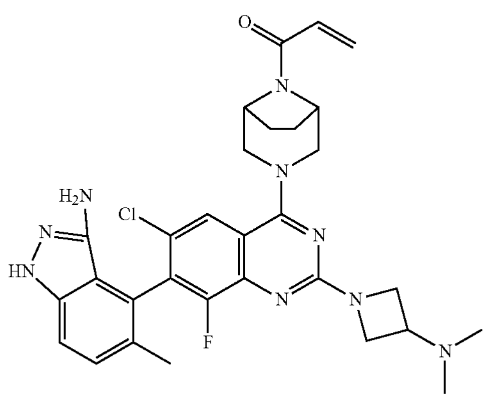 [SMILES: C=CC(=O)N1C2CCC1CN(c1nc(N3CC(N(C)C)C3)nc3c(F)c(-c4c(C)ccc5[nH]nc(N)c45)c(Cl)cc13)C2] | 1-((1R,5S)-3-(7-(3-amino-5-methyl-1H-indazol-4-yl)-6-chloro-2-(3-(dimethylamino)-azetidin-1-yl)-8-fluoroquinazolin-4-yl)-3,8-diazabicyclo[3.2.1]octan-8-yl)prop-2-en-1-one | B | 590.0 |
| 48 | 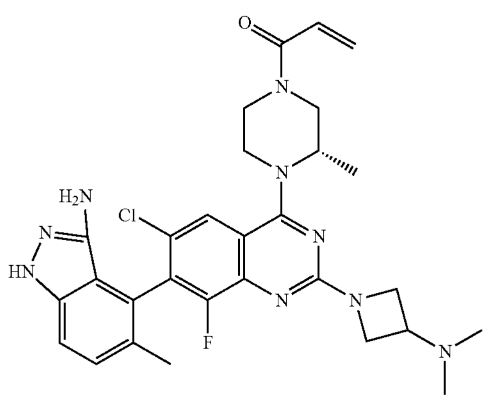 [SMILES: C=CC(=O)N1CCN(c2nc(N3CC(N(C)C)C3)nc3c(F)c(-c4c(C)ccc5[nH]nc(N)c45)c(Cl)cc23)[C@@H](C)C1] | 1-((3S)-4-(7-(3-amino-5-methyl-1H-indazol-4-yl)-6-chloro-2-(3-(dimethylamino)-azetidin-1-yl)-8-fluoroquinazolin-4-yl)-3-methylpiperazin-1-yl)prop-2-en-1-one | B | 578.0 |

TABLE 1-continued

Representative Compounds

| No. | Structure | Name | Method | [M + H]+ |
|---|---|---|---|---|
| 49 | 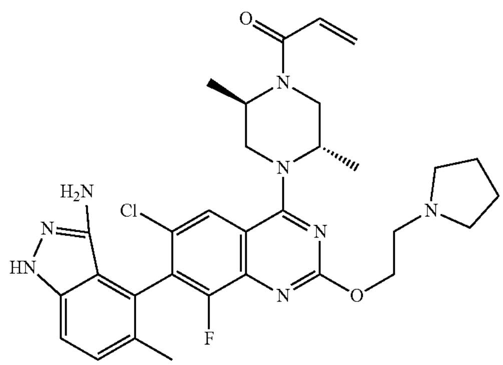 | 1-((2R,5S)-4-(7-(3-amino-5-methyl-1H-indazol-4-yl)-6-chloro-8-fluoro-2-(2-(pyrrolidin-1-yl)-ethoxy(quinazolin-4-yl)-2,5-dimethyl-piperazin-1-yl)prop-2-en-1-one | B | 608.0 |
| 50 | 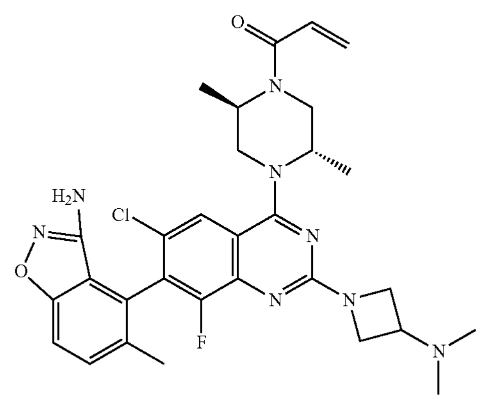 [SMILES: C=CC(=O)N1C[C@H](C)N(c2nc(N3CC(N(C)C)C3)nc3c(F)c(-c4c(C)ccc5onc(N)c45)c(Cl)cc23)C[C@H]1C] | 1-((2R,5S)-4-(7-(3-amino-5-methylbenzo-[d]isoxazol-4-yl)-6-chloro-2-(3-(dimethyl-amino)azetidin-1-yl)-8-fluoroquinazolin-4-yl)-2,5-dimethyl-piperazin-1-yl)prop-2-en-1-one | F | 593.0 |
| 51 | 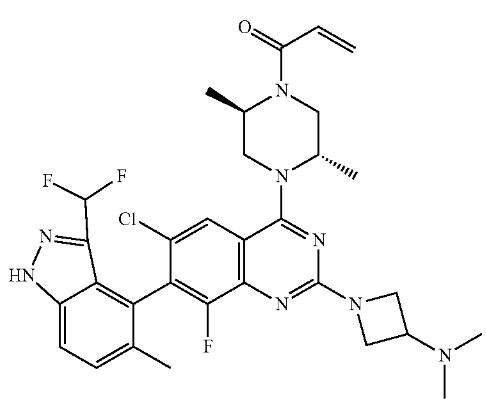 [SMILES: C=CC(=O)N1C[C@H](C)N(c2nc(N3CC(N(C)C)C3)nc3c(F)c(-c4c(C)ccc5[nH]nc(C(F)F)c45)c(Cl)cc23)C[C@H]1C] | 1-((2R,5S)-4-(6-chloro-7-(3-(difluoro-methyl)-5-methyl-1H-indazol-4-yl)-2-(3-(dimethylamino)-azetidin-1-yl)-8-fluoroquinazolin-4-yl)-2,5-dimethyl-piperazin-1-yl)prop-2-en-1-one | B | 627.0 |
| 52 | 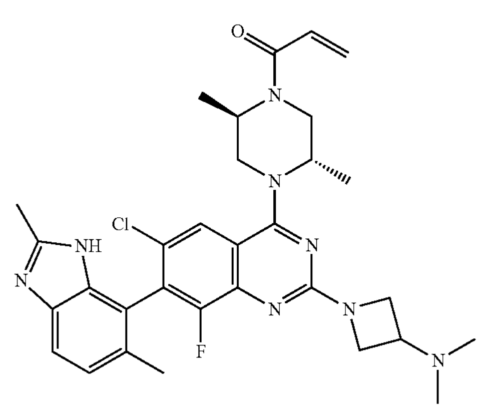 | 1-((2R,5S)-4-(6-chloro-7-(2,6-dimethyl-1H-benzo[d]imidazol-7-yl)-2-(3-(dimethyl-amino)azetidin-1-yl)-8-fluoroquinazolin-4-yl)-2,5-dimethyl-piperazin-1-yl)prop-2-en-1-one | A | 591.0 |

TABLE 1-continued

Representative Compounds

| No. | Structure | Name | Method | [M + H]+ |
|---|---|---|---|---|
| 53 | 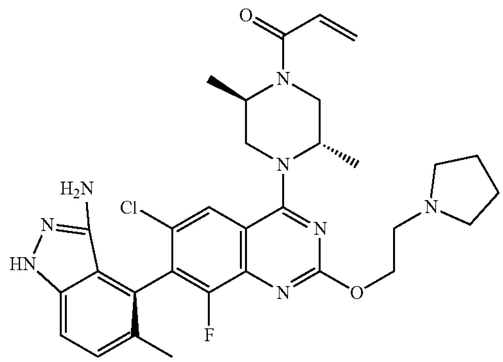 | 1-((2R,5S)-4-((S)-7-(3-amino-5-methyl-1H-indazol-4-yl)-6-chloro-8-fluoro-2-(2-(pyrrolidin-1-yl)ethoxy)quinazolin-4-yl)-2,5-dimethylpiperazin-1-yl)prop-2-en-1-one | B | 607.0 |
| 54 | 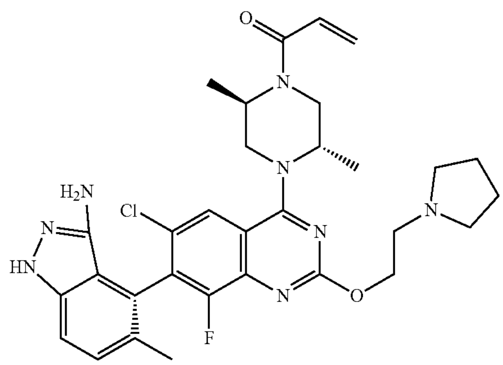 | 1-((2R,5S)-4-((R)-7-(3-amino-5-methyl-1H-indazol-4-yl)-6-chloro-8-fluoro-2-(2-(pyrrolidin-1-yl)ethoxy)quinazolin-4-yl)-2,5-dimethylpiperazin-1-yl)prop-2-en-1-one | B | 607 |
| 55 | 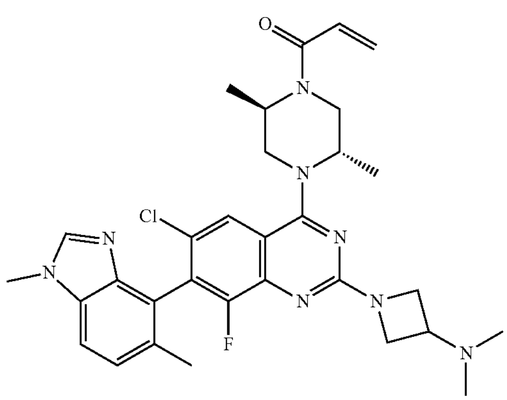 | 1-((2R,5S)-4-(6-chloro-7-(1,5-dimethyl-1H-benzo[d]imidazol-4-yl)-2-(3-(dimethylamino)azetidin-1-yl)-8-fluoroquinazolin-4-yl)-2,5-dimethylpiperazin-1-yl)prop-2-en-1-one | D | 591.2 |
| 56 | 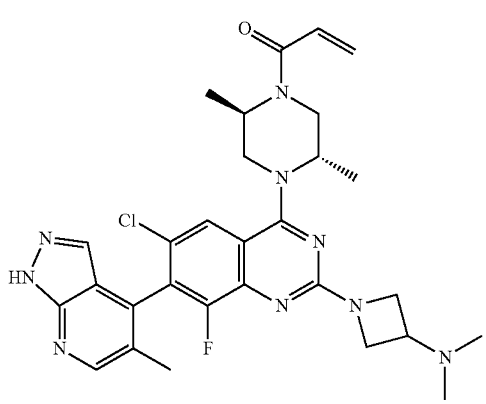 [SMILES: C=CC(=O)N1C[C@H](C)N(c2nc(N3CC(N(C)C)C3)nc3c(F)c(-c4c(C)cnc5[nH]ncc45)c(Cl)cc23)C[C@H]1C] | 1-((2R,5S)-4-(6-chloro-2-(3-(dimethylamino)azetidin-1-yl)-8-fluoro-7-(5-methyl-1H-pyrazolo[3,4-b]pyridin-4-yl)quinazolin-4-yl)-2,5-dimethylpiperazin-1-yl)prop-2-en-1-one | A | ND |

TABLE 1-continued

Representative Compounds

| No. | Structure | Name | Method | [M + H]+ |
|---|---|---|---|---|
| 57 | 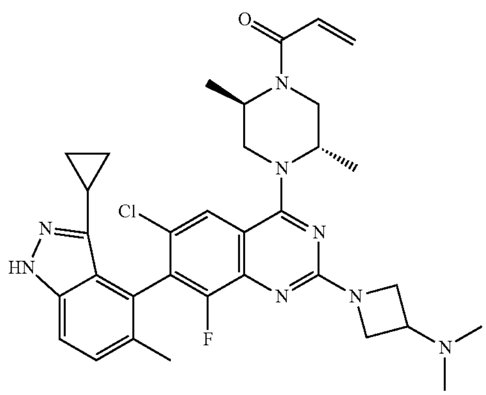 [SMILES: C=CC(=O)N1C[C@H](C)N(c2nc(N3CC(N(C)C)C3)nc3c(F)c(-c4c(C)ccc5[nH]nc(C6CC6)c45)c(Cl)cc23)C[C@H]1C] | 1-((2R,5S)-4-(6-chloro-7-(3-cyclopropyl-5-methyl-1H-indazol-4-yl)-2-(3-(dimethylamino)-azetidin-1-yl)-8-fluoroquinazolin-4-yl)-2,5-dimethyl-piperazin-1-yl)prop-2-en-1-one | C | 619.0 |
| 58 | 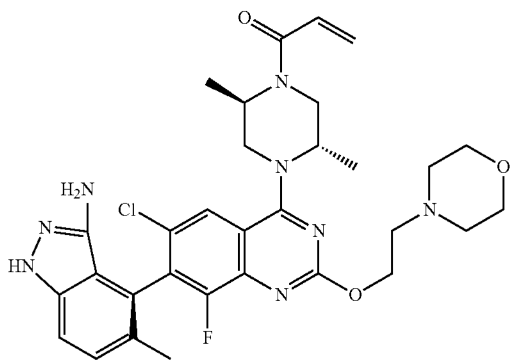 | 1-((2R,5S)-4-((S)-7-(3-amino-5-methyl-1H-indazol-4-yl)-6-chloro-8-fluoro-2-(2-morpholinoethoxy)-quinazolin-4-yl)-2,5-dimethylpiperazin-1-yl)prop-2-en-1-one | B | 623.0 |
| 59 | 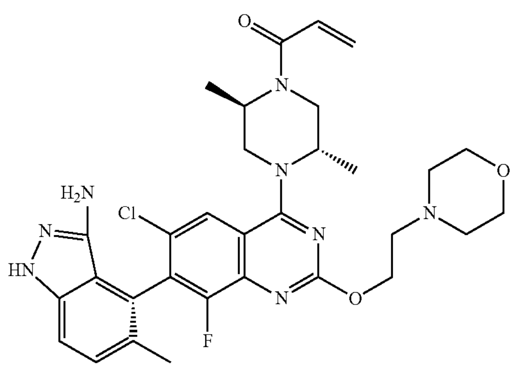 | 1-((2R,5S)-4-((R)-7-(3-amino-5-methyl-1H-indazol-4-yl)-6-chloro-8-fluoro-2-(2-morpholinoethoxy)-quinazolin-4-yl)-2,5-dimethylpiperazin-1-yl)prop-2-en-1-one | B | 623.0 |
| 60 | 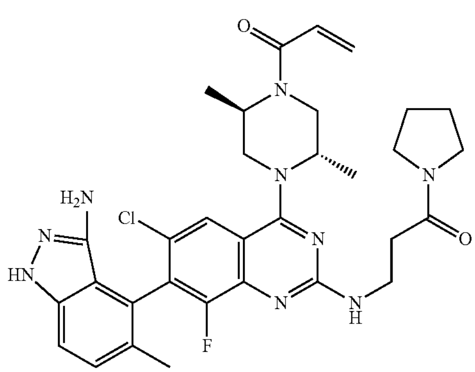 [SMILES: C=CC(=O)N1C[C@H](C)N(c2nc(NCCC(=O)N3CCCC3)nc3c(F)c(-c4c(C)ccc5[nH]nc(N)c45)c(Cl)cc23)C[C@H]1C] | 1-((2R,5S)-4-(7-(3-amino-5-methyl-1H-indazol-4-yl)-6-chloro-8-fluoro-2-(3-oxo-3-(pyrrolidin-1-yl)propylamino)-quinazolin-4-yl)-2,5-dimethylpiperazin-1-yl)prop-2-en-1-one | B | 636.0 |

TABLE 1-continued

Representative Compounds

| No. | Structure | Name | Method | [M + H]+ |
|---|---|---|---|---|
| 61 | 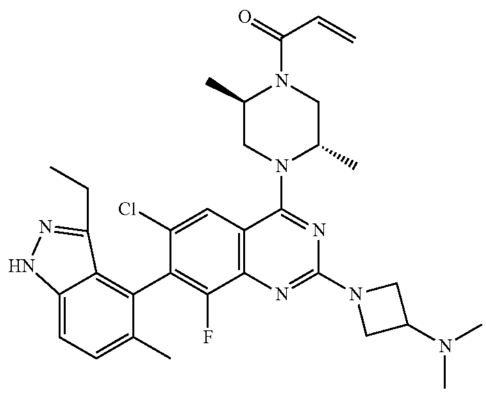 [SMILES: C=CC(=O)N1C[C@H](C)N(c2nc(N3CC(N(C)C)C3)nc3c(F)c(-c4c(C)ccc5[nH]nc(CC)c45)c(Cl)cc23)C[C@H]1C] | 1-((2R,5S)-4-(6-chloro-2-(3-(dimethyl-amino)azetidin-1-yl)-7-(3-ethyl-5-methyl-1H-indazol-4-yl)-8-fluoroquinazolin-4-yl)-2,5-dimethyl-piperazin-1-yl)prop-2-en-1-one | C | 605.2 |
| 62 | 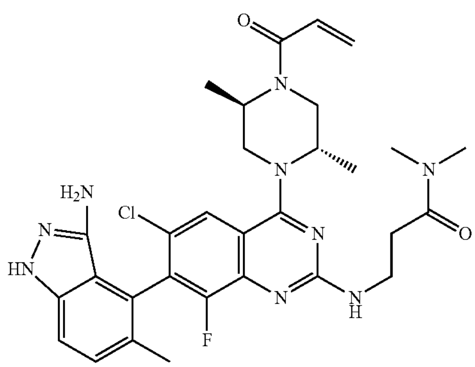 [SMILES: C=CC(=O)N1C[C@H](C)N(c2nc(NCCC(=O)N(C)C)nc3c(F)c(-c4c(C)ccc5[nH]nc(N)c45)c(Cl)cc23)C[C@H]1C] | 3-(4-((2S,5R)-4-acryloyl-2,5-dimethyl-piperazin-1-yl)-7-(3-amino-5-methyl-1H-indazol-4-yl)-6-chloro-8-fluoro-quinazolin-2-yl-amino)-N,N-dimethylpropanamide | B | 608.4 |
| 63 | 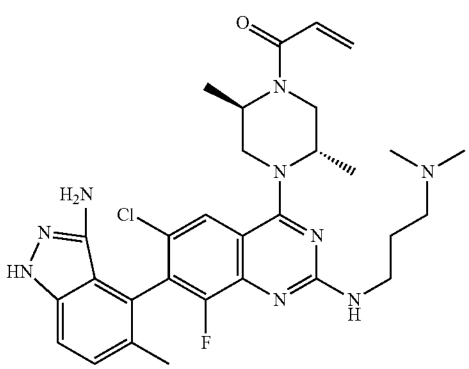 [SMILES: C=CC(=O)N1C[C@H](C)N(c2nc(NCCCN(C)C)nc3c(F)c(-c4c(C)ccc5[nH]nc(N)c45)c(Cl)cc23)C[C@H]1C] | 1-((2R,5S)-4-(7-(3-amino-5-methyl-1H-indazol-4-yl)-6-chloro-2-(3-(dimethyl-amino)propylamino)-8-fluoroquinazolin-4-yl)-2,5-dimethyl-piperazin-1-yl)prop-2-en-1-one | B | 594.4 |
| 64 | 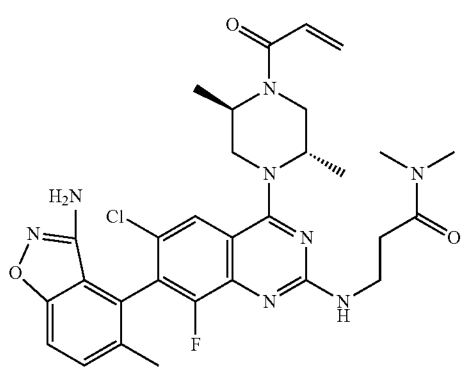 [SMILES: C=CC(=O)N1C[C@H](C)N(c2nc(NCCC(=O)N(C)C)nc3c(F)c(-c4c(C)ccc5onc(N)c45)c(Cl)cc23)C[C@H]1C] | 3-(4-((2S,5R)-4-acryloyl-2,5-dimethyl-piperazin-1-yl)-7-(3-amino-5-methylbenzo-[d]isoxazol-4-yl)-6-chloro-8-fluoro-quinazolin-2-ylamino)-N,N-dimethyl propanamide | F | 609.5 |

TABLE 1-continued

Representative Compounds

| No. | Structure | Name | Method | [M + H]+ |
|---|---|---|---|---|
| 65 | 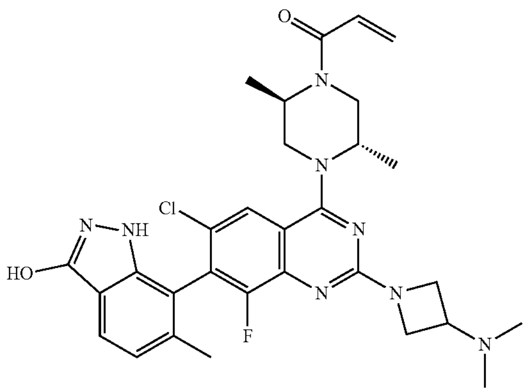 [SMILES: C=CC(=O)N1C[C@H](C)N(c2nc(N3CC(N(C)C)C3)nc3c(F)c(-c4c(C)ccc5c(O)n[nH]c45)c(Cl)cc23)C[C@H]1C] | 1-((2R,5S)-4-(6-chloro-2-(3-(dimethylamino)azetidin-1-yl)-8-fluoro-7-(3-hydroxy-6-methyl-1H-indazol-7-yl)quinazolin-4-yl)-2,5-dimethylpiperazin-1-yl)prop-2-en-1-one | G | 593.2 |
| 66 | 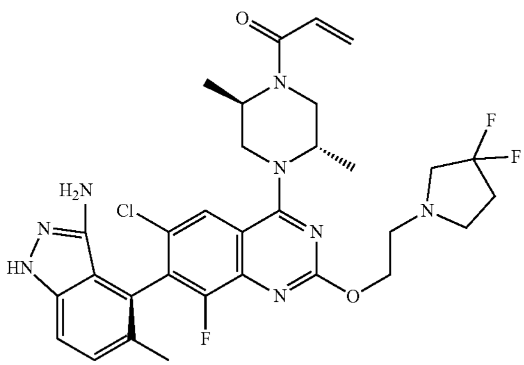 | 1-((2R,5S)-4-((S)-7-(3-amino-5-methyl-1H-indazol-4-yl)-6-chloro-2-(2-(3,3-difluoropyrrolidin-1-yl)ethoxy)-8-fluoroquinazolin-4-yl)-2,5-dimethylpiperazin-1-yl)prop-2-en-1-one | B | 643.5 |
| 67 | 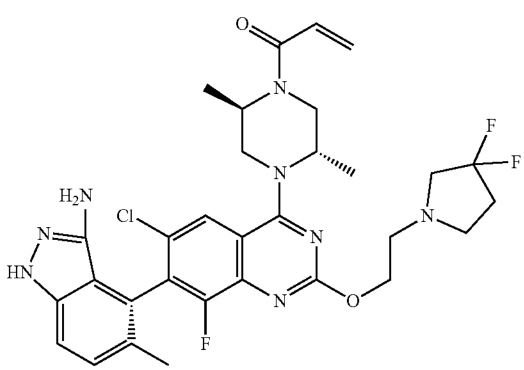 | 1-((2R,5S)-4-((R)-7-(3-amino-5-methyl-1H-indazol-4-yl)-6-chloro-2-(2-(3,3-difluoropyrrolidin-1-yl)ethoxy)-8-fluoroquinazolin-4-yl)-2,5-dimethylpiperazin-1-yl)prop-2-en-1-one | B | 643.5 |
| 68 | 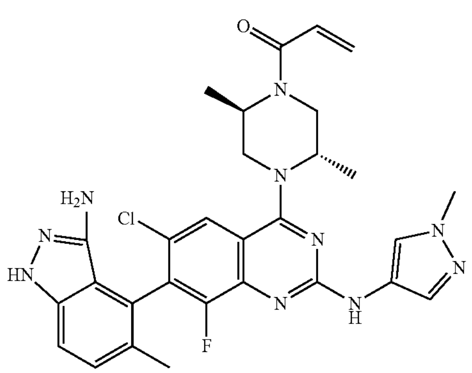 [SMILES: C=CC(=O)N1C[C@H](C)N(c2nc(Nc3cnn(C)c3)nc3c(F)c(-c4c(C)ccc5[nH]nc(N)c45)c(Cl)cc23)C[C@H]1C] | 1-((2R,5S)-4-(7-(3-amino-5-methyl-1H-indazol-4-yl)-6-chloro-8-fluoro-2-(1-methyl-1H-pyrazol-4-ylamino)quinazolin-4-yl)-2,5-dimethylpiperazin-1-yl)prop-2-en-1-one | B | 589.5 |

TABLE 1-continued

Representative Compounds

| No. | Structure | Name | Method | [M + H]+ |
|---|---|---|---|---|
| 69 | 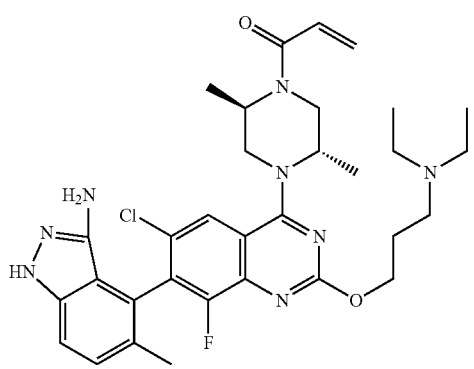 [SMILES: C=CC(=O)N1C[C@H](C)N(c2nc(OCCCN(CC)CC)nc3c(F)c(-c4c(C)ccc5[nH]nc(N)c45)c(Cl)cc23)C[C@H]1C] | 1-((2R,5S)-4-(7-(3-amino-5-methyl-1H-indazol-4-yl)-6-chloro-2-(3-(diethylamino)propoxy)-8-fluoroquinazolin-4-yl)-2,5-dimethylpiperazin-1-yl)prop-2-en-1-one | B | 623.5 |
| 70 | 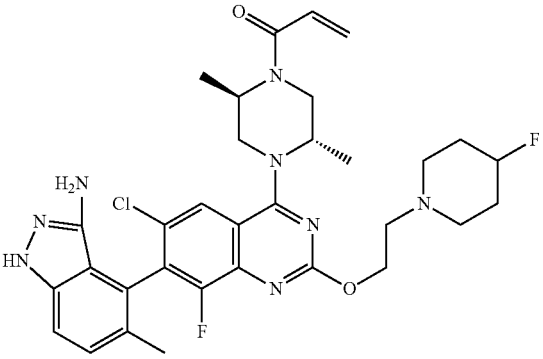 [SMILES: C=CC(=O)N1C[C@H](C)N(c2nc(OCCN3CCC(F)CC3)nc3c(F)c(-c4c(C)ccc5[nH]nc(N)c45)c(Cl)cc23)C[C@H]1C] | 1-((2R,5S)-4-(7-(3-amino-5-methyl-1H-indazol-4-yl)-6-chloro-8-fluoro-2-(2-(4-fluoropiperidin-1-yl)ethoxy)quinazolin-4-yl)-2,5-dimethylpiperazin-1-yl)prop-2-en-1-one | B | 639.5 |
| 71 | 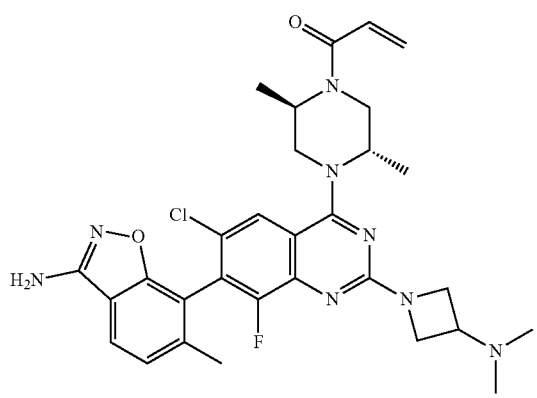 [SMILES: C=CC(=O)N1C[C@H](C)N(c2nc(N3CC(N(C)C)C3)nc3c(F)c(-c4c(C)ccc5c(N)noc45)c(Cl)cc23)C[C@H]1C] | 1-((2R,5S)-4-(7-(3-amino-6-methylbenzo[d]isoxazol-7-yl)-6-chloro-2-(3-(dimethylamino)azetidin-1-yl)-8-fluoroquinazolin-4-yl)-2,5-dimethylpiperazin-1-yl)prop-2-en-1-one | F | 593.5 |
| 72 | 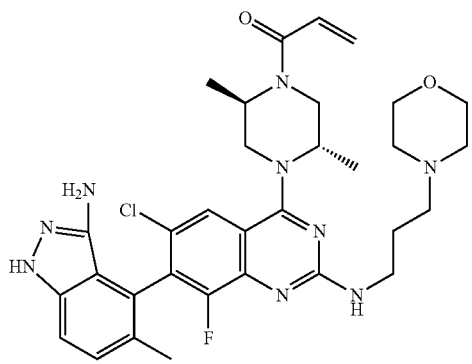 [SMILES: C=CC(=O)N1C[C@H](C)N(c2nc(NCCCN3CCOCC3)nc3c(F)c(-c4c(C)ccc5[nH]nc(N)c45)c(Cl)cc23)C[C@H]1C] | 1-((2R,5S)-4-(7-(3-amino-5-methyl-1H-indazol-4-yl)-6-chloro-8-fluoro-2-(3-morpholinopropylamino)quinazolin-4-yl)-2,5-dimethylpiperazin-1-yl)prop-2-en-1-one | B | 636.4 |

TABLE 1-continued

Representative Compounds

| No. | Structure | Name | Method | [M + H]+ |
|---|---|---|---|---|
| 73 | 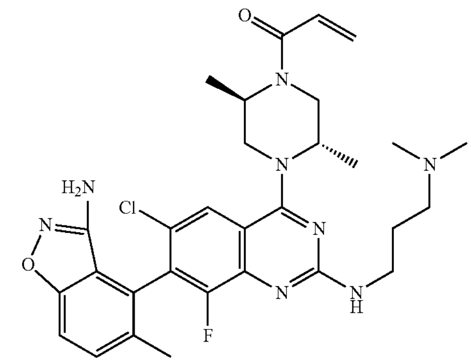 [SMILES: C=CC(=O)N1C[C@H](C)N(c2nc(NCCCN(C)C)nc3c(F)c(-c4c(C)ccc5onc(N)c45)c(Cl)cc23)C[C@H]1C] | 1-((2R,5S)-4-(7-(3-amino-5-methylbenzo[d]isoxazol-4-yl)-6-chloro-2-(3-(dimethylamino)propylamino)-8-fluoroquinazolin-4-yl)-2,5-dimethylpiperazin-1-yl)prop-2-en-1-one | F | 595.4 |
| 74 | 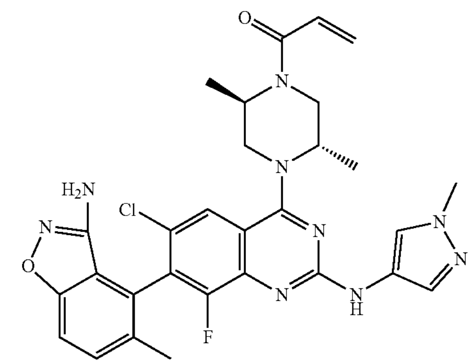 [SMILES: C=CC(=O)N1C[C@H](C)N(c2nc(Nc3cnn(C)c3)nc3c(F)c(-c4c(C)ccc5onc(N)c45)c(Cl)cc23)C[C@H]1C] | 1-((2R,5S)-4-(7-(3-amino-5-methylbenzo[d]isoxazol-4-yl)-6-chloro-8-fluoro-2-(1-methyl-1H-pyrazol-4-ylamino)quinazolin-4-yl)-2,5-dimethylpiperazin-1-yl)prop-2-en-1-one | F | 590.4 |
| 75 | 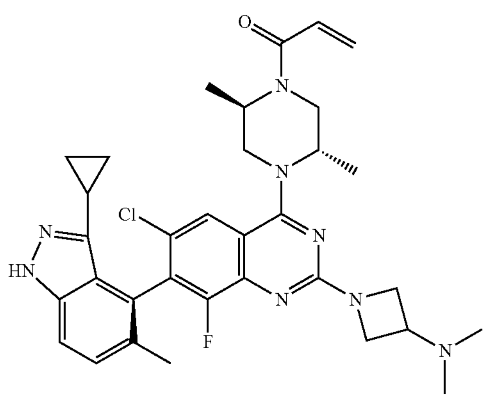 | 1-((2R,5S)-4-((S)-6-chloro-7-(3-cyclopropyl-5-methyl-1H-indazol-4-yl)-2-(3-(dimethylamino)azetidin-1-yl)-8-fluoroquinazolin-4-yl)-2,5-dimethylpiperazin-1-yl)prop-2-en-1-one | C | 617.4 |
| 76 | 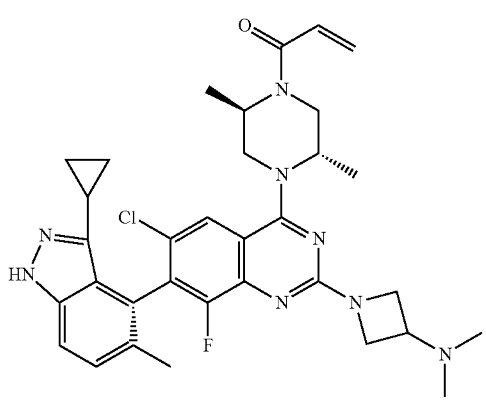 | 1-((2R,5S)-4-((R)-6-chloro-7-(3-cyclopropyl-5-methyl-1H-indazol-4-yl)-2-(3-(dimethylamino)azetidin-1-yl)-8-fluoroquinazolin-4-yl-2,5-dimethylpiperazin-1-yl)prop-2-en-1-one | C | 617.4 |

TABLE 1-continued

Representative Compounds

| No. | Structure | Name | Method | [M + H]+ |
|---|---|---|---|---|
| 77 | 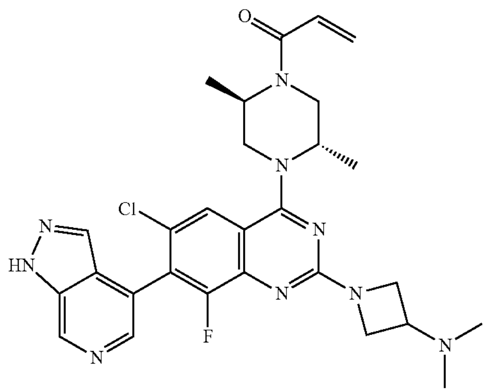 [SMILES: C=CC(=O)N1C[C@H](C)N(c2nc(N3CC(N(C)C)C3)nc3c(F)c(-c4cncc5[nH]ncc45)c(Cl)cc23)C[C@H]1C] | 1-((2R,5S)-4-(6-chloro-2-(3-(dimethyl-amino)azetidin-1-yl)-8-fluoro-7-(1H-pyrazolo[3,4-c]pyridin-4-yl)quinazolin-4-yl)-2,5-dimethylpiperazin-1-yl)prop-2-en-1-one | A | 564.2 |
| 78 | 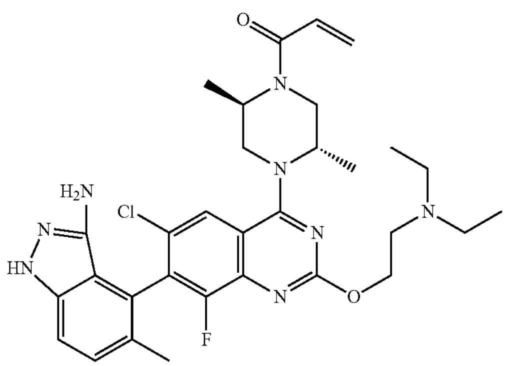 [SMILES: C=CC(=O)N1C[C@H](C)N(c2nc(OCCN(CC)CC)nc3c(F)c(-c4c(C)ccc5[nH]nc(N)c45)c(Cl)cc23)C[C@H]1C] | 1-((2R,5S)-4-(7-(3-amino-5-methyl-1H-indazol-4-yl)-6-chloro-2-(2-(diethyl-amino)ethoxy)-8-fluoroquinazolin-4-yl)-2,5-dimethyl-piperazin-1-yl)prop-2-en-1-one | B | 609.5 |
| 79 | 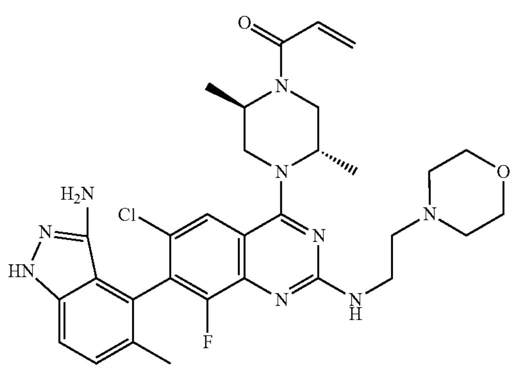 [SMILES: C=CC(=O)N1C[C@H](C)N(c2nc(NCCN3CCOCC3)nc3c(F)c(-c4c(C)ccc5[nH]nc(N)c45)c(Cl)cc23)C[C@H]1C] | 1-((2R,5S)-4-(7-(3-amino-5-methyl-1H-indazol-4-yl)-6-chloro-8-fluoro-2-(2-morpholinoethylamino)-quinazolin-4-yl)-2,5-dimethylpiperazin-1-yl)prop-2-en-1-one | B | 622.4 |
| 80 | 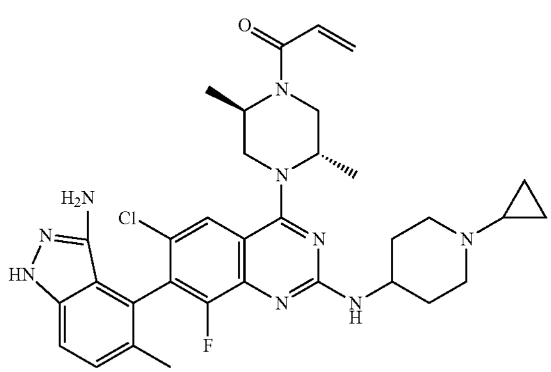 [SMILES: C=CC(=O)N1C[C@H](C)N(c2nc(NC3CCN(C4CC4)CC3)nc3c(F)c(-c4c(C)ccc5[nH]nc(N)c45)c(Cl)cc23)C[C@H]1C] | 1-((2R,5S)-4-(7-(3-amino-5-methyl-1H-indazol-4-yl)-6-chloro-2-(1-cyclo-propylpiperidin-4-ylamino)-8-fluoro-quinazolin-4-yl)-2,5-dimethylpiperazin-1-yl)prop-2-en-1-one | B | 632.4 |

TABLE 1-continued

Representative Compounds

| No. | Structure | Name | Method | [M + H]⁺ |
|---|---|---|---|---|
| 81 | 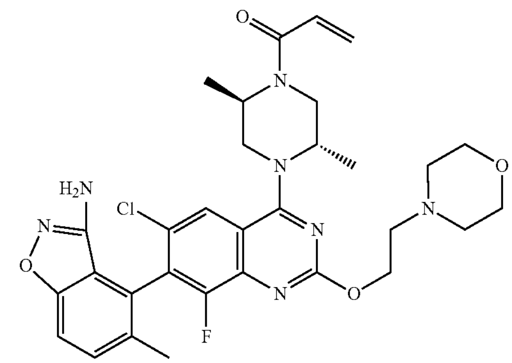 [SMILES: C=CC(=O)N1C[C@H](C)N(c2nc(OCCN3CCOCC3)nc3c(F)c(-c4c(C)ccc5onc(N)c45)c(Cl)cc23)C[C@H]1C] | 1-((2R,5S)-4-(7-(3-amino-5-methylbenzo-[d]isoxazol-4-yl)-6-chloro-8-fluoro-2-(2-morpholinoethoxy)-quinazolin-4-yl)-2,5-dimethylpiperazin-1-yl)prop-2-en-1-one | F | 632.4 |
| 82 | 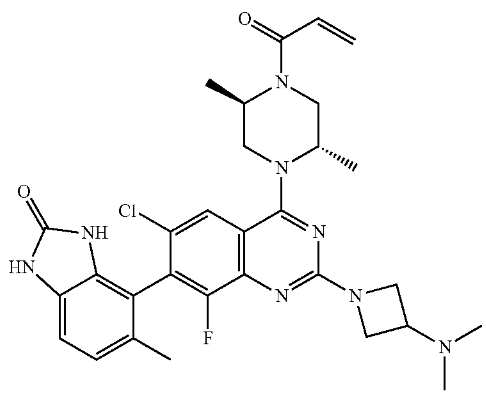 [SMILES: C=CC(=O)N1C[C@H](C)N(c2nc(N3CC(N(C)C)C3)nc3c(F)c(-c4c(C)ccc5[nH]c(=O)[nH]c45)c(Cl)cc23)C[C@H]1C] | 4-(4-((2S,5R)-4-acryloyl-2,5-dimethyl-piperazin-1-yl)-6-chloro-2-(3-(dimethyl-amino)azetidin-1-yl)-8-fluoroquinazolin-7-yl)-5-methyl-1H-benzo[d]imidazol-2(3H)-one | A | 593.4 |
| 83 | 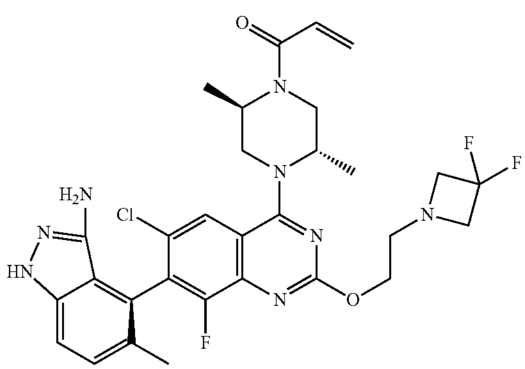 | 1-((2R,5S)-4-((S)-7-(3-amino-5-methyl-1H-indazol-4-yl)-6-chloro-2-(2-(3,3-difluoroazetidin-1-yl)ethoxy)-8-fluoro-quinazolin-4-yl)-2,5-dimethylpiperazin-1-yl)prop-2-en-1-one | B | 629.4 |
| 84 | 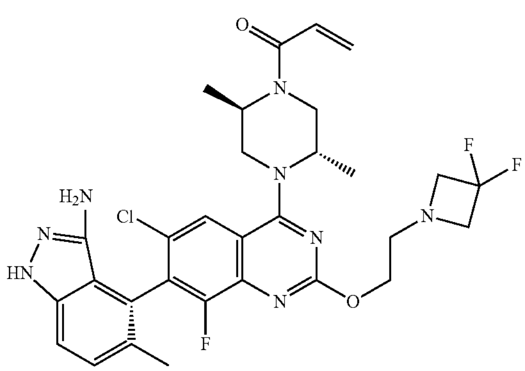 | 1-((2R,5S)-4-((R)-7-(3-amino-5-methyl-1H-indazol-4-yl)-6-chloro-2-(2-(3,3-difluoroazetidin-1-yl)ethoxy)-8-fluoro-quinazolin-4-yl)-2,5-dimethylpiperazin-1-yl)prop-2-en-1-one | B | 629.4 |

TABLE 1-continued

Representative Compounds

| No. | Structure | Name | Method | [M + H]+ |
|---|---|---|---|---|
| 85 | 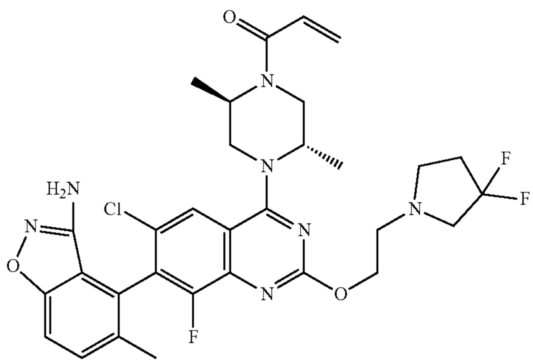 [SMILES: C=CC(=O)N1C[C@H](C)N(c2nc(OCCN3CCC(F)(F)C3)nc3c(F)c(-c4c(C)ccc5onc(N)c45)c(Cl)cc23)C[C@H]1C] | 1-((2R,5S)-4-(7-(3-amino-5-methylbenzo-[d]isoxazol-4-yl)-6-chloro-2-(2-(3,3-difluoropyrrolidin-1-yl)ethoxy)-8-fluoro-quinazolin-4-yl)-2,5-dimethylpiperazin-1-yl)prop-2-en-1-one | F | 644.2 |
| 86 | 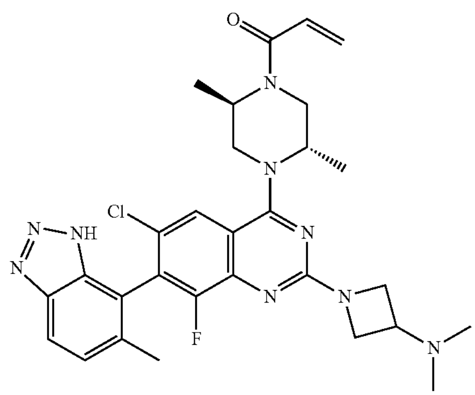 [SMILES: C=CC(=O)N1C[C@H](C)N(c2nc(N3CC(N(C)C)C3)nc3c(F)c(-c4c(C)ccc5nn[nH]c45)c(Cl)cc23)C[C@H]1C] | 1-((2R,5S)-4-(6-chloro-2-(3-(dimethyl-amino)azetidin-1-yl)-8-fluoro-7-(6-methyl-1H-benzo[d][1,2,3]-triazol-7-yl)quinazolin-4-yl)-2,5-dimethyl-piperazin-1-yl)prop-2-en-1-one | B | 564.2 |
| 87 | 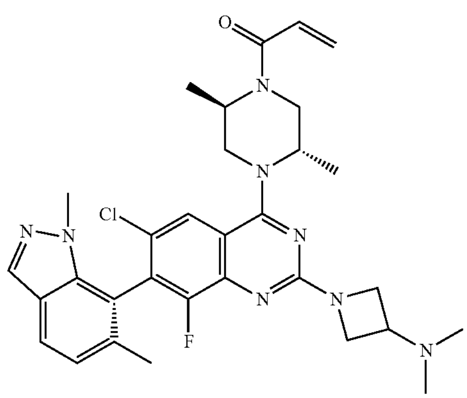 | 1-((2R,5S)-4-((R)-6-chloro-7-(1,6-dimethyl-1H-indazol-7-yl)-2-(3-(dimethylamino)-azetidin-1-yl)-8-fluoroquinazolin-4-yl)-2,5-dimethyl-piperazin-1-yl)prop-2-en-1-one | D | 591.3 |
| 88 | 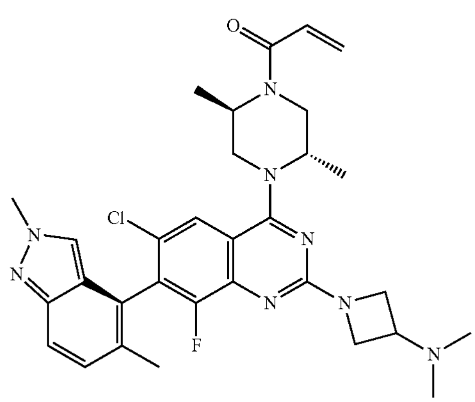 | 1-((2R,5S)-4-((R)-6-chloro-7-(2,5-dimethyl-2H-indazol-4-yl)-2-(3-(dimethylamino)-azetidin-1-yl)-8-fluoro-quinazolin-4-yl)-2,5-dimethylpiperazin-1-yl)prop-2-en-1-one | D | 591.3 |

TABLE 1-continued

Representative Compounds

| No. | Structure | Name | Method | [M + H]+ |
|---|---|---|---|---|
| 89 | 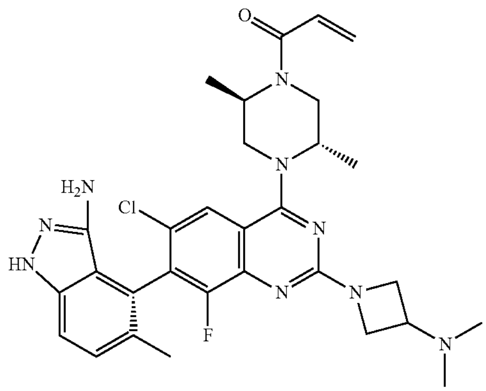 | 1-((2R,5S)-4-((R)-7-(3-amino-5-methyl-1H-indazol-4-yl)-6-chloro-2-(3-(dimethylamino)azetidin-1-yl)-8-fluoroquinazolin-4-yl)-2,5-dimethylpiperazin-1-yl)prop-2-en-1-one | B | 592.4 |
| 90 | 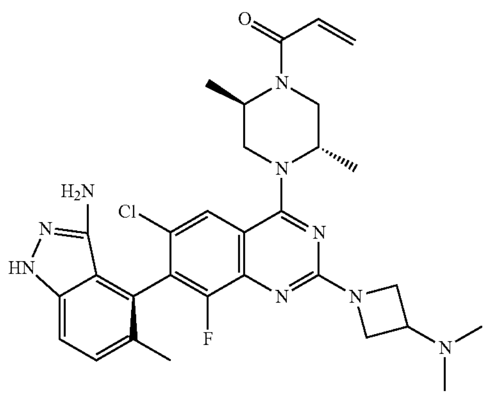 | 1-((2R,5S)-4-((S)-7-(3-amino-5-methyl-1H-indazol-4-yl)-6-chloro-2-(3-(dimethylamino)azetidin-1-yl)-8-fluoroquinazolin-4-yl)-2,5-dimethylpiperazin-1-yl)prop-2-en-1-one | B | 592.4 |
| 91 | 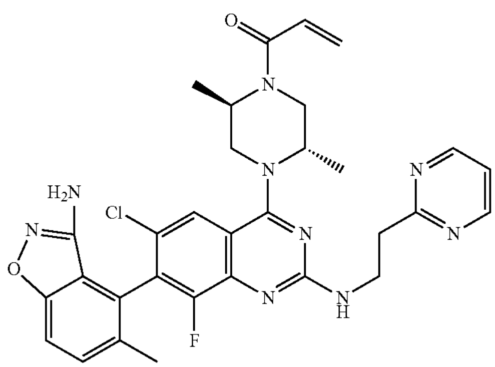 [SMILES: C=CC(=O)N1C[C@H](C)N(c2nc(NCCc3ncccn3)nc3c(F)c(-c4c(C)ccc5onc(N)c45)c(Cl)cc23)C[C@H]1C] | 1-((2R,5S)-4-(7-(3-amino-5-methylbenzo[d]isoxazol-4-yl)-6-chloro-8-fluoro-2-(2-(pyrimidin-2-yl)ethylamino)quinazolin-4-yl)-2,5-dimethylpiperazin-1-yl)prop-2-en-1-one | F | 616.3 |
| 92 | 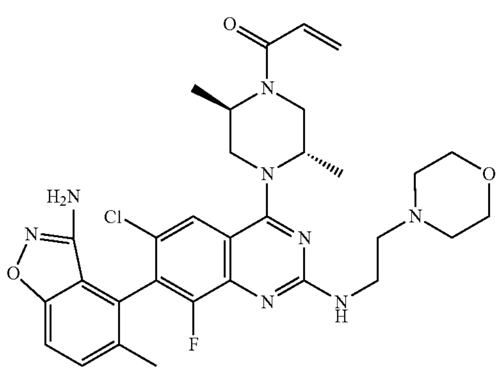 [SMILES: C=CC(=O)N1C[C@H](C)N(c2nc(NCCN3CCOCC3)nc3c(F)c(-c4c(C)ccc5onc(N)c45)c(Cl)cc23)C[C@H]1C] | 1-((2R,5S)-4-(7-(3-amino-5-methylbenzo[d]isoxazol-4-yl)-6-chloro-8-fluoro-2-(2-morpholinoethylamino)quinazolin-4-yl)-2,5-dimethylpiperazin-1-yl)prop-2-en-1-one | F | 623.4 |

TABLE 1-continued

Representative Compounds

| No. | Structure | Name | Method | [M + H]+ |
|---|---|---|---|---|
| 93 | 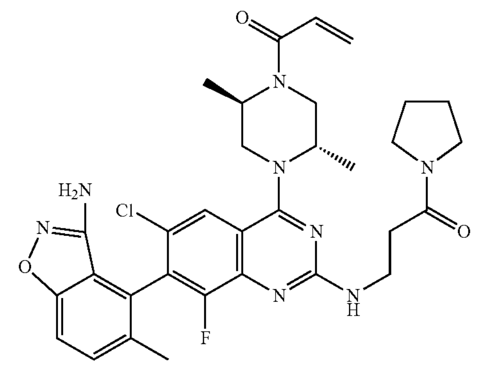 [SMILES: C=CC(=O)N1C[C@H](C)N(c2nc(NCCC(=O)N3CCCC3)nc3c(F)c(-c4c(C)ccc5onc(N)c45)c(Cl)cc23)C[C@H]1C] | 1-((2R,5S)-4-(7-(3-amino-5-methylbenzo[d]isoxazol]-4-yl)-6-chloro-8-fluoro-2-(3-oxo-3-(pyrrolidin-1-yl)propylamino)-quinazolin-4-yl)-2,5-dimethylpiperazin-1-yl)prop-2-en-1-one | F | 635.5 |
| 94 | 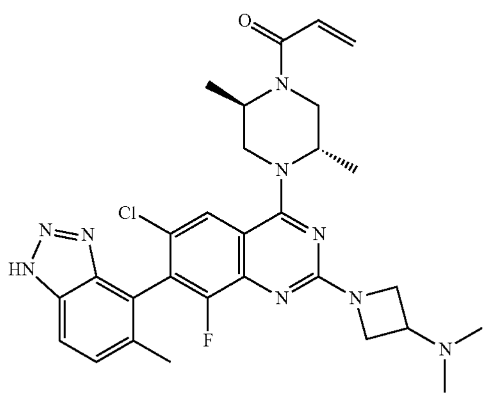 [SMILES: C=CC(=O)N1C[C@H](C)N(c2nc(N3CC(N(C)C)C3)nc3c(F)c(-c4c(C)ccc5[nH]nnc45)c(Cl)cc23)C[C@H]1C] | 1-((2R,5S)-4-(6-chloro-2-(3-(dimethyl-amino)azetidin-1-yl)-8-fluoro-7-(5-methyl-1H-benzo[d][1,2,3]-triazol-4-yl)quinazolin-4-yl)-2,5-dimethyl-piperazin-1-yl)prop-2-en-1-one | B | 578.4 |
| 95 | 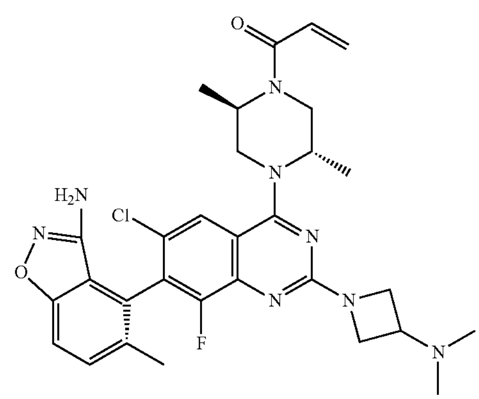 | 1-((2R,5S)-4-((R)-7-(3-amino-5-methylbenzo[d]isoxazol-4-yl)-6-chloro-2-(3-(dimethyl-amino)azetidin-1-yl)-8-fluoroquinazolin-4-yl)-2,5-dimethyl-piperazin-1-yl)prop-2-en-1-one | F | 593.8 |
| 96 | 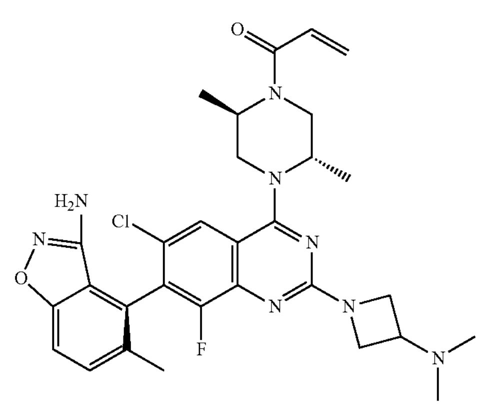 | 1-((2R,5S)-4-((S)-7-(3-amino-5-methyl-benzo[d]isoxazol-4-yl)-6-chloro-2-(3-(dimethyl-amino)azetidin-1-yl)-8-fluoroquinazolin-4-yl)-2,5-dimethyl-piperazin-1-yl)prop-2-en-1-one | F | 593.8 |

TABLE 1-continued

Representative Compounds

| No. | Structure | Name | Method | [M + H]+ |
|---|---|---|---|---|
| 97 | 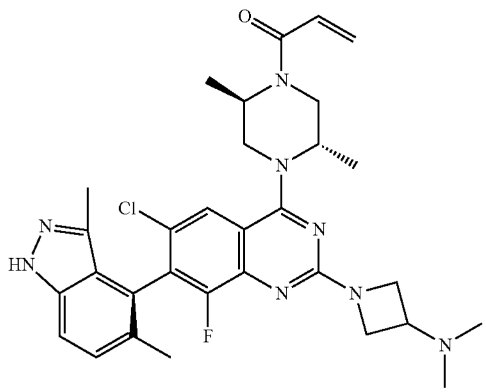 | 1-((2R,5S)-4-((S)-6-chloro-7-(3,5-dimethyl-1H-indazol-4-yl)-2-(3-(dimethylamino)-azetidin-1-yl)-8-fluoro-quinazolin-4-yl)-2,5-dimethylpiperazin-1-yl)prop-2-en-1-one | C | 591.4 |
| 98 | 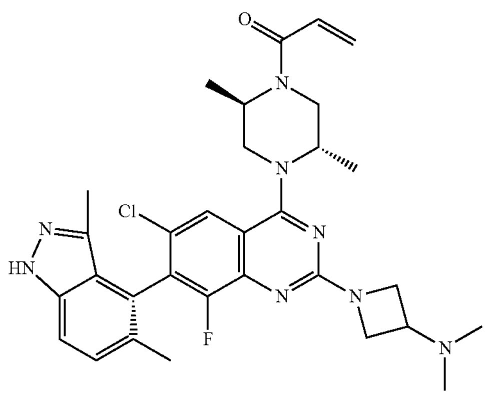 | 1-((2R,5S)-4-((R)-6-chloro-7-(3,5-dimethyl-1H-indazol-4-yl)-2-(3-(dimethylamino)-azetidin-1-yl)-8-fluoroquinazolin-4-yl)-2,5-dimethyl-piperazin-1-yl)prop-2-en-1-one | C | 591.4 |
| 99 | 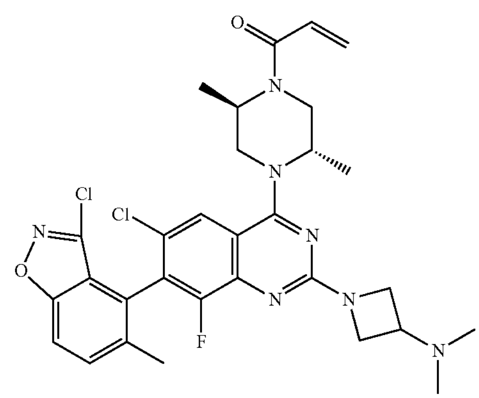 [SMILES: C=CC(=O)N1C[C@H](C)N(c2nc(N3CC(N(C)C)C3)nc3c(F)c(-c4c(C)ccc5onc(Cl)c45)c(Cl)cc23)C[C@H]1C] | 1-((2R,5S)-4-(6-chloro-7-(3-chloro-5-methylbenzo[d]isoxazol-4-yl)-2-(3-(dimethyl-amino)azetidin-1-yl)-8-fluoroquinazolin-4-yl)-2,5-dimethyl-piperazin-1-yl)prop-2-en-1-one | A | 612.4 |
| 100 | 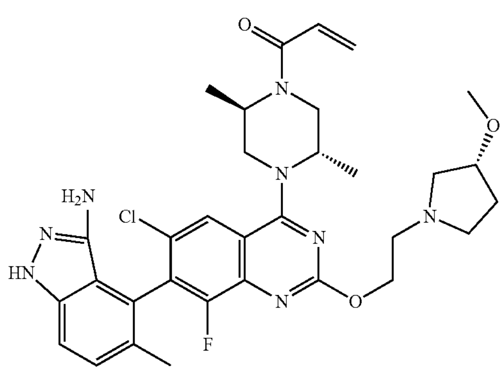 [SMILES: C=CC(=O)N1C[C@H](C)N(c2nc(OCCN3CC[C@@H](OC)C3)nc3c(F)c(-c4c(C)ccc5[nH]nc(N)c45)c(Cl)cc23)C[C@H]1C] | 1-((2R,5S)-4-(7-(3-amino-5-methyl-1H-indazol-4-yl)-6-chloro-8-fluoro-2-(2-((R)-3-methoxy-pyrrolidin-1-yl)-ethoxy)quinazolin-4-yl)-2,5-dimethyl-piperazin-1-yl)prop-2-en-1-one | B | 637.3 |

TABLE 1-continued

Representative Compounds

| No. | Structure | Name | Method | [M + H]+ |
|---|---|---|---|---|
| 101 | 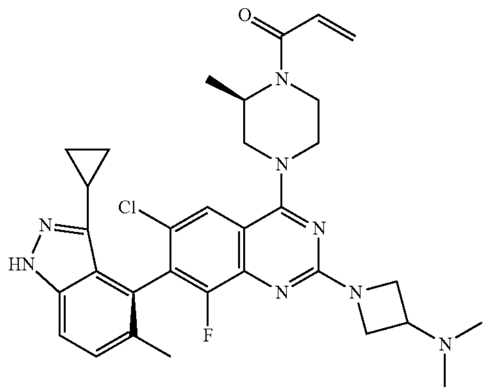 | 1-((R)-4-((S)-6-chloro-7-(3-cyclopropyl-5-methyl-1H-indazol-4-yl)-2-(3-dimethyl-amino)azetidin-1-yl)-8-fluoroquinazolin-4-yl)-2-methyl-piperazin-1-yl)prop-2-en-1-one | C | 603.4 |
| 102 | 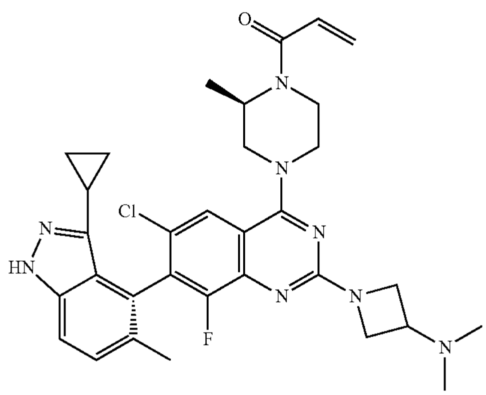 | 1-((R)-4-((R)-6-chloro-7-(3-cyclopropyl-5-methyl-1H-indazol-4-yl)-2-(3-(dimethyl-amino)azetidin-1-yl)-8-fluoroquinazolin-4-yl)-2-methylpiperazin-1-yl)prop-2-en-1-one | C | 603.4 |
| 103 | 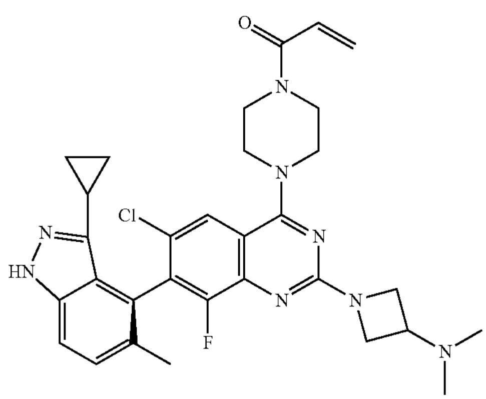 | (S)-1-(4-(6-chloro-7-(3-cyclopropyl-5-methyl-1H-indazol-4-yl)-2-(3-(dimethyl-amino)azetidin-1-yl)-8-fluoroquinazolin-4-yl)piperazin-1-yl)prop-2-en-1-one | C | 589.4 |
| 104 | 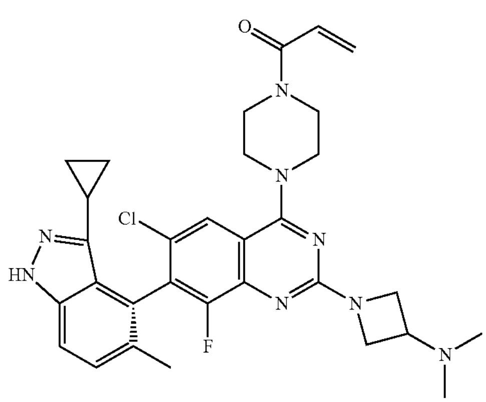 | (R)-1-(4-(6-chloro-7-(3-cyclopropyl-5-methyl-1H-indazol-4-yl)-2-(3-(dimethyl-amino)azetidin-1-yl)-8-fluoroquinazolin-4-yl)piperazin-1-yl)-prop-2-en-1-one | C | 589.4 |

TABLE 1-continued

Representative Compounds

| No. | Structure | Name | Method | [M + H]+ |
|---|---|---|---|---|
| 105 | 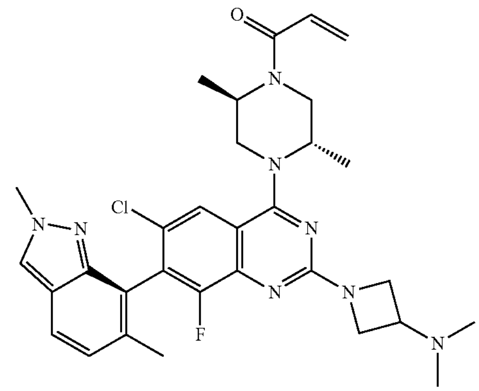 | 1-((2R,5S)-4-((R)-6-chloro-7-(2,6-dimethyl-2H-indazol-7-yl)-2-(3-(dimethylamino)-azetidin-1-yl)-8-fluoroquinazolin-4-yl)-2,5-dimethyl-piperazin-1-yl)prop-2-en-1-one | D | 591.2 |
| 106 | 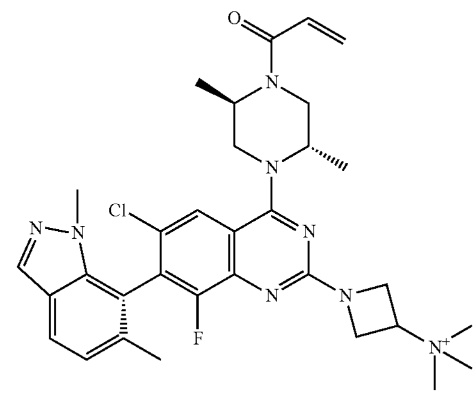 | 1-((R)-4-((2S,5R)-4-acryloyl-2,5-dimethyl-piperazin-1-yl)-6-chloro-7-(1,6-dimethyl-1H-indazol-7-yl)-8-fluoroquinazolin-2-yl)-N,N,N-trimethyl-azetidin-3-aminium | D | 605.3 |
| 107 | 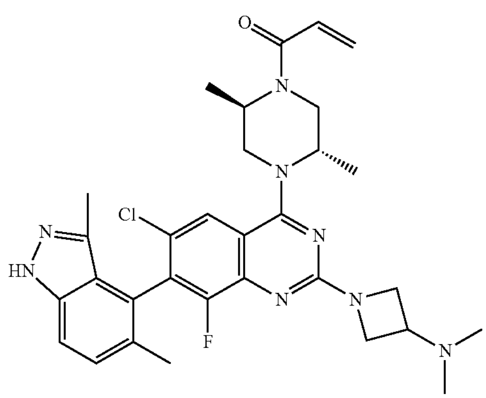 [SMILES: C=CC(=O)N1C[C@H](C)N(c2nc(N3CC(N(C)C)C3)nc3c(F)c(-c4c(C)ccc5[nH]nc(C)c45)c(Cl)cc23)C[C@H]1C] | 1-((2R,5S)-4-(6-chloro-7-(3,5-dimethyl-1H-indazol-4-yl)-2-(3-(dimethylamino)-azetidin-1-yl)-8-fluoroquinazolin-4-yl)-2,5-dimethyl-piperazin-1-yl)prop-2-en-1-one | C | 579.2 |
| 108 | 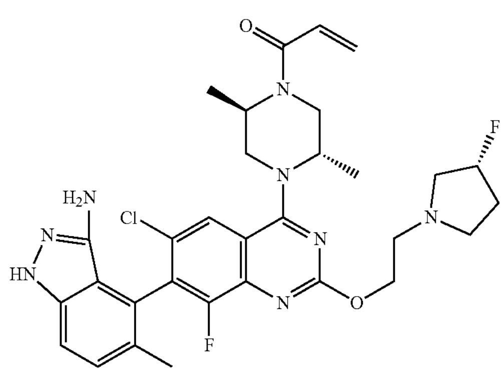 [SMILES: C=CC(=O)N1C[C@H](C)N(c2nc(OCCN3CC[C@@H](F)C3)nc3c(F)c(-c4c(C)ccc5[nH]nc(N)c45)c(Cl)cc23)C[C@H]1C] | 1-((2R,5S)-4-(7-(3-amino-5-methyl-1H-indazol-4-yl)-6-chloro-8-fluoro-2-(2-((R)-3-fluoro-pyrrolidin-1-yl)-ethoxy)quinazolin-4-yl)-2,5-dimethyl-piperazin-1-yl)prop-2-en-1-one | B | 625.3 |

TABLE 1-continued

Representative Compounds

| No. | Structure | Name | Method | [M + H]+ |
|---|---|---|---|---|
| 109 | 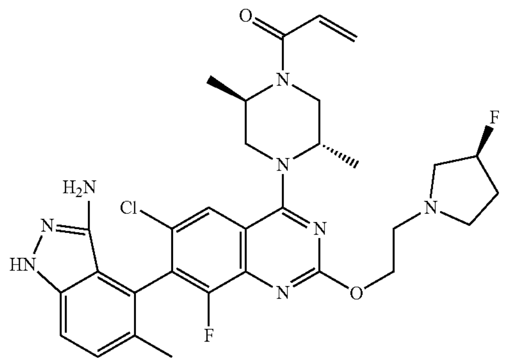 [SMILES: C=CC(=O)N1C[C@H](C)N(c2nc(OCCN3CC[C@H](F)C3)nc3c(F)c(-c4c(C)ccc5[nH]nc(N)c45)c(Cl)cc23)C[C@H]1C] | 1-((2R,5S)-4-(7-(3-amino-5-methyl-1H-indazol-4-yl)-6-chloro-8-fluoro-2-(2-((S)-3-fluoropyrrolidin-1-yl)ethoxy)quinazolin-4-yl)-2,5-dimethyl-piperazin-1-yl)prop-2-en-1-one | B | 625.4 |
| 110 | 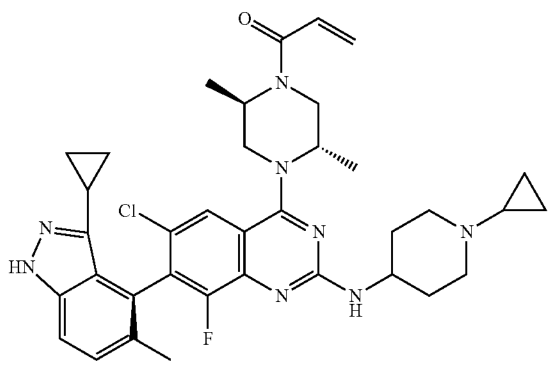 | 1-((2R,5S)-4-((S)-6-chloro-7-(3-cyclo-propyl-5-methyl-1H-indazol-4-yl)-2-(1-cyclopropylpiperidin-4-ylamino)-8-fluoro-quinazolin-4-yl)-2,5-dimethylpiperazin-1-yl)prop-2-en-1-one | C | 657.4 |
| 111 | 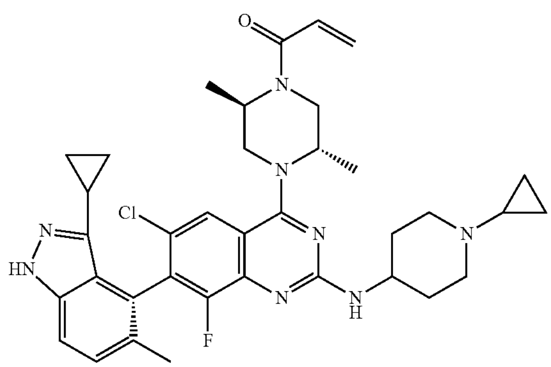 | 1-((2R,5S)-4-((R)-6-chloro-7-(3-cyclo-propyl-5-methyl-1H-indazol-4-yl)-2-(1-cyclopropylpiperidin-4-ylamino)-8-fluoro-quinazolin-4-yl)-2,5-dimethylpiperazin-1-yl)prop-2-en-1-one | C | 657.4 |
| 112 | 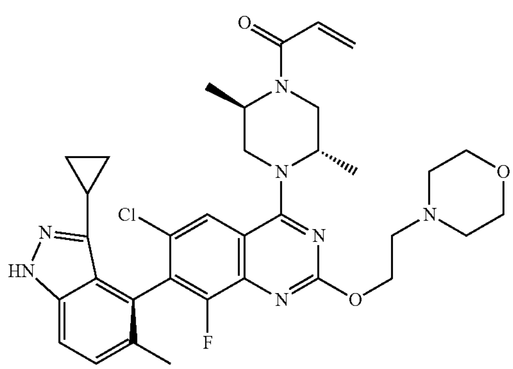 | 1-((2R,5S)-4-((S)-6-chloro-7-(3-cyclo-propyl-5-methyl-1H-indazol-4-yl)-8-fluoro-2-(2-morpholino-ethoxy)quinazolin-4-yl)-2,5-dimethyl-piperazin-1-yl)prop-2-en-1-one | C | 648.5 |

TABLE 1-continued

Representative Compounds

| No. | Structure | Name | Method | [M + H]+ |
|---|---|---|---|---|
| 113 | 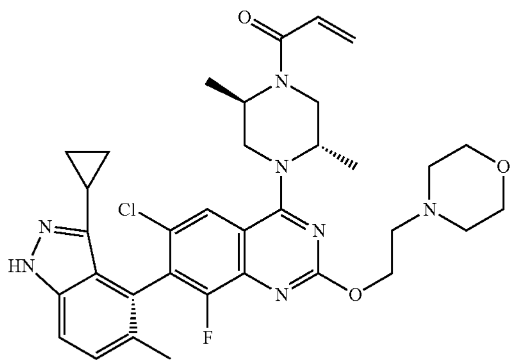 | 1-((2R,5S)-4-((R)-6-chloro-7-(3-cyclopropyl-5-methyl-1H-indazol-4-yl)-8-fluoro-2-(2-morpholinoethoxy)quinazolin-4-yl)-2,5-dimethylpiperazin-1-yl)prop-2-en-1-one | C | 648.5 |
| 114 | 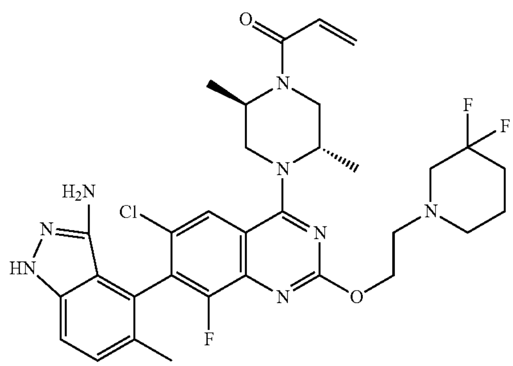 [SMILES: C=CC(=O)N1C[C@H](C)N(c2nc(OCCN3CCCC(F)(F)C3)nc3c(F)c(-c4c(C)ccc5[nH]nc(N)c45)c(Cl)cc23)C[C@H]1C] | 1-((2R,5S)-4-(7-(3-amino-5-methyl-1H-indazol-4-yl)-6-chloro-2-(2-(3,3-difluoropiperidin-1-yl)ethoxy)-8-fluoroquinazolin-4-yl)-2,5-dimethylpiperazin-1-yl)prop-2-en-1-one | B | 657.6 |
| 115 | 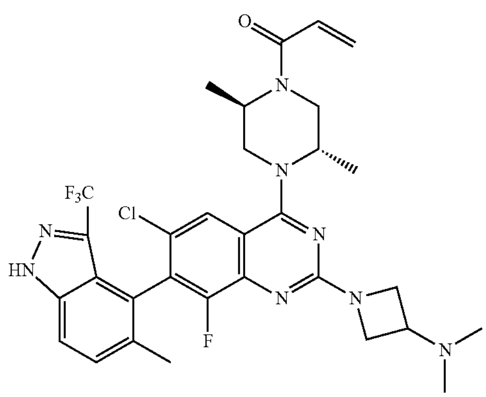 | 1-((2R,5S)-4-(6-chloro-2-(3-(dimethylamino)azetidin-1-yl)-8-fluoro-7-(5-methyl-3-(trifluoromethyl)-1H-indazol-4-yl)-quinazolin-4-yl)-2,5-dimethylpiperazin-1-yl)prop-2-en-1-one | C | 631.2 |
| 116 | 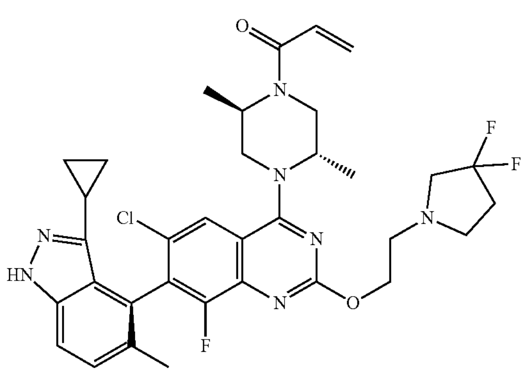 | 1-((2R,5S)-4-((S)-6-chloro-7-(3-cyclopropyl-5-methyl-1H-indazol-4-yl)-2-(2-(3,3-difluoropyrrolidin-1-yl)-ethoxy)-8-fluoroquinazolin-4-yl)-2,5-dimethylpiperazin-1-yl)prop-2-en-1-one | C | 668.4 |

TABLE 1-continued

Representative Compounds

| No. | Structure | Name | Method | [M + H]+ |
|---|---|---|---|---|
| 117 | 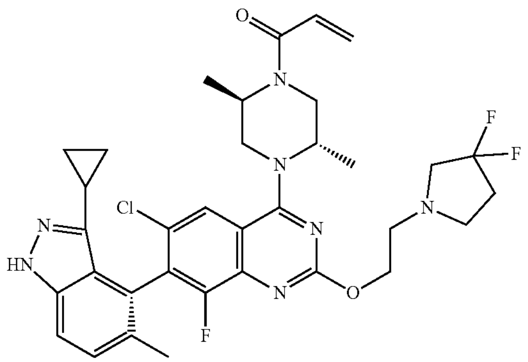 | 1-((2R,5S)-4-((R)-6-chloro-7-(3-cyclopropyl-5-methyl-1H-indazol-4-yl)-2-(2-(3,3-difluoropyrrolidin-1-yl)ethoxy)-8-fluoroquinazolin-4-yl)-2,5-dimethylpiperazin-1-yl)prop-2-en-1-one | C | 668.4 |
| 118 | 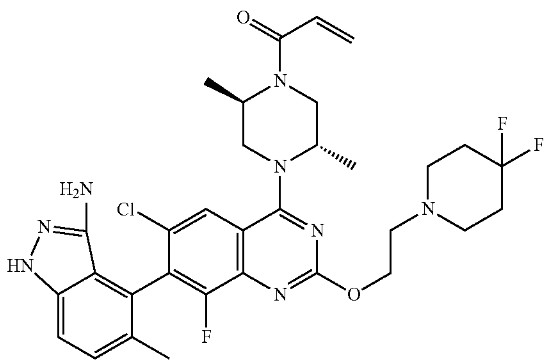 [SMILES: C=CC(=O)N1C[C@H](C)N(c2nc(OCCN3CCC(F)(F)CC3)nc3c(F)c(-c4c(C)ccc5[nH]nc(N)c45)c(Cl)cc23)C[C@H]1C] | 1-((2R,5S)-4-(7-(3-amino-5-methyl-1H-indazol-4-yl)-6-chloro-2-(2-(4,4-difluoropiperidin-1-yl)ethoxy)-8-fluoroquinazolin-4-yl)-2,5-dimethylpiperazin-1-yl)prop-2-en-1-one | B | 657.9 |
| 119 | 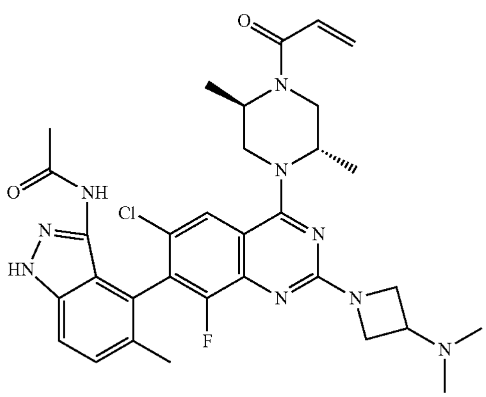 [SMILES: C=CC(=O)N1C[C@H](C)N(c2nc(N3CC(N(C)C)C3)nc3c(F)c(-c4c(C)ccc5[nH]nc(NC(C)=O)c45)c(Cl)cc23)C[C@H]1C] | N-(4-(4-((2S,5R)-4-acryloyl-2,5-dimethylpiperazin-1-yl)-6-chloro-2-(3-(dimethylamino)azetidin-1-yl)-8-fluoroquinazolin-7-yl)-5-methyl-1H-indazol-3-yl)acetamide | E | 634.5 |
| 120 | 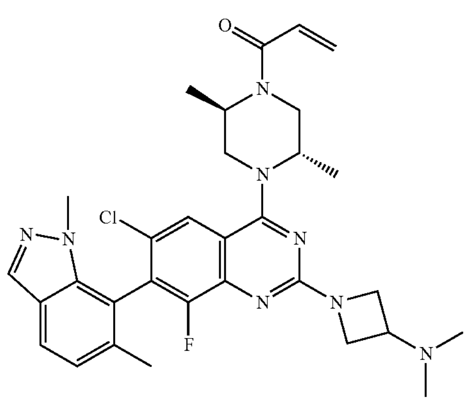 | 1-((2R,5S)-4-(6-chloro-7-(1,6-dimethyl-1H-indazol-7-yl)-2-(3-(dimethylamino)azetidin-1-yl)-8-fluoroquinazolin-4-yl)-2,5-dimethylpiperazin-1-yl)prop-2-en-1-one | D | 577.5 |

TABLE 1-continued

Representative Compounds

| No. | Structure | Name | Method | [M + H]⁺ |
|---|---|---|---|---|
| 121 | 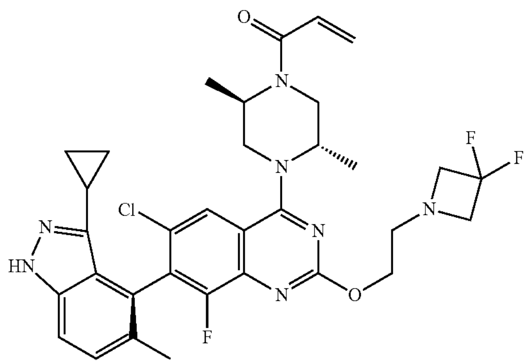 | 1-((2R,5S)-4-((S)-6-chloro-7-(3-cyclopropyl-5-methyl-1H-indazol-4-yl)-2-(2-(3,3-difluoroazetidin-1-yl)ethoxy)-8-fluoroquinazolin-4-yl)-2,5-dimethylpiperazin-1-yl)prop-2-en-1-one | C | 654.4 |
| 122 | 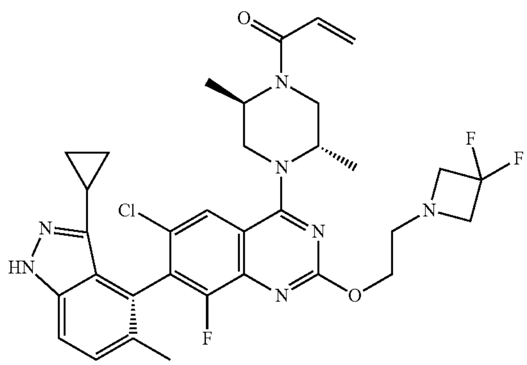 | 1-((2R,5S)-4-((R)-6-chloro-7-(3-cyclopropyl-5-methyl-1H-indazol-4-yl)-2-(2-(3,3-difluoroazetidin-1-yl)ethoxy)-8-fluoroquinazolin-4-yl)-2,5-dimethylpiperazin-1-yl)prop-2-en-1-one | C | 654.4 |
| 123 | 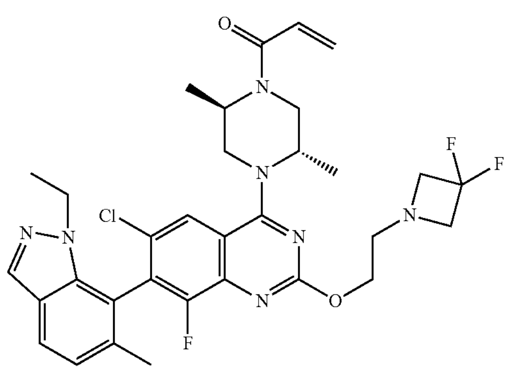 [SMILES: C=CC(=O)N1C[C@H](C)N(c2nc(OCCN3CC(F)(F)C3)nc3c(F)c(-c4c(C)ccc5cnn(CC)c45)c(Cl)cc23)C[C@H]1C] | 1-((2R,5S)-4-(6-chloro-2-(2-(3,3-difluoroazetidin-1-yl)ethoxy)-7-(1-ethyl-6-methyl-1H-indazol-7-yl)-8-fluoroquinazolin-4-yl)-2,5-dimethylpiperazin-1-yl)prop-2-en-1-one | D | 605.3 |
| 124 | 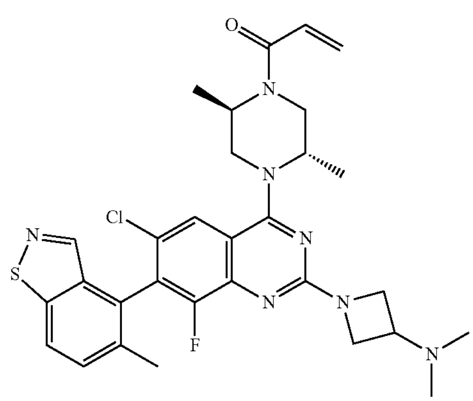 [SMILES: C=CC(=O)N1C[C@H](C)N(c2nc(N3CC(N(C)C)C3)nc3c(F)c(-c4c(C)ccc5sncc45)c(Cl)cc23)C[C@H]1C] | 1-((2R,5S)-4-(6-chloro-2-(3-(dimethylamino)azetidin-1-yl)-8-fluoro-7-(5-methylbenzo[d]isothiazol-4-yl)quinazolin-4-yl)-2,5-dimethylpiperazin-1-yl)prop-2-en-1-one | A | 594.4 |

TABLE 1-continued

Representative Compounds

| No. | Structure | Name | Method | [M + H]+ |
|---|---|---|---|---|
| 125 | 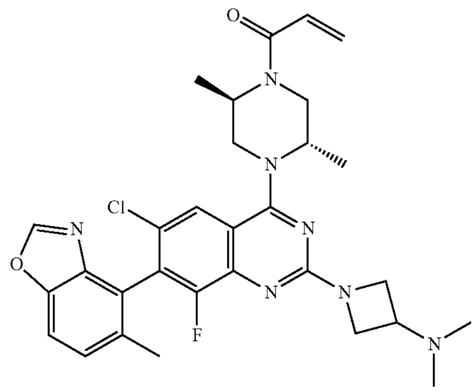 [SMILES: C=CC(=O)N1C[C@H](C)N(c2nc(N3CC(N(C)C)C3)nc3c(F)c(-c4c(C)ccc5ocnc45)c(Cl)cc23)C[C@H]1C] | 1-((2R,5S)-4-(6-chloro-2-(3-(dimethylamino)-azetidin-1-yl)-8-fluoro-7-(5-methylbenzo[d]-oxazol-4-yl)quinazolin-4-yl)-2,5-dimethyl-piperazin-1-yl)prop-2-en-1-one | A | 578.4 |
| 126 | 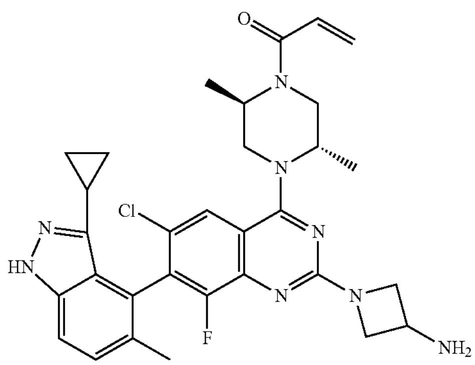 [SMILES: C=CC(=O)N1C[C@H](C)N(c2nc(N3CC(N)C3)nc3c(F)c(-c4c(C)ccc5[nH]nc(C6CC6)c45)c(Cl)cc23)C[C@H]1C] | 1-((2R,5S)-4-(2-(3-aminoazetidin-1-yl)-6-chloro-7-(3-cyclo-propyl-5-methyl-1H-indazol-4-yl)-8-fluoro-quinazolin-4-yl)-2,5-dimethylpiperazin-1-yl)prop-2-en-1-one | C | 589.5 |
| 127 | 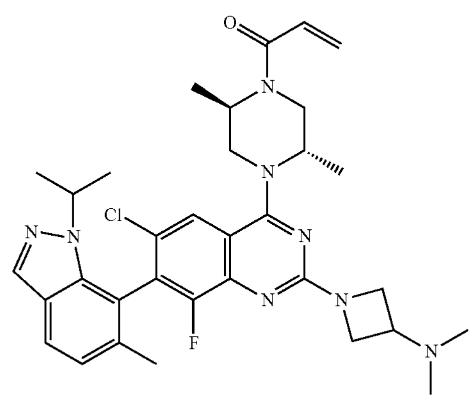 [SMILES: C=CC(=O)N1C[C@H](C)N(c2nc(N3CC(N(C)C)C3)nc3c(F)c(-c4c(C)ccc5cnn(C(C)C)c45)c(Cl)cc23)C[C@H]1C] | 1-((2R,5S)-4-(6-chloro-2-(3-(dimethylamino)-azetidin-1-yl)-8-fluoro-7-(1-isopropyl-6-methyl-1H-indazol-7-yl)quinazolin-4-yl)-2,5-dimethylpiperazin-1-yl)prop-2-en-1-one | E | 619.4 |
| 128 | 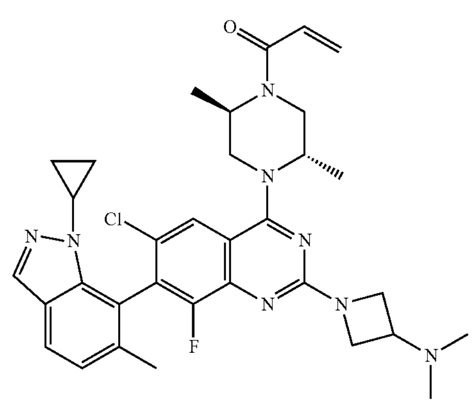 | 1-((2R,5S)-4-(6-chloro-7-(1-cyclopropyl-6-methyl-1H-indazol-7-yl)-2-(3-(dimethyl-amino)azetidin-1-yl)-8-fluoroquinazolin-4-yl)-2,5-dimethyl-piperazin-1-yl)prop-2-en-1-one | E | 617.6 |

TABLE 1-continued

Representative Compounds

| No. | Structure | Name | Method | [M + H]+ |
|---|---|---|---|---|
| 129 | 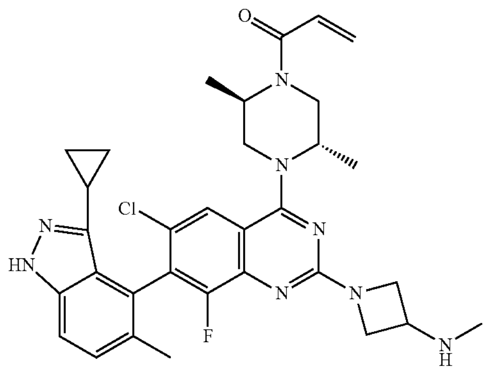 [SMILES: C=CC(=O)N1C[C@H](C)N(c2nc(N3CC(NC)C3)nc3c(F)c(-c4c(C)ccc5[nH]nc(C6CC6)c45)c(Cl)cc23)C[C@H]1C] | 1-((2R,5S)-4-(6-chloro-7-(3-cyclopropyl-5-methyl-1H-indazol-4-yl)-8-fluoro-2-(3-(methylamino)azetidin-1-yl)quinazolin-4-yl)-2,5-dimethylpiperazin-1-yl)prop-2-en-1-one | C | 603.5 |
| 130 | 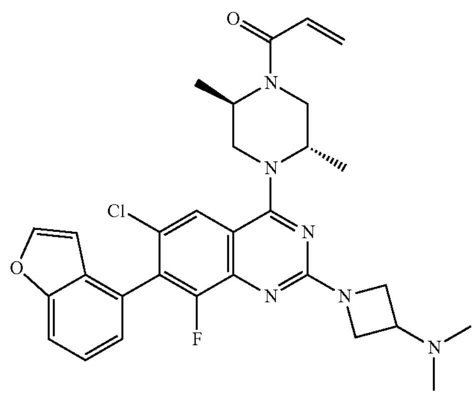 [SMILES: C=CC(=O)N1C[C@H](C)N(c2nc(N3CC(N(C)C)C3)nc3c(F)c(-c4cccc5occc45)c(Cl)cc23)C[C@H]1C] | 1-((2R,5S)-4-(7-(benzofuran-4-yl)-6-chloro-2-(3-(dimethylamino)azetidin-1-yl)-8-fluoroquinazolin-4-yl)-2,5-dimethylpiperazin-1-yl)prop-2-en-1-one | A | 563.4 |
| 131 | 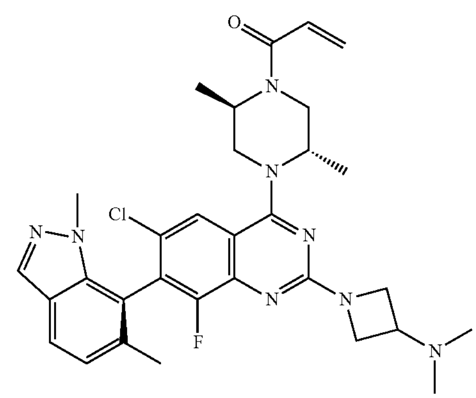 | 1-((2R,5S)-4-((S)-6-chloro-7-(1,6-dimethyl-1H-indazol-7-yl)-2-(3-(dimethylamino)azetidin-1-yl)-8-fluoroquinazolin-4-yl)-2,5-dimethylpiperazin-1-yl)prop-2-en-1-one | D | 591.5 |
| 132 | 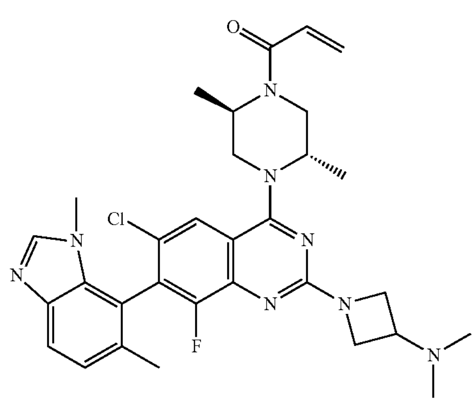 [SMILES: C=CC(=O)N1C[C@H](C)N(c2nc(N3CC(N(C)C)C3)nc3c(F)c(-c4c(C)ccc5ncn(C)c45)c(Cl)cc23)C[C@H]1C] | 1-((2R,5S)-4-(6-chloro-7-(1,6-dimethyl-1H-benzo[d]imidazol-7-yl)-2-(3-(dimethylamino)azetidin-1-yl)-8-fluoroquinazolin-4-yl)-2,5-dimethylpiperazin-1-yl)prop-2-en-1-one | D | 577.2 |

TABLE 1-continued

Representative Compounds

| No. | Structure | Name | Method | [M + H]+ |
|---|---|---|---|---|
| 133 | 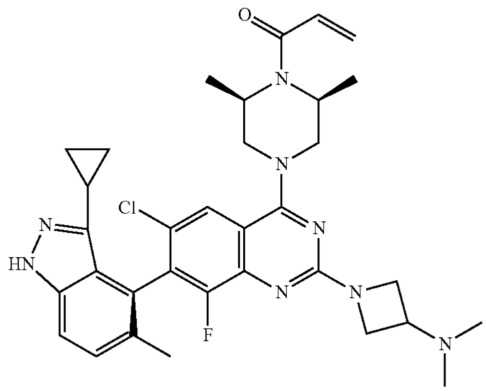 | 1-((2S,6R)-4-((S)-6-chloro-7-(3-cyclopropyl-5-methyl-1H-indazol-4-yl)-2-(3-(dimethylamino)-azetidin-1-yl)-8-fluoro-quinazolin-4-yl)-2,6-dimethylpiperazin-1-yl)prop-2-en-1-one | C | 617.5 |
| 134 | 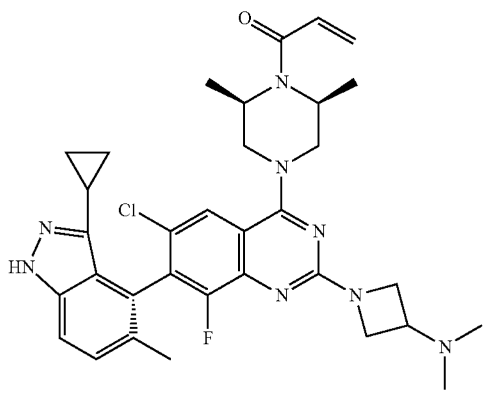 | 1-((2S,6R)-4-((R)-6-chloro-7-(3-cyclopropyl-5-methyl-1H-indazol-4-yl)-2-(3-(dimethylamino)-azetidin-1-yl)-8-fluoroquinazolin-4-yl)-2,6-dimethyl-piperazin-1-yl)prop-2-en-1-one | C | 617.5 |
| 135 | 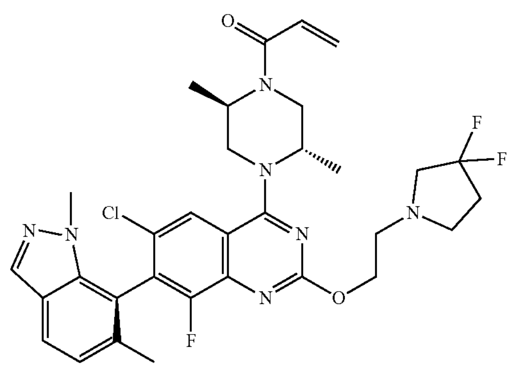 | 1-((2R,5S)-4-((S)-6-chloro-2-(2-(3,3-difluoropyrrolidin-1-yl)ethoxy)-7-(1,6-dimethyl-1H-indazol-7-yl)-8-fluoro-quinazolin-4-yl)-2,5-dimethylpiperazin-1-yl)prop-2-en-1-one | D | 642.5 |
| 136 | 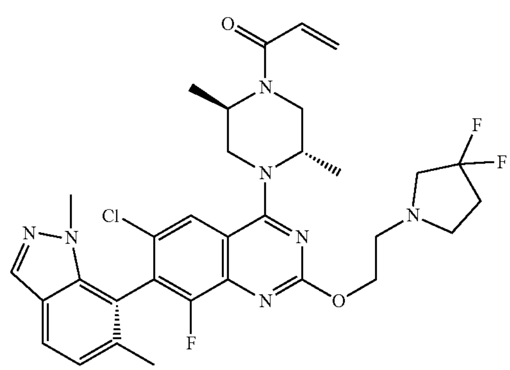 | 1-((2R,5S)-4-((R)-6-chloro-2-(2-(3,3-difluoropyrrolidin-1-yl)ethoxy)-7-(1,6-dimethyl-1H-indazol-7-yl)-8-fluoro-quinazolin-4-yl)-2,5-dimethylpiperazin-1-yl)prop-2-en-1-one | D | 642.5 |

TABLE 1-continued

Representative Compounds

| No. | Structure | Name | Method | [M + H]+ |
|---|---|---|---|---|
| 137 | 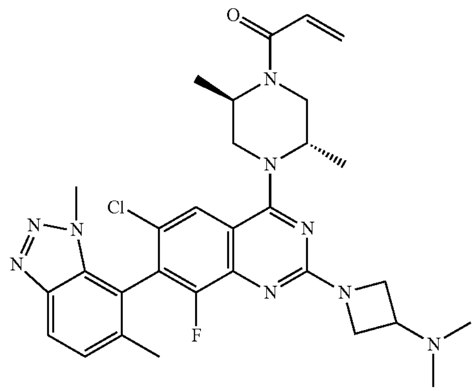 | 1-((2R,5S)-4-(6-chloro-7-(1,6-dimethyl-1H-benzo[d][1,2,3]triazol-7-yl)-2-(3-(dimethylamino)azetidin-1-yl)-8-fluoroquinazolin-4-yl)-2,5-dimethylpiperazin-1-yl)prop-2-en-1-one | D | 578.2 |
| 138 | 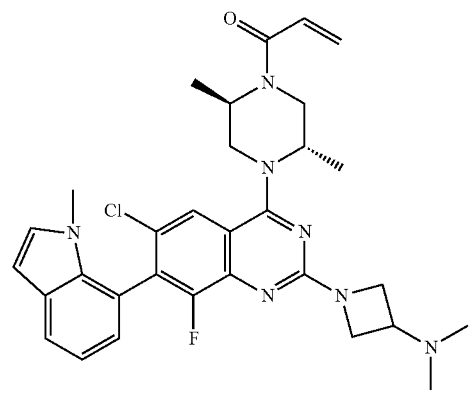 [SMILES: C=CC(=O)N1C[C@H](C)N(c2nc(N3CC(N(C)C)C3)nc3c(F)c(-c4cccc5ccn(C)c45)c(Cl)cc23)C[C@H]1C] | 1-((2R,5S)-4-(6-chloro-2-(3-(dimethylamino)-azetidin-1-yl)-8-fluoro-7-(1-methyl-1H-indol-7-yl)quinazolin-4-yl)-2,5-dimethylpiperazin-1-yl)prop-2-en-1-one | D | 576.4 |
| 139 | 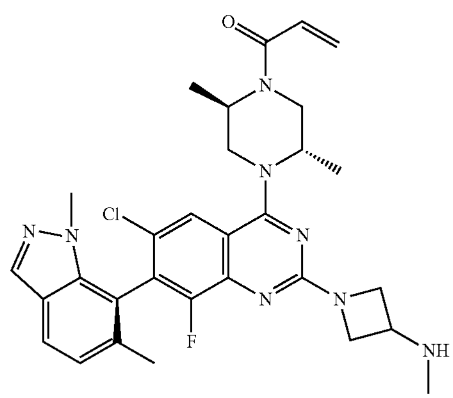 | 1-((2R,5S)-4-((S)-6-chloro-7-(1,6-dimethyl-1H-indazol-7-yl)-8-fluoro-2-(3-(methylamino)azetidin-1-yl)quinazolin-4-yl)-2,5-dimethylpiperazin-1-yl)prop-2-en-1-one | D | 577.5 |
| 140 | 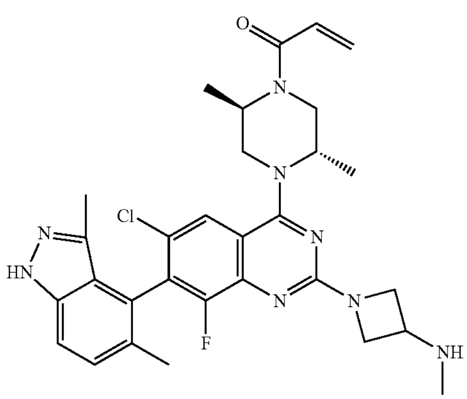 [SMILES: C=CC(=O)N1C[C@H](C)N(c2nc(N3CC(NC)C3)nc3c(F)c(-c4c(C)ccc5[nH]nc(C)c45)c(Cl)cc23)C[C@H]1C] | 1-((2R,5S)-4-(6-chloro-7-(3,5-dimethyl-1H-indazol-4-yl)-8-fluoro-2-(3-(methylamino)-azetidin-1-yl)quinazolin-4-yl)-2,5-dimethyl-piperazin-1-yl)prop-2-en-1-one | C | 577.4 |

TABLE 1-continued

Representative Compounds

| No. | Structure | Name | Method | [M + H]+ |
|---|---|---|---|---|
| 141 | 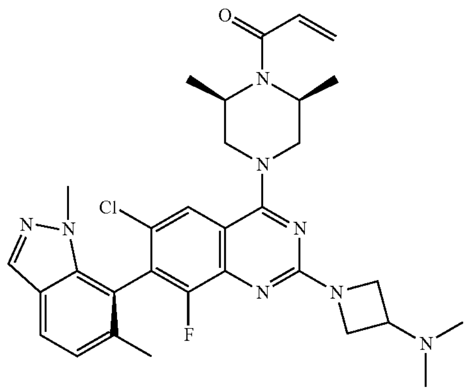 | 1-((2S,6R)-4-((S)-6-chloro-7-(1,6-dimethyl-1H-indazol-7-yl)-2-(3-(dimethylamino)-azetidin-1-yl)-8-fluoroquinazolin-4-yl)-2,6-dimethyl-piperazin-1-yl)prop-2-en-1-one | D | 591.4 |
| 142 | 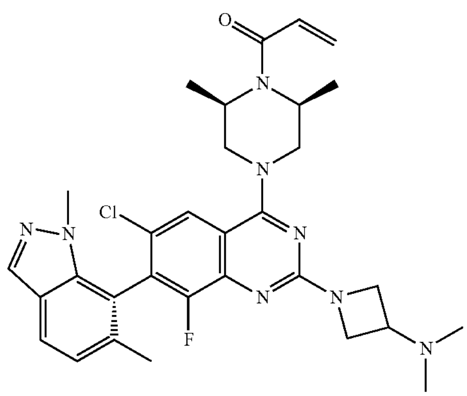 | 1-((2S,6R)-4-((R)-6-chloro-7-(1,6-dimethyl-1H-indazol-7-yl)-2-(3-(dimethylamino)-azetidin-1-yl)-8-fluoroquinazolin-4-yl)-2,6-dimethyl-piperazin-1-yl)prop-2-en-1-one | D | 591.4 |
| 143 | 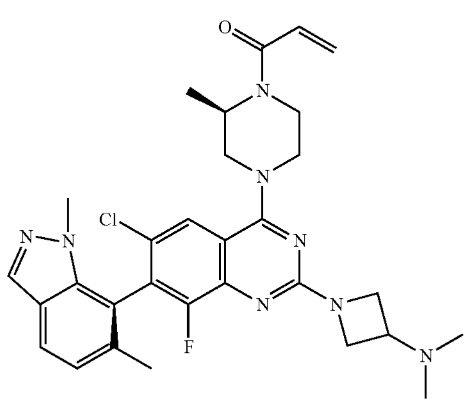 | 1-((R)-4-((S)-6-chloro-7-(1,6-dimethyl-1H-indazol-7-yl)-2-(3-(dimethylamino)-azetidin-1-yl)-8-fluoroquinazolin-4-yl)-2-methylpiperazin-1-yl)prop-2-en-1-one | D | 577.4 |

TABLE 1-continued

Representative Compounds

| No. | Structure | Name | Method | [M + H]⁺ |
|---|---|---|---|---|
| 144 | 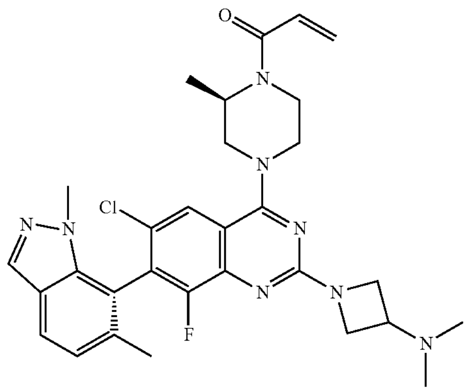 | 1-((R)-4-((R)-6-chloro-7-(1,6-dimethyl-1H-indazol-7-yl)-2-(3-(dimethylamino)-azetidin-1-yl)-8-fluoroquinazolin-4-yl)-2-methylpiperazin-1-yl)prop-2-en-1-one | D | 577.4 |
| 145 | 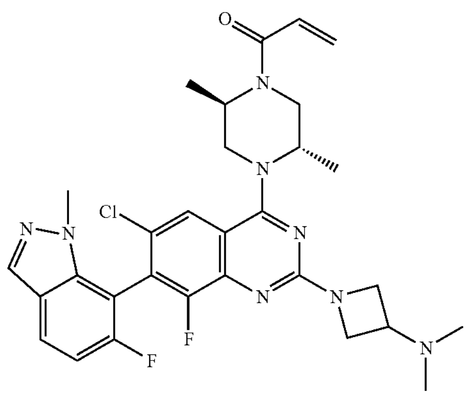 [SMILES: C=CC(=O)N1C[C@H](C)N(c2nc(N3CC(N(C)C)C3)nc3c(F)c(-c4c(F)ccc5cnn(C)c45)c(Cl)cc23)C[C@H]1C] | 1-((2R,5S)-4-(6-chloro-2-(3-(dimethyl-amino)azetidin-1-yl)-8-fluoro-7-(6-fluoro-1-methyl-1H-indazol-7-yl)quinazolin-4-yl)-2,5-dimethylpiperazin-1-yl)prop-2-en-1-one | D | 595.3 |
| 146 | 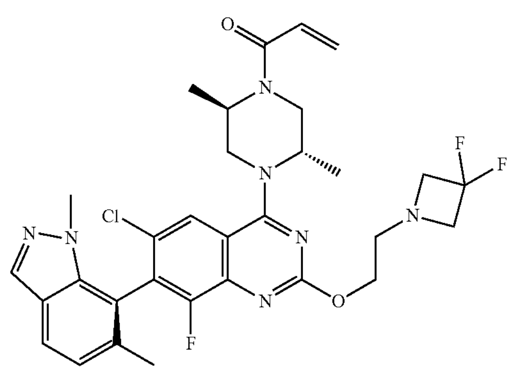 | 1-((2R,5S)-4-((S)-6-chloro-2-(2-(3,3-difluoroazetidin-1-yl)ethoxy)-7-(1,6-dimethyl-1H-indazol-7-yl)-8-fluoro-quinazolin-4-yl)-2,5-dimethylpiperazin-1-yl)prop-2-en-1-one | D | 628.4 |
| 147 | 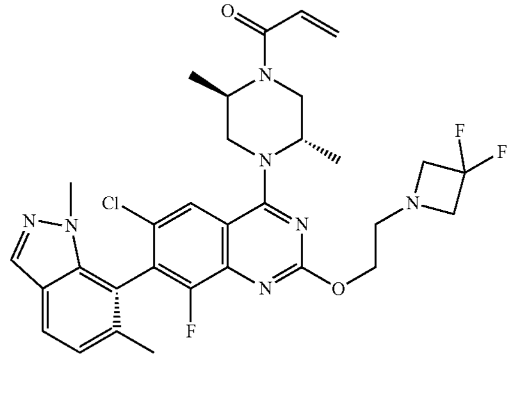 | 1-((2R,5S)-4-((R)-6-chloro-2-(2-(3,3-difluoroazetidin-1-yl)ethoxy)-7-(1,6-dimethyl-1H-indazol-7-yl)-8-fluoro-quinazolin-4-yl)-2,5-dimethylpiperazin-1-yl)prop-2-en-1-one | D | 628.4 |

TABLE 1-continued

Representative Compounds

| No. | Structure | Name | Method | [M + H]+ |
|---|---|---|---|---|
| 148 | 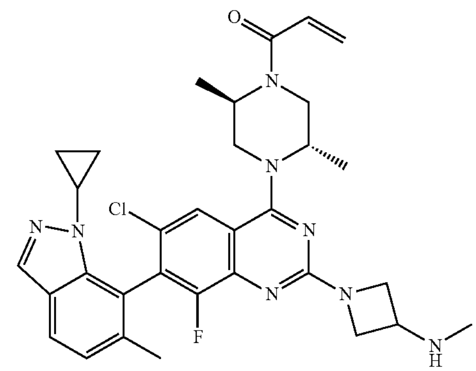 [SMILES: C=CC(=O)N1C[C@H](C)N(c2nc(N3CC(NC)C3)nc3c(F)c(-c4c(C)ccc5cnn(C6CC6)c45)c(Cl)cc23)C[C@H]1C] | 1-((2R,5S)-4-(6-chloro-7-(1-cyclopropyl-6-methyl-1H-indazol-7-yl)-8-fluoro-2-(3-(methylamino)azetidin-1-yl)quinazolin-4-yl)-2,5-dimethylpiperazin-1-yl)prop-2-en-1-one | D | 603.5 |
| 149 | 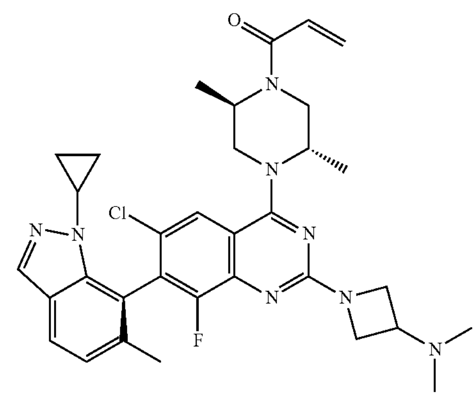 | 1-((2R,5S)-4-((S)-6-chloro-7-(1-cyclopropyl-6-methyl-1H-indazol-7-yl)-2-(3-(dimethylamino)-azetidin-1-yl)-8-fluoroquinazolin-4-yl)-2,5-dimethyl-piperazin-1-yl)prop-2-en-1-one | D | 617.4 |
| 150 | 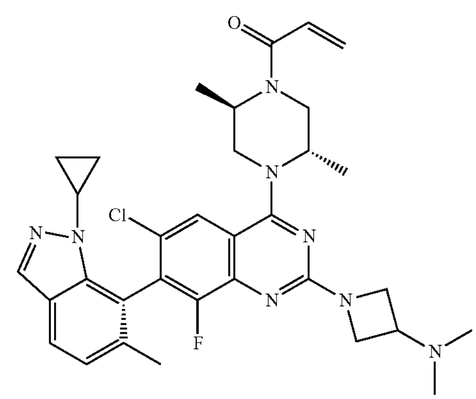 | 1-((2R,5S)-4-((R)-6-chloro-7-(1-cyclopropyl-6-methyl-1H-indazol-7-yl)-2-(3-(dimethylamino)-azetidin-1-yl)-8-fluoroquinazolin-4-yl)-2,5-dimethyl-piperazin-1-yl)prop-2-en-1-one | D | 617.4 |
| 151 | 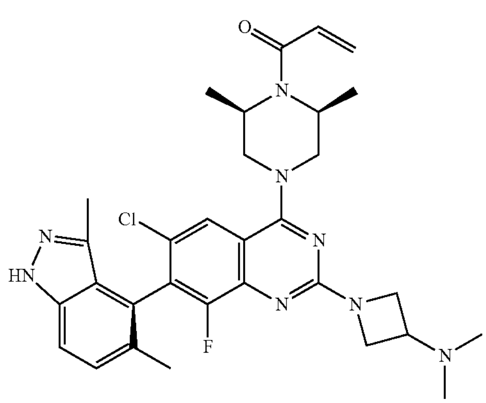 | 1-((2S,6R)-4-((S)-6-chloro-7-(3,5-dimethyl-1H-indazol-4-yl)-2-(3-(dimethylamino)-azetidin-1-yl)-8-fluoro-quinazolin-4-yl)-2,6-dimethylpiperazin-1-yl)prop-2-en-1-one | C | 591.3 |

TABLE 1-continued

Representative Compounds

| No. | Structure | Name | Method | [M + H]+ |
|---|---|---|---|---|
| 152 | 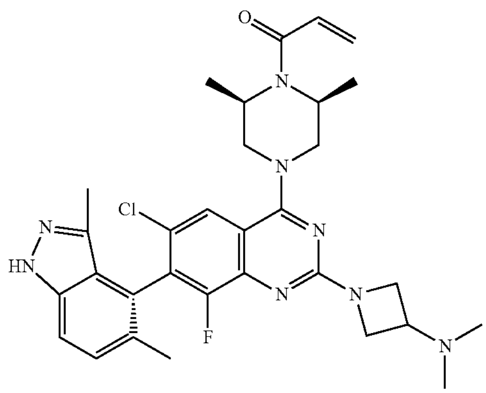 | 1-((2S,6R)-4-((R)-6-chloro-7-(3,5-dimethyl-1H-indazol-4-yl)-2-(3-(dimethylamino)-azetidin-1-yl)-8-fluoro-quinazolin-4-yl)-2,6-dimethylpiperazin-1-yl)prop-2-en-1-one | C | 591.3 |
| 153 | 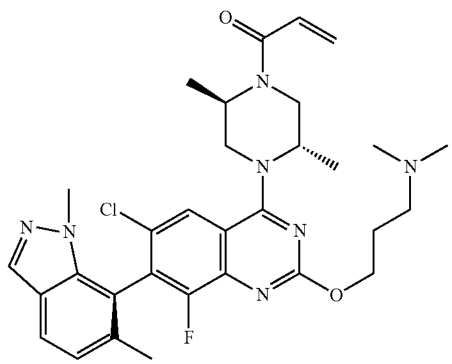 | 1-((2R,5S)-4-((S)-6-chloro-7-(1,6-dimethyl-1H-indazol-7-yl)-2-(3-(dimethylamino)-propoxy)-8-fluoro-quinazolin-4-yl)-2,5-dimethylpiperazin-1-yl)prop-2-en-1-one | D | 594.4 |
| 154 | 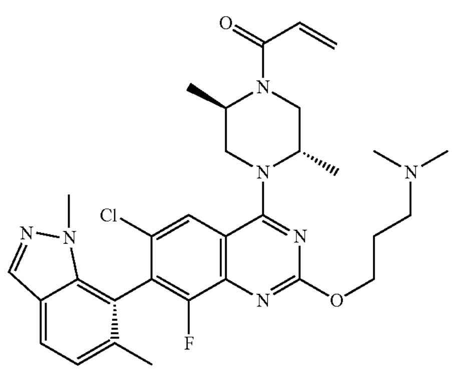 | 1-((2R,5S)-4-((R)-6-chloro-7-(1,6-dimethyl-1H-indazol-7-yl)-2-(3-(dimethylamino)-propoxy)-8-fluoro-quinazolin-4-yl)-2,5-dimethylpiperazin-1-yl)prop-2-en-1-one | D | 594.3 |
| 155 | 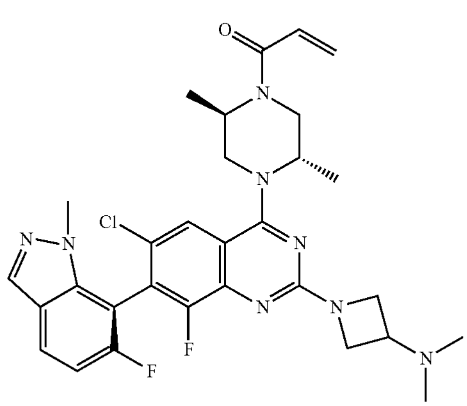 | 1-((2R,5S)-4-((R)-6-chloro-2-(3-(dimethyl-amino)azetidin-1-yl)-8-fluoro-7-(6-fluoro-1-methyl-1H-indazol-7-yl)quinazolin-4-yl)-2,5-dimethylpiperazin-1-yl)prop-2-en-1-one | D | 595.4 |

TABLE 1-continued

Representative Compounds

| No. | Structure | Name | Method | [M + H]+ |
|---|---|---|---|---|
| 156 | 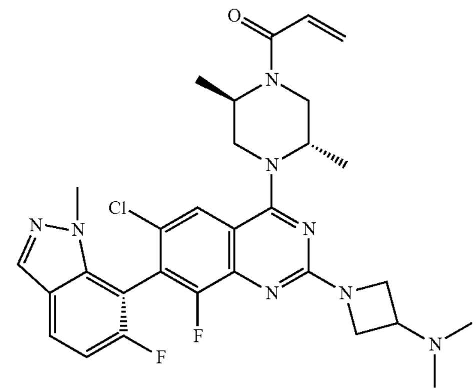 | 1-((2R,5S)-4-((S)-6-chloro-2-(3-(dimethylamino)azetidin-1-yl)-8-fluoro-7-(6-fluoro-1-methyl-1H-indazol-7-yl)quinazolin-4-yl)-2,5-dimethylpiperazin-1-yl)prop-2-en-1-one | D | 595.4 |
| 157 | 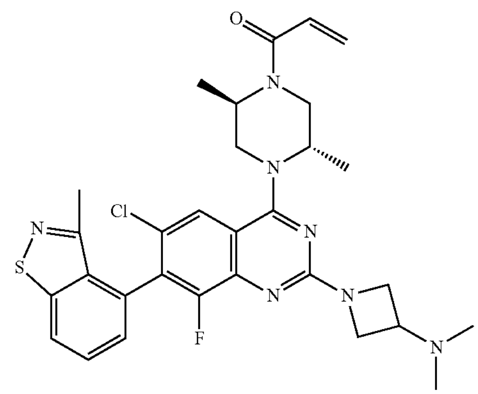 [SMILES: C=CC(=O)N1C[C@H](C)N(c2nc(N3CC(N(C)C)C3)nc3c(F)c(-c4cccc5snc(C)c45)c(Cl)cc23)C[C@H]1C] | 1-((2R,5S)-4-(6-chloro-2-(3-(dimethylamino)-azetidin-1-yl)-8-fluoro-7-(3-methylbenzo[d]-isothiazol-4-yl)-quinazolin-4-yl)-2,5-dimethylpiperazin-1-yl)prop-2-en-1-one | A | 594.4 |
| 158 | 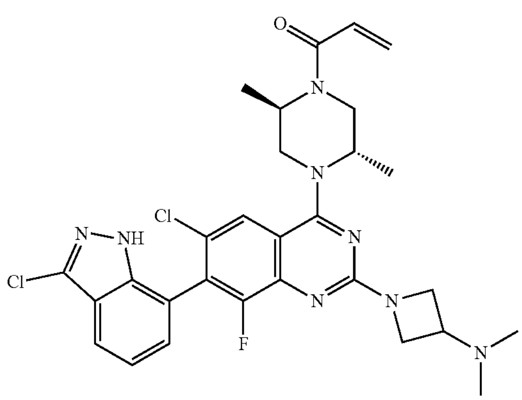 [SMILES: C=CC(=O)N1C[C@H](C)N(c2nc(N3CC(N(C)C)C3)nc3c(F)c(-c4cccc5c(Cl)n[nH]c45)c(Cl)cc23)C[C@H]1C] | 1-((2R,5S)-4-(6-chloro-7-(3-chloro-1H-indazol-7-yl)-2-(3-(dimethyl-amino)azetidin-1-yl)-8-fluoroquinazolin-4-yl)-2,5-dimethyl-piperazin-1-yl)prop-2-en-1-one | B | 611.2 |
| 159 | 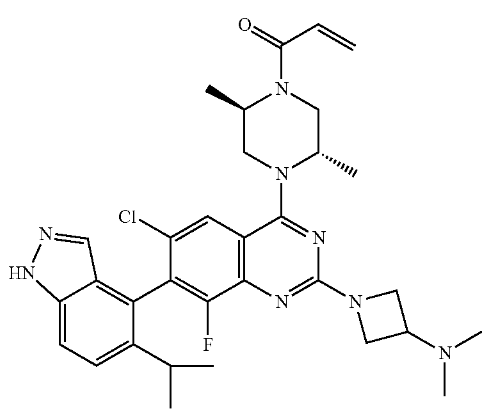 [SMILES: C=CC(=O)N1C[C@H](C)N(c2nc(N3CC(N(C)C)C3)nc3c(F)c(-c4c(C(C)C)ccc5[nH]ncc45)c(Cl)cc23)C[C@H]1C] | 1-((2R,5S)-4-(6-chloro-2-(3-(dimethyl-amino)azetidin-1-yl)-8-fluoro-7-(5-isopropyl-1H-indazol-4-yl)-quinazolin-4-yl)-2,5-dimethylpiperazin-1-yl)prop-2-en-1-one | A | 605.3 |

TABLE 1-continued

Representative Compounds

| No. | Structure | Name | Method | [M + H]+ |
|---|---|---|---|---|
| 160 | 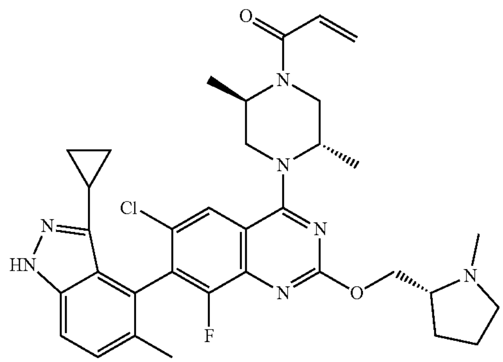 [SMILES: C=CC(=O)N1C[C@H](C)N(c2nc(OC[C@H]3CCCN3C)nc3c(F)c(-c4c(C)ccc5[nH]nc(C6CC6)c45)c(Cl)cc23)C[C@H]1C] | 1-((2R,5S)-4-(6-chloro-7-(3-cyclopropyl-5-methyl-1H-indazol-4-yl)-8-fluoro-2-(((R)-1-methylpyrrolidin-2-yl)methoxy)quinazolin-4-yl)-2,5-dimethyl-piperazin-1-yl)prop-2-en-1-one | C | 632.3 |
| 161 | 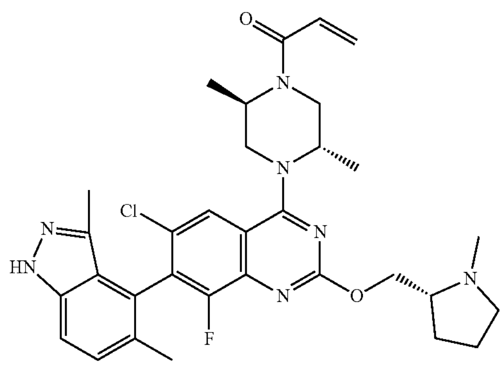 [SMILES: C=CC(=O)N1C[C@H](C)N(c2nc(OC[C@H]3CCCN3C)nc3c(F)c(-c4c(C)ccc5[nH]nc(C)c45)c(Cl)cc23)C[C@H]1C] | 1-((2R,5S)-4-(6-chloro-7-(3,5-dimethyl-1H-indazol-4-yl)-8-fluoro-2-(((R)-1-methyl-pyrrolidin-2-yl)-methoxy)quinazolin-4-yl)-2,5-dimethyl-piperazin-1-yl)prop-2-en-1-one | C | 606.4 |
| 162 | 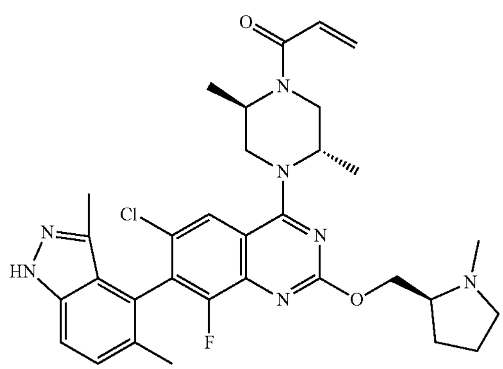 [SMILES: C=CC(=O)N1C[C@H](C)N(c2nc(OC[C@@H]3CCCN3C)nc3c(F)c(-c4c(C)ccc5[nH]nc(C)c45)c(Cl)cc23)C[C@H]1C] | 1-((2R,5S)-4-(6-chloro-7-(3,5-dimethyl-1H-indazol-4-yl)-8-fluoro-2-(((S)-1-methyl-pyrrolidin-2-yl)-methoxy)quinazolin-4-yl)-2,5-dimethyl-piperazin-1-yl)prop-2-en-1-one | C | 606.4 |
| 163 | 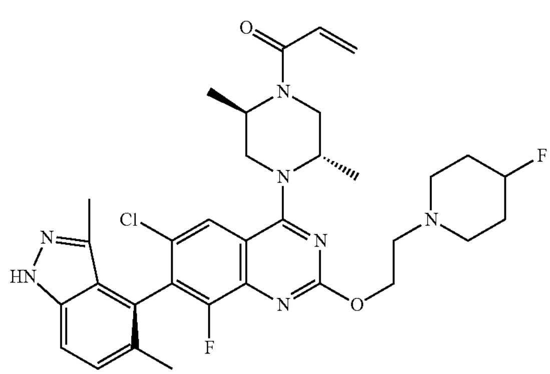 | 1-((2R,5S)-4-((S)-6-chloro-7-(3,5-dimethyl-1H-indazol-4-yl)-8-fluoro-2-(2-(4-fluoropiperidin-1-yl)ethoxy)quinazolin-4-yl)-2,5-dimethyl-piperazin-1-yl)prop-2-en-1-one | C | 639.3 |

TABLE 1-continued

Representative Compounds

| No. | Structure | Name | Method | [M + H]+ |
|---|---|---|---|---|
| 164 | 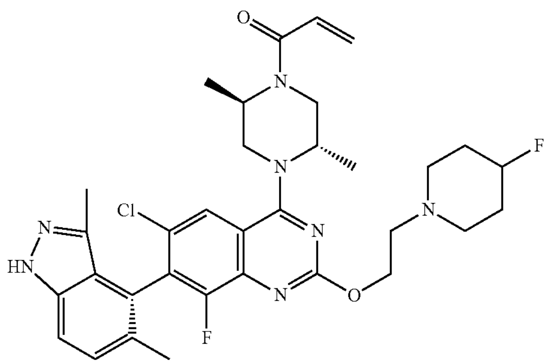 | 1-((2R,5S)-4-((R)-6-chloro-7-(3,5-dimethyl-1H-indazol-4-yl)-8-fluoro-2-(2-(4-fluoro-piperidin-1-yl)-ethoxy)quinazolin-4-yl)-2,5-dimethyl-piperazin-1-yl)prop-2-en-1-one | C | 639.3 |
| 165 | 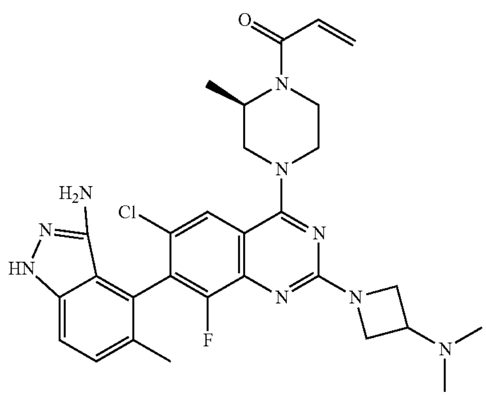 [SMILES: C=CC(=O)N1CCN(c2nc(N3CC(N(C)C)C3)nc3c(F)c(-c4c(C)ccc5[nH]nc(N)c45)c(Cl)cc23)C[C@H]1C] | 1-((2R)-4-(7-(3-amino-5-methyl-1H-indazol-4-yl)-6-chloro-2-(3-(dimethyl-amino)azetidin-1-yl)-8-fluoroquinazolin-4-yl)-2-methyl-piperazin-1-yl)prop-2-en-1-one | B | 578.0 |
| 166 | 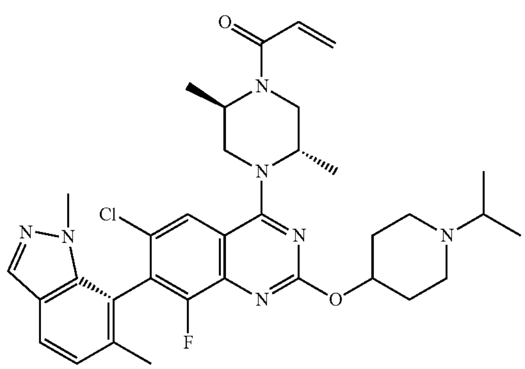 | 1-((2R,5S)-4-((S)-6-chloro-7-(1,6-dimethyl-1H-indazol-7-yl)-8-fluoro-2-(1-isopropyl-piperidin-4-yloxy)-quinazolin-4-yl)-2,5-dimethylpiperazin-1-yl)prop-2-en-1-one | D | 634.4 |
| 167 | 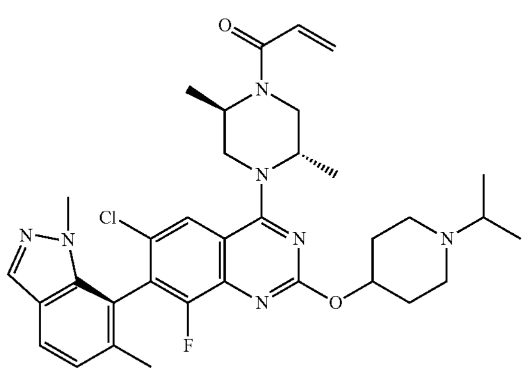 | 1-((2R,5S)-4-((R)-6-chloro-7-(1,6-dimethyl-1H-indazol-7-yl)-8-fluoro-2-(1-isopropyl-piperidin-4-yloxy)-quinazolin-4-yl)-2,5-dimethylpiperazin-1-yl)prop-2-en-1-one | D | 634.4 |

TABLE 1-continued

Representative Compounds

| No. | Structure | Name | Method | [M + H]+ |
|---|---|---|---|---|
| 168 | 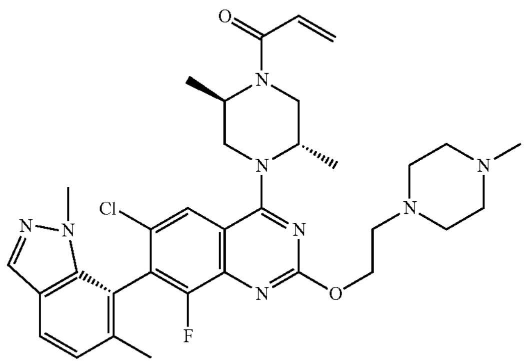 | 1-((2R,5S)-4-((S)-6-chloro-7-(1,6-dimethyl-1H-indazol-7-yl)-8-fluoro-2-(2-(4-methyl-piperazin-1-yl)-ethoxy)quinazolin-4-yl)-2,5-dimethyl-piperazin-1-yl)prop-2-en-1-one | D | 635.4 |
| 169 | 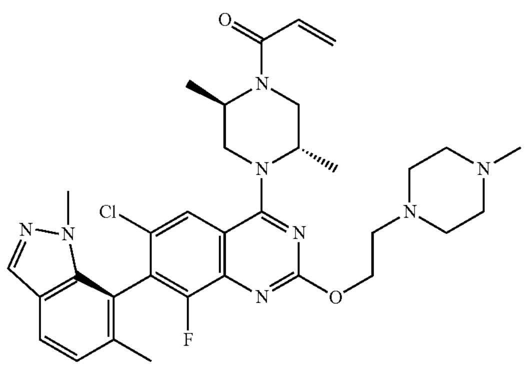 | 1-((2R,5S)-4-((R)-6-chloro-7-(1,6-dimethyl-1H-indazol-7-yl)-8-fluoro-2-(2-(4-methylpiperazin-1-yl)ethoxy)quinazolin-4-yl)-2,5-dimethyl-piperazin-1-yl)prop-2-en-1-one | D | 635.4 |
| 170 | 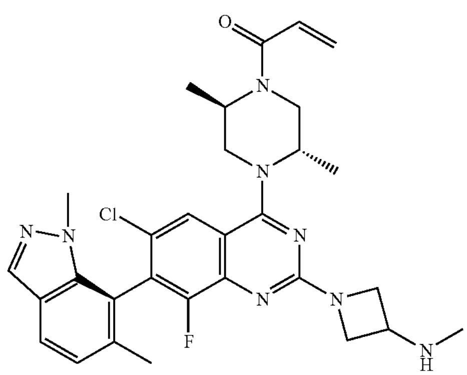 | 1-((2R,5S)-4-((R)-6-chloro-7-(1,6-dimethyl-1H-indazol-7-yl)-8-fluoro-2-(3-(methyl-amino)azetidin-1-yl)-quinazolin-4-yl)-2,5-dimethylpiperazin-1-yl)prop-2-en-1-one | D | 577.4 |
| 171 | 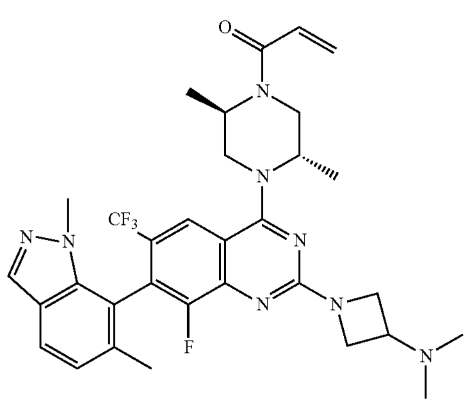 [SMILES: C=CC(=O)N1C[C@H](C)N(c2nc(N3CC(N(C)C)C3)nc3c(F)c(-c4c(C)ccc5cnn(C)c45)c(C(F)(F)F)cc23)C[C@H]1C] | 1-((2R,5S)-4-(7-(1,6-dimethyl-1H-indazol-7-yl)-2-(3-(dimethyl-amino)azetidin-1-yl)-8-fluoro-6-(trifluoro-methyl)quinazolin-4-yl)-2,5-dimethyl-piperazin-1-yl)prop-2-en-1-one | D | 625.4 |

TABLE 1-continued

Representative Compounds

| No. | Structure | Name | Method | [M + H]+ |
|---|---|---|---|---|
| 172 | 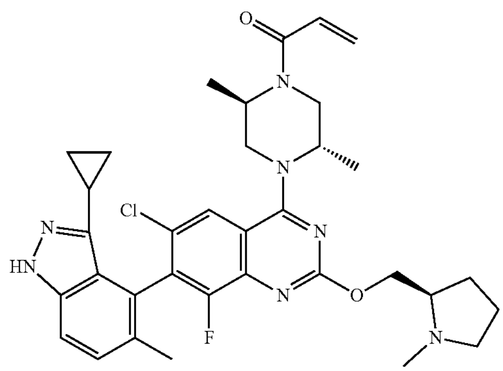 [SMILES: C=CC(=O)N1C[C@H](C)N(c2nc(OC[C@H]3CCCN3C)nc3c(F)c(-c4c(C)ccc5[nH]nc(C6CC6)c45)c(Cl)cc23)C[C@H]1C] | 1-((2R,5S)-4-(6-chloro-7-(3-cyclopropyl-5-methyl-1H-indazol-4-yl)-8-fluoro-2-(((R)-1-methylpyrrolidin-2-yl)methoxy)quinazolin-4-yl)-2,5-dimethyl-piperazin-1-yl)prop-2-en-1-one | C | 632.4 |
| 173 | 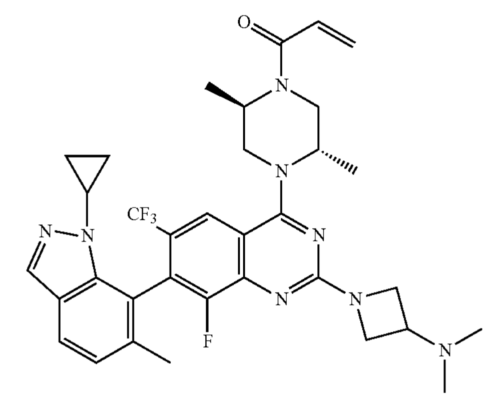 [SMILES: C=CC(=O)N1C[C@H](C)N(c2nc(N3CC(N(C)C)C3)nc3c(F)c(-c4c(C)ccc5cnn(C6CC6)c45)c(C(F)(F)F)cc23)C[C@H]1C] | 1-((2R,5S)-4-(7-(1-cyclopropyl-6-methyl-1H-indazol-7-yl)-2-(3-(dimethylamino)-azetidin-1-yl)-8-fluoro-6-(trifluoromethyl)-quinazolin-4-yl)-2,5-dimethylpiperazin-1-yl)prop-2-en-1-one | D | 651.5 |
| 174 | 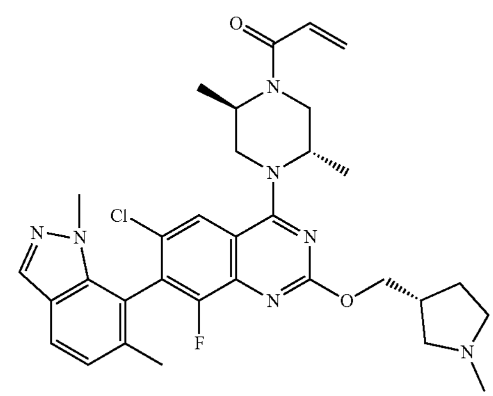 [SMILES: C=CC(=O)N1C[C@H](C)N(c2nc(OC[C@@H]3CCN(C)C3)nc3c(F)c(-c4c(C)ccc5cnn(C)c45)c(Cl)cc23)C[C@H]1C] | 1-((2R,5S)-4-(6-chloro-7-(1,6-dimethyl-1H-indazol-7-yl)-8-fluoro-2-(((R)-1-methyl-pyrrolidin-3-yl)-methoxy)quinazolin-4-yl)-2,5-dimethyl-piperazin-1-yl)prop-2-en-1-one | D | 606.4 |
| 175 | 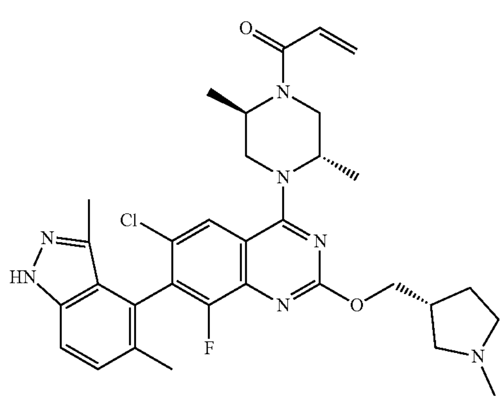 [SMILES: C=CC(=O)N1C[C@H](C)N(c2nc(OC[C@@H]3CCN(C)C3)nc3c(F)c(-c4c(C)ccc5[nH]nc(C)c45)c(Cl)cc23)C[C@H]1C] | 1-((2R,5S)-4-(6-chloro-7-(3,5-dimethyl-1H-indazol-4-yl)-8-fluoro-2-(((R)-1-methyl-pyrrolidin-3-yl)-methoxy)quinazolin-4-yl)-2,5-dimethyl-piperazin-1-yl)prop-2-en-1-one | C | 606.3 |

TABLE 1-continued

Representative Compounds

| No. | Structure | Name | Method | [M + H]+ |
|---|---|---|---|---|
| 176 | 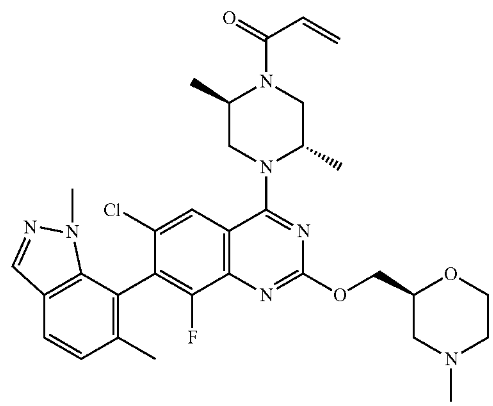 [SMILES: C=CC(=O)N1C[C@H](C)N(c2nc(OC[C@@H]3CN(C)CCO3)nc3c(F)c(-c4c(C)ccc5cnn(C)c45)c(Cl)cc23)C[C@H]1C] | 1-((2R,5S)-4-(6-chloro-7-(1,6-dimethyl-1H-indazol-7-yl)-8-fluoro-2-(((S)-4-methylmorpholin-2-yl)methoxy)-quinazolin-4-yl)-2,5-dimethylpiperazin-1-yl)prop-2-en-1-one | D | 622.4 |
| 177 | 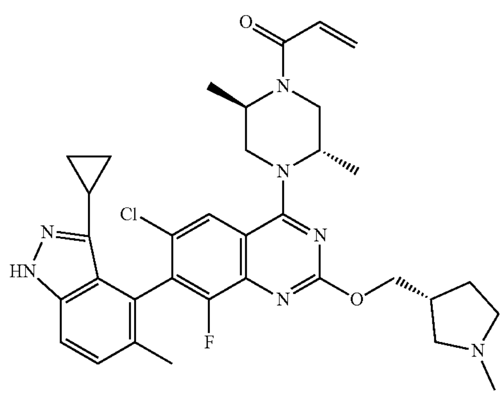 [SMILES: C=CC(=O)N1C[C@H](C)N(c2nc(OC[C@@H]3CCN(C)C3)nc3c(F)c(-c4c(C)ccc5[nH]nc(C6CC6)c45)c(Cl)cc23)C[C@H]1C] | 1-((2R,5S)-4-(6-chloro-7-(3-cyclopropyl-5-methyl-1H-indazol-4-yl)-8-fluoro-2-(((R)-1-methylpyrrolidin-3-yl)methoxy)quinazolin-4-yl)-2,5-dimethyl-piperazin-1-yl)prop-2-en-1-one | C | 632.4 |
| 178 | 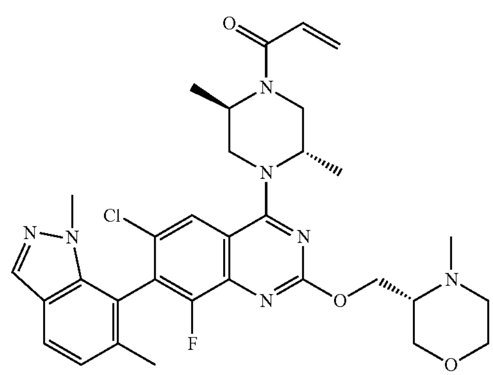 [SMILES: C=CC(=O)N1C[C@H](C)N(c2nc(OC[C@H]3COCCN3C)nc3c(F)c(-c4c(C)ccc5cnn(C)c45)c(Cl)cc23)C[C@H]1C] | 1-((2R,5S)-4-(6-chloro-7-(1,6-dimethyl-1H-indazol-7-yl)-8-fluoro-2-(((R)-4-methyl-morpholin-3-yl)-methoxy)quinazolin-4-yl)-2,5-dimethyl-piperazin-1-yl)prop-2-en-1-one | D | 622.4 |
| 179 | 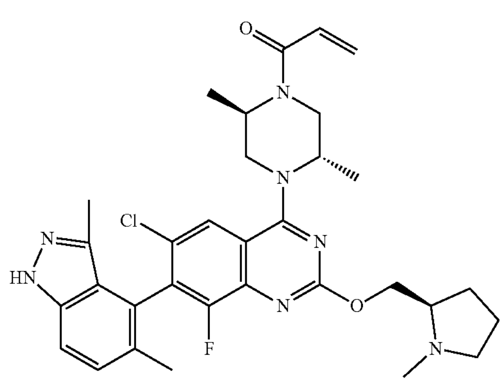 [SMILES: C=CC(=O)N1C[C@H](C)N(c2nc(OC[C@H]3CCCN3C)nc3c(F)c(-c4c(C)ccc5[nH]nc(C)c45)c(Cl)cc23)C[C@H]1C] | 1-((2R,5S)-4-(6-chloro-7-(3,5-dimethyl-1H-indazol-4-yl)-8-fluoro-2-(((R)-1-methylpyrrolidin-2-yl)methoxy)quinazolin-4-yl)-2,5-dimethyl-piperazin-1-yl)prop-2-en-1-one | C | 606.4 |

TABLE 1-continued

Representative Compounds

| No. | Structure | Name | Method | [M + H]+ |
|---|---|---|---|---|
| 180 | 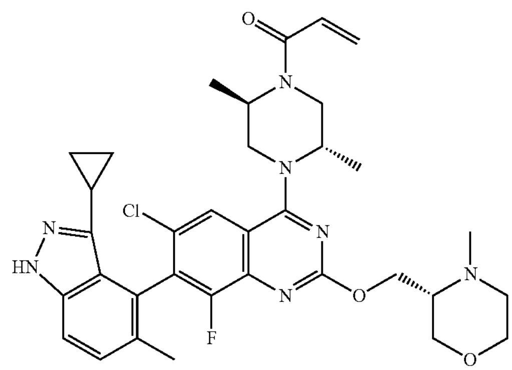 [SMILES: C=CC(=O)N1C[C@H](C)N(c2nc(OC[C@H]3COCCN3C)nc3c(F)c(-c4c(C)ccc5[nH]nc(C6CC6)c45)c(Cl)cc23)C[C@H]1C] | 1-((2R,5S)-4-(6-chloro-7-(3-cyclopropyl-5-methyl-1H-indazol-4-yl)-8-fluoro-2-(((R)-4-methylmorpholin-3-yl)methoxy)quinazolin-4-yl)-2,5-dimethyl-piperazin-1-yl)prop-2-en-1-one | C | 648.5 |
| 181 | 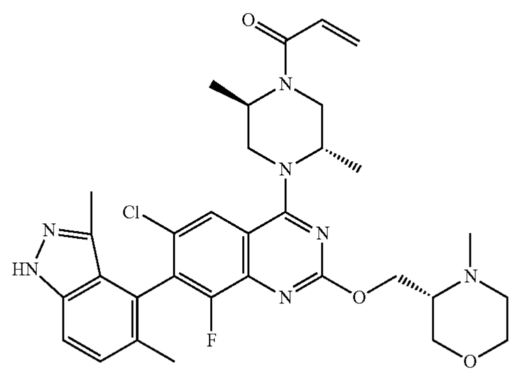 [SMILES: C=CC(=O)N1C[C@H](C)N(c2nc(OC[C@H]3COCCN3C)nc3c(F)c(-c4c(C)ccc5[nH]nc(C)c45)c(Cl)cc23)C[C@H]1C] | 1-((2R,5S)-4-(6-chloro-7-(3,5-dimethyl-1H-indazol-4-yl)-8-fluoro-2-(((R)-4-methyl-morpholin-3-yl)-methoxy)quinazolin-4-yl)-2,5-dimethyl-piperazin-1-yl)prop-2-en-1-one | C | 622.4 |
| 182 | 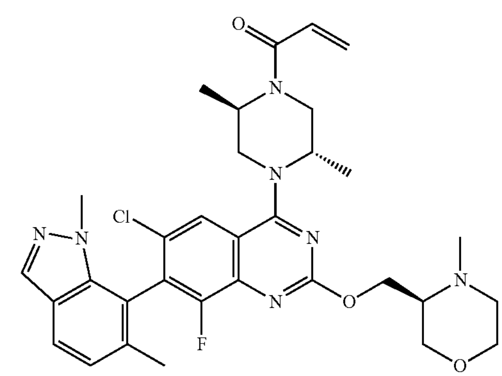 [SMILES: C=CC(=O)N1C[C@H](C)N(c2nc(OC[C@@H]3COCCN3C)nc3c(F)c(-c4c(C)ccc5cnn(C)c45)c(Cl)cc23)C[C@H]1C] | 1-((2R,5S)-4-(6-chloro-7-(1,6-dimethyl-1H-indazol-7-yl)-8-fluoro-2-(((S)-4-methyl-morpholin-3-yl)-methoxy)quinazolin-4-yl)-2,5-dimethyl-piperazin-1-yl)prop-2-en-1-one | D | 622.7 |
| 183 | 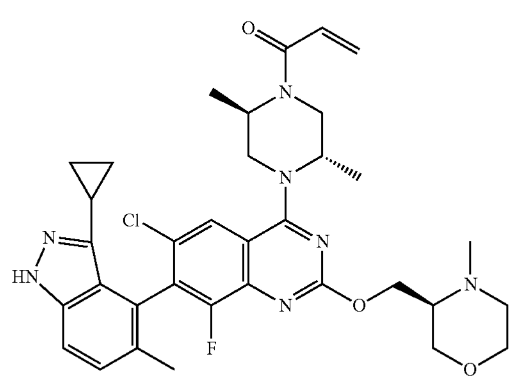 [SMILES: C=CC(=O)N1C[C@H](C)N(c2nc(OC[C@@H]3COCCN3C)nc3c(F)c(-c4c(C)ccc5[nH]nc(C6CC6)c45)c(Cl)cc23)C[C@H]1C] | 1-((2R,5S)-4-(6-chloro-7-(3-cyclopropyl-5-methyl-1H-indazol-4-yl)-8-fluoro-2-(((S)-4-methylmorpholin-3-yl)methoxy)quinazolin-4-yl)-2,5-dimethyl-piperazin-1-yl)prop-2-en-1-one | C | 648.4 |

TABLE 1-continued

Representative Compounds

| No. | Structure | Name | Method | [M + H]+ |
|---|---|---|---|---|
| 184 | 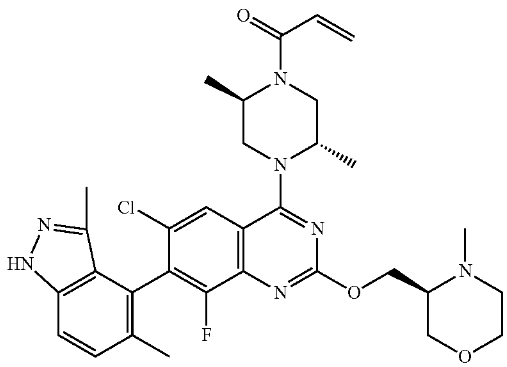 [SMILES: C=CC(=O)N1C[C@H](C)N(c2nc(OC[C@@H]3COCCN3C)nc3c(F)c(-c4c(C)ccc5[nH]nc(C)c45)c(Cl)cc23)C[C@H]1C] | 1-((2R,5S)-4-(6-chloro-7-(3,5-dimethyl-1H-indazol-4-yl)-8-fluoro-2-(((S)-4-methyl-morpholin-3-yl)-methoxy)quinazolin-4-yl)-2,5-dimethyl-piperazin-1-yl)prop-2-en-1-one | C | 622.4 |
| 185 | 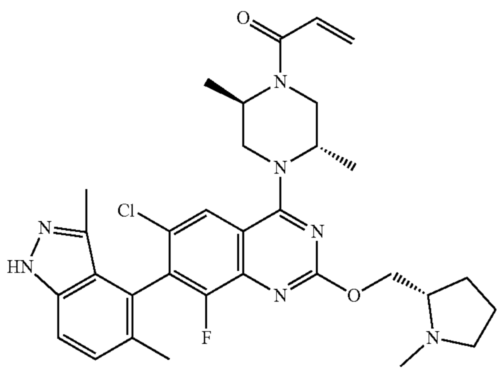 [SMILES: C=CC(=O)N1C[C@H](C)N(c2nc(OC[C@@H]3CCCN3C)nc3c(F)c(-c4c(C)ccc5[nH]nc(C)c45)c(Cl)cc23)C[C@H]1C] | 1-((2R,5S)-4-(6-chloro-7-(3,5-dimethyl-1H-indazol-4-yl)-8-fluoro-2-(((S)-1-methyl-pyrrolidin-2-yl)-methoxy)quinazolin-4-yl)-2,5-dimethyl-piperazin-1-yl)prop-2-en-1-one | C | 606.6 |
| 186 | 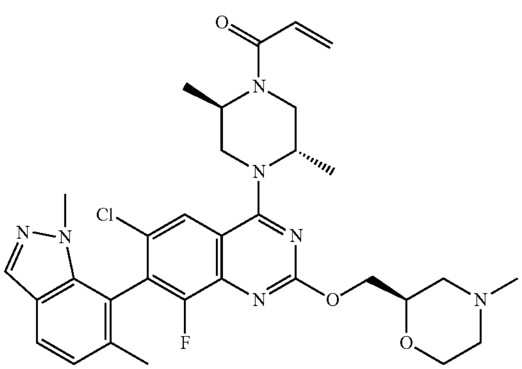 [SMILES: C=CC(=O)N1C[C@H](C)N(c2nc(OC[C@H]3CN(C)CCO3)nc3c(F)c(-c4c(C)ccc5cnn(C)c45)c(Cl)cc23)C[C@H]1C] | 1-((2R,5S)-4-(6-chloro-7-(1,6-dimethyl-1H-indazol-7-yl)-8-fluoro-2-(((R)-4-methyl-morpholin-2-yl)-methoxy)quinazolin-4-yl)-2,5-dimethyl-piperazin-1-yl)prop-2-en-1-one | D | 622.5 |
| 187 | 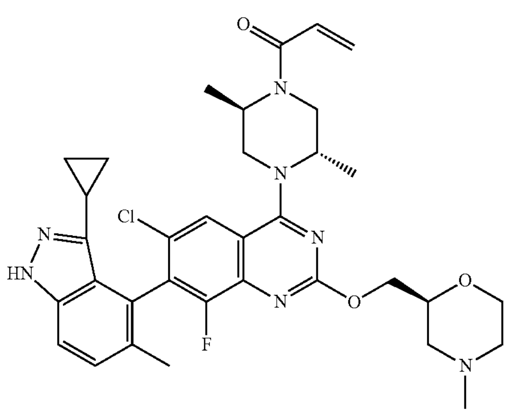 [SMILES: C=CC(=O)N1C[C@H](C)N(c2nc(OC[C@@H]3CN(C)CCO3)nc3c(F)c(-c4c(C)ccc5[nH]nc(C6CC6)c45)c(Cl)cc23)C[C@H]1C] | 1-((2R,5S)-4-(6-chloro-7-(3-cyclopropyl-5-methyl-1H-indazol-4-yl)-8-fluoro-2-(((S)-4-methylmorpholin-2-yl)methoxy)quinazolin-4-yl)-2,5-dimethyl-piperazin-1-yl)prop-2-en-1-one | C | 648.4 |

TABLE 1-continued

Representative Compounds

| No. | Structure | Name | Method | [M + H]⁺ |
|---|---|---|---|---|
| 188 | 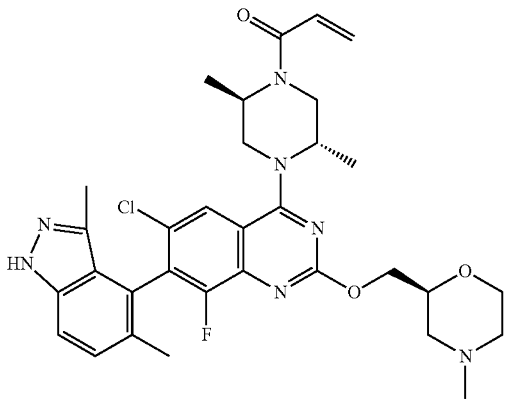 [SMILES: C=CC(=O)N1C[C@H](C)N(c2nc(OC[C@@H]3CN(C)CCO3)nc3c(F)c(-c4c(C)ccc5[nH]nc(C)c45)c(Cl)cc23)C[C@H]1C] | 1-((2R,5S)-4-(6-chloro-7-(3,5-dimethyl-1H-indazol-4-yl)-8-fluoro-2-(((S)-4-methyl-morpholin-2-yl)-methoxy)quinazolin-4-yl)-2,5-dimethyl-piperazin-1-yl)prop-2-en-1-one | C | 622.3 |
| 189 | 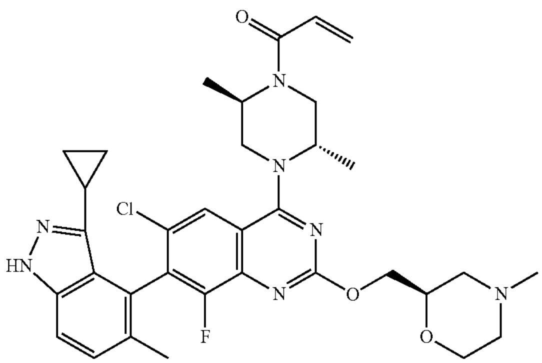 [SMILES: C=CC(=O)N1C[C@H](C)N(c2nc(OC[C@H]3CN(C)CCO3)nc3c(F)c(-c4c(C)ccc5[nH]nc(C6CC6)c45)c(Cl)cc23)C[C@H]1C] | 1-((2R,5S)-4-(6-chloro-7-(3-cyclopropyl-5-methyl-1H-indazol-4-yl)-8-fluoro-2-(((R)-4-methylmorpholin-2-yl)methoxy)quinazolin-4-yl)-2,5-dimethyl-piperazin-1-yl)prop-2-en-1-one | C | 648.5 |
| 190 | 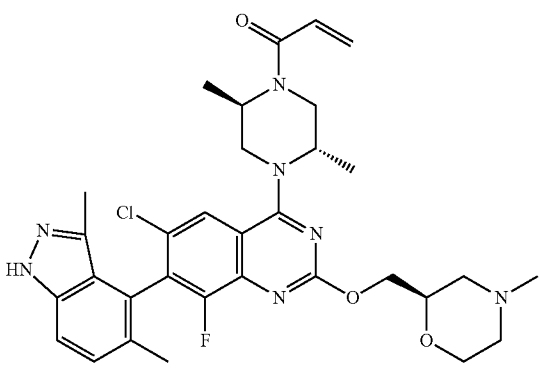 [SMILES: C=CC(=O)N1C[C@H](C)N(c2nc(OC[C@H]3CN(C)CCO3)nc3c(F)c(-c4c(C)ccc5[nH]nc(C)c45)c(Cl)cc23)C[C@H]1C] | 1-((2R,5S)-4-(6-chloro-7-(3,5-dimethyl-1H-indazol-4-yl)-8-fluoro-2-(((R)-4-methyl-morpholin-2-yl)-methoxy)quinazolin-4-yl)-2,5-dimethyl-piperazin-1-yl)prop-2-en-1-one | C | 622.4 |
| 191 | 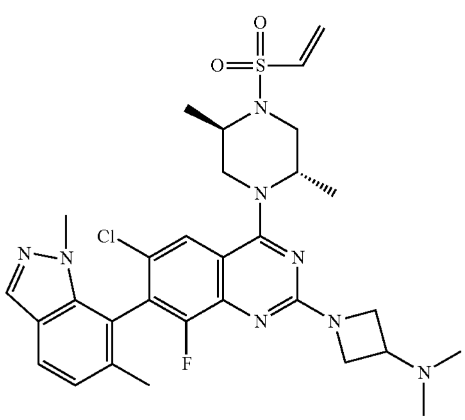 [SMILES: C=CS(=O)(=O)N1C[C@H](C)N(c2nc(N3CC(N(C)C)C3)nc3c(F)c(-c4c(C)ccc5cnn(C)c45)c(Cl)cc23)C[C@H]1C] | 1-(6-chloro-7-(1,6-dimethyl-1H-indazol-7-yl)-4-((2S,5R)-2,5-dimethyl-4-(vinyl-sulfonyl)piperazin-1-yl)-8-fluoroquinazolin-2-yl)-N,N-dimethyl-azetidin-3-amine | D | 627.4 |

TABLE 1-continued

Representative Compounds

| No. | Structure | Name | Method | [M + H]+ |
|---|---|---|---|---|
| 192 | 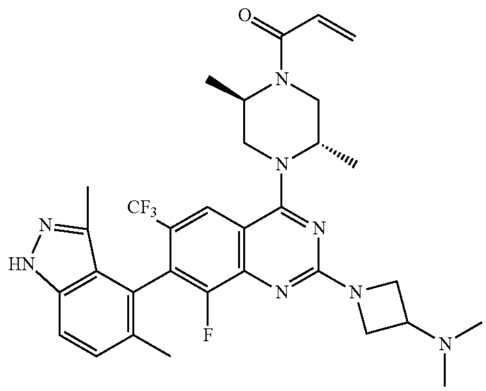 [SMILES: C=CC(=O)N1C[C@H](C)N(c2nc(N3CC(N(C)C)C3)nc3c(F)c(-c4c(C)ccc5[nH]nc(C)c45)c(C(F)(F)F)cc23)C[C@H]1C] | 1-((2R,5S)-4-(7-(3,5-dimethyl-1H-indazol-4-yl)-2-(3-(dimethylamino)azetidin-1-yl)-8-fluoro-6-(trifluoromethyl)quinazolin-4-yl)-2,5-dimethylpiperazin-1-yl)prop-2-en-1-one | C | 625.6 |
| 193 | 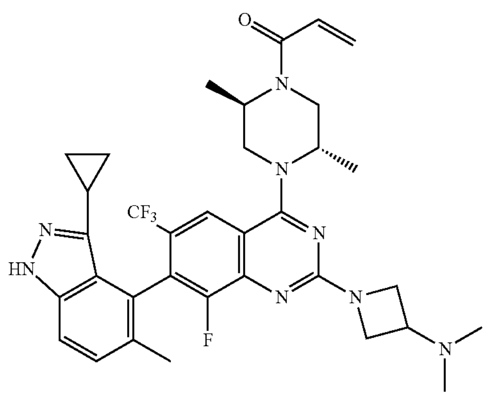 [SMILES: C=CC(=O)N1C[C@H](C)N(c2nc(N3CC(N(C)C)C3)nc3c(F)c(-c4c(C)ccc5[nH]nc(C6CC6)c45)c(C(F)(F)F)cc23)C[C@H]1C] | 1-((2R,5S)-4-(7-(3-cyclopropyl-5-methyl-1H-indazol-4-yl)-2-(3-(dimethylamino)-azetidin-1-yl)-8-fluoro-6-(trifluoromethyl)-quinazolin-4-yl)-2,5-dimethylpiperazin-1-yl)prop-2-en-1-one | C | 651.3 |
| 194 | 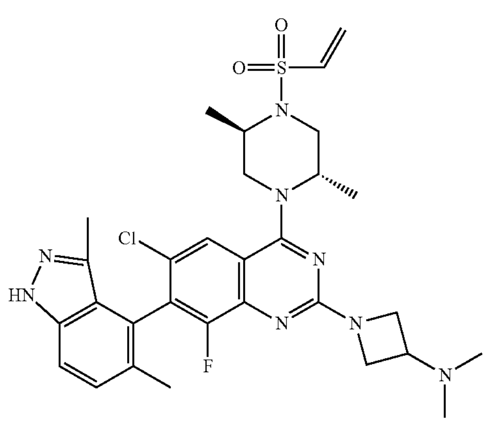 [SMILES: C=CS(=O)(=O)N1C[C@H](C)N(c2nc(N3CC(N(C)C)C3)nc3c(F)c(-c4c(C)ccc5[nH]nc(C)c45)c(Cl)cc23)C[C@H]1C] | 1-(6-chloro-7-(3,5-dimethyl-1H-indazol-4-yl)-4-((2S,5R)-2,5-dimethyl-4-(vinylsulfonyl)piperazin-1-yl)-8-fluoroquinazolin-2-yl)-N,N-dimethylazetidin-3-amine | C | 627.3 |

TABLE 1-continued

Representative Compounds

| No. | Structure | Name | Method | [M + H]+ |
|---|---|---|---|---|
| 195 | 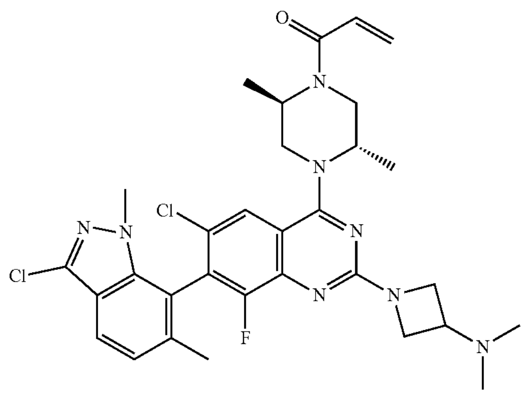 [SMILES: C=CC(=O)N1C[C@H](C)N(c2nc(N3CC(N(C)C)C3)nc3c(F)c(-c4c(C)ccc5c(Cl)nn(C)c45)c(Cl)cc23)C[C@H]1C] | 1-((2R,5S)-4-(6-chloro-7-(3-chloro-1,6-dimethyl-1H-indazol-7-yl)-2-(3-(dimethyl-amino)azetidin-1-yl)-8-fluoroquinazolin-4-yl)-2,5-dimethyl-piperazin-1-yl)prop-2-en-1-one | D | 625.2 |
| 196 | 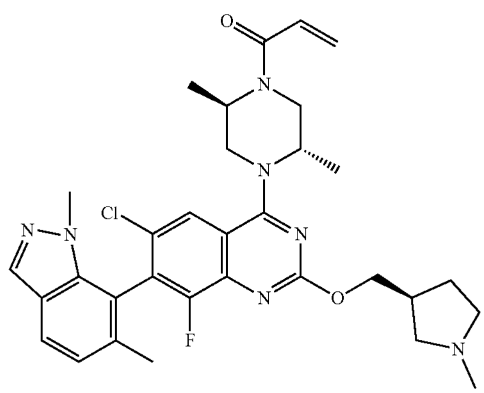 [SMILES: C=CC(=O)N1C[C@H](C)N(c2nc(OC[C@H]3CCN(C)C3)nc3c(F)c(-c4c(C)ccc5cnn(C)c45)c(Cl)cc23)C[C@H]1C] | 1-((2R,5S)-4-(6-chloro-7-(1,6-dimethyl-1H-indazol-7-yl)-8-fluoro-2-(((S)-1-methyl-pyrrolidin-3-yl)-methoxy)quinazolin-4-yl)-2,5-dimethyl-piperazin-1-yl)prop-2-en-1-one | D | 606.4 |
| 197 | 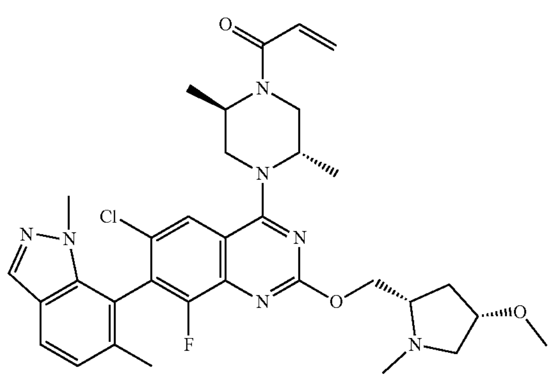 [SMILES: C=CC(=O)N1C[C@H](C)N(c2nc(OC[C@@H]3C[C@H](OC)CN3C)nc3c(F)c(-c4c(C)ccc5cnn(C)c45)c(Cl)cc23)C[C@H]1C] | 1-((2R,5S)-4-(6-chloro-7-(1,6-dimethyl-1H-indazol-7-yl)-8-fluoro-2-(((2S,4S)-4-methoxy-1-methylpyrrolidin-2-yl)methoxy)quinazolin-4-yl)-2,5-dimethyl-piperazin-1-yl)prop-2-en-1-one | D | 636.3 |
| 198 | 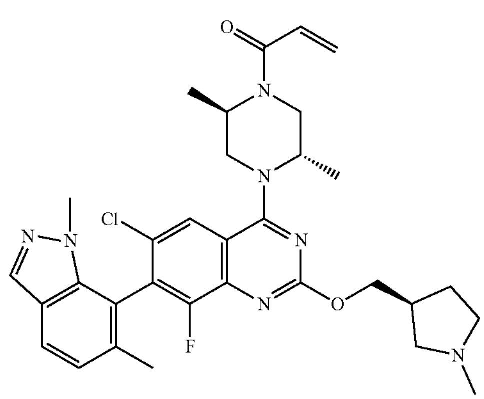 [SMILES: C=CC(=O)N1C[C@H](C)N(c2nc(OC[C@H]3CCN(C)C3)nc3c(F)c(-c4c(C)ccc5cnn(C)c45)c(Cl)cc23)C[C@H]1C] | 1-((2R,5S)-4-(6-chloro-7-(1-cyclopropyl-6-methyl-1H-indazol-7-yl)-8-fluoro-2-(((S)-1-methylpyrrolidin-3-yl)methoxy)quinazolin-4-yl)-2,5-dimethyl-piperazin-1-yl)prop-2-en-1-one | D | 632.6 |

TABLE 1-continued

Representative Compounds

| No. | Structure | Name | Method | [M + H]+ |
|---|---|---|---|---|
| 199 | 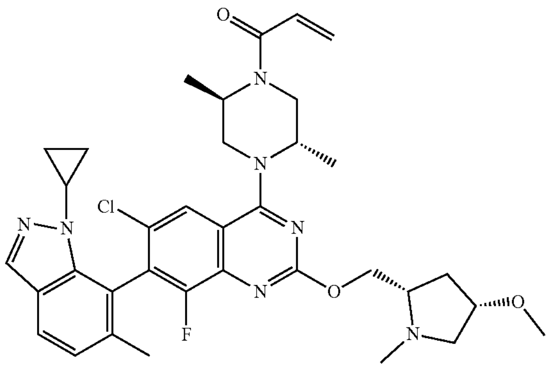 [SMILES: C=CC(=O)N1C[C@H](C)N(c2nc(OC[C@@H]3C[C@H](OC)CN3C)nc3c(F)c(-c4c(C)ccc5cnn(C6CC6)c45)c(Cl)cc23)C[C@H]1C] | 1-((2R,5S)-4-(6-chloro-7-(1-cyclopropyl-6-methyl-1H-indazol-7-yl)-8-fluoro-2-(((2S,4S)-4-methoxy-1-methyl-pyrrolidin-2-yl)-methoxy)quinazolin-4-yl)-2,5-dimethyl-piperazin-1-yl)prop-2-en-1-one | D | 661.9 |
| 200 | 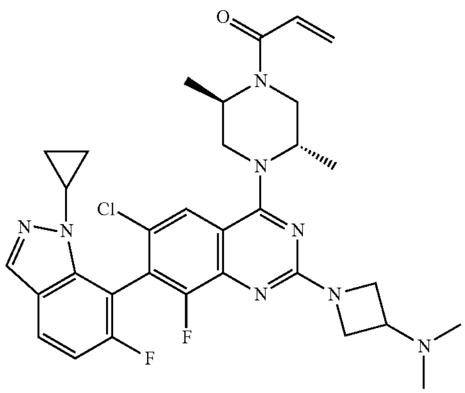 [SMILES: C=CC(=O)N1C[C@H](C)N(c2nc(N3CC(N(C)C)C3)nc3c(F)c(-c4c(F)ccc5cnn(C6CC6)c45)c(Cl)cc23)C[C@H]1C] | 1-((2R,5S)-4-(6-chloro-7-(1-cyclopropyl-6-fluoro-1H-indazol-7-yl)-2-(3-(dimethyl-amino)azetidin-1-yl)-8-fluoroquinazolin-4-yl)-2,5-dimethyl-piperazin-1-yl)prop-2-en-1-one | D | 621.3 |
| 201 | 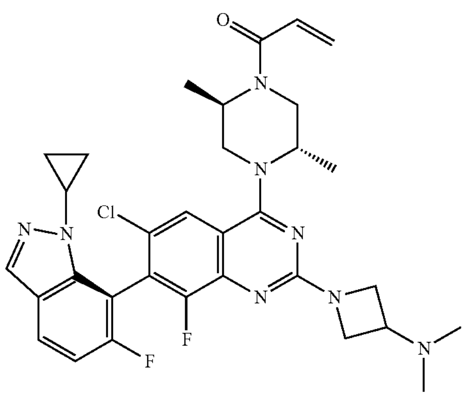 | 1-((2R,5S)-4-((S)-6-chloro-7-(1-cyclo-propyl-6-fluoro-1H-indazol-7-yl)-2-(3-(dimethylamino)-azetidin-1-yl)-8-fluoroquinazolin-4-yl)-2,5-dimethyl-piperazin-1-yl)prop-2-en-1-one | D | 621.3 |
| 202 | 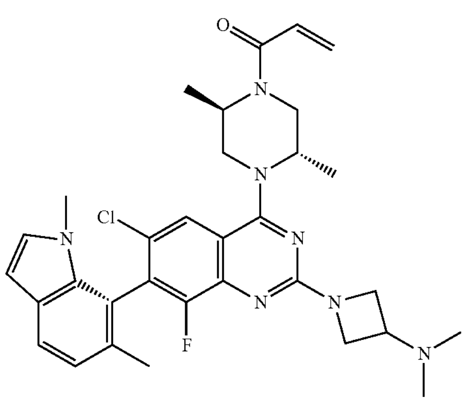 | 1-((2R,5S)-4-((S)-6-chloro-7-(1,6-dimethyl-1H-indol-7-yl)-2-(3-(dimethylamino)-azetidin-1-yl)-8-fluoroquinazolin-4-yl)-2,5-dimethyl-piperazin-1-yl)prop-2-en-1-one | D | 590.4 |

TABLE 1-continued

Representative Compounds

| No. | Structure | Name | Method | [M + H]+ |
|---|---|---|---|---|
| 203 | 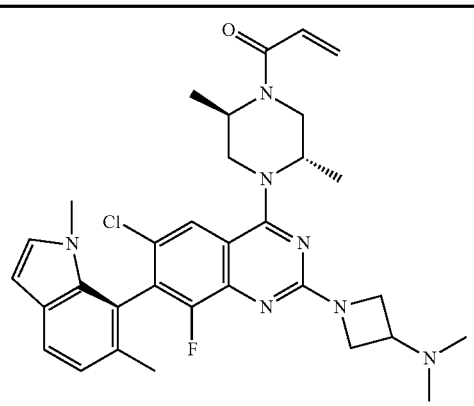 | 1-((2R,5S)-4-((R)-6-chloro-7-(1,6-dimethyl-1H-indol-7-yl)-2-(3-(dimethylamino)-azetidin-1-yl)-8-fluoroquinazolin-4-yl)-2,5-dimethyl-piperazin-1-yl)prop-2-en-1-one | D | 590.4 |
| 204 | 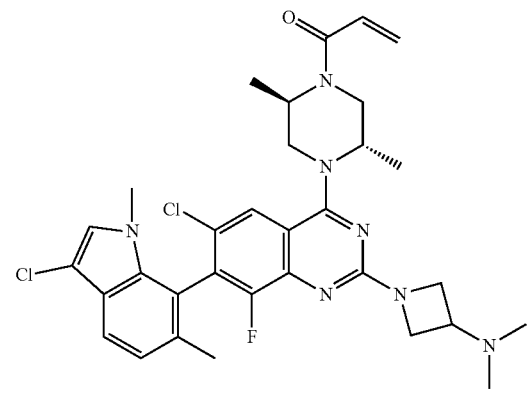 | 1-((2R,5S)-4-(6-chloro-7-(3-chloro-1,6-dimethyl-1H-indol-7-yl)-2-(3-(dimethyl-amino)azetidin-1-yl)-8-fluoroquinazolin-4-yl-2,5-dimethyl-piperazin-1-yl)prop-2-en-1-one | D | 624.3 |
| 205 | 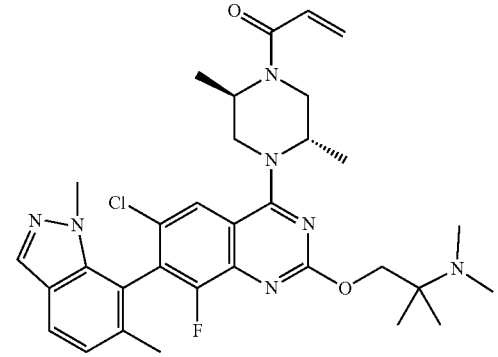 [SMILES: C=CC(=O)N1C[C@H](C)N(c2nc(OCC(C)(C)N(C)C)nc3c(F)c(-c4c(C)ccc5cnn(C)c45)c(Cl)cc23)C[C@H]1C] | 1-((2R,5S)-4-(6-chloro-7-(1,6-dimethyl-1H-indazol-7-yl)-2-(2-(dimethylamino)-2-methylpropoxy)-8-fluoroquinazolin-4-yl)-2,5-dimethyl-piperazin-1-yl)prop-2-en-1-one | D | 608.3 |
| 206 | 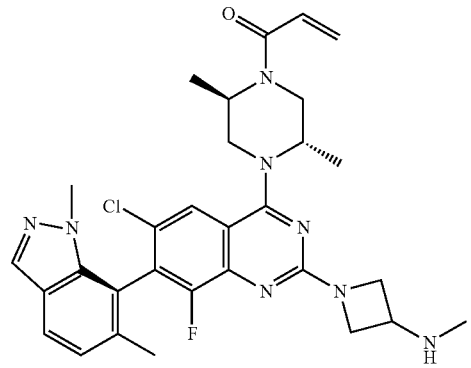 | 1-((2R,5S)-4-((R)-6-chloro-7-(1,6-dimethyl-1H-indazol-7-yl)-8-fluoro-2-(3-(methyl-amino)azetidin-1-yl)-quinazolin-4-yl)-2,5-dimethylpiperazin-1-yl)prop-2-en-1-one | D | 577.5 |

TABLE 1-continued

Representative Compounds

| No. | Structure | Name | Method | [M + H]+ |
|---|---|---|---|---|
| 207 | 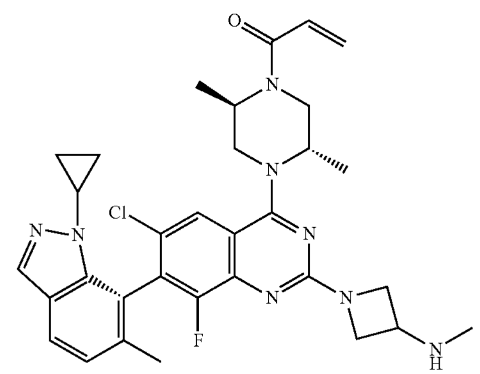 | 1-((2R,5S)-4-((S)-6-chloro-7-(1-cyclopropyl-6-methyl-1H-indazol-7-yl)-8-fluoro-2-(3-(methylamino)azetidin-1-yl)quinazolin-4-yl)-2,5-dimethylpiperazin-1-yl)prop-2-en-1-one | D | 603.3 |
| 208 | 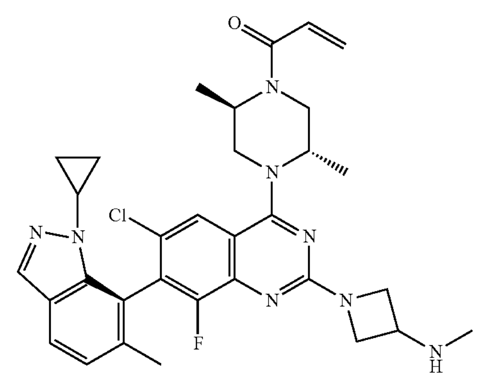 | 1-((2R,5S)-4-((R)-6-chloro-7-(1-cyclopropyl-6-methyl-1H-indazol-7-yl)-8-fluoro-2-(3-(methylamino)azetidin-1-yl)quinazolin-4-yl)-2,5-dimethylpiperazin-1-yl)prop-2-en-1-one | D | 603.3 |
| 209 | 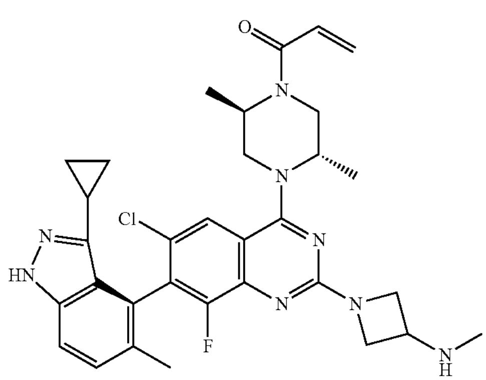 | 1-((2R,5S)-4-((R)-6-chloro-7-(3-cyclopropyl-5-methyl-1H-indazol-4-yl)-8-fluoro-2-(3-(methylamino)azetidin-1-yl)quinazolin-4-yl)-2,5-dimethylpiperazin-1-yl)prop-2-en-1-one | C | 603.3 |
| 210 | 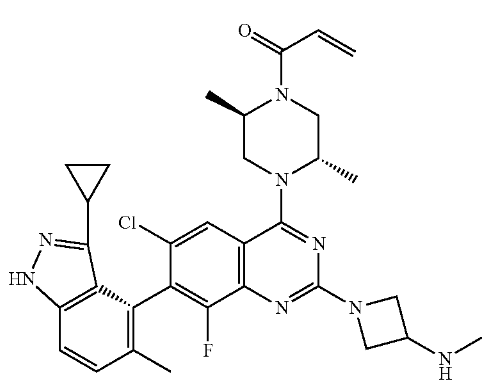 | 1-((2R,5S)-4-((S)-6-chloro-7-(3-cyclopropyl-5-methyl-1H-indazol-4-yl)-8-fluoro-2-(3-(methylamino)azetidin-1-yl)quinazolin-4-yl)-2,5-dimethylpiperazin-1-yl)prop-2-en-1-one | C | 603.3 |

TABLE 1-continued

Representative Compounds

| No. | Structure | Name | Method | [M + H]⁺ |
|---|---|---|---|---|
| 211 | 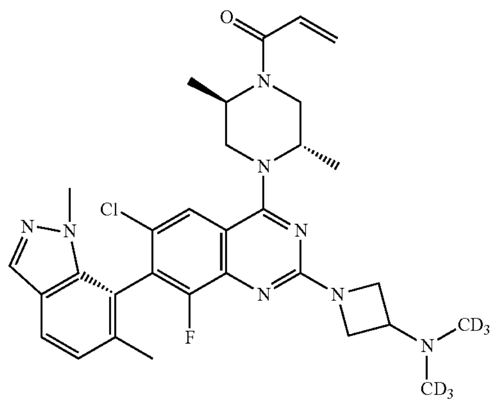 | 1-((2R,5S)-4-((S)-6-chloro-7-(1,6-dimethyl-1H-indazol-7-yl)-2-(3-(diperdeuteromethylamino)azetidin-1-yl)-8-fluoroquinazolin-4-yl)-2,5-dimethylpiperazin-1-yl)prop-2-en-1-one | D | 597.6 |
| 212 | 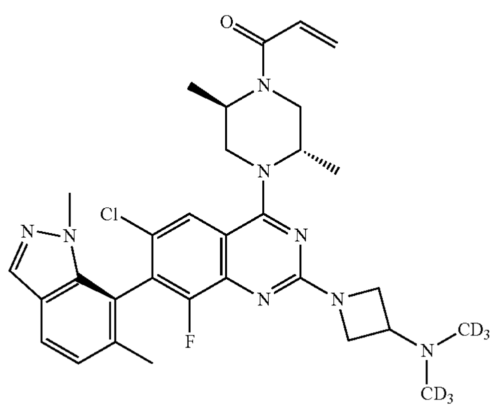 | 1-((2R,5S)-4-((R)-6-chloro-7-(1,6-dimethyl-1H-indazol-7-yl)-2-(3-(diperdeuteromethylamino)azetidin-1-yl)-8-fluoroquinazolin-4-yl)-2,5-dimethylpiperazin-1-yl)prop-2-en-1-one | D | 597.5 |
| 213 | 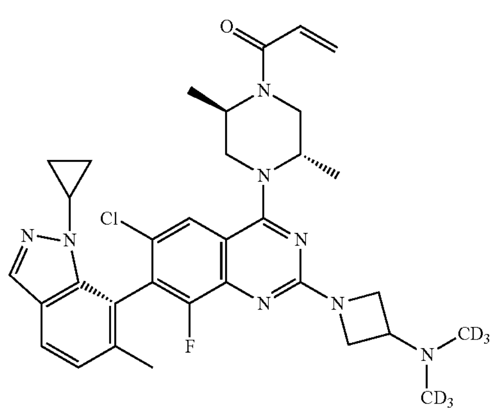 | 1-((2R,5S)-4-((S)-6-chloro-7-(1-cyclopropyl-6-methyl-1H-indazol-7-yl)-2-(3-(diperdeuteromethylamino)azetidin-1-yl)-8-fluoroquinazolin-4-yl)-2,5-dimethylpiperazin-1-yl)prop-2-en-1-one | D | 624.2 |

TABLE 1-continued

Representative Compounds

| No. | Structure | Name | Method | [M + H]+ |
|---|---|---|---|---|
| 214 | 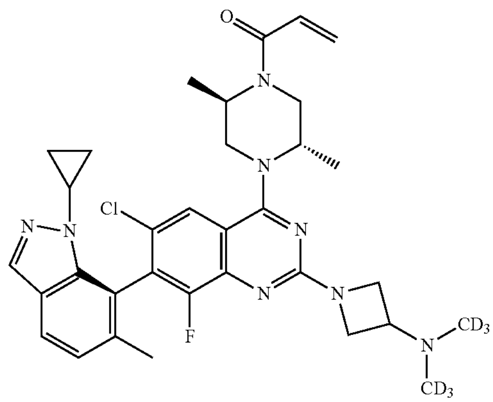 | 1-((2R,5S)-4-((R)-6-chloro-7-(1-cyclopropyl-6-methyl-1H-indazol-7-yl)-2-(3-(diperdeutero-methylamino)azetidin-1-yl)-8-fluoro-quinazolin-4-yl)-2,5-dimethylpiperazin-1-yl)prop-2-en-1-one | D | 624.2 |
| 215 | 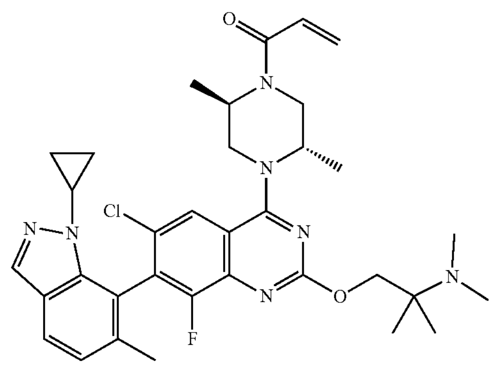 [SMILES: C=CC(=O)N1C[C@H](C)N(c2nc(OCC(C)(C)N(C)C)nc3c(F)c(-c4c(C)ccc5cnn(C6CC6)c45)c(Cl)cc23)C[C@H]1C] | 1-((2R,5S)-4-(6-chloro-7-(1-cyclopropyl-6-methyl-1H-indazol-7-yl)-2-(2-(dimethyl-amino)-2-methyl-propoxy)-8-fluoro-quinazolin-4-yl)-2,5-dimethylpiperazin-1-yl)prop-2-en-1-one | D | 634.5 |
| 216 | 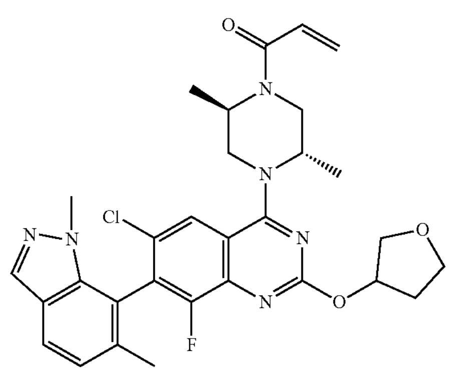 [SMILES: C=CC(=O)N1C[C@H](C)N(c2nc(OC3CCOC3)nc3c(F)c(-c4c(C)ccc5cnn(C)c45)c(Cl)cc23)C[C@H]1C] | 1-((2R,5S)-4-(6-chloro-7-(1,6-dimethyl-1H-indazol-7-yl)-8-fluoro-2-(tetrahydrofuran-3-yloxy)quinazolin-4-yl)-2,5-dimethyl-piperazin-1-yl)prop-2-en-1-one | D | 579.1 |
| 217 | 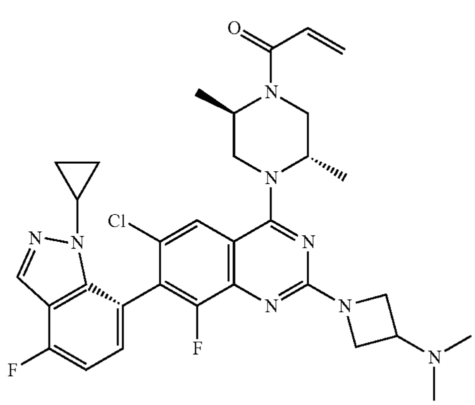 | 1-((2R,5S)-4-((S)-6-chloro-7-(1-cyclo-propyl-4-fluoro-1H-indazol-7-yl)-2-(3-(dimethylamino)-azetidin-1-yl)-8-fluoroquinazolin-4-yl)-2,5-dimethyl-piperazin-1-yl)prop-2-en-1-one | D | 621.5 |

TABLE 1-continued

Representative Compounds

| No. | Structure | Name | Method | [M + H]+ |
|---|---|---|---|---|
| 218 | 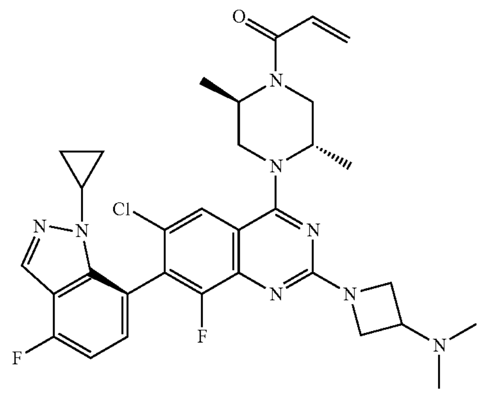 | 1-((2R,5S)-4-((R)-6-chloro-7-(1-cyclopropyl-4-fluoro-1H-indazol-7-yl)-2-(3-(dimethylamino)azetidin-1-yl)-8-fluoroquinazolin-4-yl)-2,5-dimethylpiperazin-1-yl)prop-2-en-1-one | D | 621.4 |
| 219 | 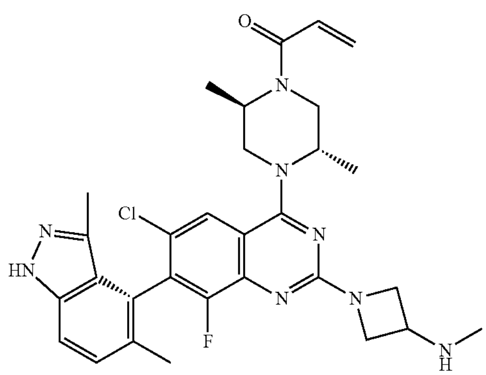 | 1-((2R,5S)-4-((S)-6-chloro-7-(3,5-dimethyl-1H-indazol-4-yl)-8-fluoro-2-(3-(methylamino)azetidin-1-yl)quinazolin-4-yl)-2,5-dimethylpiperazin-1-yl)prop-2-en-1-one | C | 577.3 |
| 220 | 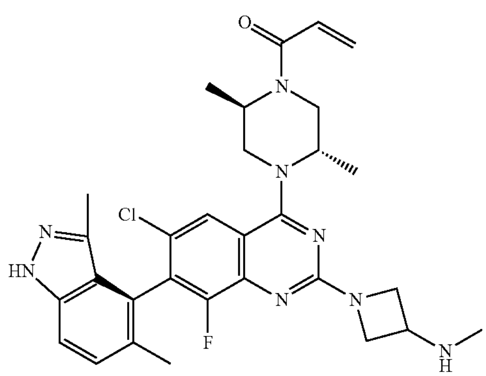 | 1-((2R,5S)-4-((R)-6-chloro-7-(3,5-dimethyl-1H-indazol-4-yl)-8-fluoro-2-(3-(methylamino)azetidin-1-yl)quinazolin-4-yl)-2,5-dimethylpiperazin-1-yl)prop-2-en-1-one | C | 577.3 |
| 221 | 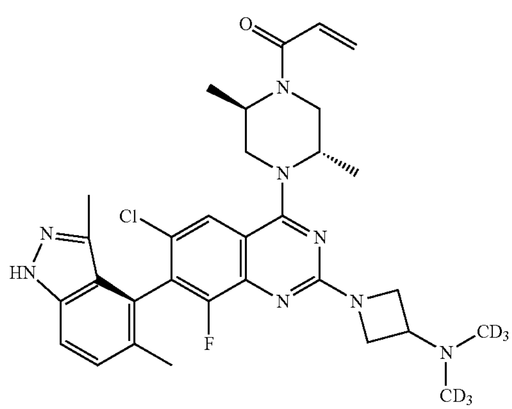 | 1-((2R,5S)-4-((R)-6-chloro-7-(3,5-dimethyl-1H-indazol-4-yl)-2-(3-(diperdeuteromethylamino)azetidin-1-yl)-8-fluoroquinazolin-4-yl)-2,5-dimethylpiperazin-1-yl)prop-2-en-1-one | C | 597.4 |

TABLE 1-continued

Representative Compounds

| No. | Structure | Name | Method | [M + H]+ |
|---|---|---|---|---|
| 222 | 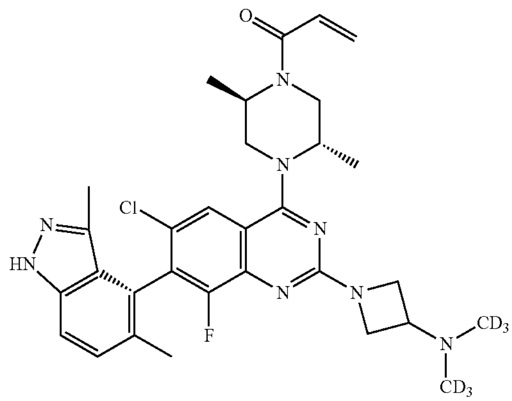 | 1-((2R,5S)-4-((S)-6-chloro-7-(3,5-dimethyl-1H-indazol-4-yl)-2-(3-(diperdeuteromethyl-amino)azetidin-1-yl)-8-fluoroquinazolin-4-yl)-2,5-dimethyl-piperazin-1-yl)prop-2-en-1-one | C | 597.4 |
| 223 | 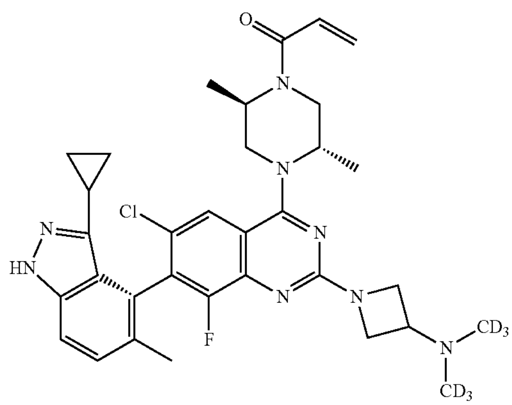 | 1-((2R,5S)-4-((S)-6-chloro-7-(3-cyclo-propyl-5-methyl-1H-indazol-4-yl)-2-(3-(diperdeuteromethyl-amino)azetidin-1-yl)-8-fluoroquinazolin-4-yl)-2,5-dimethyl-piperazin-1-yl)prop-2-en-1-one | C | 623.3 |
| 224 | 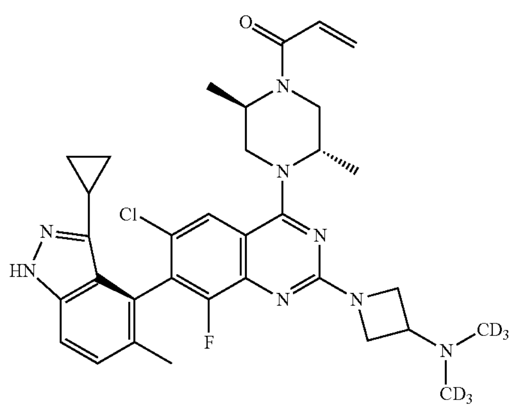 | 1-((2R,5S)-4-((R)-6-chloro-7-(3-cyclo-propyl-5-methyl-1H-indazol-4-yl)-2-(3-(diperdeuteromethyl-amino)azetidin-1-yl)-8-fluoroquinazolin-4-yl)-2,5-dimethyl-piperazin-1-yl)prop-2-en-1-one | C | 623.3 |
| 225 | 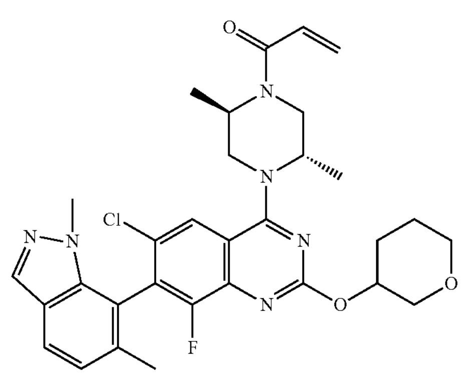 [SMILES: C=CC(=O)N1C[C@H](C)N(c2nc(OC3CCCOC3)nc3c(F)c(-c4c(C)ccc5cnn(C)c45)c(Cl)cc23)C[C@H]1C] | 1-((2R,5S)-4-(6-chloro-7-(1,6-dimethyl-1H-indazol-7-yl)-8-fluoro-2-(tetrahydro-2H-pyran-3-yloxy)-quinazolin-4-yl)-2,5-dimethylpiperazin-1-yl)prop-2-en-1-one | D | 593.3 |

TABLE 1-continued

Representative Compounds

| No. | Structure | Name | Method | [M + H]+ |
|---|---|---|---|---|
| 226 | 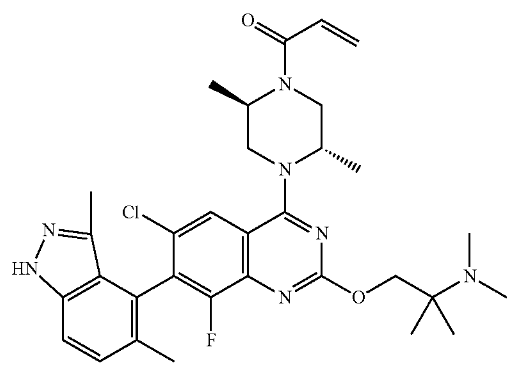 [SMILES: C=CC(=O)N1C[C@H](C)N(c2nc(OCC(C)(C)N(C)C)nc3c(F)c(-c4c(C)ccc5[nH]nc(C)c45)c(Cl)cc23)C[C@H]1C] | 1-((2R,5S)-4-(6-chloro-7-(3,5-dimethyl-1H-indazol-4-yl)-2-(2-(dimethylamino)-2-methylpropoxy)-8-fluoroquinazolin-4-yl)-2,5-dimethyl-piperazin-1-yl)prop-2-en-1-one | C | 610.4 |
| 227 | 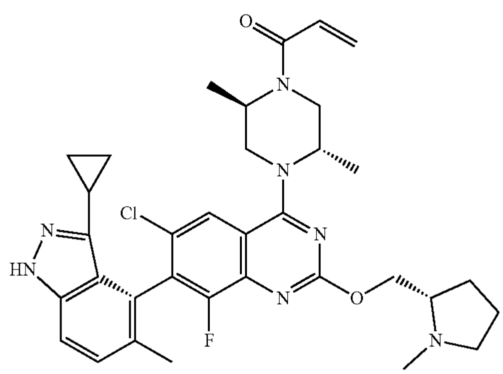 | 1-((2R,5S)-4-((S)-6-chloro-7-(3-cyclo-propyl-5-methyl-1H-indazol-4-yl)-8-fluoro-2-(((S)-1-methylpyrrolidin-2-yl)methoxy)quinazolin-4-yl)-2,5-dimethyl-piperazin-1-yl)prop-2-en-1-one | C | 632.4 |
| 228 | 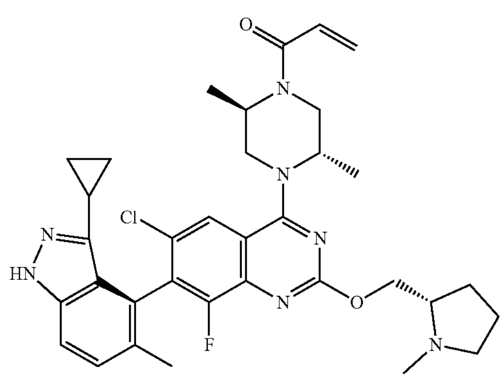 | 1-((2R,5S)-4-((R)-6-chloro-7-(3-cyclo-propyl-5-methyl-1H-indazol-4-yl)-8-fluoro-2-(((S)-1-methyl-pyrrolidin-2-yl)-methoxy)quinazolin-4-yl)-2,5-dimethyl-piperazin-1-yl)prop-2-en-1-one | C | 632.4 |
| 229 | 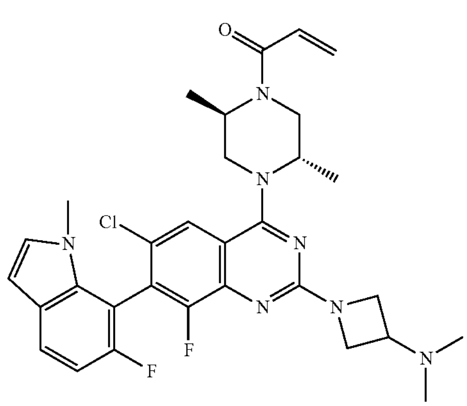 | 1-((2R,5S)-4-(6-chloro-2-(3-(dimethylamino)-azetidin-1-yl)-8-fluoro-7-(6-fluoro-1-methyl-1H-indol-7-yl)-quinazolin-4-yl)-2,5-dimethylpiperazin-1-yl)prop-2-en-1-one | D | 594.4 |

TABLE 1-continued

Representative Compounds

| No. | Structure | Name | Method | [M + H]+ |
|---|---|---|---|---|
| 230 | 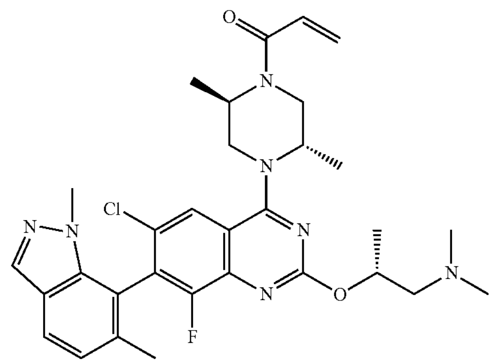 [SMILES: C=CC(=O)N1C[C@H](C)N(c2nc(O[C@H](C)CN(C)C)nc3c(F)c(-c4c(C)ccc5cnn(C)c45)c(Cl)cc23)C[C@H]1C] | 1-((2R,5S)-4-(6-chloro-7-(1,6-dimethyl-1H-indazol-7-yl)-2-((R)-1-(dimethylamino)-propan-2-yloxy)-8-fluoroquinazolin-4-yl)-2,5-dimethyl-piperazin-1-yl)prop-2-en-1-one | D | 594.6 |
| 231 | 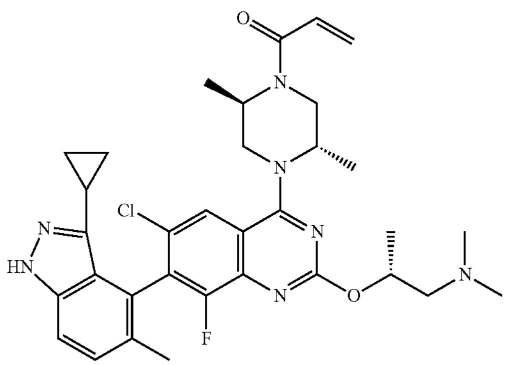 [SMILES: C=CC(=O)N1C[C@H](C)N(c2nc(O[C@H](C)CN(C)C)nc3c(F)c(-c4c(C)ccc5[nH]nc(C6CC6)c45)c(Cl)cc23)C[C@H]1C] | 1-((2R,5S)-4-(6-chloro-7-(3-cyclopropyl-5-methyl-1H-indazol-4-yl)-2-((R)-1-(dimethylamino)propan-2-yloxy)-8-fluoroquinazolin-4-yl)-2,5-dimethyl-piperazin-1-yl)prop-2-en-1-one | C | 620.4 |
| 232 | 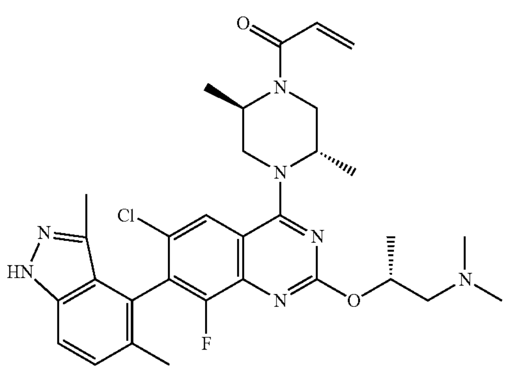 [SMILES: C=CC(=O)N1C[C@H](C)N(c2nc(O[C@H](C)CN(C)C)nc3c(F)c(-c4c(C)ccc5[nH]nc(C)c45)c(Cl)cc23)C[C@H]1C] | 1-((2R,5S)-4-(6-chloro-7-(3,5-dimethyl-1H-indazol-4-yl)-2-((R)-1-(dimethylamino)-propan-2-yloxy)-8-fluoroquinazolin-4-yl)-2,5-dimethyl-piperazin-1-yl)prop-2-en-1-one | C | 594.5 |
| 233 | 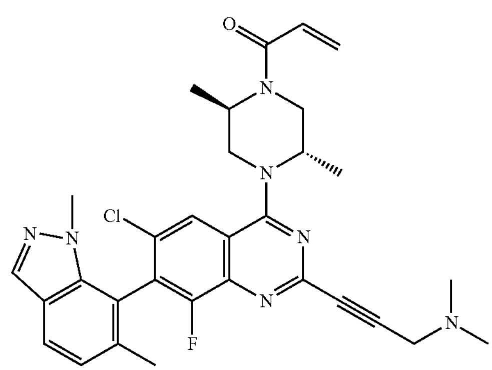 [SMILES: C=CC(=O)N1C[C@H](C)N(c2nc(C#CCN(C)C)nc3c(F)c(-c4c(C)ccc5cnn(C)c45)c(Cl)cc23)C[C@H]1C] | 1-((2R,5S)-4-(6-chloro-7-(1,6-dimethyl-1H-indazol-7-yl)-2-(3-(dimethylamino)prop-1-ynyl)-8-fluoro-quinazolin-4-yl)-2,5-dimethylpiperazin-1-yl)prop-2-en-1-one | D | 574.5 |

TABLE 1-continued

Representative Compounds

| No. | Structure | Name | Method | [M + H]+ |
|---|---|---|---|---|
| 234 | 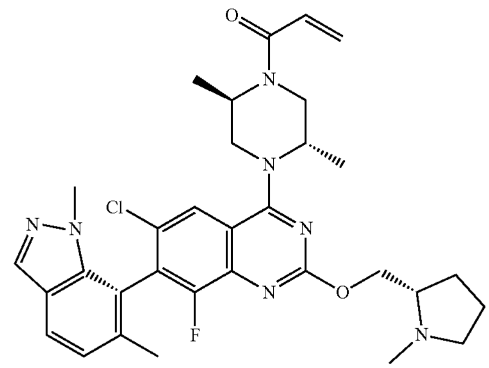 | 1-((2R,5S)-4-((S)-6-chloro-7-(1,6-dimethyl-1H-indazol-7-yl)-8-fluoro-2-(((S)-1-methylpyrrolidin-2-yl)methoxy)quinazolin-4-yl)-2,5-dimethyl-piperazin-1-yl)prop-2-en-1-one | D | 606.5 |
| 235 | 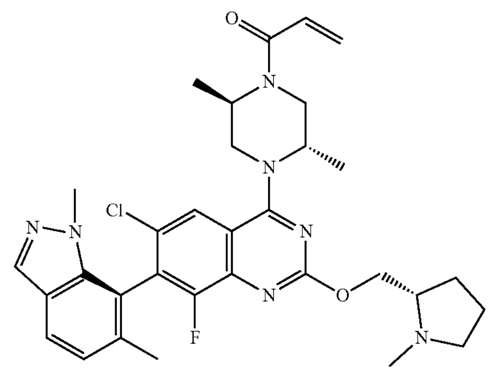 | 1-((2R,5S)-4-((R)-6-chloro-7-(1,6-dimethyl-1H-indazol-7-yl)-8-fluoro-2-(((S)-1-methylpyrrolidin-2-yl)methoxy)quinazolin-4-yl)-2,5-dimethyl-piperazin-1-yl)prop-2-en-1-one | D | 606.5 |
| 236 | 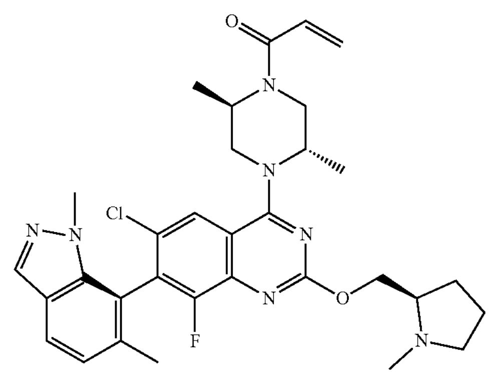 | 1-((2R,5S)-4-((R)-6-chloro-7-(1,6-dimethyl-1H-indazol-7-yl)-8-fluoro-2-(((R)-1-methylpyrrolidin-2-yl)methoxy)quinazolin-4-yl)-2,5-dimethyl-piperazin-1-yl)prop-2-en-1-one | D | 606.5 |
| 237 | 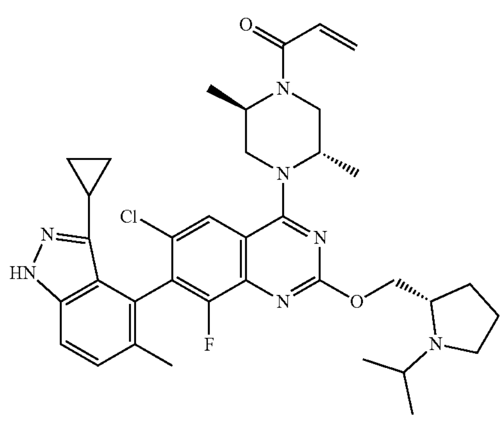 [SMILES: C=CC(=O)N1C[C@H](C)N(c2nc(OC[C@@H]3CCCN3C(C)C)nc3c(F)c(-c4c(C)ccc5[nH]nc(C6CC6)c45)c(Cl)cc23)C[C@H]1C] | 1-((2R,5S)-4-(6-chloro-7-(3-cyclopropyl-5-methyl-1H-indazol-4-yl)-8-fluoro-2-(((S)-1-isopropylpyrrolidin-2-yl)methoxy)quinazolin-4-yl)-2,5-dimethyl-piperazin-1-yl)prop-2-en-1-one | C | 660.6 |

TABLE 1-continued

Representative Compounds

| No. | Structure | Name | Method | [M + H]+ |
|---|---|---|---|---|
| 238 | 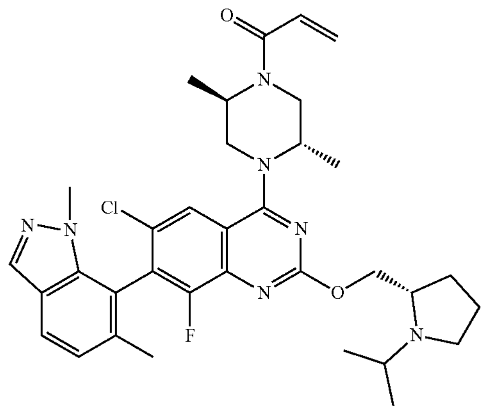 [SMILES: C=CC(=O)N1C[C@H](C)N(c2nc(OC[C@@H]3CCCN3C(C)C)nc3c(F)c(-c4c(C)ccc5cnn(C)c45)c(Cl)cc23)C[C@H]1C] | 1-((2R,5S)-4-(6-chloro-7-(1,6-dimethyl-1H-indazol-7-yl)-8-fluoro-2-(((S)-1-isopropylpyrrolidin-2-yl)methoxy)quinazolin-4-yl)-2,5-dimethyl-piperazin-1-yl)prop-2-en-1-one | D | 634.5 |
| 239 | 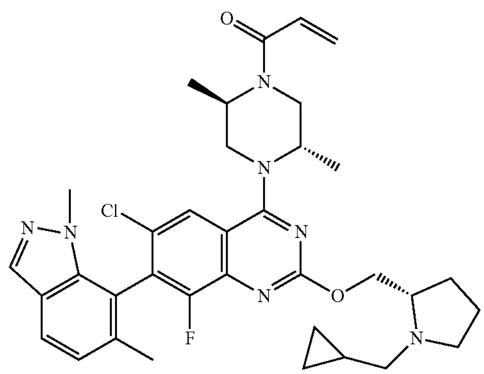 [SMILES: C=CC(=O)N1C[C@H](C)N(c2nc(OC[C@@H]3CCCN3CC3CC3)nc3c(F)c(-c4c(C)ccc5cnn(C)c45)c(Cl)cc23)C[C@H]1C] | 1-((2R,5S)-4-(6-chloro-2-(((S)-1-(cyclopropyl-methyl)pyrrolidin-2-yl)methoxy)-7-(1,6-dimethyl-1H-indazol-7-yl)-8-fluoro-quinazolin-4-yl)-2,5-dimethylpiperazin-1-yl)prop-2-en-1-one | D | 646.5 |
| 240 | 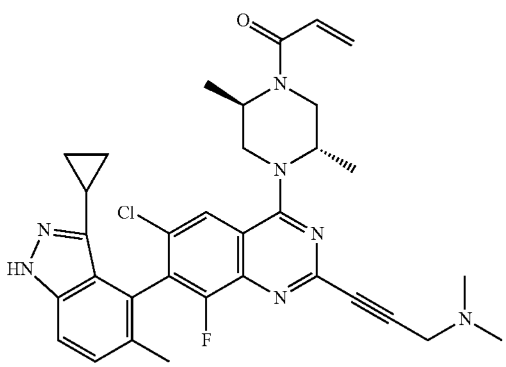 [SMILES: C=CC(=O)N1C[C@H](C)N(c2nc(C#CCN(C)C)nc3c(F)c(-c4c(C)ccc5[nH]nc(C6CC6)c45)c(Cl)cc23)C[C@H]1C] | 1-((2R,5S)-4-(6-chloro-7-(3-cyclopropyl-5-methyl-1H-indazol-4-yl)-2-(3-(dimethyl-amino)prop-1-ynyl)-8-fluoroquinazolin-4-yl)-2,5-dimethyl-piperazin-1-yl)prop-2-en-1-one | C | 600.5 |
| 241 | 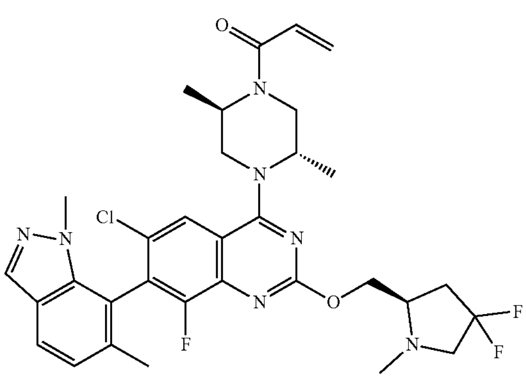 [SMILES: C=CC(=O)N1C[C@H](C)N(c2nc(OC[C@H]3CC(F)(F)CN3C)nc3c(F)c(-c4c(C)ccc5cnn(C)c45)c(Cl)cc23)C[C@H]1C] | 1-((2R,5S)-4-(6-chloro-2-(((R)-4,4-difluoro-1-methylpyrrolidin-2-yl)methoxy)-7-(1,6-dimethyl-1H-indazol-7-yl)-8-fluoro-quinazolin-4-yl)-2,5-dimethylpiperazin-1-yl)prop-2-en-1-one | D | 642.2 |

TABLE 1-continued

Representative Compounds

| No. | Structure | Name | Method | [M + H]+ |
|---|---|---|---|---|
| 242 | 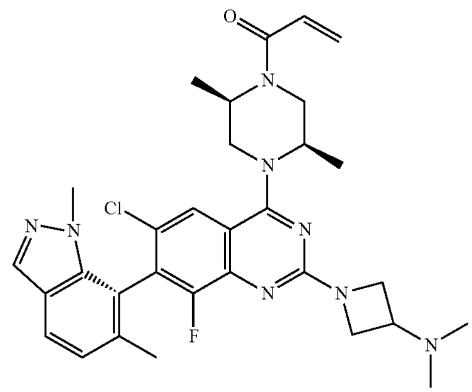 | 1-((2R,5R)-4-((S)-6-chloro-7-(1,6-dimethyl-1H-indazol-7-yl)-2-(3-(dimethylamino)-azetidin-1-yl)-8-fluoroquinazolin-4-yl)-2,5-dimethyl-piperazin-1-yl)prop-2-en-1-one | D | 591.5 |
| 243 | 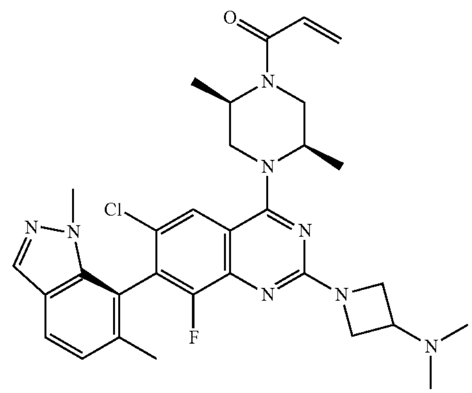 | 1-((2R,5R)-4-((R)-6-chloro-7-(1,6-dimethyl-1H-indazol-7-yl)-2-(3-(dimethylamino)-azetidin-1-yl)-8-fluoroquinazolin-4-yl)-2,5-dimethyl-piperazin-1-yl)prop-2-en-1-one | D | 591.5 |
| 244 | 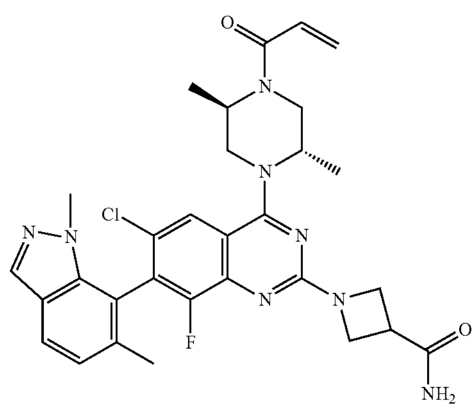 [SMILES: C=CC(=O)N1C[C@H](C)N(c2nc(N3CC(C(N)=O)C3)nc3c(F)c(-c4c(C)ccc5cnn(C)c45)c(Cl)cc23)C[C@H]1C] | 1-(4-((2S,5R)-4-acryloyl-2,5-dimethyl-piperazin-1-yl)-6-chloro-7-(1,6-dimethyl-1H-indazol-7-yl)-8-fluoroquinazolin-2-yl)azetidine-3-carboxamide | D | 591.4 |
| 245 | 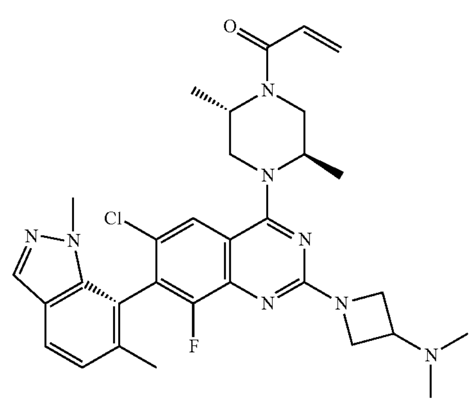 | 1-((2S,5R)-4-((S)-6-chloro-7-(1,6-dimethyl-1H-indazol-7-yl)-2-(3-(dimethylamino)-azetidin-1-yl)-8-fluoroquinazolin-4-yl)-2,5-dimethyl-piperazin-1-yl)prop-2-en-1-one | D | 591.6 |

TABLE 1-continued

Representative Compounds

| No. | Structure | Name | Method | [M + H]+ |
|---|---|---|---|---|
| 246 | 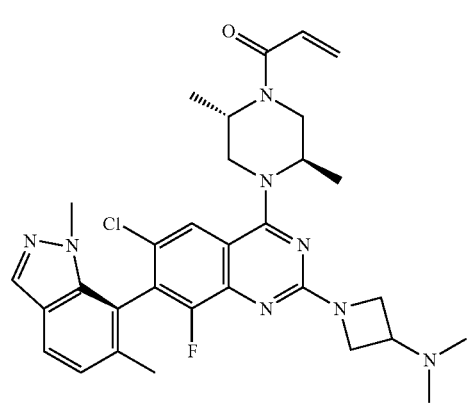 | 1-((2S,5R)-4-((R)-6-chloro-7-(1,6-dimethyl-1H-indazol-7-yl)-2-(3-(dimethylamino)-azetidin-1-yl)-8-fluoroquinazolin-4-yl)-2,5-dimethyl-piperazin-1-yl)prop-2-en-1-one | D | 591.6 |
| 247 | 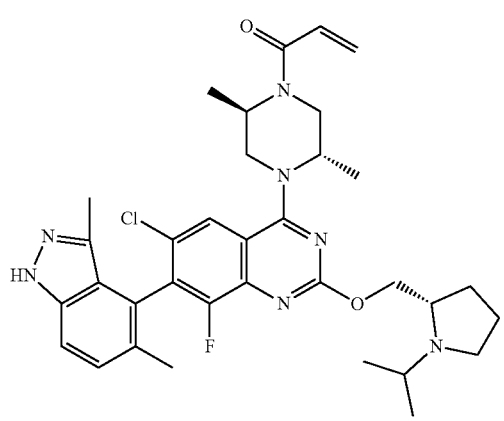 [SMILES: C=CC(=O)N1C[C@H](C)N(c2nc(OC[C@@H]3CCCN3C(C)C)nc3c(F)c(-c4c(C)ccc5[nH]nc(C)c45)c(Cl)cc23)C[C@H]1C] | 1-((2R,5S)-4-(6-chloro-7-(3,5-dimethyl-1H-indazol-4-yl)-8-fluoro-2-(((S)-1-isopropyl-pyrrolidin-2-yl)-methoxy)quinazolin-4-yl)-2,5-dimethyl-piperazin-1-yl)prop-2-en-1-one | C | 634.5 |
| 248 | 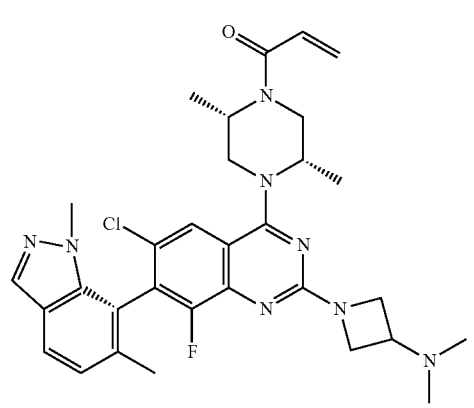 | 1-((2S,5S)-4-((S)-6-chloro-7-(1,6-dimethyl-1H-indazol-7-yl)-2-(3-(dimethylamino)-azetidin-1-yl)-8-fluoroquinazolin-4-yl)-2,5-dimethyl-piperazin-1-yl)prop-2-en-1-one | D | 591.5 |

TABLE 1-continued

Representative Compounds

| No. | Structure | Name | Method | [M + H]+ |
|---|---|---|---|---|
| 249 | 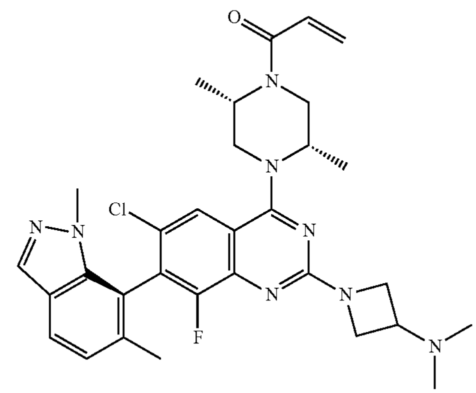 | 1-((2S,5S)-4-((R)-6-chloro-7-(1,6-dimethyl-1H-indazol-7-yl)-2-(3-(dimethylamino)-azetidin-1-yl)-8-fluoroquinazolin-4-yl)-2,5-dimethyl-piperazin-1-yl)prop-2-en-1-one | D | 591.5 |
| 250 | 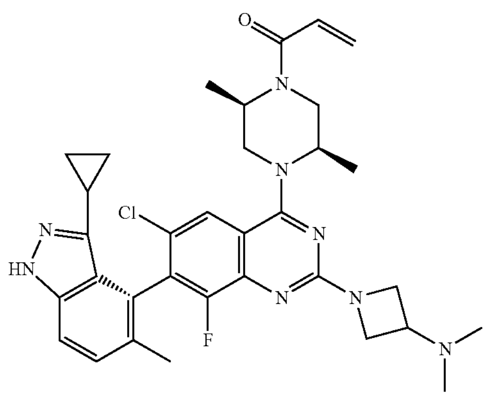 | 1-((2R,5R)-4-((S)-6-chloro-7-(3-cyclopropyl-5-methyl-1H-indazol-4-yl)-2-(3-(dimethyl-amino)azetidin-1-yl)-8-fluoroquinazolin-4-yl)-2,5-dimethyl-piperazin-1-yl)prop-2-en-1-one | C | 617.4 |
| 251 | 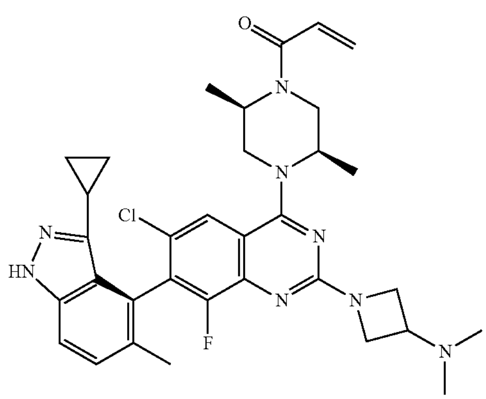 | 1-((2R,5R)-4-((R)-6-chloro-7-(3-cyclo-propyl-5-methyl-1H-indazol-4-yl)-2-(3-(dimethylamino)-azetidin-1-yl)-8-fluoroquinazolin-4-yl)-2,5-dimethyl-piperazin-1-yl)prop-2-en-1-one | C | 617.4 |
| 252 | 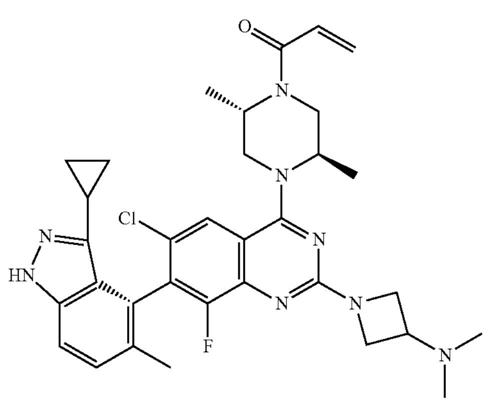 | 1-((2S,5R)-4-((S)-6-chloro-7-(3-cyclo-propyl-5-methyl-1H-indazol-4-yl)-2-(3-(dimethylamino)-azetidin-1-yl)-8-fluoroquinazolin-4-yl)-2,5-dimethyl-piperazin-1-yl)prop-2-en-1-one | C | 617.4 |

TABLE 1-continued

Representative Compounds

| No. | Structure | Name | Method | [M + H]+ |
|---|---|---|---|---|
| 253 | 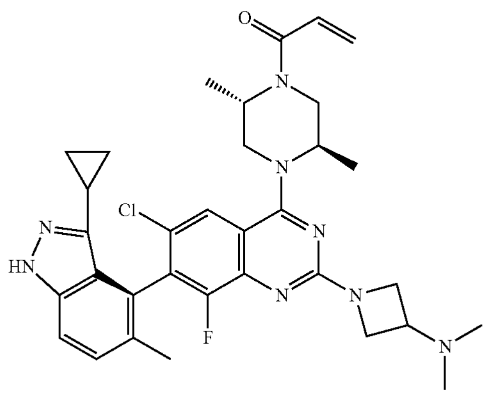 | 1-((2S,5R)-4-((R)-6-chloro-7-(3-cyclopropyl-5-methyl-1H-indazol-4-yl)-2-(3-(dimethylamino)-azetidin-1-yl)-8-fluoroquinazolin-4-yl)-2,5-dimethyl-piperazin-1-yl)prop-2-en-1-one | C | 617.4 |
| 254 | 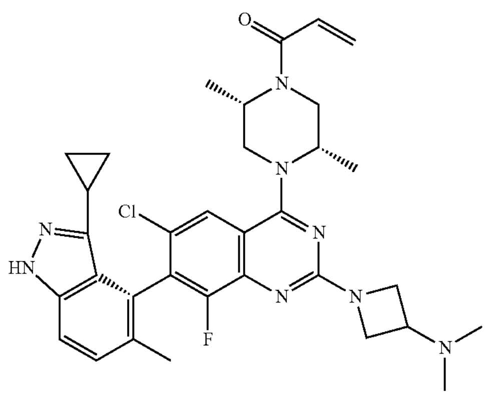 | 1-((2S,5S)-4-((S)-6-chloro-7-(3-cyclopropyl-5-methyl-1H-indazol-4-yl)-2-(3-(dimethylamino)-azetidin-1-yl)-8-fluoroquinazolin-4-yl)-2,5-dimethylpiperazin-1-yl)prop-2-en-1-one | C | 617.5 |
| 255 | 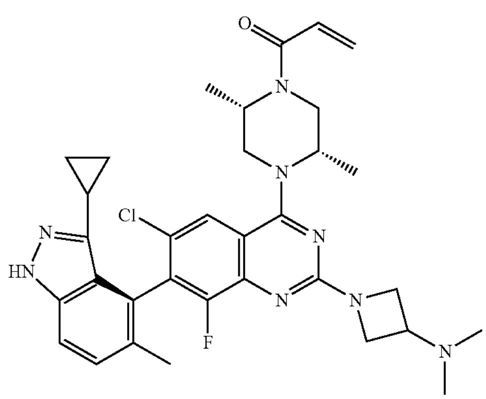 | 1-((2S,5S)-4-((R)-6-chloro-7-(3-cyclopropyl-5-methyl-1H-indazol-4-yl)-2-(3-(dimethylamino)-azetidin-1-yl)-8-fluoroquinazolin-4-yl)-2,5-dimethyl-piperazin-1-yl)prop-2-en-1-one | C | 617.5 |
| 256 | 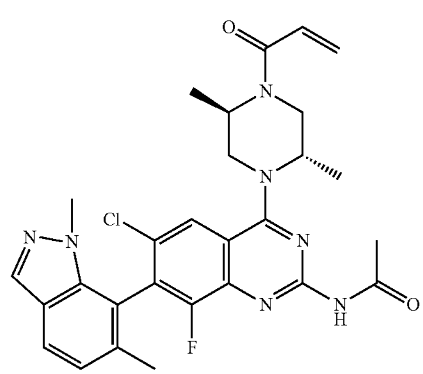 [SMILES: C=CC(=O)N1C[C@H](C)N(c2nc(NC(C)=O)nc3c(F)c(-c4c(C)ccc5cnn(C)c45)c(Cl)cc23)C[C@H]1C] | N-(4-((2S,5R)-4-acryloyl-2,5-dimethyl-piperazin-1-yl)-6-chloro-7-(1,6-dimethyl-1H-indazol-7-yl)-8-fluoroquinazolin-2-yl)acetamide | D | 550.4 |

| No. | Structure | Name | Method | [M + H]+ |
|---|---|---|---|---|
| 257 | 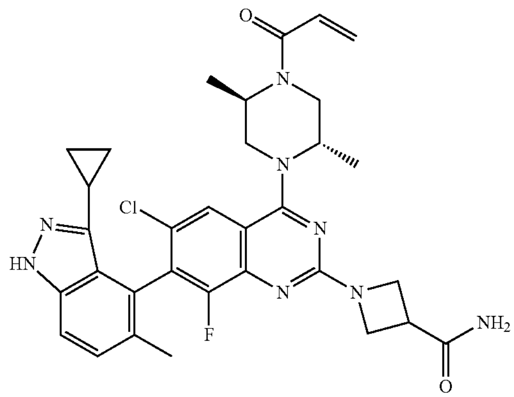 [SMILES: C=CC(=O)N1C[C@H](C)N(c2nc(N3CC(C(N)=O)C3)nc3c(F)c(-c4c(C)ccc5[nH]nc(C6CC6)c45)c(Cl)cc23)C[C@H]1C] | 1-(4-((2S,5R)-4-acryloyl-2,5-dimethyl-piperazin-1-yl)-6-chloro-7-(3-cyclopropyl-5-methyl-1H-indazol-4-yl)-8-fluoroquinazolin-2-yl)-azetidine-3-carboxamide | C | 617.4 |
| 258 | 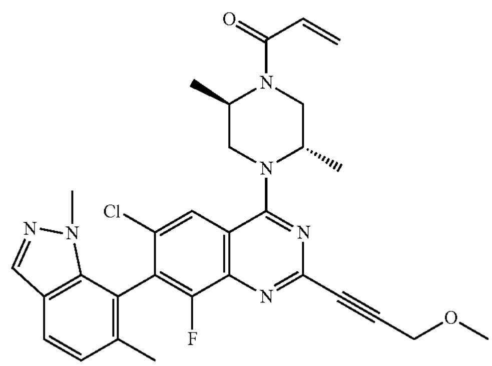 [SMILES: C=CC(=O)N1C[C@H](C)N(c2nc(C#CCOC)nc3c(F)c(-c4c(C)ccc5cnn(C)c45)c(Cl)cc23)C[C@H]1C] | 1-((2R,5S)-4-(6-chloro-7-(1,6-dimethyl-1H-indazol-7-yl)-8-fluoro-2-(3-methoxyprop-1-ynyl)quinazolin-4-yl)-2,5-dimethylpiperazin-1-yl)prop-2-en-1-one | D | 561.4 |
| 259 | 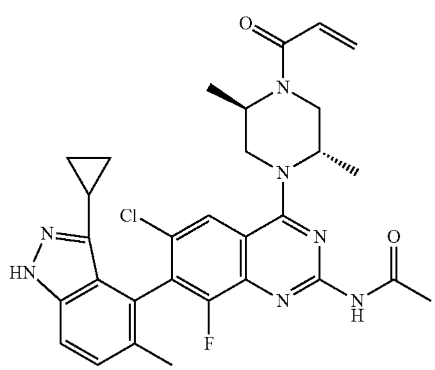 [SMILES: C=CC(=O)N1C[C@H](C)N(c2nc(NC(C)=O)nc3c(F)c(-c4c(C)ccc5[nH]nc(C6CC6)c45)c(Cl)cc23)C[C@H]1C] | N-(4-((2S,5R)-4-acryloyl-2,5-dimethyl-piperazin-1-yl)-6-chloro-7-(3-cyclopropyl-5-methyl-1H-indazol-4-yl)-8-fluoroquinazolin-2-yl)acetamide | C | 576.4 |
| 260 | 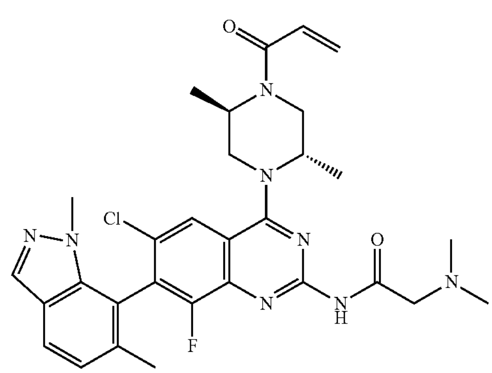 [SMILES: C=CC(=O)N1C[C@H](C)N(c2nc(NC(=O)CN(C)C)nc3c(F)c(-c4c(C)ccc5cnn(C)c45)c(Cl)cc23)C[C@H]1C] | N-(4-((2S,5R)-4-acryloyl-2,5-dimethyl-piperazin-1-yl)-6-chloro-7-(1,6-dimethyl-1H-indazol-7-yl)-8-fluoro-quinazolin-2-yl)-2-(dimethylamino)-acetamide | D | 595.3 |

TABLE 1-continued

Representative Compounds

| No. | Structure | Name | Method | [M + H]+ |
|---|---|---|---|---|
| 261 | 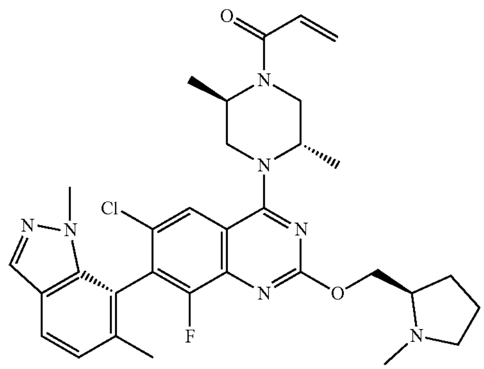 | 1-((2R,5S)-4-((S)-6-chloro-7-(1,6-dimethyl-1H-indazol-7-yl)-8-fluoro-2-(((R)-1-methylpyrrolidin-2-yl)methoxy)quinazolin-4-yl)-2,5-dimethyl-piperazin-1-yl)prop-2-en-1-one | D | 606.5 |
| 262 | 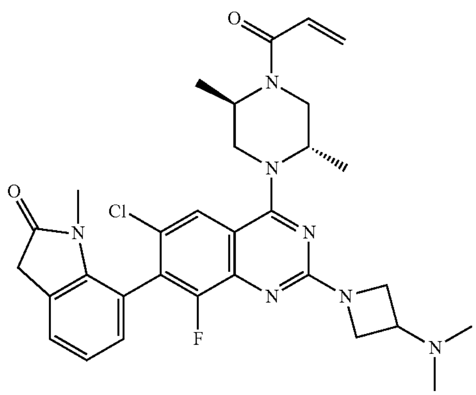 [SMILES: C=CC(=O)N1C[C@H](C)N(c2nc(N3CC(N(C)C)C3)nc3c(F)c(-c4cccc5c4N(C)C(=O)C5)c(Cl)cc23)C[C@H]1C] | 7-(4-((2S,5R)-4-acryloyl-2,5-dimethyl-piperazin-1-yl)-6-chloro-2-(3-(dimethyl-amino)azetidin-1-yl)-8-fluoroquinazolin-7-yl)-1-methylindolin-2-one | A | 592.2 |
| 263 | 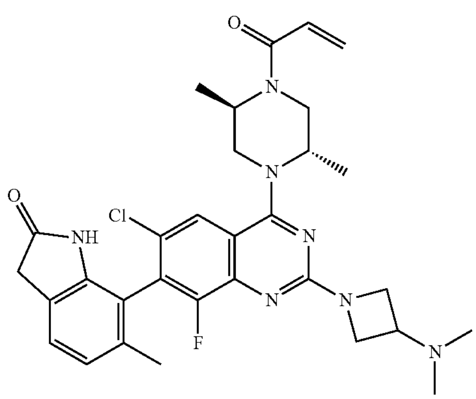 [SMILES: C=CC(=O)N1C[C@H](C)N(c2nc(N3CC(N(C)C)C3)nc3c(F)c(-c4c(C)ccc5c4NC(=O)C5)c(Cl)cc23)C[C@H]1C] | 7-(4-((2S,5R)-4-acryloyl-2,5-dimethyl-piperazin-1-yl)-6-chloro-2-(3-(dimethyl-amino)azetidin-1-yl)-8-fluoroquinazolin-7-yl)-6-methylindolin-2-one | A | 592.5 |
| 264 | 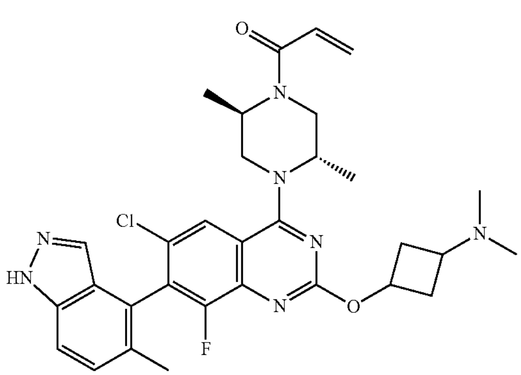 [SMILES: C=CC(=O)N1C[C@H](C)N(c2nc(OC3CC(N(C)C)C3)nc3c(F)c(-c4c(C)ccc5[nH]ncc45)c(Cl)cc23)C[C@H]1C] | 1-((2R,5S)-4-(6-chloro-2-(3-(dimethylamino)-cyclobutoxy)-8-fluoro-7-(5-methyl-1H-indazol-4-yl)quinazolin-4-yl)-2,5-dimethylpiperazin-1-yl)prop-2-en-1-one | A | 592.2 |

TABLE 1-continued

Representative Compounds

| No. | Structure | Name | Method | [M + H]+ |
|---|---|---|---|---|
| 265 | 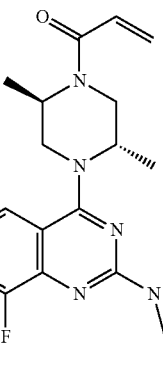 | 1-((2R,5S)-4-(6-chloro-7-(3,4-dihydroquinolin-1(2H)-yl)-2-(3-(dimethylamino)-azetidin-1-yl)-8-fluoro-quinazolin-4-yl)-2,5-dimethylpiperazin-1-yl)prop-2-en-1-one | A | 578.3 |
| 266 | 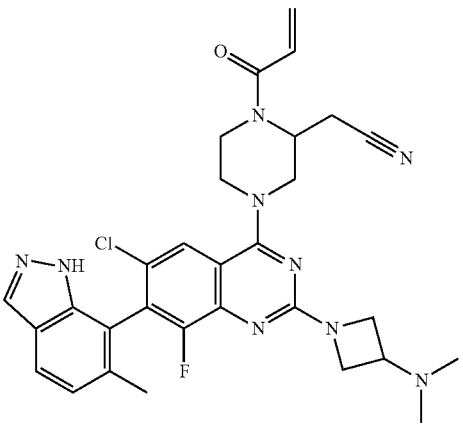 [SMILES: C=CC(=O)N1CCN(c2nc(N3CC(N(C)C)C3)nc3c(F)c(-c4c(C)ccc5cn[nH]c45)c(Cl)cc23)CC1CC#N] | 2-(1-acryloyl-4-(6-chloro-2-(3-(dimethyl-amino)azetidin-1-yl)-8-fluoro-7-(6-methyl-1H-indazol-7-yl)quinazolin-4-yl)piperazin-2-yl)-acetonitrile | A | 588.4 |
| 267 | 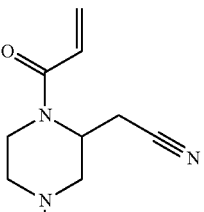 | 2-(1-acryloyl-4-(6-chloro-2-(3-(dimethyl-amino)azetidin-1-yl)-8-fluoro-7-(5-methyl-1H-indazol-4-yl)-quinazolin-4-yl)-piperazin-2-yl)-acetonitrile | A | 588.4 |

TABLE 1-continued

Representative Compounds

| No. | Structure | Name | Method | [M + H]+ |
|---|---|---|---|---|
| 268 | 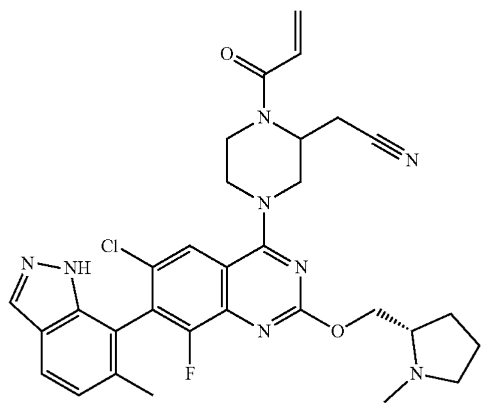 [SMILES: C=CC(=O)N1CCN(c2nc(OC[C@@H]3CCCN3C)nc3c(F)c(-c4c(C)ccc5cn[nH]c45)c(Cl)cc23)CC1CC#N] | 2-(1-acryloyl-4-(6-chloro-8-fluoro-7-(6-methyl-1H-indazol-7-yl)-2-(((S)-1-methyl-pyrrolidin-2-yl)-methoxy)quinazolin-4-yl)piperazin-2-yl)-acetonitrile | A | 603.4 |
| 269 | 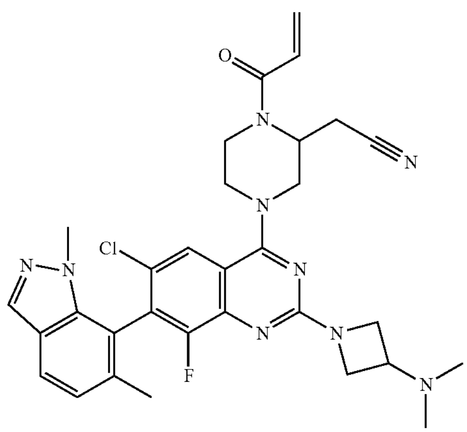 [SMILES: C=CC(=O)N1CCN(c2nc(N3CC(N(C)C)C3)nc3c(F)c(-c4c(C)ccc5cnn(C)c45)c(Cl)cc23)CC1CC#N] | 2-(1-acryloyl-4-(6-chloro-7-(1,6-dimethyl-1H-indazol-7-yl)-2-(3-(dimethylamino)azetidin-1-yl)-8-fluoroquinazolin-4-yl)piperazin-2-yl)-acetonitrile | A | 602.4 |
| 270 | 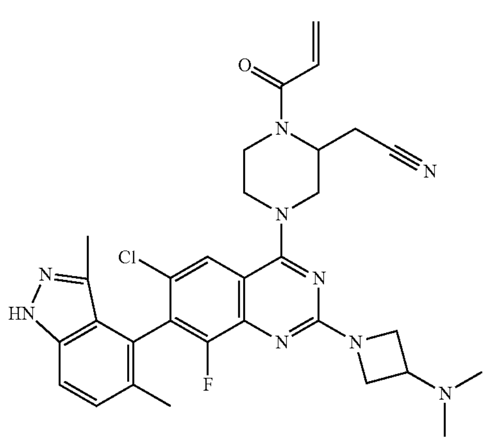 [SMILES: C=CC(=O)N1CCN(c2nc(N3CC(N(C)C)C3)nc3c(F)c(-c4c(C)ccc5[nH]nc(C)c45)c(Cl)cc23)CC1CC#N] | 2-(1-acryloyl-4-(6-chloro-7-(3,5-dimethyl-1H-indazol-4-yl)-2-(3-(dimethylamino)-azetidin-1-yl)-8-fluoroquinazolin-4-yl)piperazin-2-yl)-acetonitrile | A | 602.5 |

TABLE 1-continued

Representative Compounds

| No. | Structure | Name | Method | [M + H]+ |
|---|---|---|---|---|
| 271 | 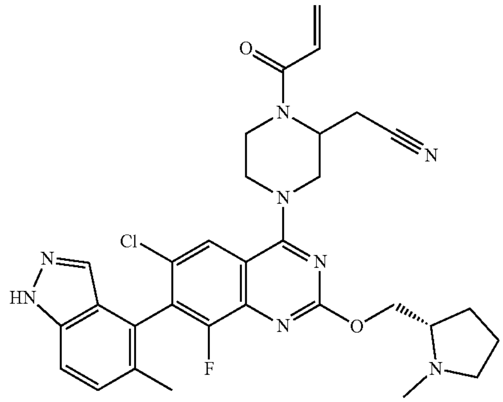 [SMILES: C=CC(=O)N1CCN(c2nc(OC[C@@H]3CCCN3C)nc3c(F)c(-c4c(C)ccc5[nH]ncc45)c(Cl)cc23)CC1CC#N] | 2-(1-acryloyl-4-(6-chloro-8-fluoro-7-(5-methyl-1H-indazol-4-yl)-2-(((S)-1-methylpyrrolidin-2-yl)methoxy)quinazolin-4-yl)piperazin-2-yl)-acetonitrile | A | 603.5 |
| 272 | 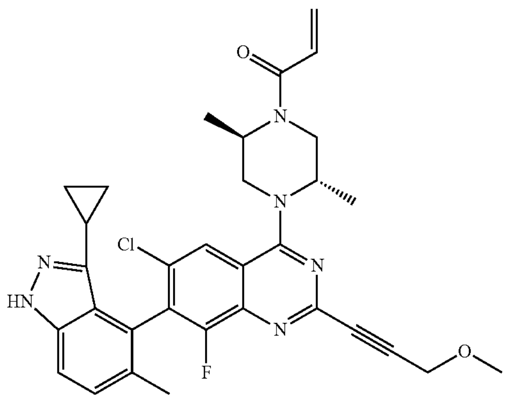 [SMILES: C=CC(=O)N1C[C@H](C)N(c2nc(C#CCOC)nc3c(F)c(-c4c(C)ccc5[nH]nc(C6CC6)c45)c(Cl)cc23)C[C@H]1C] | 1-((2R,5S)-4-(6-chloro-7-(3-cyclopropyl-5-methyl-1H-indazol-4-yl)-8-fluoro-2-(3-methoxyprop-1-yn-1-yl)quinazolin-4-yl)-2,5-dimethylpiperazin-1-yl)prop-2-en-1-one | C | 587.4 |
| 273 | 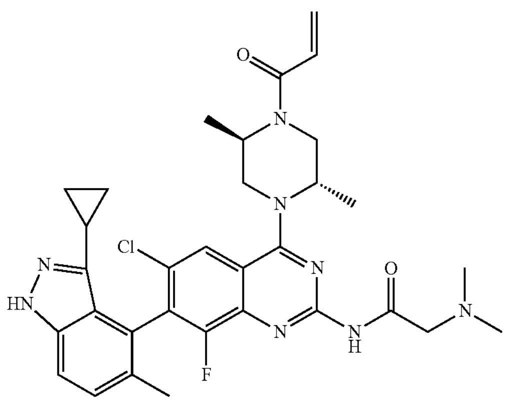 [SMILES: C=CC(=O)N1C[C@H](C)N(c2nc(NC(=O)CN(C)C)nc3c(F)c(-c4c(C)ccc5[nH]nc(C6CC6)c45)c(Cl)cc23)C[C@H]1C] | N-(4-((2S,5R)-4-acryloyl-2,5-dimethyl-piperazin-1-yl)-6-chloro-7-(3-cyclopropyl-5-methyl-1H-indazol-4-yl)-8-fluoroquinazolin-2-yl)-2-(dimethyl-amino)acetamide | C | 619.5 |
| 274 | 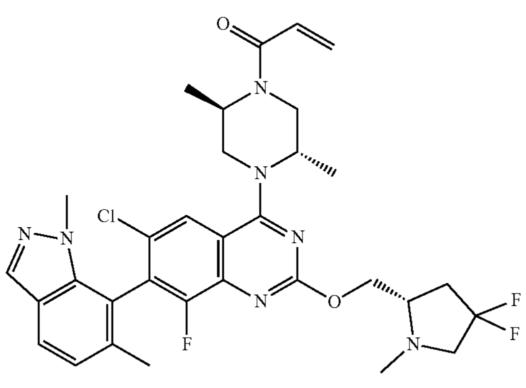 [SMILES: C=CC(=O)N1C[C@H](C)N(c2nc(OC[C@@H]3CC(F)(F)CN3C)nc3c(F)c(-c4c(C)ccc5cnn(C)c45)c(Cl)cc23)C[C@H]1C] | 1-((2R,5S)-4-(6-chloro-2-(((S)-4,4-difluoro-1-methylpyrrolidin-2-yl)methoxy)-7-(1,6-dimethyl-1H-indazol-7-yl)-8-fluoro-quinazolin-4-yl)-2,5-dimethylpiperazin-1-yl)prop-2-en-1-one | D | 642.2 |

TABLE 1-continued

Representative Compounds

| No. | Structure | Name | Method | [M + H]+ |
|-----|-----------|------|--------|----------|
| 275 | 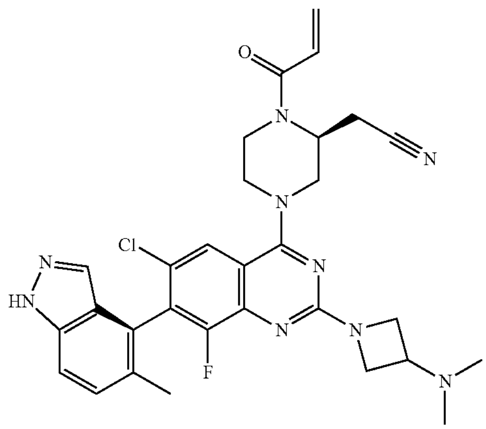 | 2-((S)-1-acryloyl-4-((R)-6-chloro-2-(3-(dimethyl-amino)azetidin-1-yl)-8-fluoro-7-(5-methyl-1H-indazol-4-yl)quinazolin-4-yl)-piperazin-2-yl)-acetonitrile | A | 588.6 |
| 276 | 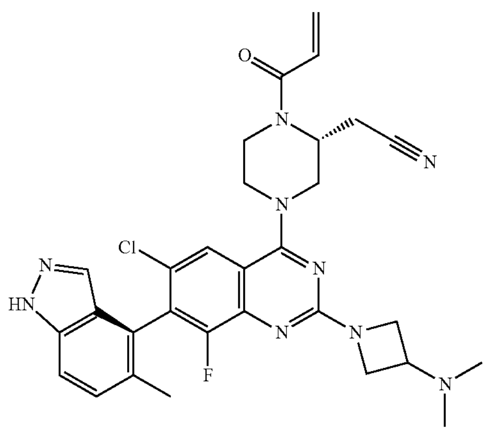 | 2-((R)-1-acryloyl-4-((R)-6-chloro-2-(3-(dimethyl-amino)azetidin-1-yl)-8-fluoro-7-(5-methyl-1H-indazol-4-yl)quinazolin-4-yl)-piperazin-2-yl)-acetonitrile | A | 588.6 |
| 277 | 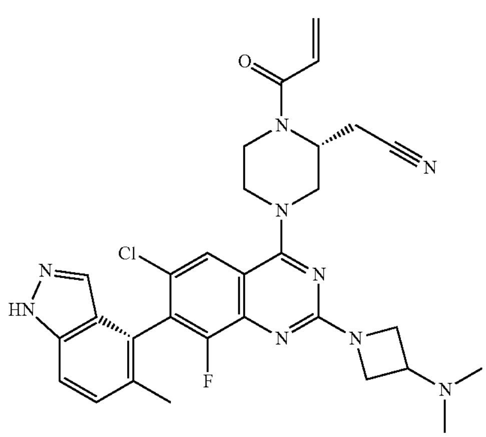 | 2-((R)-1-acryloyl-4-((S)-6-chloro-2-(3-(dimethyl-amino)azetidin-1-yl)-8-fluoro-7-(5-methyl-1H-indazol-4-yl)quinazolin-4-yl)piperazin-2-yl)-acetonitrile | A | 588.6 |

TABLE 1-continued

Representative Compounds

| No. | Structure | Name | Method | [M + H]+ |
|---|---|---|---|---|
| 278 | 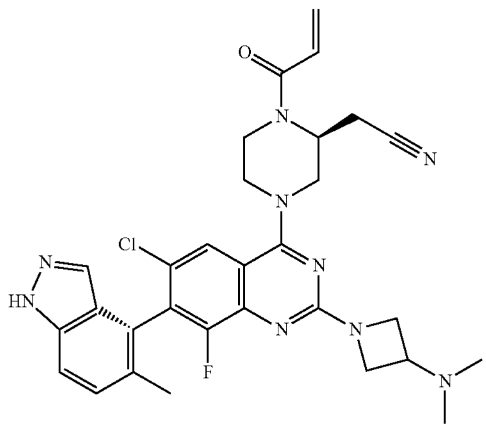 | 2-((S)-1-acryloyl-4-((S)-6-chloro-2-(3-(dimethylamino)-azetidin-1-yl)-8-fluoro-7-(5-methyl-1H-indazol-4-yl)-quinazolin-4-yl)-piperazin-2-yl)acetonitrile | A | 588.6 |
| 279 | 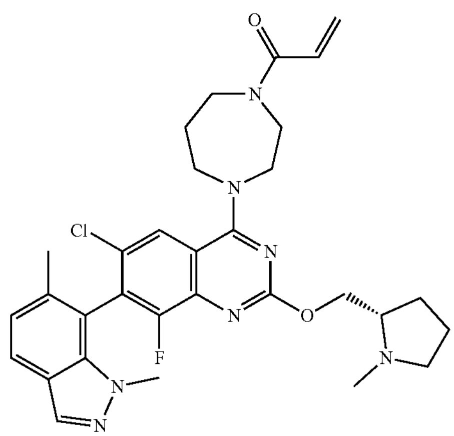 [SMILES: C=CC(=O)N1CCCN(c2nc(OC[C@@H]3CCCN3C)nc3c(F)c(-c4c(C)ccc5cnn(C)c45)c(Cl)cc23)CC1] | 1-(4-(6-chloro-7-(1,6-dimethyl-1H-indazol-7-yl)-8-fluoro-2-(((S)-1-methylpyrrolidin-2-yl)methoxy)quinazolin-4-yl)-1,4-diazepan-1-yl)prop-2-en-1-one | D | 592.5 |
| 280 | 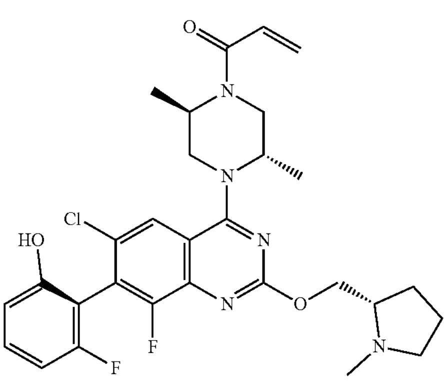 | 1-((2R,5S)-4-((S)-6-chloro-8-fluoro-7-(2-fluoro-6-hydroxy-phenyl)-2-(((S)-1-methylpyrrolidin-2-yl)-methoxy)quinazolin-4-yl)-2,5-dimethyl-piperazin-1-yl)prop-2-en-1-one | A | 572.4 |

TABLE 1-continued

Representative Compounds

| No. | Structure | Name | Method | [M + H]+ |
|---|---|---|---|---|
| 281 | 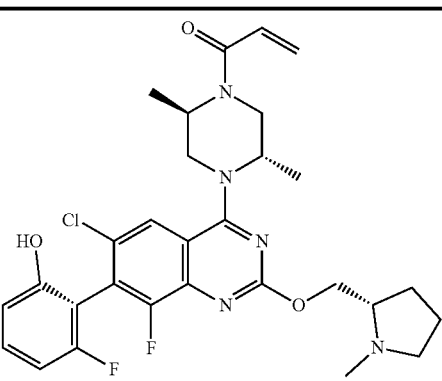 | 1-((2R,5S)-4-((R)-6-chloro-8-fluoro-7-(2-fluoro-6-hydroxy-phenyl)-2-(((S)-1-methylpyrrolidin-2-yl)-methoxy)quinazolin-4-yl)-2,5-dimethyl-piperazin-1-yl)prop-2-en-1-one | A | 572.4 |

In some embodiments, the compounds do not include the compounds set forth in Table 2.

TABLE 2

Compounds Excluded from Certain Embodiments

| No. | Structure | Name |
|---|---|---|
| A | 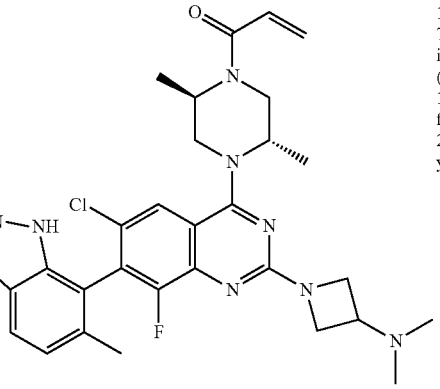 | 1-((2R,5S)-4-(6-chloro-7-(3,6-dimethyl-1H-indazol-7-yl)-2-(3-(dimethylamino)azetidin-1-yl)-8-fluoroquinazolin-4-yl)-2,5-dimethylpiperazin-1-yl)prop-2-en-1-one |
| B | 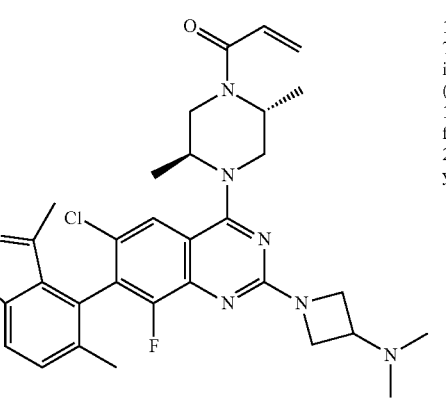 | 1-((2R,5S)-4-(6-chloro-7-(3,5-dimethyl-1H-indazol-4-yl)-2-(3-(dimethylamino)azetidin-1-yl)-8-fluoroquinazolin-4-yl)-2,5-dimethylpiperazin-1-yl)prop-2-en-1-one |

TABLE 2-continued

Compounds Excluded from Certain Embodiments

| No. | Structure | Name |
| --- | --- | --- |
| C | 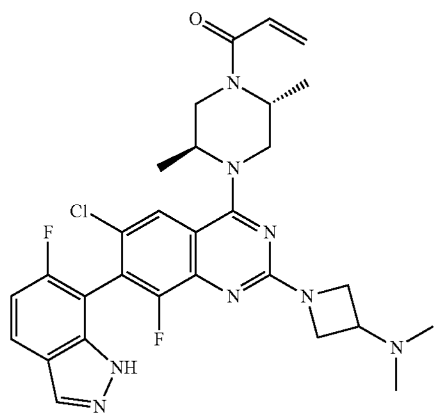 [SMILES: C=CC(=O)N1C[C@H](C)N(c2nc(N3CC(N(C)C)C3)nc3c(F)c(-c4c(F)ccc5cn[nH]c45)c(Cl)cc23)C[C@H]1C] | 1-((2R,5S)-4-(6-chloro-2-(3-(dimethylamino)azetidin-1-yl)-8-fluoro-7-(6-fluoro-1H-indazol-7-yl)quinazolin-4-yl)-2,5-dimethylpiperazin-1-yl)prop-2-en-1-one |
| D | 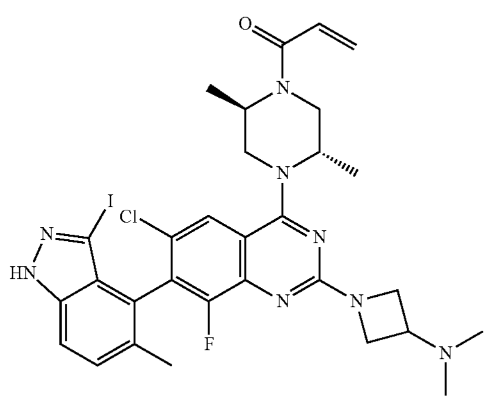 [SMILES: C=CC(=O)N1C[C@H](C)N(c2nc(N3CC(N(C)C)C3)nc3c(F)c(-c4c(C)ccc5[nH]nc(I)c45)c(Cl)cc23)C[C@H]1C] | 1-((2R,5S)-4-(6-chloro-2-(3-(dimethylamino)azetidin-1-yl)-8-fluoro-7-(3-iodo-5-methyl-1H-indazol-4-yl)quinazolin-4-yl)-2,5-dimethylpiperazin-1-yl)prop-2-en-1-one |
| E | 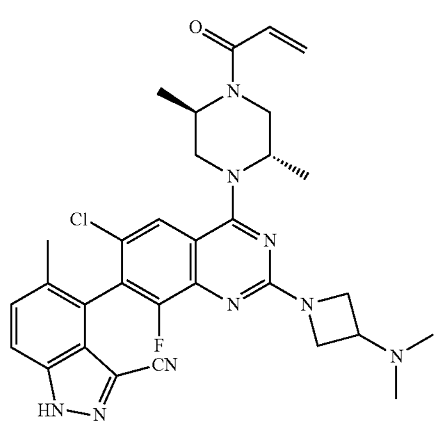 [SMILES: C=CC(=O)N1C[C@H](C)N(c2nc(N3CC(N(C)C)C3)nc3c(F)c(-c4c(C)ccc5[nH]nc(C#N)c45)c(Cl)cc23)C[C@H]1C] | 4-(4-((2S,5R)-4-acryloyl-2,5-dimethylpiperazin-1-yl)-6-chloro-2-(3-(dimethylamino)azetidin-1-yl)-8-fluoroquinazolin-7-yl)-5-methyl-1H-indazole-3-carbonitrile |

TABLE 2-continued

Compounds Excluded from Certain Embodiments

| No. | Structure | Name |
|---|---|---|
| F | 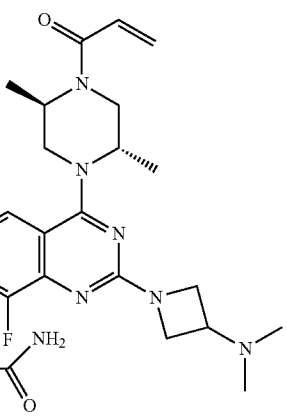 | 4-(4-((2S,5R)-4-acryloyl-2,5-dimethylpiperazin-1-yl)-6-chloro-2-(3-(dimethylamino)azetidin-1-yl)-8-fluoroquinazolin-7-yl)-5-methyl-1H-indazole-3-carboxamide |
| G | 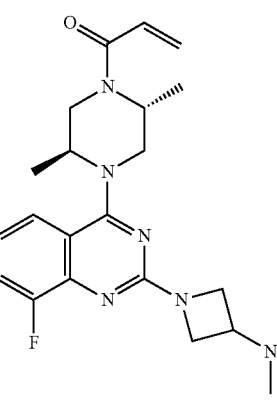 | 1-((2R,5S)-4-(7-(3-amino-5-methyl-1H-indazol-4-yl)-6-chloro-2-(3-(dimethylamino)azetidin-1-yl)-8-fluoroquinazolin-4-yl)-2,5-dimethylpiperazin-1-yl)prop-2-en-1-one |
| H | 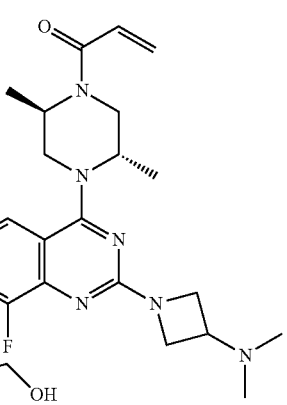 | 1-((2R,5S)-4-(6-chloro-2-(3-(dimethylamino)azetidin-1-yl)-8-fluoro-7-(3-(hydroxymethyl)-5-methyl-1H-indazol-4-yl)quinazolin-4-yl)-2,5-dimethylpiperazin-1-yl)prop-2-en-1-one |

TABLE 2-continued

Compounds Excluded from Certain Embodiments

| No. | Structure | Name |
|---|---|---|
| I | (structure) | 1-((2R,5S)-4-(6-chloro-2-(3-(dimethylamino)azetidin-1-yl)-8-fluoro-7-(5-methyl-1H-benzo[d]imidazol-4-yl)quinazolin-4-yl)-2,5-dimethylpiperazin-1-yl)prop-2-en-1-one |
| J | (structure) | 1-((2R,5S)-4-(6-chloro-2-(3-(dimethylamino)azetidin-1-yl)-8-fluoro-7-(5-methyl-1H-indol-4-yl)quinazolin-4-yl)-2,5-dimethylpiperazin-1-yl)prop-2-en-1-one |

It is understood that in the present description, combinations of substituents and/or variables of the depicted formulae are permissible only if such contributions result in stable compounds.

Furthermore, all compounds of the invention which exist in free base or acid form can be converted to their pharmaceutically acceptable salts by treatment with the appropriate inorganic or organic base or acid by methods known to one skilled in the art. Salts of the compounds of the invention can be converted to their free base or acid form by standard techniques.

The following General Reaction Schemes illustrate exemplary methods of making compounds of compounds of structure (I):

Compounds of structure (I) can be prepared according to methods known in the art. For example, compounds of structure (I) may be prepared according to methods analogous to those disclosed in WO 2015/054572, the full disclosure of which is hereby incorporated by reference in its entirety. In general, starting components may be obtained from sources such as Sigma Aldrich, Lancaster Synthesis, Inc., Maybridge, Matrix Scientific, TCI, and Fluorochem USA, etc. or synthesized according to sources known to those skilled in the art (see, for example, Advanced Organic Chemistry: Reactions, Mechanisms, and Structure, 5th edition (Wiley, December 2000)) or prepared as described herein.

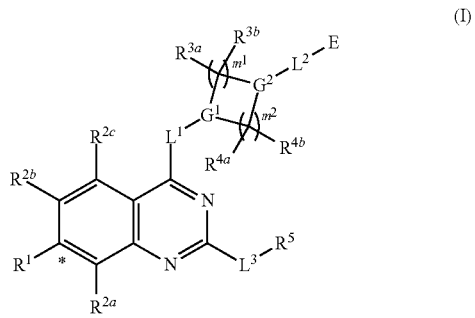

(I)

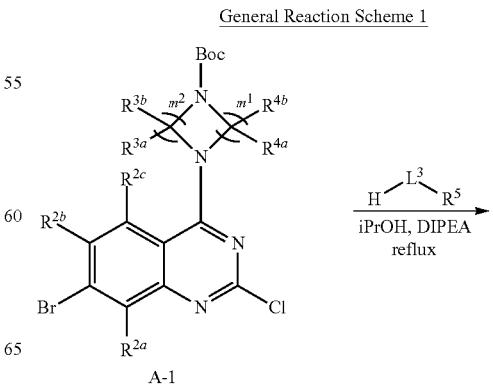

General Reaction Scheme 1 or a pharmaceutically acceptable salt, stereoisomer or prodrug thereof, wherein $R^1$, $R^{2a}$, $R^{2b}$, $R^{2c}$, $R^{3a}$, $R^{3b}$, $R^{4a}$, $R^{4b}$, $R^5$, $G^1$, $G^2$, $L^1$, $L^2$, $L^3$, $m^1$, $m^2$ and E are as defined herein.

General Reaction Scheme 2

Embodiments of the compound of structure (I) (e.g., compound A-3) can be prepared according to General Reaction Scheme 1 ("Method A"), wherein $R^1$, $R^{3a}$, $R^{3b}$, $R^{4a}$, $R^{4b}$, $R^5$, $R^9$, $R^{10}$ and $L^3$ are as defined herein. As shown in General Reaction Scheme 1, compound A-1 is prepared according to the general methods described in WO 2015/054572 and coupled with an appropriate nucleophile (H-$L^3$-$R^5$) to form A-2. The desired $R^1$ substituent may then be added by way of Suzuki coupling to yield A-3. Removal of the boc protecting group, followed by reaction with an appropriately substituted acryloyl chloride yields the desired compound A-4.

-continued

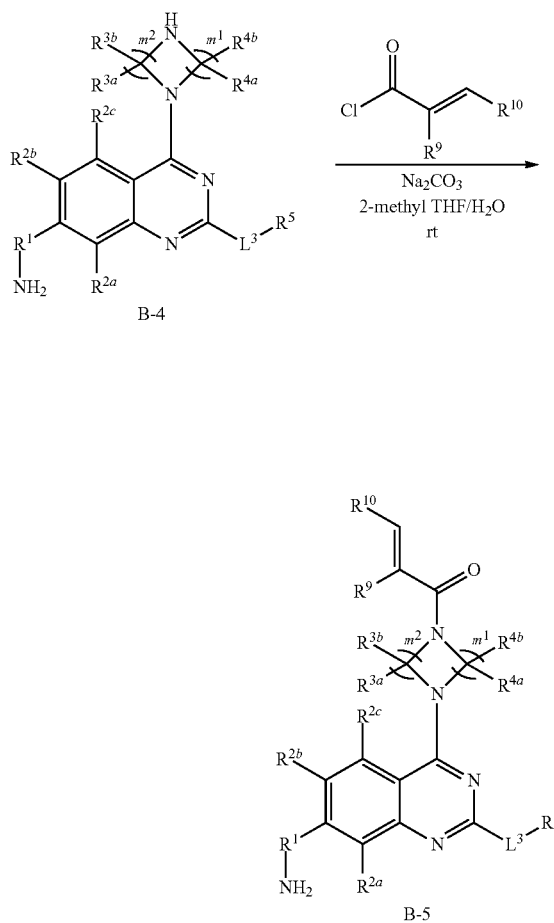

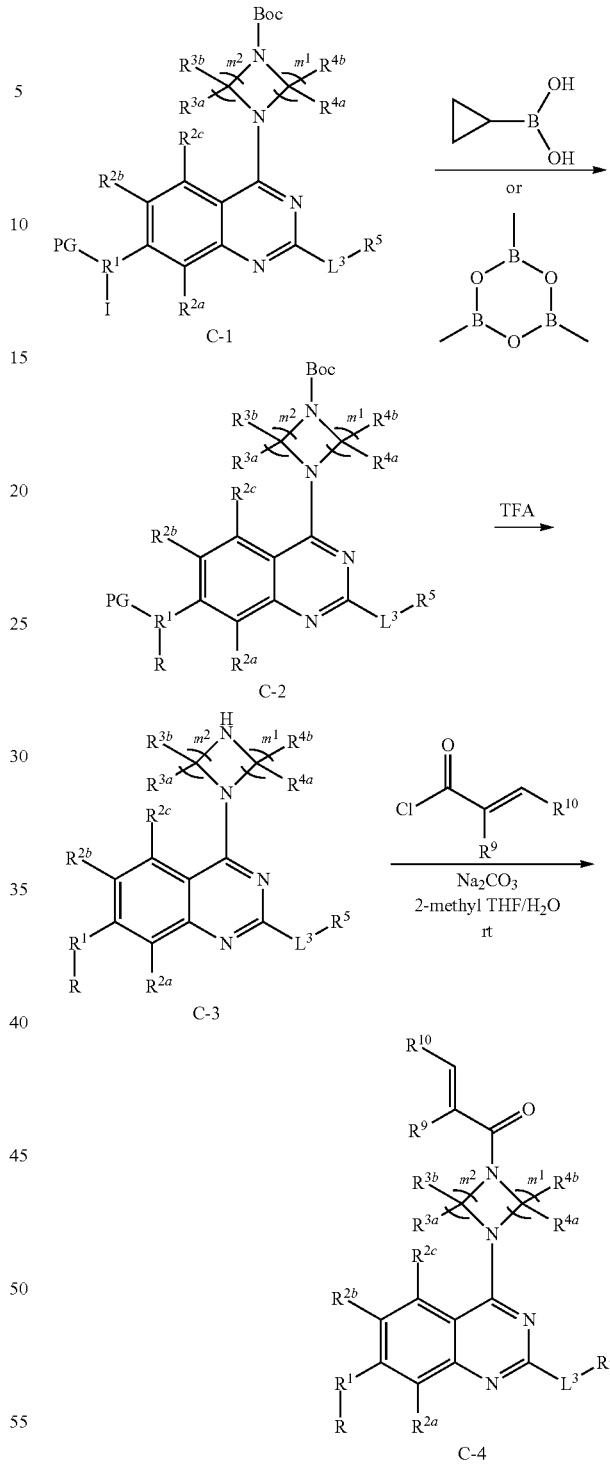

Embodiments of the compound of structure (I) (e.g., compound B-5) can be prepared according to General Reaction Scheme 2 ("Method B"), wherein $R^1$, $R^{3a}$, $R^{3b}$, $R^{4a}$, $R^{4b}$, $R^5$, $R^9$, $R^{10}$ and $L^3$ are as defined herein. Referring to General Reaction Scheme 2, compounds of structure A-11 can be obtained according to Method A above and converted to B-1 under appropriate conditions (e.g., $I_2$ and KOH). B-1 is then trityl protected and coupled with diphenylmethanimine to afford B-3. Following a global deprotection, B-4 is reacted with an appropriately substituted acryloyl chloride yields the desired compound B-5.

General Reaction Scheme 3

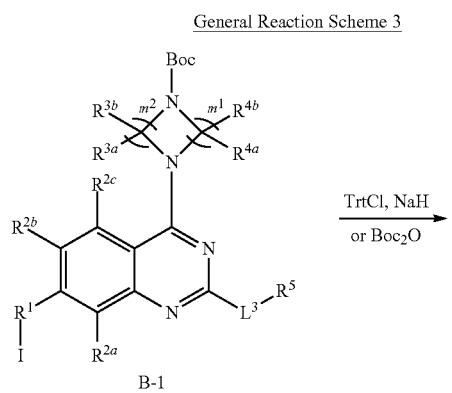

Embodiments of the compound of structure (I) (e.g., compound C-4) can be prepared according to General Reaction Scheme 3 ("Method C"), wherein $R^1$, $R^{3a}$, $R^{3b}$, $R^{4a}R^{4b}$, $R^5$, $R^9$, $R^{10}$ and $L^3$ are as defined herein. Referring to General Reaction Scheme 3, compounds of structure B-1 are protected followed by coupling under Suzuki conditions to yield C-2. C-2 is deprotected and the desired compound prepared according to the general methods described herein.

General Reaction Scheme 4

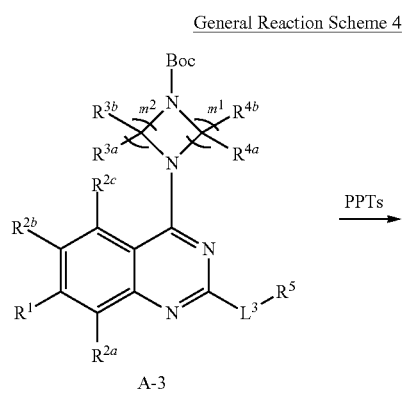

A-3

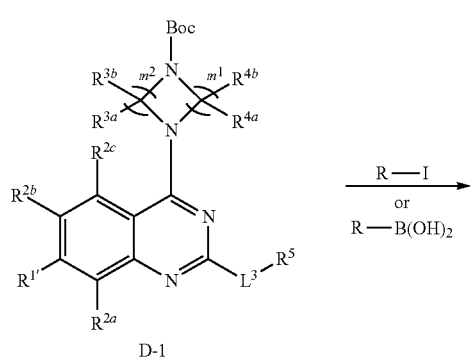

D-1

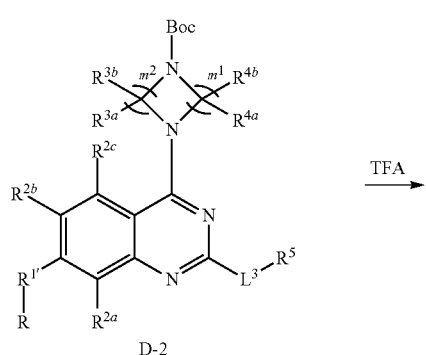

D-2

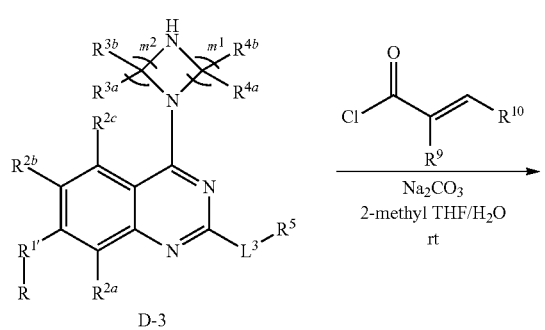

D-3

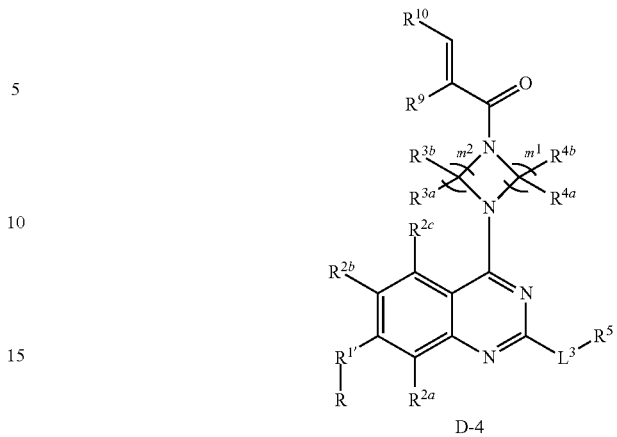

D-4

Embodiments of the compound of structure (I) (e.g., compound D-4) can be prepared according to General Reaction Scheme 4 ("Method D"), wherein $R^1$, $R^{3a}$, $R^{3b}$, $R^{4a}$, $R^{4b}$, $R^5$, $R^9$, $R^{10}$ and $L^3$ are as defined herein. Referring to General Reaction Scheme 4, compounds of structure A-3 are protected followed by coupling under Suzuki conditions to yield D-2. D-2 is deprotected and the desired compound prepared according to the general methods described herein.

General Reaction Scheme 5

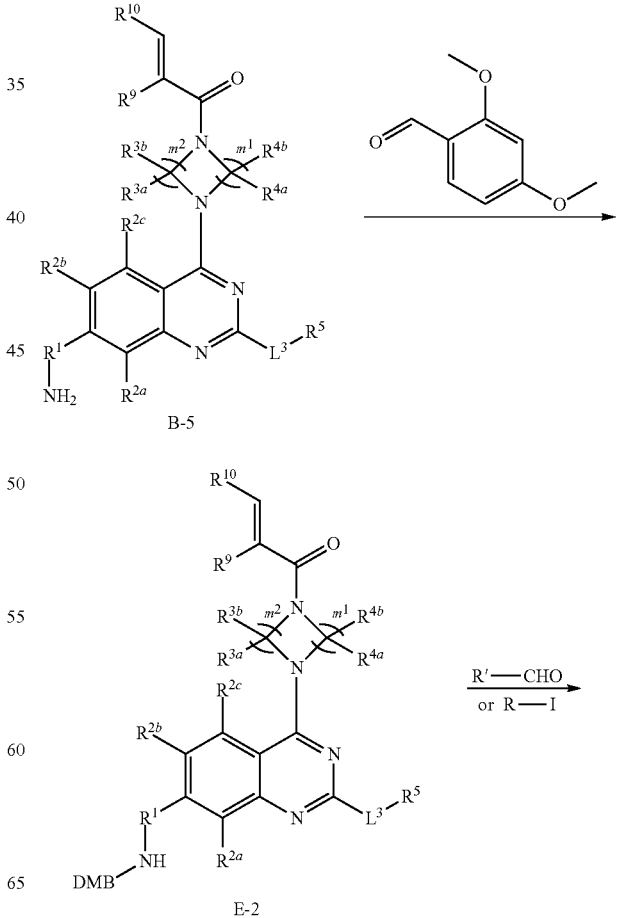

B-5

E-2

219

-continued

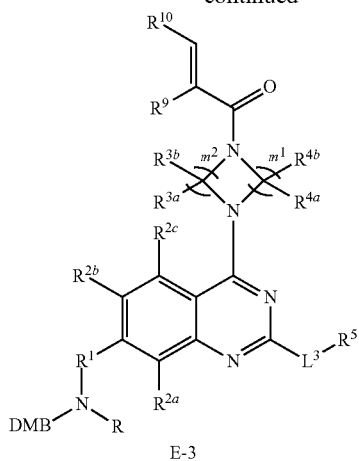

E-3

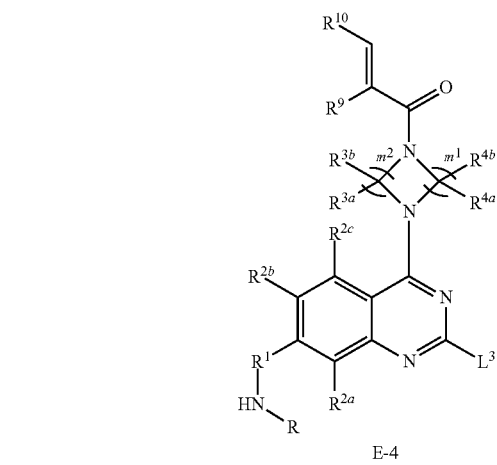

E-4

Embodiments of the compound of structure (I) (e.g., compound E-4) can be prepared according to General Reaction Scheme 5 ("Method E"), wherein $R^1$, $R^{3a}$, $R^{3b}$, $R^{4a}$, $R^{4b}$, $R^5$, $R^9$, $R^{10}$ and $L^3$ are as defined herein. Referring to General Reaction Scheme 5, compounds of structure B-5 are protected followed by reductive amination to yield E-3. E-3 is then deprotected to yield the desired compound.

General Reaction Scheme 6

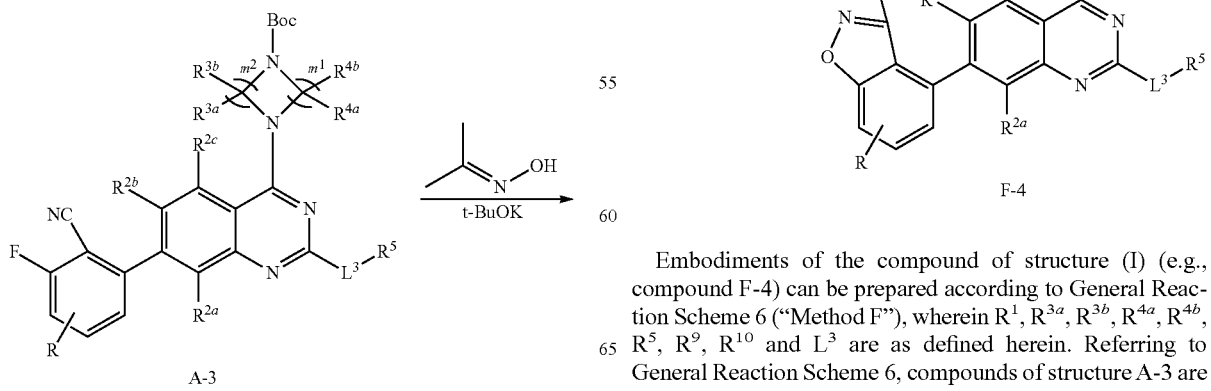

220

-continued

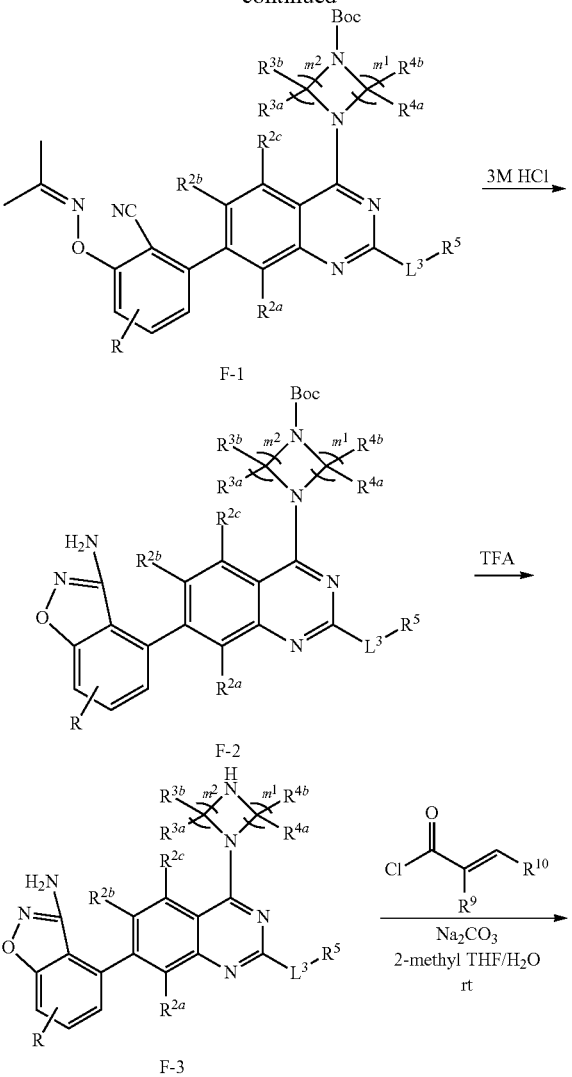

Embodiments of the compound of structure (I) (e.g., compound F-4) can be prepared according to General Reaction Scheme 6 ("Method F"), wherein $R^1$, $R^{3a}$, $R^{3b}$, $R^{4a}$, $R^{4b}$, $R^5$, $R^9$, $R^{10}$ and $L^3$ are as defined herein. Referring to General Reaction Scheme 6, compounds of structure A-3 are treated with propan-2-one oxime followed by cyclization to yield F-2. F-2 is deprotected and the desired compound prepared according to the general methods described herein.

General Reaction Scheme 7

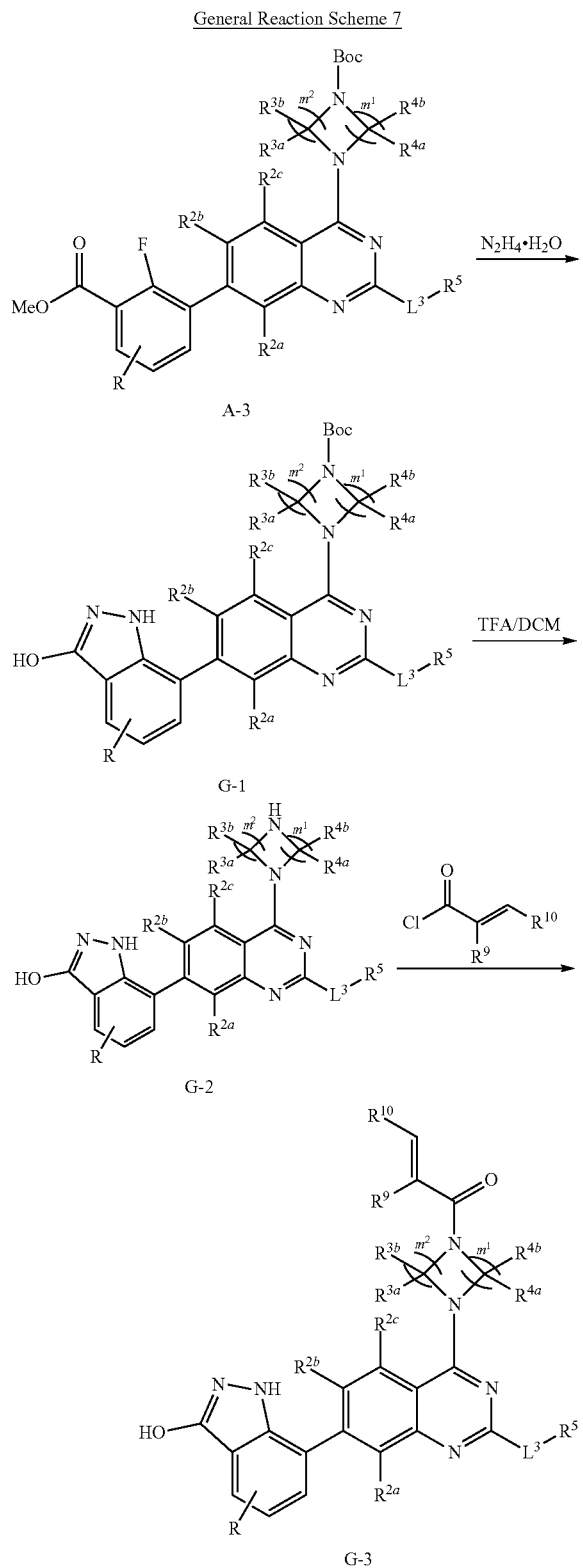

Embodiments of the compound of structure (I) (e.g., compound G-3) can be prepared according to General Reaction Scheme 7 ("Method G"), wherein $R^1$, $R^{3a}$, $R^{3b}$, $R^{4a}$, $R^{4b}$, $R^5$, $R^9$, $R^{10}$ and $L^3$ are as defined herein. Referring to General Reaction Scheme 7, compounds of structure A-3 are treated with hydrazine followed by cyclization to yield G-2. G-2 is then treated according to the general methods described herein to obtain the desired compound.

It is understood that one skilled in the art may be able to make these compounds by similar methods or by combining other methods known to one skilled in the art. It is also understood that one skilled in the art would be able to make, in a similar manner as described below, other compounds of structure (I) not specifically illustrated below by using the appropriate starting components and modifying the parameters of the synthesis as needed. In general, starting components may be obtained from sources such as Sigma Aldrich, Lancaster Synthesis, Inc., Maybridge, Matrix Scientific, TCI, and Fluorochem USA, etc. or synthesized according to sources known to those skilled in the art (see, for example, Advanced Organic Chemistry: Reactions, Mechanisms, and Structure, $5^{th}$ edition (Wiley, December 2000)) or prepared as described herein.

It will be apparent to one of ordinary skill in the art that all compounds of structure (I) can be prepared according to one or more of the methods described herein or otherwise known in the art. It will also be apparent that in some instances it will be necessary to use a differently substituted starting material and/or protecting groups to arrive at the desired compound when following the general procedures described herein. Various substituents may also be added at various points in the synthetic scheme to prepare the desired compound.

Further, one skilled in the art will recognize that certain modifications to the above schemes and those provided in the examples are possible to prepare different embodiments of compounds of structure (I). For example, for ease of illustration the General Reaction Schemes above depict preparation of compounds of structure (I) wherein $R^{2a}$, $R^{2b}$ and $R^{2c}$ are fluoro, chloro and H, respectively. However, it will be apparent to one of ordinary skill in the art that differently substituted compounds of structure (I) can be prepared according the general methods provided herein by using differently substituted starting materials and/or adding the desired substituent using methods known in the art.

One of ordinary skill in the art will also readily recognize that compounds wherein $L^1$ is $NR^7$ can be prepared by substituting the piperazine illustrated in the above schemes with a heterocycle having the following structure:

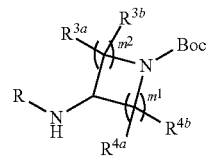

where R is H, a protecting group or $C_1$-$C_6$ alkyl.

It will also be appreciated by those skilled in the art that in the processes for preparing the compounds described herein the functional groups of intermediate compounds may need to be protected by suitable protecting groups. Such functional groups include, but are not limited to, hydroxy, amino, mercapto and carboxylic acid. Suitable protecting groups for hydroxy include trialkylsilyl or diarylalkylsilyl (for example, t-butyldimethylsilyl, t-butyldiphenylsilyl or trimethylsilyl), tetrahydropyranyl, benzyl, and the like. Suitable protecting groups for amino, amidino and guanidino include t-butoxycarbonyl, benzyloxycarbonyl, and the like. Suitable protecting groups for mercapto include —C(O)—R" (where R" is alkyl, aryl or arylalkyl), p-methoxybenzyl, trityl and the like. Suitable protecting groups for carboxylic acid include alkyl, aryl or arylalkyl esters. Protecting groups are optionally added or removed in accordance with standard techniques, which are known to one skilled in the art and as described herein. The use of protecting groups is described in detail in Green, T. W. and P.G.M. Wutz, *Protective Groups in Organic Synthesis* (1999), $3^{rd}$ Ed., Wiley. As one of skill in the art would appreciate, the protecting group may also be a polymer resin such as a Wang resin, Rink resin or a 2-chlorotrityl-chloride resin.

It will also be appreciated by those skilled in the art, although such protected derivatives of compounds of this invention may not possess pharmacological activity as such, they may be administered to a mammal and thereafter metabolized in the body to form compounds of the invention which are pharmacologically active. Such derivatives may therefore be described as "prodrugs". Embodiments include prodrugs of compounds disclosed herein.

Pharmaceutical Compositions

Other embodiments are directed to pharmaceutical compositions. The pharmaceutical composition comprises any one (or more) of the foregoing compounds and a pharmaceutically acceptable carrier. In some embodiments, the pharmaceutical composition is formulated for oral administration. In other embodiments, the pharmaceutical composition is formulated for injection. In still more embodiments, the pharmaceutical compositions comprise a compound as disclosed herein and an additional therapeutic agent (e.g., anticancer agent). Non-limiting examples of such therapeutic agents are described herein below.

Suitable routes of administration include, but are not limited to, oral, intravenous, rectal, aerosol, parenteral, ophthalmic, pulmonary, transmucosal, transdermal, vaginal, otic, nasal, and topical administration. In addition, by way of example only, parenteral delivery includes intramuscular, subcutaneous, intravenous, intramedullary injections, as well as intrathecal, direct intraventricular, intraperitoneal, intralymphatic, and intranasal injections.

In certain embodiments, a compound as described herein is administered in a local rather than systemic manner, for example, via injection of the compound directly into an organ, often in a depot preparation or sustained release formulation. In specific embodiments, long acting formulations are administered by implantation (for example subcutaneously or intramuscularly) or by intramuscular injection. Furthermore, in other embodiments, the drug is delivered in a targeted drug delivery system, for example, in a liposome coated with organ-specific antibody. In such embodiments, the liposomes are targeted to and taken up selectively by the organ. In yet other embodiments, the compound as described herein is provided in the form of a rapid release formulation, in the form of an extended release formulation, or in the form of an intermediate release formulation. In yet other embodiments, the compound described herein is administered topically.

The compounds according to the invention are effective over a wide dosage range. For example, in the treatment of adult humans, dosages from 0.01 to 1000 mg, from 0.5 to 100 mg, from 1 to 50 mg per day, and from 5 to 40 mg per day are examples of dosages that are used in some embodiments. An exemplary dosage is 10 to 30 mg per day. The exact dosage will depend upon the route of administration, the form in which the compound is administered, the subject to be treated, the body weight of the subject to be treated, and the preference and experience of the attending physician.

In some embodiments, a compound of the invention is administered in a single dose. Typically, such administration will be by injection, e.g., intravenous injection, in order to introduce the agent quickly. However, other routes are used as appropriate. A single dose of a compound of the invention may also be used for treatment of an acute condition.

In some embodiments, a compound of the invention is administered in multiple doses. In some embodiments, dosing is about once, twice, three times, four times, five times, six times, or more than six times per day. In other embodiments, dosing is about once a month, once every two weeks, once a week, or once every other day. In another embodiment a compound of the invention and another agent are administered together about once per day to about 6 times per day. In another embodiment the administration of a compound of the invention and an agent continues for less than about 7 days. In yet another embodiment the administration continues for more than about 6, 10, 14, 28 days, two months, six months, or one year. In some cases, continuous dosing is achieved and maintained as long as necessary.

Administration of the compounds of the invention may continue as long as necessary. In some embodiments, a compound of the invention is administered for more than 1, 2, 3, 4, 5, 6, 7, 14, or 28 days. In some embodiments, a compound of the invention is administered for less than 28, 14, 7, 6, 5, 4, 3, 2, or 1 day. In some embodiments, a compound of the invention is administered chronically on an ongoing basis, e.g., for the treatment of chronic effects.

In some embodiments, the compounds of the invention are administered in dosages. It is known in the art that due to intersubject variability in compound pharmacokinetics, individualization of dosing regimen is necessary for optimal therapy. Dosing for a compound of the invention may be found by routine experimentation in light of the instant disclosure.

In some embodiments, the compounds described herein are formulated into pharmaceutical compositions. In specific embodiments, pharmaceutical compositions are formulated in a conventional manner using one or more physiologically acceptable carriers comprising excipients and auxiliaries which facilitate processing of the active compounds into preparations which can be used pharmaceutically. Proper formulation is dependent upon the route of administration chosen. Any pharmaceutically acceptable techniques, carriers, and excipients are used as suitable to formulate the pharmaceutical compositions described herein: Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999).

Provided herein are pharmaceutical compositions comprising a compound of structure (I) and a pharmaceutically acceptable diluent(s), excipient(s), or carrier(s). In certain embodiments, the compounds described are administered as pharmaceutical compositions in which compounds of structure (I) are mixed with other active ingredients, as in combination therapy. Encompassed herein are all combinations of actives set forth in the combination therapies section below and throughout this disclosure. In specific embodiments, the pharmaceutical compositions include one or more compounds of structure (I).

A pharmaceutical composition, as used herein, refers to a mixture of a compound of structure (I) with other chemical components, such as carriers, stabilizers, diluents, dispersing agents, suspending agents, thickening agents, and/or excipients. In certain embodiments, the pharmaceutical composition facilitates administration of the compound to an organism. In some embodiments, practicing the methods of treatment or use provided herein, therapeutically effective amounts of compounds of structure (I) provided herein are administered in a pharmaceutical composition to a mammal having a disease, disorder or medical condition to be treated. In specific embodiments, the mammal is a human. In certain embodiments, therapeutically effective amounts vary depending on the severity of the disease, the age and relative health of the subject, the potency of the compound used and other factors. The compounds described herein are used singly or in combination with one or more therapeutic agents as components of mixtures.

In one embodiment, one or more compounds of structure (I) is formulated in an aqueous solutions. In specific embodiments, the aqueous solution is selected from, by way of example only, a physiologically compatible buffer, such as Hank's solution, Ringer's solution, or physiological saline buffer. In other embodiments, one or more compound of structure (I) is/are formulated for transmucosal administration. In specific embodiments, transmucosal formulations include penetrants that are appropriate to the barrier to be permeated. In still other embodiments wherein the compounds described herein are formulated for other parenteral injections, appropriate formulations include aqueous or non-aqueous solutions. In specific embodiments, such solutions include physiologically compatible buffers and/or excipients.

In another embodiment, compounds described herein are formulated for oral administration. Compounds described herein are formulated by combining the active compounds with, e.g., pharmaceutically acceptable carriers or excipients. In various embodiments, the compounds described herein are formulated in oral dosage forms that include, by way of example only, tablets, powders, pills, dragees, capsules, liquids, gels, syrups, elixirs, slurries, suspensions and the like.

In certain embodiments, pharmaceutical preparations for oral use are obtained by mixing one or more solid excipient with one or more of the compounds described herein, optionally grinding the resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as: for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. In specific embodiments, disintegrating agents are optionally added. Disintegrating agents include, by way of example only, cross-linked croscarmellose sodium, polyvinylpyrrolidone, agar, or alginic acid or a salt thereof such as sodium alginate.

In one embodiment, dosage forms, such as dragee cores and tablets, are provided with one or more suitable coating. In specific embodiments, concentrated sugar solutions are used for coating the dosage form. The sugar solutions, optionally contain additional components, such as by way of example only, gum arabic, talc, polyvinylpyrrolidone, carbopol gel, polyethylene glycol, and/or titanium dioxide, lacquer solutions, and suitable organic solvents or solvent mixtures. Dyestuffs and/or pigments are also optionally added to the coatings for identification purposes. Additionally, the dyestuffs and/or pigments are optionally utilized to characterize different combinations of active compound doses.

In certain embodiments, therapeutically effective amounts of at least one of the compounds described herein are formulated into other oral dosage forms. Oral dosage forms include push-fit capsules made of gelatin, as well as soft, sealed capsules made of gelatin and a plasticizer, such as glycerol or sorbitol. In specific embodiments, push-fit capsules contain the active ingredients in admixture with one or more filler. Fillers include, by way of example only, lactose, binders such as starches, and/or lubricants such as talc or magnesium stearate and, optionally, stabilizers. In other embodiments, soft capsules, contain one or more active compound that is dissolved or suspended in a suitable liquid. Suitable liquids include, by way of example only, one or more fatty oil, liquid paraffin, or liquid polyethylene glycol. In addition, stabilizers are optionally added.

In other embodiments, therapeutically effective amounts of at least one of the compounds described herein are formulated for buccal or sublingual administration. Formulations suitable for buccal or sublingual administration include, by way of example only, tablets, lozenges, or gels. In still other embodiments, the compounds described herein are formulated for parental injection, including formulations suitable for bolus injection or continuous infusion. In specific embodiments, formulations for injection are presented in unit dosage form (e.g., in ampoules) or in multi-dose containers. Preservatives are, optionally, added to the injection formulations. In still other embodiments, the pharmaceutical compositions are formulated in a form suitable for parenteral injection as sterile suspensions, solutions or emulsions in oily or aqueous vehicles. Parenteral injection formulations optionally contain formulatory agents such as suspending, stabilizing and/or dispersing agents. In specific embodiments, pharmaceutical formulations for parenteral administration include aqueous solutions of the active compounds in water-soluble form. In additional embodiments, suspensions of the active compounds (e.g., compounds of structure (I)) are prepared as appropriate oily injection suspensions. Suitable lipophilic solvents or vehicles for use in the pharmaceutical compositions described herein include, by way of example only, fatty oils such as sesame oil, or synthetic fatty acid esters, such as ethyl oleate or triglycerides, or liposomes. In certain specific embodiments, aqueous injection suspensions contain substances which increase the viscosity of the suspension, such as sodium carboxymethyl cellulose, sorbitol, or dextran. Optionally, the suspension contains suitable stabilizers or agents which increase the solubility of the compounds to allow for the preparation of highly concentrated solutions. Alternatively, in other embodiments, the active ingredient is in powder form for constitution with a suitable vehicle, e.g., sterile pyrogen-free water, before use.

In still other embodiments, the compounds of structure (I) are administered topically. The compounds described herein are formulated into a variety of topically administrable compositions, such as solutions, suspensions, lotions, gels, pastes, medicated sticks, balms, creams or ointments. Such pharmaceutical compositions optionally contain solubilizers, stabilizers, tonicity enhancing agents, buffers and preservatives.

In yet other embodiments, the compounds of structure (I) are formulated for transdermal administration. In specific embodiments, transdermal formulations employ transdermal delivery devices and transdermal delivery patches and can be lipophilic emulsions or buffered, aqueous solutions, dissolved and/or dispersed in a polymer or an adhesive. In various embodiments, such patches are constructed for continuous, pulsatile, or on demand delivery of pharmaceutical agents. In additional embodiments, the transdermal delivery of the compounds of structure (I) is accomplished by means of iontophoretic patches and the like. In certain embodiments, transdermal patches provide controlled delivery of the compounds of structure (I). In specific embodiments, the rate of absorption is slowed by using rate-controlling membranes or by trapping the compound within a polymer matrix or gel. In alternative embodiments, absorption enhancers are used to increase absorption. Absorption enhancers or carriers include absorbable pharmaceutically acceptable solvents that assist passage through the skin. For example, in one embodiment, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin.

In other embodiments, the compounds of structure (I) are formulated for administration by inhalation. Various forms suitable for administration by inhalation include, but are not limited to, aerosols, mists or powders. Pharmaceutical compositions of any of compound of structure (I) are conveniently delivered in the form of an aerosol spray presentation from pressurized packs or a nebulizer, with the use of a suitable propellant (e.g., dichlorodifluoromethane, trichlorofluoromethane, dichlorotetrafluoroethane, carbon dioxide or other suitable gas). In specific embodiments, the dosage unit of a pressurized aerosol is determined by providing a valve to deliver a metered amount. In certain embodiments, capsules and cartridges of, such as, by way of example only, gelatin for use in an inhaler or insufflator is formulated containing a powder mix of the compound and a suitable powder base such as lactose or starch.

In still other embodiments, the compounds of structure (I) are formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, PEG, and the like. In suppository forms of the compositions, a low-melting wax such as, but not limited to, a mixture of fatty acid glycerides, optionally in combination with cocoa butter is first melted.

In certain embodiments, pharmaceutical compositions are formulated in any conventional manner using one or more physiologically acceptable carriers comprising excipients and auxiliaries which facilitate processing of the active compounds into preparations which can be used pharmaceutically. Proper formulation is dependent upon the route of administration chosen. Any pharmaceutically acceptable techniques, carriers, and excipients are optionally used as suitable. Pharmaceutical compositions comprising a compound of structure (I) are manufactured in a conventional manner, such as, by way of example only, by means of conventional mixing, dissolving, granulating, dragee-making, levigating, emulsifying, encapsulating, entrapping or compression processes.

Pharmaceutical compositions include at least one pharmaceutically acceptable carrier, diluent or excipient and at least one compound of structure (I), described herein as an active ingredient. The active ingredient is in free-acid or free-base form, or in a pharmaceutically acceptable salt form. In addition, the methods and pharmaceutical compositions described herein include the use of N-oxides, crystalline forms (also known as polymorphs), as well as active metabolites of these compounds having the same type of activity. All tautomers of the compounds described herein are included within the scope of the compounds presented herein. Additionally, the compounds described herein encompass unsolvated as well as solvated forms with pharmaceutically acceptable solvents such as water, ethanol, and the like. The solvated forms of the compounds presented herein are also considered to be disclosed herein. In addition, the pharmaceutical compositions optionally include other medicinal or pharmaceutical agents, carriers, adjuvants, such as preserving, stabilizing, wetting or emulsifying agents, solution promoters, salts for regulating the osmotic pressure, buffers, and/or other therapeutically valuable substances.

Methods for the preparation of compositions comprising the compounds described herein include formulating the compounds with one or more inert, pharmaceutically acceptable excipients or carriers to form a solid, semi-solid or liquid. Solid compositions include, but are not limited to, powders, tablets, dispersible granules, capsules, cachets, and suppositories. Liquid compositions include solutions in which a compound is dissolved, emulsions comprising a compound, or a solution containing liposomes, micelles, or nanoparticles comprising a compound as disclosed herein. Semi-solid compositions include, but are not limited to, gels, suspensions and creams. The form of the pharmaceutical compositions described herein include liquid solutions or suspensions, solid forms suitable for solution or suspension in a liquid prior to use, or as emulsions. These compositions also optionally contain minor amounts of nontoxic, auxiliary substances, such as wetting or emulsifying agents, pH buffering agents, and so forth.

In some embodiments, pharmaceutical composition comprising at least one compound of structure (I) illustratively takes the form of a liquid where the agents are present in solution, in suspension or both. Typically when the composition is administered as a solution or suspension a first portion of the agent is present in solution and a second portion of the agent is present in particulate form, in suspension in a liquid matrix. In some embodiments, a liquid composition includes a gel formulation. In other embodiments, the liquid composition is aqueous.

In certain embodiments, useful aqueous suspensions contain one or more polymers as suspending agents. Useful polymers include water-soluble polymers such as cellulosic polymers, e.g., hydroxypropyl methylcellulose, and water-insoluble polymers such as cross-linked carboxyl-containing polymers. Certain pharmaceutical compositions described herein comprise a mucoadhesive polymer, selected for example from carboxymethylcellulose, carbomer (acrylic acid polymer), poly(methylmethacrylate), polyacrylamide, polycarbophil, acrylic acid/butyl acrylate copolymer, sodium alginate and dextran.

Useful pharmaceutical compositions also, optionally, include solubilizing agents to aid in the solubility of a compound of structure (I). The term "solubilizing agent"

generally includes agents that result in formation of a micellar solution or a true solution of the agent. Certain acceptable nonionic surfactants, for example polysorbate 80, are useful as solubilizing agents, as can ophthalmically acceptable glycols, polyglycols, e.g., polyethylene glycol 400, and glycol ethers.

Furthermore, useful pharmaceutical compositions optionally include one or more pH adjusting agents or buffering agents, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

Additionally, useful compositions also, optionally, include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

Other useful pharmaceutical compositions optionally include one or more preservatives to inhibit microbial activity. Suitable preservatives include mercury-containing substances such as merfen and thiomersal; stabilized chlorine dioxide; and quaternary ammonium compounds such as benzalkonium chloride, cetyltrimethylammonium bromide and cetylpyridinium chloride.

Still other useful compositions include one or more surfactants to enhance physical stability or for other purposes. Suitable nonionic surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40.

Still other useful compositions include one or more antioxidants to enhance chemical stability where required. Suitable antioxidants include, by way of example only, ascorbic acid and sodium metabisulfite.

In certain embodiments, aqueous suspension compositions are packaged in single-dose non-reclosable containers. Alternatively, multiple-dose reclosable containers are used, in which case it is typical to include a preservative in the composition.

In alternative embodiments, other delivery systems for hydrophobic pharmaceutical compounds are employed. Liposomes and emulsions are examples of delivery vehicles or carriers useful herein. In certain embodiments, organic solvents such as N-methylpyrrolidone are also employed. In additional embodiments, the compounds described herein are delivered using a sustained-release system, such as semipermeable matrices of solid hydrophobic polymers containing the therapeutic agent. Various sustained-release materials are useful herein. In some embodiments, sustained-release capsules release the compounds for a few weeks up to over 100 days. Depending on the chemical nature and the biological stability of the therapeutic reagent, additional strategies for protein stabilization are employed.

In certain embodiments, the formulations described herein comprise one or more antioxidants, metal chelating agents, thiol containing compounds and/or other general stabilizing agents. Examples of such stabilizing agents, include, but are not limited to: (a) about 0.5% to about 2% w/v glycerol, (b) about 0.1% to about 1% w/v methionine, (c) about 0.1% to about 2% w/v monothioglycerol, (d) about 1 mM to about 10 mM EDTA, (e) about 0.01% to about 2% w/v ascorbic acid, (f) 0.003% to about 0.02% w/v polysorbate 80, (g) 0.001% to about 0.05% w/v. polysorbate 20, (h) arginine, (i) heparin, (j) dextran sulfate, (k) cyclodextrins, (l) pentosan polysulfate and other heparinoids, (m) divalent cations such as magnesium and zinc; or (n) combinations thereof.

In some embodiments, the concentration of one or more compounds provided in the pharmaceutical compositions of the present invention is less than 100%, 90%, 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, 2%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v or v/v.

In some embodiments, the concentration of one or more compounds of the invention is greater than 90%, 80%, 70%, 60%, 50%, 40%, 30%, 20%, 19.75%, 19.50%, 19.25% 19%, 18.75%, 18.50%, 18.25% 18%, 17.75%, 17.50%, 17.25% 17%, 16.75%, 16.50%, 16.25% 16%, 15.75%, 15.50%, 15.25% 15%, 14.75%, 14.50%, 14.25% 14%, 13.75%, 13.50%, 13.25% 13%, 12.75%, 12.50%, 12.25% 12%, 11.75%, 11.50%, 11.25% 11%, 10.75%, 10.50%, 10.25% 10%, 9.75%, 9.50%, 9.25% 9%, 8.75%, 8.50%, 8.25% 8%, 7.75%, 7.50%, 7.25% 7%, 6.75%, 6.50%, 6.25% 6%, 5.75%, 5.50%, 5.25% 5%, 4.75%, 4.50%, 4.25%, 4%, 3.75%, 3.50%, 3.25%, 3%, 2.75%, 2.50%, 2.25%, 2%, 1.75%, 1.50%, 125%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v, or v/v.

In some embodiments, the concentration of one or more compounds of the invention is in the range from approximately 0.0001% to approximately 50%, approximately 0.001% to approximately 40%, approximately 0.01% to approximately 30%, approximately 0.02% to approximately 29%, approximately 0.03% to approximately 28%, approximately 0.04% to approximately 27%, approximately 0.05% to approximately 26%, approximately 0.06% to approximately 25%, approximately 0.07% to approximately 24%, approximately 0.08% to approximately 23%, approximately 0.09% to approximately 22%, approximately 0.1% to approximately 21%, approximately 0.2% to approximately 20%, approximately 0.3% to approximately 19%, approximately 0.4% to approximately 18%, approximately 0.5% to approximately 17%, approximately 0.6% to approximately 16%, approximately 0.7% to approximately 15%, approximately 0.8% to approximately 14%, approximately 0.9% to approximately 12%, approximately 1% to approximately 10% w/w, w/v or v/v.

In some embodiments, the concentration of one or more compounds of the invention is in the range from approximately 0.001% to approximately 10%, approximately 0.01% to approximately 5%, approximately 0.02% to approximately 4.5%, approximately 0.03% to approximately 4%, approximately 0.04% to approximately 3.5%, approximately 0.05% to approximately 3%, approximately 0.06% to approximately 2.5%, approximately 0.07% to approximately 2%, approximately 0.08% to approximately 1.5%, approximately 0.09% to approximately 1%, approximately 0.1% to approximately 0.9% w/w, w/v or v/v.

In some embodiments, the amount of one or more compounds of the invention is equal to or less than 10 g, 9.5 g, 9.0 g, 8.5 g, 8.0 g, 7.5 g, 7.0 g, 6.5 g, 6.0 g, 5.5 g, 5.0 g, 4.5 g, 4.0 g, 3.5 g, 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g, or 0.0001 g.

In some embodiments, the amount of one or more compounds of the invention is more than 0.0001 g, 0.0002 g, 0.0003 g, 0.0004 g, 0.0005 g, 0.0006 g, 0.0007 g, 0.0008 g, 0.0009 g, 0.001 g, 0.0015 g, 0.002 g, 0.0025 g, 0.003 g, 0.0035 g, 0.004 g, 0.0045 g, 0.005 g, 0.0055 g, 0.006 g, 0.0065 g, 0.007 g, 0.0075 g, 0.008 g, 0.0085 g, 0.009 g, 0.0095 g, 0.01 g, 0.015 g, 0.02 g, 0.025 g, 0.03 g, 0.035 g, 0.04 g, 0.045 g, 0.05 g, 0.055 g, 0.06 g, 0.065 g, 0.07 g, 0.075 g, 0.08 g, 0.085 g, 0.09 g, 0.095 g, 0.1 g, 0.15 g, 0.2 g, 0.25 g, 0.3 g, 0.35 g, 0.4 g, 0.45 g, 0.5 g, 0.55 g, 0.6 g, 0.65 g, 0.7 g, 0.75 g, 0.8 g, 0.85 g, 0.9 g, 0.95 g, 1 g, 1.5 g, 2 g, 2.5, 3 g, 3.5, 4 g, 4.5 g, 5 g, 5.5 g, 6 g, 6.5 g, 7 g, 7.5 g, 8 g, 8.5 g, 9 g, 9.5 g, or 10 g.

In some embodiments, the amount of one or more compounds of the invention is in the range of 0.0001-10 g, 0.0005-9 g, 0.001-8 g, 0.005-7 g, 0.01-6 g, 0.05-5 g, 0.1-4 g, 0.5-4 g, or 1-3 g.

Kits/Articles of Manufacture

For use in the therapeutic applications described herein, kits and articles of manufacture are also provided. In some embodiments, such kits comprise a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. The containers are formed from a variety of materials such as glass or plastic.

The articles of manufacture provided herein contain packaging materials. Packaging materials for use in packaging pharmaceutical products include those found in, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. For example, the container(s) includes one or more compounds described herein, optionally in a composition or in combination with another agent as disclosed herein. The container(s) optionally have a sterile access port (for example the container is an intravenous solution bag or a vial having a stopper pierceable by a hypodermic injection needle). Such kits optionally comprise a compound with an identifying description or label or instructions relating to its use in the methods described herein.

For example, a kit typically includes one or more additional containers, each with one or more of various materials (such as reagents, optionally in concentrated form, and/or devices) desirable from a commercial and user standpoint for use of a compound described herein. Non-limiting examples of such materials include, but not limited to, buffers, diluents, filters, needles, syringes; carrier, package, container, vial and/or tube labels listing contents and/or instructions for use, and package inserts with instructions for use. A set of instructions will also typically be included. A label is optionally on or associated with the container. For example, a label is on a container when letters, numbers or other characters forming the label are attached, molded or etched into the container itself, a label is associated with a container when it is present within a receptacle or carrier that also holds the container, e.g., as a package insert. In addition, a label is used to indicate that the contents are to be used for a specific therapeutic application. In addition, the label indicates directions for use of the contents, such as in the methods described herein. In certain embodiments, the pharmaceutical compositions are presented in a pack or dispenser device which contains one or more unit dosage forms containing a compound provided herein. The pack for example contains metal or plastic foil, such as a blister pack. Or, the pack or dispenser device is accompanied by instructions for administration. Or, the pack or dispenser is accompanied with a notice associated with the container in form prescribed by a governmental agency regulating the manufacture, use, or sale of pharmaceuticals, which notice is reflective of approval by the agency of the form of the drug for human or veterinary administration. Such notice, for example, is the labeling approved by the U.S. Food and Drug Administration for prescription drugs, or the approved product insert. In some embodiments, compositions containing a compound provided herein formulated in a compatible pharmaceutical carrier are prepared, placed in an appropriate container, and labeled for treatment of an indicated condition.

Methods

Embodiments of the present invention provide a method of inhibiting RAS-mediated cell signaling comprising contacting a cell with an effective amount of one or more compounds disclosed herein. Inhibition of RAS-mediated signal transduction can be assessed and demonstrated by a wide variety of ways known in the art. Non-limiting examples include a showing of (a) a decrease in GTPase activity of RAS; (b) a decrease in GTP binding affinity or an increase in GDP binding affinity; (c) an increase in K off of GTP or a decrease in K off of GDP; (d) a decrease in the levels of signaling transduction molecules downstream in the RAS pathway, such as a decrease in pMEK level; and/or (e) a decrease in binding of RAS complex to downstream signaling molecules including but not limited to Raf. Kits and commercially available assays can be utilized for determining one or more of the above.

Embodiments also provide methods of using the compounds or pharmaceutical compositions of the present invention to treat disease conditions, including but not limited to conditions implicated by G12C KRAS, HRAS or NRAS mutation, G12C HRAS mutation and/or G12C NRAS mutation (e.g., cancer).

In some embodiments, a method for treatment of cancer is provided, the method comprising administering an effective amount of any of the foregoing pharmaceutical compositions comprising a compound of structure (I) to a subject in need thereof. In some embodiments, the cancer is mediated by a KRAS, HRAS or NRAS G12C mutation. In other embodiments, the cancer is pancreatic cancer, colon cancer, MYH associated polyposis, colorectal cancer or lung cancer.

In some embodiments the invention provides method of treating a disorder in a subject in need thereof, wherein the said method comprises determining if the subject has a KRAS, HRAS or NRAS G12C mutation and if the subject is determined to have the KRAS, HRAS or NRAS G12C mutation, then administering to the subject a therapeutically effective dose of at least one compound of structure (I) or a pharmaceutically acceptable salt, ester, prodrug, tautomer, solvate, hydrate or derivative thereof.

The disclosed compounds strongly inhibit anchorage-independent cell growth and therefore have the potential to inhibit tumor metastasis. Accordingly, in another embodiment the disclosure provides a method for inhibiting tumor metastasis, the method comprising administering an effective amount a pharmaceutical composition of comprising any of the compounds disclosed herein and a pharmaceutically acceptable carrier to a subject in need thereof.

KRAS, HRAS or NRAS G12C mutations have also been identified in hematological malignancies (e.g., cancers that affect blood, bone marrow and/or lymph nodes). Accordingly, certain embodiments are directed to administration of a disclosed compounds (e.g., in the form of a pharmaceutical composition) to a patient in need of treatment of a hematological malignancy. Such malignancies include, but are not limited to leukemias and lymphomas. For example, the presently disclosed compounds can be used for treatment of diseases such as Acute lymphoblastic leukemia (ALL), Acute myelogenous leukemia (AML), Chronic lymphocytic leukemia (CLL), small lymphocytic lymphoma (SLL), Chronic myelogenous leukemia (CML), Acute monocytic leukemia (AMoL) and/or other leukemias. In other embodiments, the compounds are useful for treatment of lymphomas such as all subtypes of Hodgkin's lymphoma or non-Hodgkin's lymphoma.

Determining whether a tumor or cancer comprises a G12C KRAS, HRAS or NRAS mutation can be undertaken by assessing the nucleotide sequence encoding the KRAS, HRAS or NRAS protein, by assessing the amino acid sequence of the KRAS, HRAS or NRAS protein, or by assessing the characteristics of a putative KRAS, HRAS or NRAS mutant protein. The sequence of wild-type human KRAS, HRAS or NRAS is known in the art, (e.g., Accession No. NP203524).

Methods for detecting a mutation in a KRAS, HRAS or NRAS nucleotide sequence are known by those of skill in the art. These methods include, but are not limited to, polymeRASe chain reaction-restriction fragment length polymorphism (PCR-RFLP) assays, polymeRASe chain reaction-single strand conformation polymorphism (PCR-SSCP) assays, real-time PCR assays, PCR sequencing, mutant allele-specific PCR amplification (MASA) assays, direct sequencing, primer extension reactions, electrophoresis, oligonucleotide ligation assays, hybridization assays, TaqMan assays, SNP genotyping assays, high resolution melting assays and microarray analyses. In some embodiments, samples are evaluated for G12C KRAS, HRAS or NRAS mutations by real-time PCR. In real-time PCR, fluorescent probes specific for the KRAS, HRAS or NRAS G12C mutation are used. When a mutation is present, the probe binds and fluorescence is detected. In some embodiments, the KRAS, HRAS or NRAS G12C mutation is identified using a direct sequencing method of specific regions (e.g., exon 2 and/or exon 3) in the KRAS, HRAS or NRAS gene. This technique will identify all possible mutations in the region sequenced.

Methods for detecting a mutation in a KRAS, HRAS or NRAS protein are known by those of skill in the art. These methods include, but are not limited to, detection of a KRAS, HRAS or NRAS mutant using a binding agent (e.g., an antibody) specific for the mutant protein, protein electrophoresis and Western blotting, and direct peptide sequencing.

Methods for determining whether a tumor or cancer comprises a G12C KRAS, HRAS or NRAS mutation can use a variety of samples. In some embodiments, the sample is taken from a subject having a tumor or cancer. In some embodiments, the sample is taken from a subject having a cancer or tumor. In some embodiments, the sample is a fresh tumor/cancer sample. In some embodiments, the sample is a frozen tumor/cancer sample. In some embodiments, the sample is a formalin-fixed paraffin-embedded sample. In some embodiments, the sample is processed to a cell lysate. In some embodiments, the sample is processed to DNA or RNA.

Embodiments of the invention also relate to a method of treating a hyperproliferative disorder in a mammal that comprises administering to said mammal a therapeutically effective amount of a compound of the present invention, or a pharmaceutically acceptable salt, ester, prodrug, solvate, hydrate or derivative thereof. In some embodiments, said method relates to the treatment of cancer such as acute myeloid leukemia, cancer in adolescents, adrenocortical carcinoma childhood, AIDS-related cancers (e.g., Lymphoma and Kaposi's Sarcoma), anal cancer, appendix cancer, astrocytomas, atypical teratoid, basal cell carcinoma, bile duct cancer, bladder cancer, bone cancer, brain stem glioma, brain tumor, breast cancer, bronchial tumors, burkitt lymphoma, carcinoid tumor, atypical teratoid, embryonal tumors, germ cell tumor, primary lymphoma, cervical cancer, childhood cancers, chordoma, cardiac tumors, chronic lymphocytic leukemia (CLL), chronic myelogenous leukemia (CML), chronic myleoproliferative disorders, colon cancer, colorectal cancer, craniopharyngioma, cutaneous T-cell lymphoma, extrahepatic ductal carcinoma in situ (DCIS), embryonal tumors, CNS cancer, endometrial cancer, ependymoma, esophageal cancer, esthesioneuroblastoma, Ewing sarcoma, extracranial germ cell tumor, extragonadal germ cell tumor, eye cancer, fibrous histiocytoma of bone, gall bladder cancer, gastric cancer, gastrointestinal carcinoid tumor, gastrointestinal stromal tumors (GIST), germ cell tumor, gestational trophoblastic tumor, hairy cell leukemia, head and neck cancer, heart cancer, liver cancer, Hodgkin's lymphoma, hypopharyngeal cancer, intraocular melanoma, islet cell tumors, pancreatic neuroendocrine tumors, kidney cancer, laryngeal cancer, lip and oral cavity cancer, liver cancer, lobular carcinoma in situ (LCIS), lung cancer, lymphoma, metastatic squamous neck cancer with occult primary, midline tract carcinoma, mouth cancer, multiple endocrine neoplasia syndromes, multiple myeloma/plasma cell neoplasm, mycosis fungoides, myelodysplastic syndromes, myelodysplastic/myeloproliferative neoplasms, multiple myeloma, merkel cell carcinoma, malignant mesothelioma, malignant fibrous histiocytoma of bone and osteosarcoma, nasal cavity and paranasal sinus cancer, nasopharyngeal cancer, neuroblastoma, non-Hodgkin's lymphoma, non-small cell lung cancer (NSCLC), oral cancer, lip and oral cavity cancer, oropharyngeal cancer, ovarian cancer, pancreatic cancer, papillomatosis, paraganglioma, paranasal sinus and nasal cavity cancer, parathyroid cancer, penile cancer, pharyngeal cancer, pleuropulmonary blastoma, primary central nervous system (CNS) lymphoma, prostate cancer, rectal cancer, transitional cell cancer, retinoblastoma, rhabdomyosarcoma, salivary gland cancer, skin cancer, stomach (gastric) cancer, small cell lung cancer, small intestine cancer, soft tissue sarcoma, T-Cell lymphoma, testicular cancer, throat cancer, thymoma and thymic carcinoma, thyroid cancer, transitional cell cancer of the renal pelvis and ureter, trophoblastic tumor, unusual cancers of childhood, urethral cancer, uterine sarcoma, vaginal cancer, vulvar cancer, or Viral-Induced cancer. In some embodiments, said method relates to the treatment of a non-cancerous hyperproliferative disorder such as benign hyperplasia of the skin (e.g., psoriasis), restenosis, or prostate (e.g., benign prostatic hypertrophy (BPH)).

In certain particular embodiments, the invention relates to methods for treatment of lung cancers, the methods comprise administering an effective amount of any of the above described compound (or a pharmaceutical composition comprising the same) to a subject in need thereof. In certain embodiments the lung cancer is a non-small cell lung carcinoma (NSCLC), for example adenocarcinoma, squamous-cell lung carcinoma or large-cell lung carcinoma. In other embodiments, the lung cancer is a small cell lung carcinoma. Other lung cancers treatable with the disclosed compounds include, but are not limited to, glandular tumors, carcinoid tumors and undifferentiated carcinomas.

Subjects that can be treated with compounds of the invention, or pharmaceutically acceptable salt, ester, prodrug, solvate, tautomer, hydrate or derivative of said compounds, according to the methods of this invention include, for example, subjects that have been diagnosed as having acute myeloid leukemia, acute myeloid leukemia, cancer in adolescents, adrenocortical carcinoma childhood, AIDS-related cancers (e.g., Lymphoma and Kaposi's Sarcoma), anal cancer, appendix cancer, astrocytomas, atypical teratoid, basal cell carcinoma, bile duct cancer, bladder cancer, bone cancer, brain stem glioma, brain tumor, breast cancer, bronchial tumors, burkitt lymphoma, carcinoid tumor, atypical teratoid, embryonal tumors, germ cell tumor, primary lymphoma, cervical cancer, childhood cancers, chordoma, cardiac tumors, chronic lymphocytic leukemia (CLL), chronic myelogenous leukemia (CML), chronic myeloproliferative disorders, colon cancer, colorectal cancer, craniopharyngioma, cutaneous T-cell lymphoma, extrahepatic ductal carcinoma in situ (DCIS), embryonal tumors, CNS cancer, endometrial cancer, ependymoma, esophageal cancer, esthesioneuroblastoma, Ewing sarcoma, extracranial germ cell tumor, extragonadal germ cell tumor, eye cancer, fibrous histiocytoma of bone, gall bladder cancer, gastric cancer, gastrointestinal carcinoid tumor, gastrointestinal stromal tumors (GIST), germ cell tumor, gestational trophoblastic tumor, hairy cell leukemia, head and neck cancer, heart cancer, liver cancer, Hodgkin's lymphoma, hypopharyngeal cancer, intraocular melanoma, islet cell tumors, pancreatic neuroendocrine tumors, kidney cancer, laryngeal cancer, lip and oral cavity cancer, liver cancer, lobular carcinoma in situ (LCIS), lung cancer, lymphoma, metastatic squamous neck cancer with occult primary, midline tract carcinoma, mouth cancer multiple endocrine neoplasia syndromes, multiple myeloma/plasma cell neoplasm, mycosis fungoides, myelodysplastic syndromes, myelodysplastic/myeloproliferative neoplasms, multiple myeloma, merkel cell carcinoma, malignant mesothelioma, malignant fibrous histiocytoma of bone and osteosarcoma, nasal cavity and paranasal sinus cancer, nasopharyngeal cancer, neuroblastoma, non-Hodgkin's lymphoma, non-small cell lung cancer (NSCLC), oral cancer, lip and oral cavity cancer, oropharyngeal cancer, ovarian cancer, pancreatic cancer, papillomatosis, paraganglioma, paranasal sinus and nasal cavity cancer, parathyroid cancer, penile cancer, pharyngeal cancer, pleuropulmonary blastoma, primary central nervous system (CNS) lymphoma, prostate cancer, rectal cancer, transitional cell cancer, retinoblastoma, rhabdomyosarcoma, salivary gland cancer, skin cancer, stomach (gastric) cancer, small cell lung cancer, small intestine cancer, soft tissue sarcoma, T-Cell lymphoma, testicular cancer, throat cancer, thymoma and thymic carcinoma, thyroid cancer, transitional cell cancer of the renal pelvis and ureter, trophoblastic tumor, unusual cancers of childhood, urethral cancer, uterine sarcoma, vaginal cancer, vulvar cancer, or Viral-Induced cancer. In some embodiments subjects that are treated with the compounds of the invention include subjects that have been diagnosed as having a non-cancerous hyperproliferative disorder such as benign hyperplasia of the skin (e.g., psoriasis), restenosis, or prostate (e.g., benign prostatic hypertrophy (BPH)).

Embodiments of the invention further provide methods of modulating a G12C Mutant KRAS, HRAS or NRAS protein activity by contacting the protein with an effective amount of a compound of the invention. Modulation can be inhibiting or activating protein activity. In some embodiments, the invention provides methods of inhibiting protein activity by contacting the G12C Mutant KRAS, HRAS or NRAS protein with an effective amount of a compound of the invention in solution. In some embodiments, the invention provides methods of inhibiting the G12C Mutant KRAS, HRAS or NRAS protein activity by contacting a cell, tissue, organ that express the protein of interest. In some embodiments, the invention provides methods of inhibiting protein activity in subject including but not limited to rodents and mammal (e.g., human) by administering into the subject an effective amount of a compound of the invention. In some embodiments, the percentage modulation exceeds 25%, 30%, 40%, 50%, 60%, 70%, 80%, or 90%. In some embodiments, the percentage of inhibiting exceeds 25%, 30%, 40%, 50%, 60%, 70%, 80%, or 90%.

In some embodiments, the invention provides methods of inhibiting KRAS, HRAS or NRAS G12C activity in a cell by contacting said cell with an amount of a compound of the invention sufficient to inhibit the activity of KRAS, HRAS or NRAS G12C in said cell. In some embodiments, the invention provides methods of inhibiting KRAS, HRAS or NRAS G12C activity in a tissue by contacting said tissue with an amount of a compound of the invention sufficient to inhibit the activity of KRAS, HRAS or NRAS G12C in said tissue. In some embodiments, the invention provides methods of inhibiting KRAS, HRAS or NRAS G12C activity in an organism by contacting said organism with an amount of a compound of the invention sufficient to inhibit the activity of KRAS, HRAS or NRAS G12C in said organism. In some embodiments, the invention provides methods of inhibiting KRAS, HRAS or NRAS G12C activity in an animal by contacting said animal with an amount of a compound of the invention sufficient to inhibit the activity of KRAS, HRAS or NRAS G12C in said animal. In some embodiments, the invention provides methods of inhibiting KRAS, HRAS or NRAS G12C activity in a mammal by contacting said mammal with an amount of a compound of the invention sufficient to inhibit the activity of KRAS, HRAS or NRAS G12C in said mammal. In some embodiments, the invention provides methods of inhibiting KRAS, HRAS or NRAS G12C activity in a human by contacting said human with an amount of a compound of the invention sufficient to inhibit the activity of KRAS, HRAS or NRAS G12C in said human. In other embodiments, the present invention provides methods of treating a disease mediated by KRAS, HRAS or NRAS G12C activity in a subject in need of such treatment.

Other embodiments provide methods for combination therapies in which an agent known to modulate other pathways, or other components of the same pathway, or even overlapping sets of target enzymes are used in combination with a compound of the present invention, or a pharmaceutically acceptable salt, ester, prodrug, solvate, tautomer, hydrate or derivative thereof. In one aspect, such therapy includes but is not limited to the combination of one or more compounds of the invention with chemotherapeutic agents, therapeutic antibodies, and radiation treatment, to provide a synergistic or additive therapeutic effect.

Many chemotherapeutics are presently known in the art and can be used in combination with the compounds of the invention. In some embodiments, the chemotherapeutic is selected from the group consisting of mitotic inhibitors, alkylating agents, anti-metabolites, intercalating antibiotics, growth factor inhibitors, cell cycle inhibitors, enzymes, topoisomeRASe inhibitors, biological response modifiers, anti-hormones, angiogenesis inhibitors, and anti-androgens.

Non-limiting examples are chemotherapeutic agents, cytotoxic agents, and non-peptide small molecules such as Gleevec® (Imatinib Mesylate), Velcade® (bortezomib), Casodex (bicalutamide), Iressa® (gefitinib), and Adriamycin as well as a host of chemotherapeutic agents. Non-limiting examples of chemotherapeutic agents include alkylating agents such as thiotepa and cyclosphosphamide (CYTOXAN®); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, Casodex®, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfomithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g. paclitaxel (TAXOL™, Bristol-Myers Squibb Oncology, Princeton, N.J.) and docetaxel (TAXOTERE™, Rhone-Poulenc Rorer, Antony, France); retinoic acid; esperamicins; capecitabine; and pharmaceutically acceptable salts, acids or derivatives of any of the above. Also included as suitable chemotherapeutic cell conditioners are anti-hormonal agents that act to regulate or inhibit hormone action on tumors such as anti-estrogens including for example tamoxifen, (Nolvadex™), raloxifene, aromatase inhibiting 4(5)-imidazoles, 4-hydroxytamoxifen, trioxifene, keoxifene, LY 117018, onapristone, and toremifene (Fareston); and anti-androgens such as flutamide, nilutamide, bicalutamide, leuprolide, and goserelin; chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; camptothecin-11 (CPT-11); topoisomeRASe inhibitor RFS 2000; difluoromethylornithine (DMFO). Where desired, the compounds or pharmaceutical composition of the present invention can be used in combination with commonly prescribed anti-cancer drugs such as Herceptin®, Avastin®, Erbitux®, Rituxan®, Taxol®, Arimidex®, Taxotere®, ABVD, AVICINE, Abagovomab, Acridine carboxamide, Adecatumumab, 17-N-Allylamino-17-demethoxygeldanamycin, Alpharadin, Alvocidib, 3-Aminopyridine-2-carboxaldehyde thiosemicarbazone, Amonafide, Anthracenedione, Anti-CD22 immunotoxins, Antineoplastic, Antitumorigenic herbs, Apaziquone, Atiprimod, Azathioprine, Belotecan, Bendamustine, BIBW 2992, Biricodar, Brostallicin, Bryostatin, Buthionine sulfoximine, CBV (chemotherapy), Calyculin, cell-cycle nonspecific antineoplastic agents, Dichloroacetic acid, Discodermolide, Elsamitrucin, Enocitabine, Epothilone, Eribulin, Everolimus, Exatecan, Exisulind, Ferruginol, Forodesine, Fosfestrol, ICE chemotherapy regimen, IT-101, Imexon, Imiquimod, Indolocarbazole, Irofulven, Laniquidar, Larotaxel, Lenalidomide, Lucanthone, Lurtotecan, Mafosfamide, Mitozolomide, Nafoxidine, Nedaplatin, Olaparib, Ortataxel, PAC-1, Pawpaw, Pixantrone, Proteasome inhibitor, Rebeccamycin, Resiquimod, Rubitecan, SN-38, Salinosporamide A, Sapacitabine, Stanford V, Swainsonine, Talaporfin, Tariquidar, Tegafur-uracil, Temodar, Tesetaxel, Triplatin tetranitrate, Tris(2-chloroethyl)amine, Troxacitabine, Uramustine, Vadimezan, Vinflunine, ZD6126 or Zosuquidar.

Embodiments further relate to a method for using the compounds or pharmaceutical compositions provided herein, in combination with radiation therapy for inhibiting abnormal cell growth or treating the hyperproliferative disorder in the mammal. Techniques for administering radiation therapy are known in the art, and these techniques can be used in the combination therapy described herein. The administration of the compound of the invention in this combination therapy can be determined as described herein.

Radiation therapy can be administered through one of several methods, or a combination of methods, including without limitation external-beam therapy, internal radiation therapy, implant radiation, stereotactic radiosurgery, systemic radiation therapy, radiotherapy and permanent or temporary interstitial brachytherapy. The term "brachytherapy," as used herein, refers to radiation therapy delivered by a spatially confined radioactive material inserted into the body at or near a tumor or other proliferative tissue disease site. The term is intended without limitation to include exposure to radioactive isotopes (e.g., At-211, I-131, I-125, Y-90, Re-186, Re-188, Sm-153, Bi-212, P-32, and radioactive isotopes of Lu). Suitable radiation sources for use as a cell conditioner of the present invention include both solids and liquids. By way of non-limiting example, the radiation source can be a radionuclide, such as I-125, I-131, Yb-169, Ir-192 as a solid source, I-125 as a solid source, or other radionuclides that emit photons, beta particles, gamma radiation, or other therapeutic rays. The radioactive material can also be a fluid made from any solution of radionuclide(s), e.g., a solution of I-125 or I-131, or a radioactive fluid can be produced using a slurry of a suitable fluid containing small particles of solid radionuclides, such as Au-198, Y-90. Moreover, the radionuclide(s) can be embodied in a gel or radioactive micro spheres.

Without being limited by any theory, the compounds of the present invention can render abnormal cells more sensitive to treatment with radiation for purposes of killing and/or inhibiting the growth of such cells. Accordingly, this invention further relates to a method for sensitizing abnormal cells in a mammal to treatment with radiation which comprises administering to the mammal an amount of a compound of the present invention or pharmaceutically acceptable salt, ester, prodrug, solvate, hydrate or derivative thereof, which amount is effective is sensitizing abnormal cells to treatment with radiation. The amount of the compound, salt, or solvate in this method can be determined according to the means for ascertaining effective amounts of such compounds described herein.

The compounds or pharmaceutical compositions of the invention can be used in combination with an amount of one or more substances selected from anti-angiogenesis agents, signal transduction inhibitors, antiproliferative agents, glycolysis inhibitors, or autophagy inhibitors.

Anti-angiogenesis agents, such as MMP-2 (matrix-metalloproteinase 2) inhibitors, MMP-9 (matrix-metalloproteinase 9) inhibitors, and COX-11 (cyclooxygenase 11) inhibitors, can be used in conjunction with a compound of the invention and pharmaceutical compositions described herein. Anti-angiogenesis agents include, for example, rapamycin, temsirolimus (CCI-779), everolimus (RAD001), sorafenib, sunitinib, and bevacizumab. Examples of useful COX-II inhibitors include CELEBREX™ (alecoxib), valdecoxib, and rofecoxib. Examples of useful matrix metalloproteinase inhibitors are described in WO 96/33172 (published Oct. 24, 1996), WO 96/27583 (published Mar. 7, 1996), European Patent Application No. 97304971.1 (filed Jul. 8, 1997), European Patent Application No. 99308617.2 (filed Oct. 29, 1999), WO 98/07697 (published Feb. 26, 1998), WO 98/03516 (published Jan. 29, 1998), WO 98/34918 (published Aug. 13, 1998), WO 98/34915 (published Aug. 13, 1998), WO 98/33768 (published Aug. 6, 1998), WO 98/30566 (published Jul. 16, 1998), European Patent Publication 606,046 (published Jul. 13, 1994), European Patent Publication 931, 788 (published Jul. 28, 1999), WO 90/05719 (published May 31, 1990), WO 99/52910 (published Oct. 21, 1999), WO 99/52889 (published Oct. 21, 1999), WO 99/29667 (published Jun. 17, 1999), PCT International Application No. PCT/IB98/01113 (filed Jul. 21, 1998), European Patent Application No. 99302232.1 (filed Mar. 25, 1999), Great Britain Patent Application No. 9912961.1 (filed Jun. 3, 1999), U.S. Provisional Application No. 60/148,464 (filed Aug. 12, 1999), U.S. Pat. No. 5,863,949 (issued Jan. 26, 1999), U.S. Pat. No. 5,861,510 (issued Jan. 19, 1999), and European Patent Publication 780,386 (published Jun. 25, 1997), all of which are incorporated herein in their entireties by reference. Preferred MMP-2 and MMP-9 inhibitors are those that have little or no activity inhibiting MMP-1. More preferred, are those that selectively inhibit MMP-2 and/or AMP-9 relative to the other matrix-metalloproteinases (i.e., MAP-1, MMP-3, MMP-4, MMP-5, MMP-6, MMP-7, MMP-8, MMP-10, MMP-11, MMP-12, and MMP-13). Some specific examples of MMP inhibitors useful in the invention are AG-3340, RO 32-3555, and RS 13-0830.

Autophagy inhibitors include, but are not limited to chloroquine, 3-methyladenine, hydroxychloroquine (Plaquenil™), bafilomycin A1, 5-amino-4-imidazole carboxamide riboside (AICAR), okadaic acid, autophagy-suppressive algal toxins which inhibit protein phosphatases of type 2A or type 1, analogues of cAMP, and drugs which elevate cAMP levels such as adenosine, LY204002, N6-mercaptopurine riboside, and vinblastine. In addition, antisense or siRNA that inhibits expression of proteins including but not limited to ATG5 (which are implicated in autophagy), may also be used.

Embodiments also relate to a method of and to a pharmaceutical composition for treating a cardiovascular disease in a mammal which comprises an amount of a compound of the invention, or a pharmaceutically acceptable salt, ester, prodrug, solvate, tautomer, hydrate or derivative thereof, or an isotopically-labeled derivative thereof, and an amount of one or more therapeutic agents use for the treatment of cardiovascular diseases.

Exemplary agents for use in cardiovascular disease applications are anti-thrombotic agents, e.g., prostacyclin and salicylates, thrombolytic agents, e.g., streptokinase, urokinase, tissue plasminogen activator (TPA) and anisoylated plasminogen-streptokinase activator complex (APSAC), anti-platelets agents, e.g., acetyl-salicylic acid (ASA) and clopidrogel, vasodilating agents, e.g., nitrates, calcium channel blocking drugs, anti-proliferative agents, e.g., colchicine and alkylating agents, intercalating agents, growth modulating factors such as interleukins, transformation growth factor-beta and congeners of platelet derived growth factor, monoclonal antibodies directed against growth factors, anti-inflammatory agents, both steroidal and non-steroidal, and other agents that can modulate vessel tone, function, arteriosclerosis, and the healing response to vessel or organ injury post intervention. Antibiotics can also be included in combinations or coatings comprised by the invention. Moreover, a coating can be used to affect therapeutic delivery focally within the vessel wall. By incorporation of the active agent in a swellable polymer, the active agent will be released upon swelling of the polymer.

In some embodiments, the compounds described herein are formulated or administered in conjunction with liquid or solid tissue barriers also known as lubricants. Examples of tissue barriers include, but are not limited to, polysaccharides, polyglycans, seprafilm, interceed and hyaluronic acid.

In some embodiments, medicaments which are administered in conjunction with the compounds described herein include any suitable drugs usefully delivered by inhalation for example, analgesics, e.g. codeine, dihydromorphine, ergotamine, fentanyl or morphine; anginal preparations, e.g. diltiazem; antiallergics, e.g. cromoglycate, ketotifen or nedocromil; anti-infectives, e.g. cephalosporins, penicillins, streptomycin, sulphonamides, tetracyclines or pentamidine; antihistamines, e.g. methapyrilene; anti-inflammatories, e.g. beclomethasone, flunisolide, budesonide, tipredane, triamcinolone acetonide or fluticasone; antitussives, e.g. noscapine; bronchodilators, e.g. ephedrine, adrenaline, fenoterol, formoterol, isoprenaline, metaproterenol, phenylephrine, phenylpropanolamine, pirbuterol, reproterol, rimiterol, salbutamol, salmeterol, terbutalin, isoetharine, tulobuterol, orciprenaline or (−)-4-amino-3,5-dichloro-α-[[[6-[2-(2-pyridinyl)ethoxy]hexyl]-amino]methyl]benzenemethanol; diuretics, e.g., amiloride; anticholinergics, e.g., ipratropium, atropine or oxitropium; hormones, e.g., cortisone, hydrocortisone or prednisolone; xanthines, e.g., aminophylline, choline theophyllinate, lysine theophyllinate or theophylline; and therapeutic proteins and peptides, e.g., insulin or glucagon. It will be clear to a person skilled in the art that, where appropriate, the medicaments are used in the form of salts (e.g., as alkali metal or amine salts or as acid addition salts)

or as esters (e.g., lower alkyl esters) or as solvates (e.g., hydrates) to optimize the activity and/or stability of the medicament.

Other exemplary therapeutic agents useful for a combination therapy include but are not limited to agents as described above, radiation therapy, hormone antagonists, hormones and their releasing factors, thyroid and antithyroid drugs, estrogens and progestins, androgens, adrenocorticotropic hormone; adrenocortical steroids and their synthetic analogs; inhibitors of the synthesis and actions of adrenocortical hormones, insulin, oral hypoglycemic agents, and the pharmacology of the endocrine pancreas, agents affecting calcification and bone turnover: calcium, phosphate, parathyroid hormone, vitamin D, calcitonin, vitamins such as water-soluble vitamins, vitamin B complex, ascorbic acid, fat-soluble vitamins, vitamins A, K, and E, growth factors, cytokines, chemokines, muscarinic receptor agonists and antagonists; anticholinesterase agents; agents acting at the neuromuscular junction and/or autonomic ganglia; catecholamines, sympathomimetic drugs, and adrenergic receptor agonists or antagonists; and 5-hydroxytryptamine (5-HT, serotonin) receptor agonists and antagonists.

Therapeutic agents can also include agents for pain and inflammation such as histamine and histamine antagonists, bradykinin and bradykinin antagonists, 5-hydroxytryptamine (serotonin), lipid substances that are generated by biotransformation of the products of the selective hydrolysis of membrane phospholipids, eicosanoids, prostaglandins, thromboxanes, leukotrienes, aspirin, nonsteroidal anti-inflammatory agents, analgesic-antipyretic agents, agents that inhibit the synthesis of prostaglandins and thromboxanes, selective inhibitors of the inducible cyclooxygenase, selective inhibitors of the inducible cyclooxygenase-2, autacoids, paracrine hormones, somatostatin, gastrin, cytokines that mediate interactions involved in humoral and cellular immune responses, lipid-derived autacoids, eicosanoids, β-adrenergic agonists, ipratropium, glucocorticoids, methylxanthines, sodium channel blockers, opioid receptor agonists, calcium channel blockers, membrane stabilizers and leukotriene inhibitors.

Additional therapeutic agents contemplated herein include diuretics, vasopressin, agents affecting the renal conservation of water, rennin, angiotensin, agents useful in the treatment of myocardial ischemia, anti-hypertensive agents, angiotensin converting enzyme inhibitors, β-adrenergic receptor antagonists, agents for the treatment of hypercholesterolemia, and agents for the treatment of dyslipidemia.

Other therapeutic agents contemplated include drugs used for control of gastric acidity, agents for the treatment of peptic ulcers, agents for the treatment of gastroesophageal reflux disease, prokinetic agents, antiemetics, agents used in irritable bowel syndrome, agents used for diarrhea, agents used for constipation, agents used for inflammatory bowel disease, agents used for biliary disease, agents used for pancreatic disease. Therapeutic agents used to treat protozoan infections, drugs used to treat Malaria, Amebiasis, Giardiasis, Trichomoniasis, Trypanosomiasis, and/or Leishmaniasis, and/or drugs used in the chemotherapy of helminthiasis. Other therapeutic agents include antimicrobial agents, sulfonamides, trimethoprim-sulfamethoxazole quinolones, and agents for urinary tract infections, penicillins, cephalosporins, and other, β-lactam antibiotics, an agent comprising an aminoglycoside, protein synthesis inhibitors, drugs used in the chemotherapy of tuberculosis, *Mycobacterium avium* complex disease, and leprosy, antifungal agents, antiviral agents including non-retroviral agents and antiretroviral agents.

Examples of therapeutic antibodies that can be combined with a compound of the invention include but are not limited to anti-receptor tyrosine kinase antibodies (cetuximab, panitumumab, trastuzumab), anti CD20 antibodies (rituximab, tositumomab), and other antibodies such as alemtuzumab, bevacizumab, and gemtuzumab.

Moreover, therapeutic agents used for immunomodulation, such as immunomodulators, immunosuppressive agents, tolerogens, and immunostimulants are contemplated by the methods herein. In addition, therapeutic agents acting on the blood and the blood-forming organs, hematopoietic agents, growth factors, minerals, and vitamins, anticoagulant, thrombolytic, and antiplatelet drugs.

For treating renal carcinoma, one may combine a compound of the present invention with sorafenib and/or avastin. For treating an endometrial disorder, one may combine a compound of the present invention with doxorubicin, taxotere (taxol), and/or cisplatin (carboplatin). For treating ovarian cancer, one may combine a compound of the present invention with cisplatin (carboplatin), taxotere, doxorubicin, topotecan, and/or tamoxifen. For treating breast cancer, one may combine a compound of the present invention with taxotere (taxol), gemcitabine (capecitabine), tamoxifen, letrozole, tarceva, lapatinib, PD0325901, avastin, herceptin, OSI-906, and/or OSI-930. For treating lung cancer, one may combine a compound of the present invention with taxotere (taxol), gemcitabine, cisplatin, pemetrexed, Tarceva, PD0325901, and/or avastin.

In other embodiments, agents useful in methods for combination therapy with one or more compounds of structure (I) include, but are not limited to: Erlotinib, Afatinib, Iressa, GDC0941, MLN1117, BYL719 (Alpelisib), BKM120 (Buparlisib), CYT387, GLPG0634, Baricitinib, Lestaurtinib, momelotinib, Pacritinib, Ruxolitinib, TG101348, Crizotinib, tivantinib, AMG337, cabozantinib, foretinib, onartuzumab, NVP-AEW541, Dasatinib, Ponatinib, saracatinib, bosutinib, trametinib, selumetinib, cobimetinib, PD0325901, RO5126766, Axitinib, Bevacizumab, Bostutinib, Cetuximab, Crizotinib, Fostamatinib, Gefitinib, Imatinib, Lapatinib, Lenvatinib, Ibrutinib, Nilotinib, Panitumumab, Pazopanib, Pegaptanib, Ranibizumab, Ruxolitinib, Sorafenib, Sunitinib, SU6656, Trastuzumab, Tofacitinib, Vandetanib, Vemurafenib, Irinotecan, Taxol, Docetaxel, Rapamycin or MLN0128.

Further therapeutic agents that can be combined with a compound of the invention are found in Goodman and Gilman's "The Pharmacological Basis of Therapeutics" Tenth Edition edited by Hardman, Limbird and Gilman or the Physician's Desk Reference, both of which are incorporated herein by reference in their entirety.

The compounds described herein can be used in combination with the agents disclosed herein or other suitable agents, depending on the condition being treated. Hence, in some embodiments the one or more compounds of the invention will be co-administered with other agents as described above. When used in combination therapy, the compounds described herein are administered with the second agent simultaneously or separately. This administration in combination can include simultaneous administration of the two agents in the same dosage form, simultaneous administration in separate dosage forms, and separate administration. That is, a compound described herein and any of the agents described above can be formulated together in the same dosage form and administered simultaneously. Alternatively, a compound of the invention and any of the agents described above can be simultaneously administered, wherein both the agents are present in separate formulations. In another alternative, a compound of the present invention can be administered just followed by and any of the agents described above, or vice versa. In some embodiments of the separate administration protocol, a compound of the invention and any of the agents described above are administered a few minutes apart, or a few hours apart, or a few days apart.

The examples and preparations provided below further illustrate and exemplify the compounds of the present invention and methods of preparing such compounds. It is to be understood that the scope of the present invention is not limited in any way by the scope of the following examples and preparations. In the following examples, and throughout the specification and claims, molecules with a single stereocenter, unless otherwise noted, exist as a racemic mixture. Those molecules with two or more stereocenters, unless otherwise noted, exist as a racemic mixture of diastereomers. Single enantiomers/diastereomers may be obtained by methods known to those skilled in the art.

EXAMPLES

The following examples are provided for exemplary purposes. Methods for preparation of compounds of structure (I) are known in the art or can be derived by one of ordinary skill in the art.

Example 1

Biochemical Assay of the Compounds

Test compounds were prepared as 10 mM stock solutions in DMSO (Fisher cat # BP-231-100). KRAS G12C 1-169, his-tagged protein, GDP-loaded is diluted to 2 µM or 0.5 µM in buffer (20 mM Hepes, 150 mM NaCl, 1 mM $MgCl_2$). Compounds were tested for activity as follows:

Compounds were diluted to 50× final test concentration in DMSO in 96-well storage plates. Compound stock solutions were vortexed before use and observed carefully for any sign of precipitation. Dilutions are as follow:

For 100 µM final compound concentration, compounds were diluted to 5000 µM (5 µL 10 mM compound stock+5 µL DMSO and mixed well by pipetting.

For 30 µM final compound concentration, compounds were diluted to 1500 µM (3 µL 10 mM compound stock+17 µL DMSO) and mixed well by pipetting.

For 10 µM final compound concentration, compounds were diluted to 500 µM (2 µL 10 mM compound stock+38 µL DMSO) and mixed well by pipetting.

49 µL of the stock protein solution was added to each well of a 96-well PCR plate (Fisher cat #1423027). 1 µL of the diluted 50× compounds were added to appropriate wells in the PCR plate using 12-channel pipettor. Reactions were mixed carefully and thoroughly by pipetting up/down with a 200 µL multi-channel pipettor. The plate was sealed well with aluminum plate seal, and stored in drawer at room temperature for 10 minutes, 30 minutes, 2 hours or 24 hours. 5 µL of 2% formic acid (Fisher cat # A117) in de-ionized $H_2O$ was then added to each well followed by mixing with a pipette. The plate was then resealed with aluminum seal and stored on dry ice until analyzed as described below.

The above described assays were analyzed by mass spectrometry according to one of the following two procedures:

RapidFire/TOF Assay:

The MS instrument was set to positive polarity, 2 GHz resolution, and low mass (1700) mode and allowed to equilibrate for 30 minutes. The instrument was then calibrated, switched to acquisition mode and the appropriate method loaded.

After another 30 minute equilibration time, a blank batch (i.e., buffer) was run to ensure equipment is operating properly. The samples were thawed at 37° C. for 10 minutes, briefly centrifuged, and transfer to the bench top. Wells A1 and H12 were spiked with 1 L 500 µM internal standard peptide, and the plates centrifuged at 2000×g for 5 minutes. The method was then run and masses of each individual well recorded.

The masses (for which integration data is desired) for each well were pasted into the platemap and exported from the analysis. Masses for the internal standards were exported as well. The data at 50 ppm was extracted for the +19 charge state, and identity of well A1 was assigned using the internal standard spike and integrated. Peak data was exported as a TOF list and the above steps were repeated individually, for the +20, 21, 22, 23, 24, and 25 charge states.

Q-Exactive Assay:

The masses and peak intensities of KRAS G12C protein species were measured using a Dionex RSLCnano system (Thermo Scientific) connected to a Q Exactive Plus mass spectrometer (Thermo Scientific).

20 mL of sample was each loaded onto a Aeris™ 3.6 m WIDEPORE C4 200 Å, LC Column 50×2.1 mm column maintained at 40° C. at a flow rate of 600 µL/min with 20% Solvent A (0.1% formic acid in $H_2O$) and 80% Solvent B (0.1% formic acid in acetonitrile). The liquid chromatography conditions were 20% solvent B for 1 minute, 20% to 60% solvent B for 1.5 minutes, 60% to 90% solvent for 0.5 minute, 90% solvent B for 0.2 minute, 90% to 20% solvent B for 0.2 minute, and then equilibrated for 1.6 minutes before the following sample injection. The flow rate was maintained at 600 µL/min throughout the sample analysis.

The mass spectrometer was operated in profile mode at a resolution of 17500, 5 microscans, using 50 msec max injection time and an AGC target of $1\times10^6$, and a full mass range from 800-1850 m/z was recorded. The HCD trapping gas was optimized for maximum sensitivity for intact proteins. The ionization method was electrospray ionization, which used a spray voltage of 4 kV, sheath gas flow set to 50 AU, auxiliary gas flow set to 10 AU and sweep gas flow set to 1 AU. The capillary ion transfer temperature was 320° C. and the S-lens RF level is set to 50 voltage. Protein Deconvolution software (Thermo Scientific) was used for quantitative deconvolution of the charge envelopes of each protein species in samples to determine the mass and intensity of each parent species (modified or unmodified protein). The modification percentages were calculated based on deconvoluted peak intensities.

Other in vitro analyses are as follows:
Inhibition of Cell Growth:

The ability of the subject compounds to inhibit RAS-mediated cell growth was assessed and demonstrated as follows. Cells expressing a wildtype or a mutant RAS were plated in white, clear bottom 96 well plates at a density of 5,000 cells per well. Cells were allowed to attach for about 2 hours after plating before a compound disclosed herein is added. After certain hours (e.g., 24 hours, 48 hours, or 72 hours of cell growth), cell proliferation was determined by measuring total ATP content using the Cell Titer Glo reagent (Promega) according to manufacturer's instructions. Proliferation $EC_{50}$ was determined by analyzing 8 point compound dose responses at half-log intervals decreasing from 100 μM.

Inhibition of RAS-Mediated Signaling Transduction:

The ability of the compounds disclosed herein in inhibiting RAS-mediated signaling was assessed and demonstrated as follows. Cells expressing wild type or a mutant RAS (such as G12C, G12V, or G12A) were treated with or without (control cells) a subject compound. Inhibition of RAS signaling by one or more subject compounds was demonstrated by a decrease in the steady-state level of phosphorylated MEK, phosphorylated ERK, phosphorylated RSK, and/or Raf binding in cells treated with the one or more of the subject compounds as compared to the control cells.

Representative compounds in Table 1 were tested according to the above methods and found to covalently bind to (or modify) KRAS G12C to the extent indicated in Table 3 after a ten minute incubation period.

TABLE 3

Modification Activity of Representative Compounds

| No. | Binding % | No. | Binding % | No. | Binding % | No. | Binding % | No. | Binding % |
|---|---|---|---|---|---|---|---|---|---|
| 1 | ++ | 2 | ++ | 3 | +++ | 4 |  | 5 |  |
| 6 |  | 7 |  | 8 |  | 9 |  | 10 |  |
| 11 |  | 12 |  | 13 | ++ | 14 |  | 15 |  |
| 16 |  | 17 |  | 18 |  | 19 |  | 20 |  |
| 21 |  | 22 | + | 23 | +++ | 24 |  | 25 |  |
| 26 |  | 27 |  | 28 |  | 29 | + | 30 | + |
| 31 |  | 32 |  | 33 |  | 34 |  | 35 | +++ |
| 36 | + | 37 | +++ | 38 | + | 39 | + | 40 | +++ |
| 41 | +++ | 42 | + | 43 | + | 44 | ++ | 45 | +++ |
| 46 | ++ | 47 | ++ | 48 | +++ | 49 | +++ | 50 | +++ |
| 51 |  | 52 | ++ | 53 | + | 54 |  | 55 | + |
| 56 | + | 57 | +++ | 58 | + | 59 | +++ | 60 | +++ |
| 61 | +++ | 62 | +++ | 63 | ++ | 64 | ++ | 65 | + |
| 66 | + | 67 | +++ | 68 | +++ | 69 | +++ | 70 | +++ |
| 71 | + | 72 | +++ | 73 | + | 74 | + | 75 | + |
| 76 | +++ | 77 | + | 78 | +++ | 79 | +++ | 80 | +++ |
| 81 | ++ | 82 | +++ | 83 | + | 84 | +++ | 85 | +++ |
| 86 | + | 87 | +++ | 88 | ++ | 89 | +++ | 90 | + |
| 91 | +++ | 92 | ++ | 93 | ++ | 94 | ++ | 95 | +++ |
| 96 | + | 97 | + | 98 | +++ | 99 | + | 100 | +++ |
| 101 | + | 102 | +++ | 103 | + | 104 | +++ | 105 | ++ |
| 106 | +++ | 107 | + | 108 | +++ | 109 | +++ | 110 | + |
| 111 | ++ | 112 | + | 113 | ++ | 114 | +++ | 115 | + |
| 116 | + | 117 | +++ | 118 | +++ | 119 | + | 120 | ++ |
| 121 | + | 122 | +++ | 123 | +++ | 124 | ++ | 125 | ++ |
| 126 | +++ | 127 | ++ | 128 | +++ | 129 | +++ | 130 | ++ |
| 131 | + | 132 | + | 133 | + | 134 | +++ | 135 | + |
| 136 | +++ | 137 | + | 138 | +++ | 139 | + | 140 | +++ |
| 141 | + | 142 | +++ | 143 | + | 144 | +++ | 145 | +++ |
| 146 | + | 147 | +++ | 148 | +++ | 149 | + | 150 | +++ |
| 151 | + | 152 | +++ | 153 | + | 154 | +++ | 155 | + |
| 156 | +++ | 157 | +++ | 158 | ++ | 159 | + | 160 | +++ |
| 161 | +++ | 162 | +++ | 163 | + | 164 | +++ | 165 | +++ |
| 166 | + | 167 | +++ | 168 | + | 169 | +++ | 170 | +++ |
| 171 | +++ | 172 | +++ | 173 | +++ | 174 | +++ | 175 | ++ |
| 176 | +++ | 177 | +++ | 178 | ++ | 179 | +++ | 180 | ++ |
| 181 | + | 182 | ++ | 183 | +++ | 184 | +++ | 185 | +++ |
| 186 | +++ | 187 | +++ | 188 | +++ | 189 | +++ | 190 | +++ |
| 191 | + | 192 | +++ | 193 | +++ | 194 | + | 195 | + |
| 196 | ++ | 197 | +++ | 198 | ++ | 199 | +++ | 200 | + |
| 201 | +++ | 202 | + | 203 | +++ | 204 | ND | 205 | +++ |
| 206 | +++ | 207 | + | 208 | +++ | 209 | +++ | 210 | + |
| 211 | + | 212 | +++ | 213 | + | 214 | +++ | 215 | +++ |
| 216 | ++ | 217 | + | 218 | +++ | 219 | + | 220 | +++ |
| 221 | +++ | 222 | + | 223 | + | 224 | + | 225 | ++ |
| 226 | ++ | 227 | + | 228 | +++ | 229 | +++ | 230 | + |
| 231 | ++ | 232 | ++ | 233 | +++ | 234 | ++ | 235 | +++ |
| 236 | + | 237 | ++ | 238 | ++ | 239 | +++ | 240 | + |
| 241 | + | 242 | + | 243 | +++ | 244 | ++ | 245 | + |
| 246 | + | 247 | ++ | 248 | + | 249 | + | 250 | + |

TABLE 3-continued

Modification Activity of Representative Compounds

| No. | Binding % | No. | Binding % | No. | Binding % | No. | Binding % | No. | Binding % |
|---|---|---|---|---|---|---|---|---|---|
| 251 | +++ | 252 | + | 253 | + | 254 | + | 255 | + |
| 256 | ++ | 257 | ++ | 258 | +++ | 259 | ++ | 260 | +++ |
| 261 | +++ | 262 | + | 263 | + | 264 | +++ | 265 | ++ |
| 266 | ++ | 267 | +++ | 268 | +++ | 269 | +++ | 270 | +++ |
| 271 | +++ |  |  |  |  |  |  |  |  |

+ indicates binding activity greater than 0% and up to 50%
++ indicates binding activity from 50 to 80%
+++ indicates binding activity greater than 80%
ND = Not determined Example 2

Synthesis of 1-((2R,5S)-4-(7-(3-amino-1H-indazol-4-yl)-6-chloro-2-(3-(dimethylamino)azetidin-1-yl)-8-fluoroquinazolin-4-yl)-2,5-dimethylpiperazin-1-yl)prop-2-en-1-one (Compound 2)

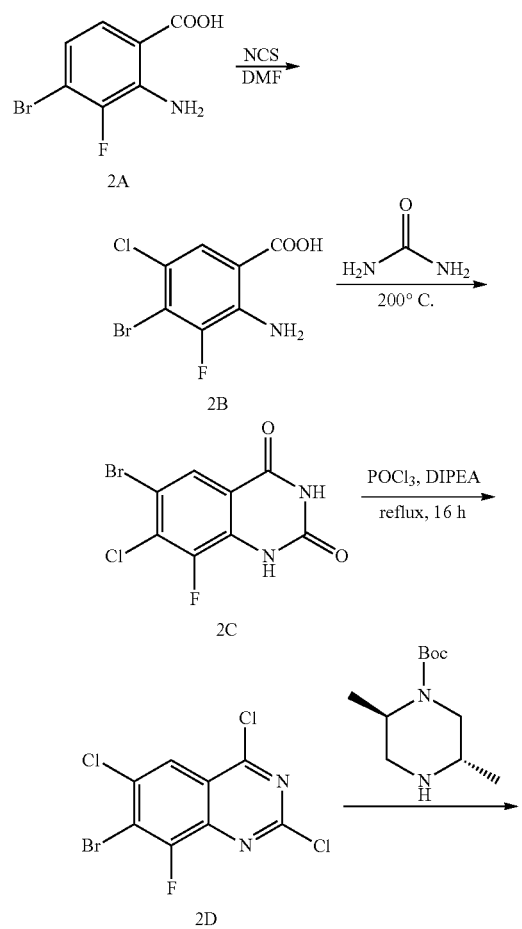

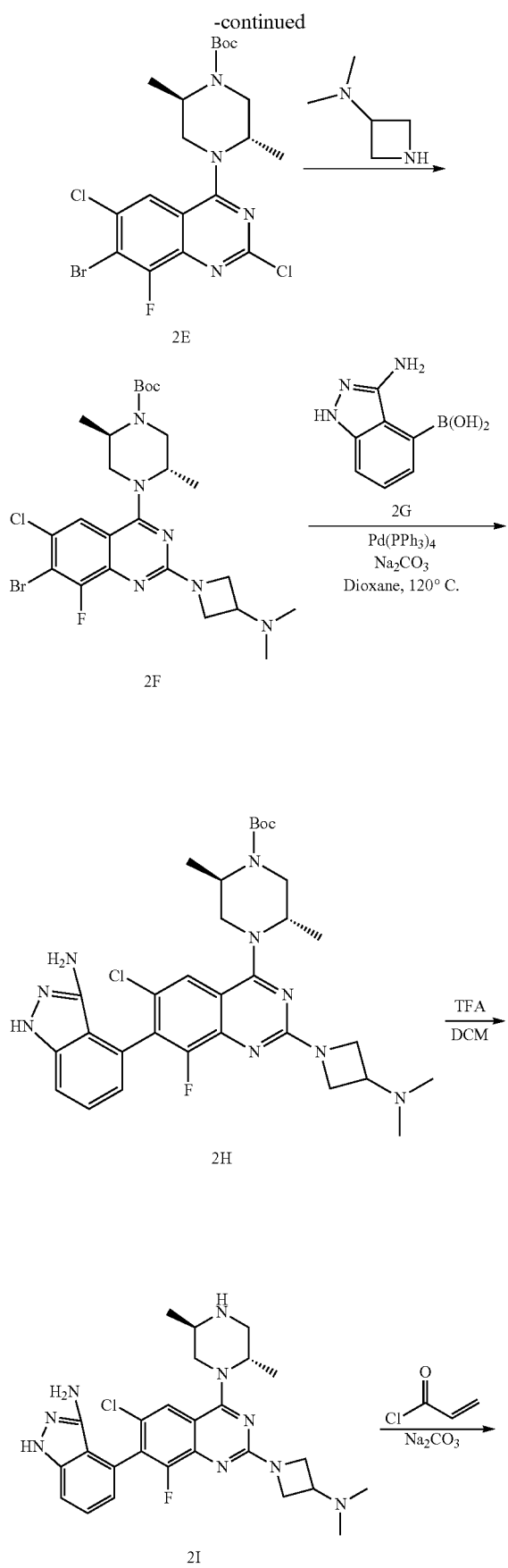

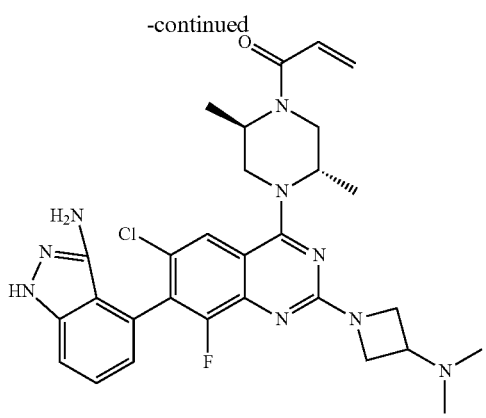

Compound 2 was prepared according to Method A as illustrated above and described below.

2-Amino-4-bromo-5-chloro-3-fluorobenzoic acid (2B)

To a solution of 2-amino-4-bromo-3-fluorobenzoic acid (234 mg, 1.00 mmol) in dimethylformamide (DMF, 10 mL) at room temperature, was added N-chlorosuccinimide (NCS, 134 mg, 1 mmol) and the resulting mixture was stirred at 70° C. for 16 hours. The mixture was poured into ice-water. The resultant precipitate was collected by filtration, washed with water and dried to afford the desired product 2B (209 mg, 78%). ESI-MS m/z: 269.8 [M+H]⁺.

6-Bromo-7-chloro-8-fluoroquinazoline-2,4(1H, 3H)-dione (2C)

A mixture of compound 2B (10.0 g, 39.9 mmol) and urea (12 g, 199.6 mmol) was stirred at 200° C. for 3 hours. The mixture was allowed to cool to room temperature, triturated with ethyl acetate and dried to afford the desired product 2C (13 g, 100%).

6-Bromo-2,4,7-trichloro-8-fluoroquinazoline (2D)

The mixture of compound 2C (13 g, 44.5 mmol) in POCl₃ (200 mL) and diisopropyl ethyl amine (DIPEA, 20 mL) was stirred at reflux for 16 hours. The mixture was allowed to cool to room temperature and concentrated in vacuo to remove POCl₃. The residue was purified by flash column chromatography on silica gel (5% ethyl acetate/petroleum ether) to afford the desired product 2D (10.4 g, 74%).

(2R,5S)-tert-Butyl4-(7-bromo-2,6-dichloro-8-fluoro-quinazolin-4-yl)-2,5-dimethylpiperazine-1-carboxylate (2E)

To a stirred solution of compound 2D (5.0 g, 15.20 mmol) in dichloromethane (100 mL) and triethylamine (4.61 g, 45.6 mmol), was added (2R,5S)-tert-butyl 2,5-dimethylpiperazine-1-carboxylate (3.25 g, 15.20 mmol). The mixture was stirred at room temperature for 1.5 hours, extracted with dichloromethane and washed with aqueous saturated sodium bicarbonate. The organic layer was dried over sodium sulfate and concentrated in vacuo to afford the desired product 2E (7.7 g, 100%). ESI-MS m/z: 509.3 [M+H]⁺.

(2R,5S)-tert-Butyl 4-(7-bromo-6-chloro-2-(3-(dimethylamino)azetidin-1-yl)-8-fluoroquinazolin-4-yl)-2,5-dimethylpiperazine-1-carboxylate (2F)

A mixture of compound 2E (7.7 g, 15.20 mmol) in isopropanol (150 mL) and DIPEA (9.80 g, 76.0 mmol), was added N,N-dimethylazetidin-3-amine dihydrochloride (3.16 g, 18.24 mmol). The mixture was stirred at reflux for 16 hours. The mixture was concentrated in vacuo. The residue was extracted with ethyl acetate and washed with water. The organic layer was dried over sodium sulfate and concentrated in vacuo. The residue was purified by flash column chromatography on silica gel to afford the desired product 2F (8.52 g, 98%).

ESI-MS m/z: 573.1 [M+H]$^+$.

(3-amino-1H-indazol-4-yl)boronic acid (2G)

The mixture of 4-iodo-1H-indazol-3-amine (150 mg, 0.58 mmol), 4,4,4',4',5,5,5',5'-octamethyl-2,2'-bi(1,3,2-dioxaborolane) (224 mg, 0.88 mmol) and potassium acetate (290.4 mg, 2.96 mmol) in 3 mL of dioxane was purged with nitrogen for 5 minutes and then PdCl$_2$(PPh$_3$)$_2$ (41.3 mg, 0.06 mmol) was added. The mixture was purged with nitrogen for 5 minutes and stirred at 100° C. overnight to afford the crude product 2G. ESI-MS m/z: 178.2 [M+H]$^+$.

tert-Butyl (2R,5S)-4-(7-(3-amino-1H-indazol-4-yl)-6-chloro-2-(3-(dimethylamino)azetidin-1-yl)-8-fluoroquinazolin-4-yl)-2,5-dimethylpiperazine-1-carboxylate (2H)

To above reaction mixture containing compound 2G, 2F (220 mg, 0.39 mmol), Pd(PPh$_3$)$_4$ (45.2 mg, 0.04 mmol) and Na$_2$CO$_3$ (1 mL of 1M solution) were added. The mixture was purged with nitrogen for 5 minutes and then stirred in microwave reactor at 120° C. for 1 hour. The mixture was diluted with water and extracted with dichloromethane. The organic layer was dried over sodium sulfate and concentrated in vacuo. The residue was purified via Isolera One (10% methanol and 0.035% ammonia in dichloromethane) to afford the desired product 2H (103 mg, 12%, two steps). ESI-MS m/z: 624.3 [M+H]$^+$.

4-(6-chloro-2-(3-(dimethylamino)azetidin-1-yl)-4-((2S,5R)-2,5-dimethylpiperazin-1-yl)-8-fluoroquinazolin-7-yl)-1H-indazol-3-amine (2I)

The above obtained compound 2H (103 mg) was dissolved in 5 mL of 50% trifluoroacetic acid in dichloromethane. The mixture was stirred for 30 minutes. The mixture was concentrated in vacuo. The residue was dissolved in dichloromethane and washed with aqueous saturated sodium bicarbonate. The organic layer was dried over magnesium sulfate, filtered and concentrated in vacuo to afford the desired product 2I. The crude product 2I was used in the next step without further purification. ESI-MS m/z: 524.2 [M+H]$^+$.

1-((2R,5S)-4-(7-(3-amino-H-indazol-4-yl)-6-chloro-2-(3-(dimethylamino)azetidin-1-yl)-8-fluoroquinazolin-4-yl)-2,5-dimethylpiperazin-1-yl)prop-2-en-1-one (2J)

To a solution of compound 2I in 2-methyl-THF (5 mL), was added 2 mL of 1M Na$_2$CO$_3$ aqueous solution, followed by addition of acryloyl chloride (1.75 eq). The reaction mixture was diluted in 30% isopropanol/dichloromethane and washed with water. The organic layer was dried over sodium sulfate, filtered and concentrated in vacuo. The residue was purified via prep-HPLC to afford the desired product 2J (12.7 mg, 13%, two steps). ESI-MS m/z: 578.2 [M+H]$^+$; $^1$H NMR (500 MHz, DMSO-d$_6$) δ: 11.77 (s, 1H), 7.72 (s, 1H), 7.33-7.40 (m, 2H), 6.75-6.90 (m, 2H), 6.18 (d, J=16.5 Hz, 1H), 5.70-5.77 (m, 1H), 4.35-4.75 (m, 2H), 3.7-4.25 (m, 8H), 3.14 (m, 1H), 2.11 (s, 6H), 1.13-1.35 (m, 6H).

Example 3

Synthesis of 1-((2R,5S)-4-(7-(3-amino-5-methyl-1H-indazol-4-yl)-6-chloro-2-(3-(dimethylamino)azetidin-1-yl)-8-fluoroquinazolin-4-YL)-2,5-dimethylpiperazin-1-yl)prop-2-en-1-one (Compound 3)

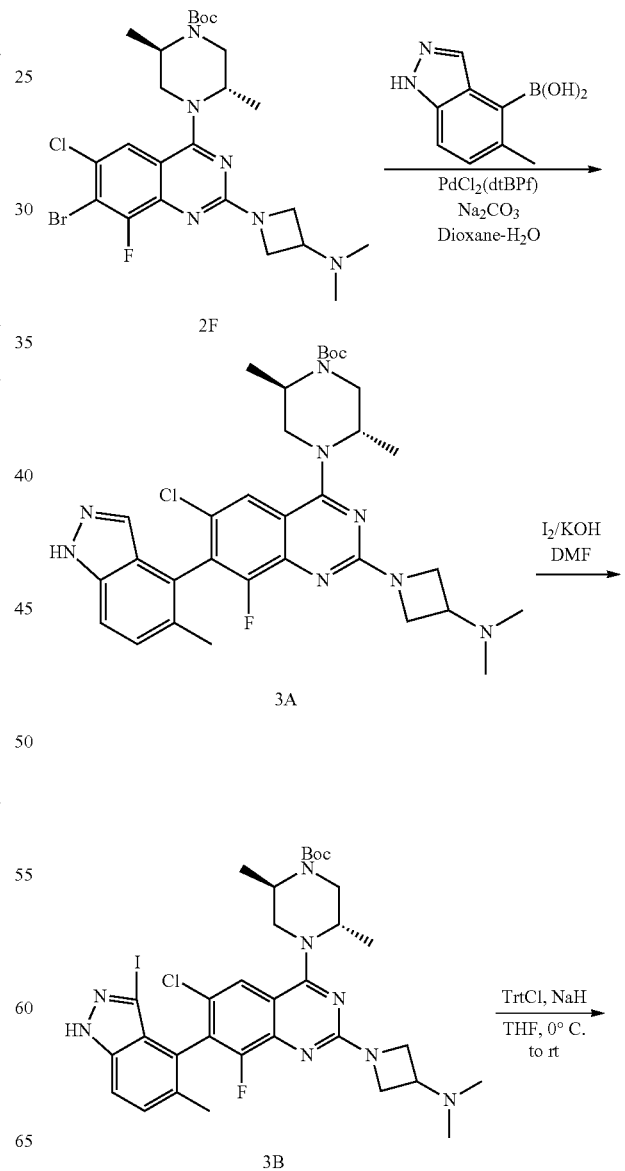

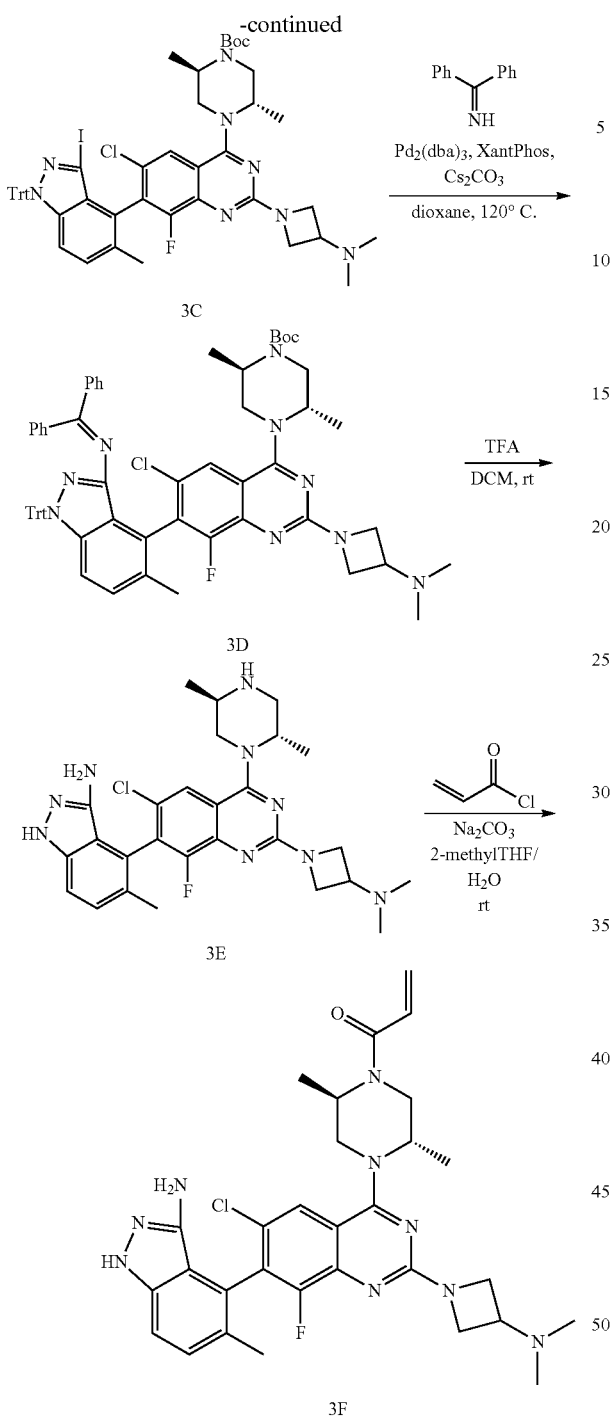

Compound 3 was prepared according to Method B as illustrated above and described below.

tert-Butyl (2R,5S)-4-(6-chloro-2-(3-(dimethylamino) azetidin-1-yl)-8-fluoro-7-(5-methyl-1H-indazol-4-yl) quinazolin-4-yl)-2,5-dimethylpiperazine-1-carboxylate (3A)

The mixture of compound 2F (500 mg, 0.87 mmol), (5-methyl-1H-indazol-4-yl)boronic acid (184 mg, 1.04 mmol) and PdCl$_2$(dtBPf) (60 mg, 0.09 mmol) in 5 mL of 1,4-dioxane and 3 mL of 1 M Na$_2$CO$_3$ was stirred at 120° C. in microwave reactor for 2 hours. The mixture was partitioned between dichloromethane and water. The organic layer was dried over sodium sulfate, filtered and concentrated in vacuo. The residue was purified via Isolera One (10% methanol and 0.035% ammonia in dichloromethane) to afford the desired product 3A (487 mg, 90%). ESI-MS m/z: 623.3 [M+H]$^+$.

tert-Butyl (2R,5S)-4-(6-chloro-2-(3-(dimethylamino) azetidin-1-yl)-8-fluoro-7-(3-iodo-5-methyl-1H-indazol-4-yl)quinazolin-4-yl)-2,5-dimethylpiperazine-1-carboxylate (3B)

To a solution of compound 3A (1.1 g, 1.76 mmol) in 15 mL of dimethylformamide (DMF), were added I$_2$ (0.9 g, 3.55 mmol) and 1.8 mL of 4 M potassium hydroxide and the resulting mixture was stirred at room temperature overnight. The reaction was quenched by adding aqueous Na$_2$SO$_3$ solution (1 M, 40 mL). The mixture was extracted with ethyl acetate and washed with water. The organic layer was dried over sodium sulfate, filtered and concentrated in vacuo. The residue was purified via Isolera One (10% methanol and 0.035% ammonia in dichloromethane) to afford the desired product 3B (1.18 g, 88.7%). ESI-MS m/z: 749.1 [M+H]$^+$. $^1$H NMR (500 MHz, DMSO-d$_6$) δ: 13.57 and 13.56 (s, s, split singlet from rotamers, 1H), 7.77 and 7.74 (s, s, split singlet from rotamers, 1H), 7.59 (d, J=8.5 Hz, 1H), 7.42 (dd, J=8.5, 1.0 Hz, 1H), 4.59 (dr. s, 1H), 3.35-4.39 (m, 9H), 3.12 (m, 1H), 2.12 (s, 9H), 1.44 (s, 9H), 1.14-1.35 (m, 6H).

tert-Butyl (2R,5S)-4-(6-chloro-2-(3-(dimethylamino) azetidin-1-yl)-8-fluoro-7-(3-iodo-5-methyl-1-trityl-1H-indazol-4-yl)quinazolin-4-yl)-2,5-dimethylpiperazine-1-carboxylate (3C)

To a stirred solution of compound 3B (300 mg, 0.40 mmol) in 3.0 mL of dry tetrahydrofuran at 0° C., was added 60% sodium hydride (15 mg, 0.60 mmol) and the reaction mixture was stirred at 0° C. for 30 minutes. Trityl chloride (125 mg, 0.45 mmol) was then added at the same temperature. The reaction mixture was stirred at room temperature overnight. The mixture was concentrated in vacuo. The residue was dissolved in ethyl acetate and washed with brine. The organic layer was dried and concentrated in vacuo. The residue was purified by flash chromatography on silica gel (0 to 10% methanol in dichloromethane) to afford the desired product 3C (about 320 mg).

tert-Butyl (2R,5S)-4-(6-chloro-2-(3-(dimethylamino) azetidin-1-yl)-7-(3-((diphenylmethylene)amino)-5-methyl-1-trityl-1H-indazol-4-yl)-8-fluoroquinazolin-4-yl)-2,5-dimethylpiperazine-1-carboxylate (3D)

To a solution of compound 3C (25 mg, 0.025 mmol) and diphenylmethanimine (13 µL, 0.075 mmol) in 3.0 mL of 1,4-dioxane at room temperature, were added Pd$_2$(dba)$_3$ (9 mg, 0.01 mmol), XantPhos (12 mg, 0.02 mmol) and Cs$_2$CO$_3$ (16 mg, 0.05 mmol). The reaction mixture was degassed and backfilled with nitrogen and stirred at 120° C. in microwave reactor for 1 hour. The mixture was concentrated in vacuo and the resultant residue was purified by flash column chromatography on silica gel to afford the desired product 3D.

4-(6-Chloro-2-(3-(dimethylamino)azetidin-1-yl)-4-((2S,5R)-2,5-dimethylpiperazin-1-yl)-8-fluoroquinazolin-7-yl)-5-methyl-1H-indazol-3-amine (3E)

Compound 3D (75 mg, 0.072 mmol) was dissolved in 15 mL of dry dichloromethane and 1.0 mL of trifluoroacetic acid was added to the solution slowly. The reaction was stirred at room temperature for 6 hours. The reaction was quenched with aqueous saturated sodium bicarbonate. The mixture was extracted with 20% isopropanol/dichloromethane (×3). The organic layer was dried with anhydrous sodium sulfate, filtered and concentrated in vacuo. The residue was purified by flash chromatography on silica gel to afford the desired product 3E.

1-((2R,5S)-4-(7-(3-Amino-5-methyl-1H-indazol-4-yl)-6-chloro-2-(3-(dimethylamino)azetidin-1-yl)-8-fluoroquinazolin-4-yl)-2,5-dimethylpiperazin-1-yl)prop-2-en-1-one (3F)

To a stirred solution of compound 3E (31 mg, 0.058 mmol) in 8 mL of 2-methyl-THF and 4 mL of 1M $Na_2CO_3$ aqueous solution at room temperature, was added slowly acryloyl chloride (4.2 μL, 0.063 mmol). The reaction was stirred at room temperature for 30 minutes and extracted with 20% isopropanol/dichloromethane (×3). The organic layer was combined, dried with anhydrous sodium sulfate and concentrated in vacuo. The residue was purified by column chromatography to afford the desired product 3F (14 mg). ESI m/z 592.2 [M+H]$^+$; $^1$H NMR (500 MHz, DMSO-$d_6$) δ: 11.6 (s, 1H), 7.76 (s, 1H), 7.27 (d, J=8.5 Hz, 1H), 7.24 (d, J=8.5 Hz, 1H), 6.82 (m, 1H), 6.17 (dd, J=5.0, 16.5 Hz, 1H), 5.73 (dd, J=5.2, 7.6 Hz, 1H), 4.44-4.74 (m, 2H), 4.09-4.13 (m, 2H), 4.00-4.03 (m, 1H), 3.77-3.95, (m, 4H), 3.46-3.48 (m, 1H), 3.12-3.14 (m, 1H), 2.12 (s, 6H), 2.06 and 2.95 (s, s, split singlet from rotamers, 3H), 1.20-1.31 (m, 6H).

Example 4

Synthesis of 1-((2R,5S)-4-(7-(3-amino-5-methyl-benzo[d]isoxazol-4-yl)-6-chloro-8-fluoro-2-(2-morpholinoethoxy)quinazolin-4-yl)-2,5-dimethylpiperazin-1-yl)prop-2-en-1-one

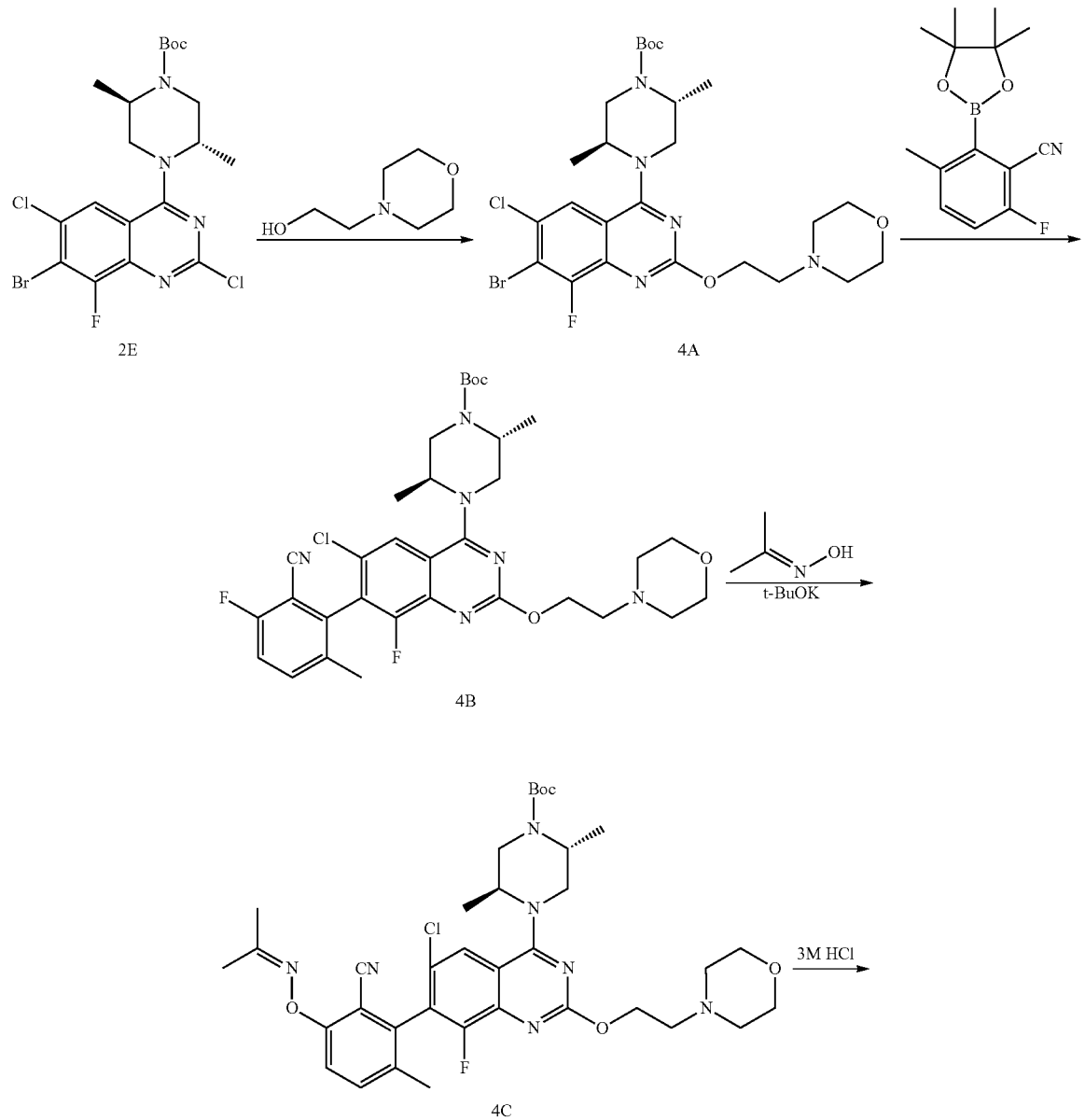

-continued

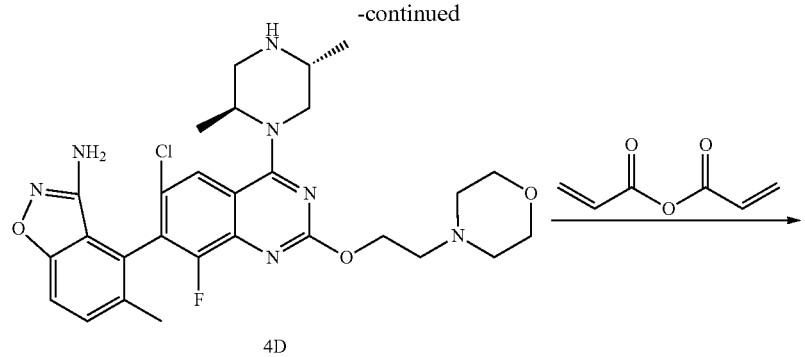

4D

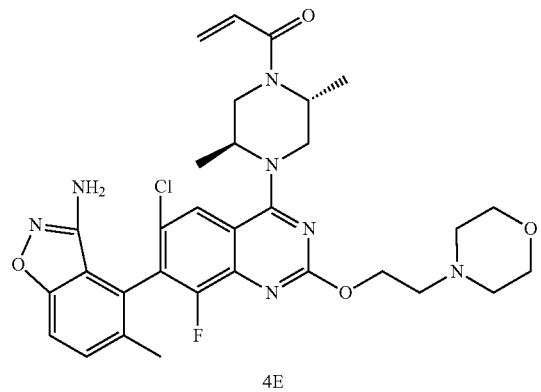 [SMILES: C=CC(=O)N1C[C@H](C)N(c2nc(OCCN3CCOCC3)nc3c(F)c(-c4c(C)ccc5onc(N)c45)c(Cl)cc23)C[C@H]1C]

4E

Example 4 provides an exemplary synthetic method according to general method F.

(2R,5S)-tert-butyl 4-(7-bromo-6-chloro-8-fluoro-2-(2-morpholinoethoxy)quinazolin-4-yl)-2,5-dimethyl-piperazine-1-carboxylate (4A)

To a stirred solution of compound 2E (5.0 g, 9.84 mmol) in DMSO (50 mL), KF (4.57 g, 78.74 mmol) and 2-morpholinoethanol (3.87 g, 29.53 mmol) were added. The mixture was stirred at 120° C. overnight. The resulting mixture was allowed to cool to RT, poured into water, and extracted with EtOAc. The organic layer was washed with water and brine, dried over $Na_2SO_4$, filtered and concentrated in vacuo. The residue was purified by flash column chromatography on silica gel to afford the desired product (2.2 g, 37%). ESI-MS m/z: 602.2 $[M+H]^+$.

(2R,5S)-tert-butyl 4-(6-chloro-7-(2-cyano-3-fluoro-6-methylphenyl)-8-fluoro-2-(2-morpholinoethoxy) quinazolin-4-yl)-2,5-dimethylpiperazine-1-carboxy-late (4B)

To a stirred solution of compound 4A (1.0 g, 1.66 mmol) in toluene (20 mL), were added 6-fluoro-3-methyl-2-(4,4,5,5-tetramethyl-1,3,2-dioxaborolan-2-yl)benzonitrile (1.30 g, 4.98 mmol), $K_3PO_4$ (1.41 g, 6.63 mmol) and bis(dtpp)$PdCl_2$ (200 mg) under argon. The mixture was stirred at 100° C. overnight. The mixture was concentrated in vacuo. The residue was purified by flash column chromatography on silica gel to afford the desired product (300 mg, 27.5%). ESI-MS m/z: 657.2 $[M+H]^+$.

(2R,5S)-tert-butyl 4-(6-chloro-7-(2-cyano-6-methyl-3-((propan-2-ylideneamino)oxy)phenyl)-8-fluoro-2-(2-morpholinoethoxy)quinazolin-4-yl)-2,5-dimethyl-piperazine-1-carboxylate (4C)

To a stirred solution of propan-2-one oxime (34 mg, 0.46 mmol) in DMF (5 mL), was added t-BuOK (51 mg, 0.457 mmol). The mixture was stirred at RT for 1 h. Compound 4B (150 mg, 0.23 mmol) was added to the reaction mixture. The mixture was stirred at RT overnight. The mixture was extracted with EtOAc and water. The solvent was removed. The residue was purified by flash column chromatography on silica gel to afford the desired product (60 mg, 37%). ESI-MS m/z: 710.25 $[M+H]^+$.

4-(6-chloro-4-((2S,5R)-2,5-dimethylpiperazin-1-yl)-8-fluoro-2-(2-morpholinoethoxy)quinazolin-7-yl)-5-methylbenzo[d]isoxazol-3-amine (4D)

The mixture of compound 4C (170 mg, 0.24 mmol) in EtOH (10 mL) and 3M HCl (10 mL) was stirred at reflux for 1 h. The solvent was removed, the residue was basified to PH to 10-11, and then extracted with EtOAc and water. The solvent was removed. The residue was purified by flash column chromatography on silica gel to afford the desired product (90 mg, 66%). ESI-MS m/z: 570.35 $[M+H]^+$.

1-((2R,5S)-4-(7-(3-amino-5-methylbenzo[d]isox-azol-4-yl)-6-chloro-8-fluoro-2-(2-morpholinoethoxy) quinazolin-4-yl)-2,5-dimethylpiperazin-1-yl)prop-2-en-1-one (4E)

To a stirred solution of compound 4D (90 mg, 0.16 mmol) in DCM (30 mL) at 0° C. were added $Et_3N$ (80 mg, 0.79 mmol) and acrylic anhydride (20 mg, 0.16 mmol). The mixture was stirred at 0° C. for 15 min. The mixture was extracted with DCM and NaHCO₃. The solvent was removed. The residue was purified by flash chromatography on silica gel to afford the desired product (50 mg, 51%). ESI-MS m/z: 624.2 [M+H]⁺; 1H NMR (400 MHz, DMSO-d₆) δ: 7.95 (s, 1H), 7.55 (dd, J=8.4, 16.2 Hz, 2H), 6.8 (m, 1H) 6.2 (m, 1H), 5.75 (m, 1H), 5.2-5.1 (m, 2H), 4.8-4.7 (m, 2H), 4.6-4.4 (m, 3H), 4.2-4.05 (m, 2H), 4.0-3.75 (m, 3H), 3.7-3.5 (m, 6H), 2.8-2.65 (m, 2H), 2.2-2.1 (m, 3H), 1.3-1.2 (m, 6H).

Example 5

Synthesis of 1-((2R,5S)-4-(6-chloro-2-(3-(dimethylamino)azetidin-1-yl)-8-fluoro-7-(6-methyl-1H-benzo[d][1,2,3]triazol-7-yl)quinazolin-4-yl)-2,5-dimethylpiperazin-1-yl)prop-2-en-1-one

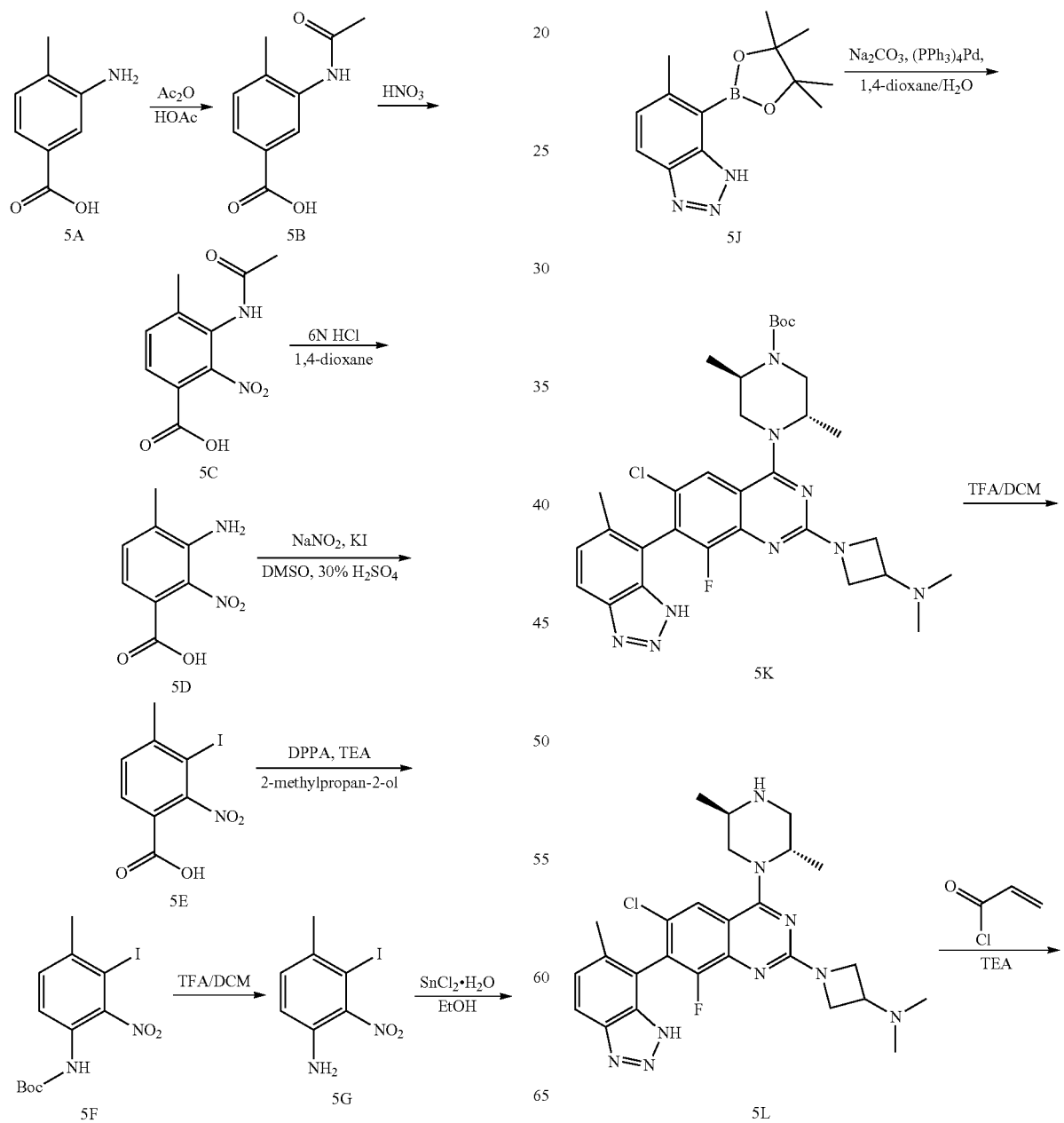

-continued

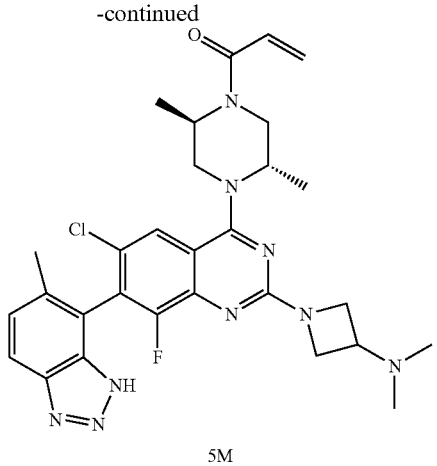

5M

3-acetamido-4-methylbenzoic acid (5B)

To a solution of 3-amino-4-methylbenzoic acid (10 g, 66 mmol) in HOAc (150 mL) at RT, was added Ac$_2$O (41.8 g, 410 mmol) slowly and the resulting mixture was stirred at RT for 16 h. The resulting precipitate was collected by filtration, rinsed with HOAc and Et$_2$O. The solid was dried to afford the desired product 5B (11.6 g, 90%). ESI-MS m/z: 194 [M+H]$^+$.

3-acetamido-4-methyl-2-nitrobenzoic acid (5C)

To a solution of HNO$_3$ (47 mL, 98%) in ice-water, was added 3-acetamido-4-methylbenzoic acid (11.6 g, 60 mmol) in portions over 1 h and the resulting mixture was stirred in ice-water for 1.5 h. Then ice was added slowly and the mixture was stirred for 0.5 h. The resulting precipitate was collected by filtration and dried to afford the desired product 5C (11 g, 77%). ESI-MS m/z: 239 [M+H]$^+$.

3-amino-4-methyl-2-nitrobenzoic acid (5D)

To a solution of 5C (11 g, 49 mmol) in 1,4-dioxane (110 mL) at RT, was added HCl (6N, 200 mmol) slowly and the resulting mixture was stirred at reflux for 16 h. The mixture was concentrated in vacuo. The residue was extracted with ethyl acetate and washed with brine. The organic layer was dried over sodium sulfate and concentrated in vacuo. The residue was triturated with PE/EA (10/1) and dried to afford the desired product (9 g, 93%). ESI-MS m/z: 197 [M+H]$^+$.

3-iodo-4-methyl-2-nitrobenzoic acid (5E)

To a solution of 5D (4 g, 20.4 mmol) in DMSO (40 mL) in an ice-water bath, was added H$_2$SO$_4$ (30%, 40 mL) slowly followed by slow addition of NaNO$_2$ (2.11 g, 30.6 mmol) in water (10 mL). The resulting mixture was stirred in ice-water bath for 1 h. KI (8.47 g, 51 mmol) in water (20 mL) was added slowly to the reaction mixture and the resulting mixture was stirred at RT for 16 h. The mixture was extracted with ethyl acetate and washed with brine. The organic layer was dried over sodium sulfate and concentrated in vacuo. The residue was purified by flash column chromatography on silica gel to afford the desired product 5E (4.3 g, 70%). ESI-MS m/z: 308 [M+H]$^+$.

tert-butyl (3-iodo-4-methyl-2-nitrophenyl)carbamate (5F)

To a solution of 5E (4 g, 13 mmol) in 2-methylpropan-2-ol (40 mL) at RT, was added 4A molecular sieves (4 g) and the resulting mixture was stirred at RT for 1 h. DPPA (5.36 g, 19.5 mmol) and TEA (1.97 g, 19.5 mmol) were added to the mixture. The resulting mixture was stirred at reflux for 16 h. The mixture was concentrated in vacuo. The residue was extracted with ethyl acetate and washed with brine. The organic layer was dried over sodium sulfate and concentrated in vacuo. The residue was purified by flash column chromatography on silica gel to afford the desired product 5F (3.68 g, 75%). ESI-MS m/z: 379 [M+H]$^+$.

3-iodo-4-methyl-2-nitroaniline (5G)

Compound 5F (2.5 g, 6.61 mmol) was dissolved in 30 mL of 50% trifluoroacetic acid in dichloromethane. The mixture was stirred for 30 min. The mixture was concentrated in vacuo. The residue was dissolved in dichloromethane and washed with aqueous saturated sodium bicarbonate. The organic layer was dried over magnesium sulfate, filtered and concentrated in vacuo to afford the desired product 5G (1.74 g, 95%). ESI-MS m/z: 279 [M+H]$^+$.

3-iodo-4-methylbenzene-1,2-diamine (5H)

To a solution of 5G (1.74 g, 6.25 mmol) in EtOH (20 mL) at RT, was added SnCl$_2$.2H$_2$O (4.23 g, 18.75 mmol) and the resulting mixture was stirred at reflux for 16 h. The mixture was concentrated in vacuo. The residue was quenched by adding aqueous Na$_2$CO$_3$ solution and the mixture was extracted with ethyl acetate and washed with brine. The organic layer was dried over sodium sulfate, filtered and concentrated in vacuo. The residue was purified by flash column chromatography on silica gel to afford the desired product 5H (1.39 g, 90%). ESI-MS m/z: 249 [M+H]$^+$.

7-iodo-6-methyl-1H-benzo[d][1,2,3]triazole (5I)

To a solution of 5H (1.39 g, 5.6 mmol) in HOAc (15 mL) in an ice-water bath. NaNO$_2$ (502 mg, 7.28 mmol) in water (4 mL) was added slowly and the resulting mixture was stirred at RT for 16 h. The mixture was extracted with ethyl acetate and washed with brine. The organic layer was dried over sodium sulfate and concentrated in vacuo. The residue was purified by flash column chromatography on silica gel to afford the desired product 5I (1.23 g, 85%). ESI-MS m/z: 260 [M+H]$^+$.

6-methyl-7-(4,4,5,5-tetramethyl-1,3,2-dioxaborolan-2-yl)-1H-benzo[d][1,2,3]triazole (5J)

The mixture of 5I (600 mg, 2.31 mmol), 4,4,4',4',5,5,5',5'-octamethyl-2,2'-bi(1,3,2-dioxaborolane) (1.77 g, 6.96 mmol) and potassium acetate (683 mg, 6.96 mmol) in 10 mL of dioxane was purged with nitrogen for 5 min and then PdCl$_2$(dppf) (253 mg, 0.35 mmol) was added. The mixture was purged with nitrogen for 5 min and stirred at 100° C. overnight. The mixture was extracted with ethyl acetate and washed with brine. The organic layer was dried over sodium sulfate and concentrated in vacuo. The residue was purified by flash column chromatography on silica gel to afford the desired product 5J (480 mg, 80%). ESI-MS m/z: 260 [M+H]$^+$.

tert-butyl (2R,5S)-4-(6-chloro-2-(3-(dimethylamino) azetidin-1-yl)-8-fluoro-7-(6-methyl-1H-benzo[d][1,2,3]triazol-7-yl)quinazolin-4-yl)-2,5-dimethylpiperazine-1-carboxylate (5K)

To a solution of 2F (150 mg, 0.26 mmol) in dioxane-water (12 mL/1 mL) at RT, 5J (202 mg, 0.78 mmol), Na$_2$CO$_3$ (69 mg, 0.65 mmol) and Pd(PPh$_3$)$_4$(60 mg, 0.052 mmol) were added. The mixture was purged with nitrogen for 3 min and stirred at 90° C. overnight. The mixture was extracted with ethyl acetate and washed with brine. The organic layer was dried over sodium sulfate and concentrated in vacuo. The residue was purified by flash column chromatography on silica gel to afford the desired product 5K (137 mg, 85%). ESI-MS m/z: 624 [M+H]$^+$.

1-(6-chloro-4-((2S,5R)-2,5-dimethylpiperazin-1-yl)-8-fluoro-7-(6-methyl-1H-benzo[d][1,2,3]triazol-7-yl)quinazolin-2-yl)-N,N-dimethylazetidin-3-amine (5L)

Compound 5K (137 mg, 0.22 mmol) was dissolved in 10 mL of 50% trifluoroacetic acid in dichloromethane. The mixture was stirred for 30 min. The mixture was concentrated in vacuo. The residue was dissolved in dichloromethane and washed with aqueous saturated sodium bicarbonate. The organic layer was dried over magnesium sulfate, filtered and concentrated in vacuo to afford the desired product 5L (103 mg, 90%). ESI-MS m/z: 524 [M+H]$^+$.

1-((2R,5S)-4-(6-chloro 11-2-(3-(dimethylamino) azetidin-1-yl)-8-fluoro-7-(6-methyl-1H-benzo[d][1,2,3]triazol-7-yl)quinazolin-4-yl)-2,5-dimethylpiperazin-1-yl)prop-2-en-1-one (5M)

To a stirred solution of 5L (50 mg, 0.08 mmol) in DCM (8 mL) in an ice-water bath, TEA (24 mg, 0.24 mmol) was added followed by addition of acryloyl chloride (11 mg, 0.12 mmol) in DCM (1 mL). The reaction mixture was stirred at RT for 30 min and extracted with DCM. The organic layer was combined, dried with anhydrous sodium sulfate and concentrated in vacuo. The residue was purified by column chromatography on silica gel to afford the desired product 5M (16 mg, 35%). ESI-MS m/z: 578 [M+H]$^+$; $^1$H NMR (400 MHz, DMSO-d$_6$): 7.94 (m, 1H), 7.81 (s, 1H), 7.49-7.47 (m, 1H), 6.88-6.78 (m, 1H), 6.21-6.17 (m, 1H), 5.76-5.73 (m, 1H), 4.77-4.46 (m, 2H), 4.12-3.84 (m, 7H), 3.48 (m, 1H), 3.17-3.13 (m, 2H), 2.27-2.24 (m, 3H), 2.10 (s, 6H), 1.30-1.18 (m, 6H).

Example 6

Synthesis of 1-((2R,5S)-4-(2-(1-cyclopropylpiperidin-4-ylamino)-6-chloro-7-(3-cyclopropyl-5-methyl-1H-indazol-4-yl)-8-fluoroquinazolin-4-yl)-2,5-dimethylpiperazin-1-yl)prop-2-en-1-one

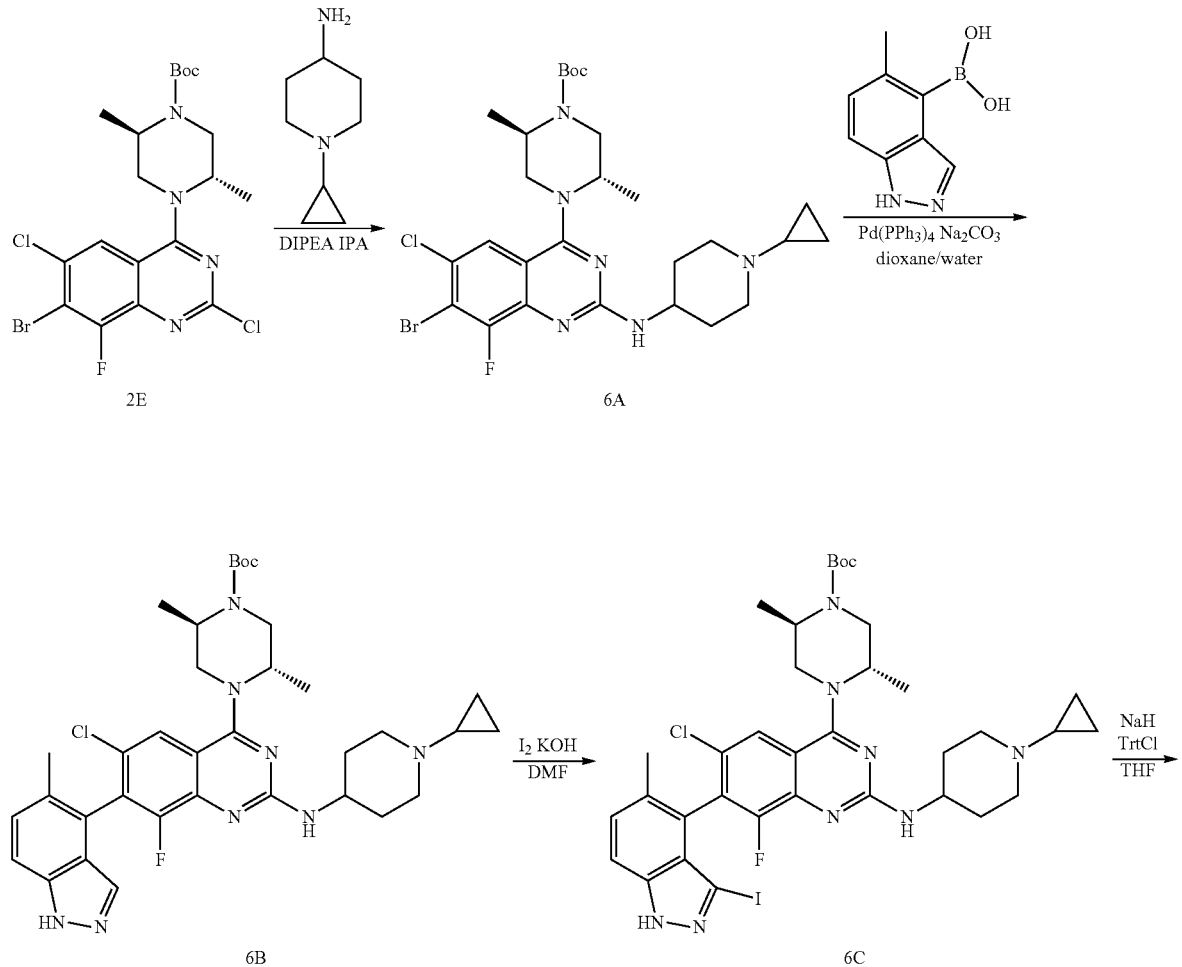

-continued
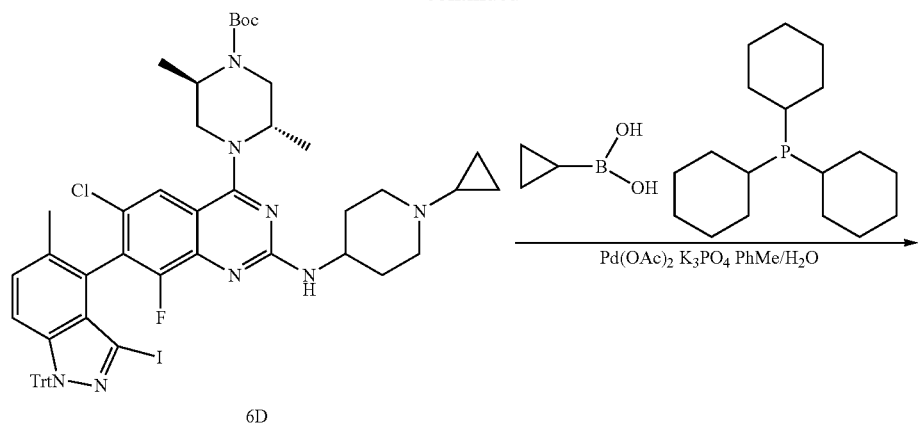
6D
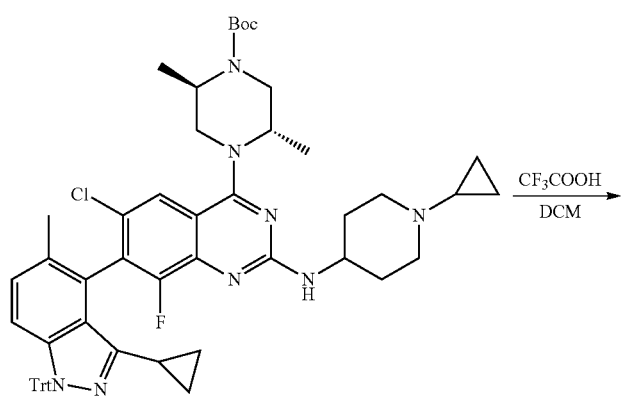
6E
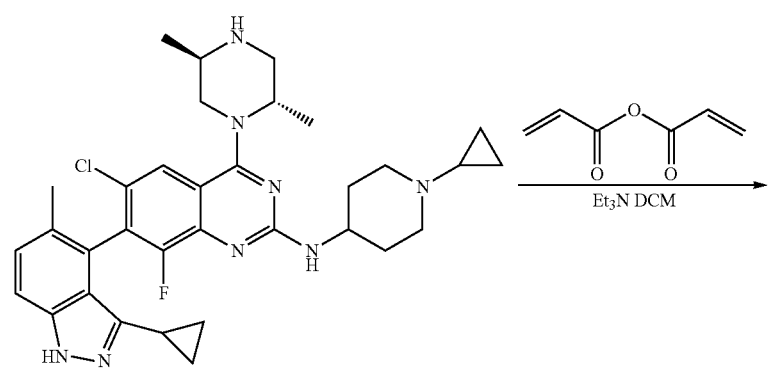
6F

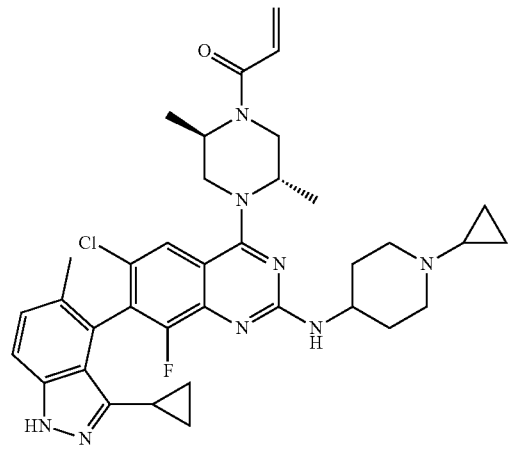

6G

Example 6 provides an exemplary synthetic method according to general method C.

(2R,5S)-tert-butyl4-(2-(1-cyclopropylpiperidin-4-ylamino)-7-bromo-6-chloro-8-fluoroquinazolin-4-yl)-2,5-dimethylpiperazine-1-carboxylate (6A)

The mixture of (2R,5S)-tert-butyl 4-(7-bromo-2,6-dichloro-8-fluoroquinazolin-4-yl)-2,5-dimethylpiperazine-1-carboxylate (5 g, 9.84 mmol), 1-cyclopropylpiperidin-4-amine (2.76 g, 19.69 mmol), DIPEA (6.35 g, 49.2 g) in IPA (50 mL) was stirred at reflux for 16 h. The mixture was extracted with EA, dried over $Na_2SO_4$ and concentrated in vacuo. The residue was purified by flash column chromatography on silica gel to afford the desire product (3.7 g, 61%). ESI-MS m/z: 612.19 [M+H]$^+$.

(2R,5S)-tert-butyl4-(2-(1-cyclopropylpiperidin-4-ylamino)-6-chloro-8-fluoro-7-(-methyl-1H-indazol-4-yl)quinazolin-4-yl)-2,5-dimethylpiperazine-1-carboxylate (6B)

To a solution of (2R,5S)-tert-butyl 4-(2-(1-cyclopropylpiperidin-4-ylamino)-7-bromo-6-chloro-8-fluoroquinazolin-4-yl)-2,5-dimethylpiperazine-1-carboxylate (3.7 g, 6.06 mmol), 5-methyl-1H-indazol-4-yl-4-boronicacid (5.33 g, 30.28 mmol) in dioxane/water (80 mL/20 mL), Pd(PPh$_3$)$_4$ (0.7 g, 0.61 mmol) and $Na_2CO_3$ (1.93 g, 18.18 mmol) were added. The mixture was stirred at reflux overnight. The mixture was extracted with EA, dried over $Na_2SO_4$ and concentrated in vacuo. The residue was purified by flash column chromatography on silica gel to afford the desire product (3.4 g, 84%). ESI-MS m/z: 662.39 [M+H]$^+$.

(2R,5S)-tert-butyl4-(2-(1-cyclopropylpiperidin-4-ylamino)-6-chloro-8-fluoro-7-(3-iodo-5-methyl-1H-indazol-4-yl)quinazolin-4-yl)-2,5-dimethylpiperazine-1-carboxylate (6C)

To a solution of (2R,5S)-tert-butyl 4-(2-(1-cyclopropylpiperidin-4-ylamino)-6-chloro-8-fluoro-7-(5-methyl-1H-indazol-4-yl)quinazolin-4-yl)-2,5-dimethylpiperazine-1-carboxylate (3.4 g, 5.14 mmol) in DMF (50 mL), KOH (1.68 g, 25.68 mmol) and iodine (2.61 g, 10.28 mmol) were added. The mixture was stirred at RT for 2 h. The mixture was extracted with EA, washed with $Na_2S_2O_3$, dried over $Na_2SO_4$ and concentrated in vacuo to get crude product (3.9 g, 96% yield). ESI-MS m/z: 789.1 [M+H]$^+$.

(2R,5S)-tert-butyl4-(2-(1-cyclopropylpiperidin-4-ylamino)-6-chloro-8-fluoro-7-(3-iodo-5-methyl-1-trityl-1H-indazol-4-yl)quinazolin-4-yl)-2,5-dimethylpiperazine-1-carboxylate (6D)

To a solution of (2R,5S)-tert-butyl 4-(2-(1-cyclopropylpiperidin-4-ylamino)-6-chloro-8-fluoro-7-(3-iodo-5-methyl-1H-indazol-4-yl)quinazolin-4-yl)-2,5-dimethylpiperazine-1-carboxylate (3.9 g, 4.94 mmol) in THF at 0° C., NaH (0.4 g, 9.89 mmol) was added slowly, and the resulting mixture was stirred at RT for 0.5 h. To this mixture, TrtCl (2.75 g, 9.89 mmol) was added. The mixture was stirred at RT overnight. The mixture was extracted with EA, dried over $Na_2SO_4$ and concentrated in vacuo. The residue was purified by flash column chromatography on silica gel to afford the desire product (2.8 g, 53%). ESI-MS m/z: 1031.3 [M+H]$^+$.

(2R,5S)-tert-butyl4-(2-(1-cyclopropylpiperidin-4-ylamino)-6-chloro-7-(3-cyclopropyl-5-methyl-1-trityl-1H-indazol-4-yl)-8-fluoroquinazolin-4-yl)-2,5-dimethylpiperazine-1-carboxylate (6E)

To a solution of (2R,5S)-tert-butyl 4-(2-(1-cyclopropylpiperidin-4-ylamino)-6-chloro-8-fluoro-7-(3-iodo-5-methyl-1-trityl-1H-indazol-4-yl)quinazolin-4-yl)-2,5-dimethylpiperazine-1-carboxylate (2.7 g, 2.62 mmol) in toluene/water (40 mL/4 mL), cyclopropylboronic acid (2.25 g, 26.19 mmol), $K_3PO_4$ (2.78 g, 13.1 mmol), tricyclohexylphosphine (72.8 mg, 0.26 mmol) and Pd(OAC)$_2$ (58.24 mg, 0.26 mmol) were added. The mixture was stirred at 120° C. overnight. The mixture was extracted with EA, dried over $Na_2SO_4$ and concentrated in vacuo. The residue was purified by flash column chromatography on silica gel to afford the desire product (1.3 g, 52% yield). ESI-MS m/z: 944.6 [M+H]$^+$.

6-chloro-7-(3-cyclopropyl-5-methyl-1H-indazol-4-yl)-N-(1-cyclopropylpiperidin-4-yl)-8-fluoro-4-((2S,5R)-2,5-dimethylpiperazin-1-yl)quinazolin-2-amine (6F)

To a solution of (2R,5S)-tert-butyl 4-(2-(1-cyclopropylpiperidin-4-ylamino)-6-chloro-7-(3-cyclopropyl-5-methyl-1- trityl-1H-indazol-4-yl)-8-fluoroquinazolin-4-yl)-2,5-dimethylpiperazine-1-carboxylate (1.3 g, 1.37 mmol) in DCM (20 mL), CF$_3$COOH (10 mL) was added and the resulting mixture was stirred at RT overnight. The mixture was quenched with NaHCO$_3$, extracted with EA and concentrated in vacuo to get the crude product (1.1 g, 100% yield).

1-((2R,5S)-4-(2-(1-cyclopropylpiperidin-4-ylamino)-6-chloro-7-(3-cyclopropyl-5-methyl-1H-indazol-4-yl)-8-fluoroquinazolin-4-yl)-2,5-dimethylpiperazin-1-yl)prop-2-en-1-one (6G)

To a solution of 6-chloro-7-(3-cyclopropyl-5-methyl-1H-indazol-4-yl)-N-(1-cyclopropylpiperidin-4-yl)-8-fluoro-4-((2 S,5R)-2,5-dimethylpiperazin-1-yl)quinazolin-2-amine (1.1 g, 1.83 mmol) in DCM (10 mL) at 0° C., acrylic anhydride (242.13 mg, 1.92 mmol) and Et$_3$N (554.49 mg, 5.49 mmol) were added. The mixture was stirred for 0.5 h. The mixture was extracted with EA, dried over Na$_2$SO$_4$ and concentrated in vacuo. The residue was purified by flash column chromatography on silica gel to afford the desire product (480 mg, 62% yield). ESI-MS m/z: 658.2 [M+H]$^+$.

Example 7

Synthesis of 1-((2R, 5S)-4-(6-chloro-2-(3-(dimethylamino)azetidin-1-yl)-7-(1-ethyl-6-methyl-1H-indazol-7-yl)-8-fluoroquinazolin-4-yl)-2,5-dimethylpiperazin-1-yl)prop-2-en-1-one 1-((2R, 5S)-4-(6-chloro-2-(3-(dimethylamino)azetidin-1-yl)-7-(1-ethyl-6-methyl-1H-indazol-7-yl)-8-fluoroquinazolin-4-yl)-2,5-dimethylpiperazin-1-yl)prop-2-en-1-one To a solution of 1-((2R,5S)-4-(6-chloro-2-(3-(dimethylamino)azetidin-1-yl)-8-fluoro-7-(6-methyl-1H-indazol-7-yl)quinazolin-4-yl)-2,5-dimethylpiperazin-1-yl)prop-2-en-1-one (100 mg, 0.17 mmol) in 3 mL of THF at 0° C., was added 1.0 N NaOH (0.4 mL, 0.35 mmol) followed by CH$_3$CH$_2$I (32 mg, 0.21 mmol) dropwise. The reaction mixture was allowed to warm to RT and stirred for 16 h. The mixture was concentrated in vacuo, and the residue was partitioned between EA and water. The organic layer was dried and concentrated in vacuo. The residue was purified by flash chromatography on silica gel (0-10% methanol in DCM) followed by Prep-TLC to give the desire product (9 mg, 8.5% yield). ESI-MS m/z: 605.3 [M+H]$^+$; $^1$HNMR (400 MHz, DMSO-d$_6$): δ 8.11 (m, 1H), 7.85-7.84 (m, 1H), 7.80-7.77 (m, 1H), 7.20-7.18 (m, 1H), 6.85-6.82 (m, 1H), 6.21-6.17 (m, 1H), 5.77-5.73 (m, 1H), 4.76-4.46 (m, 2H), 4.12-3.97 (m, 3H), 3.90-3.71 (m, 5H), 3.51-3.38 (m, 2H), 3.15-3.10 (m, 1H), 2.13-2.09 (m, 6H), 1.34-1.20 (m, 6H), 1.04-0.98 (m, 3H).

Example 8

Synthesis of 1-((2R,5S)-4-(6-chloro-2-(3-(dimethylamino)azetidin-1-yl)-8-fluoro-7-(5-methylbenzo[d]isothiazol-4-yl)quinazolin-4-yl)-2,5-dimethylpiperazin-1-yl)prop-2-en-1-one

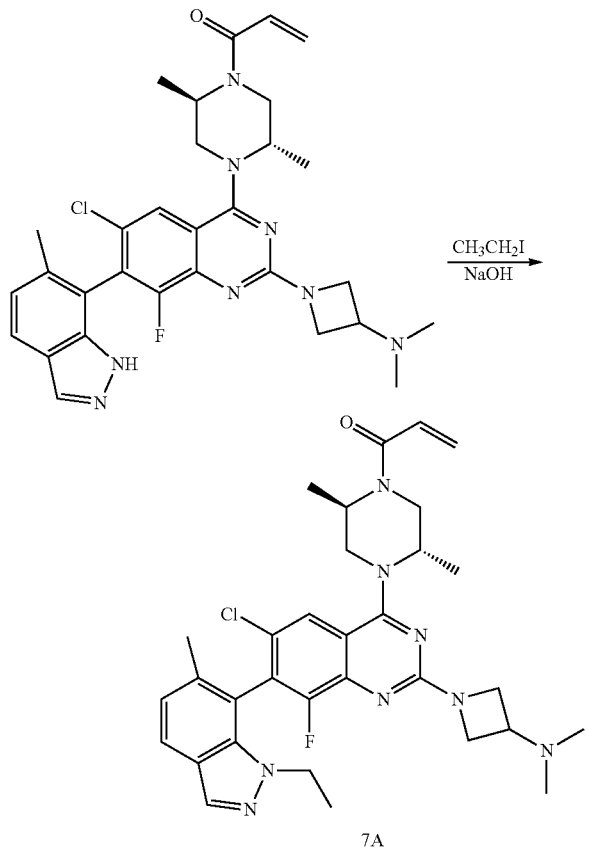

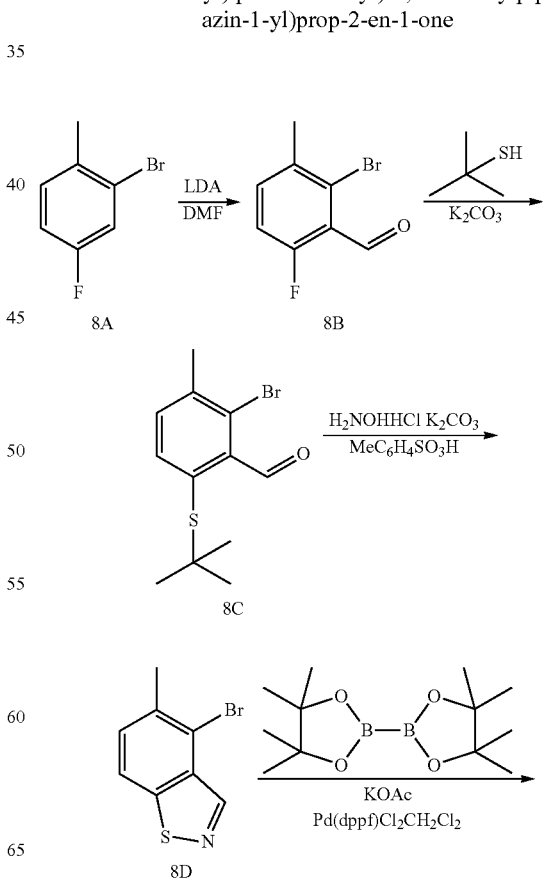

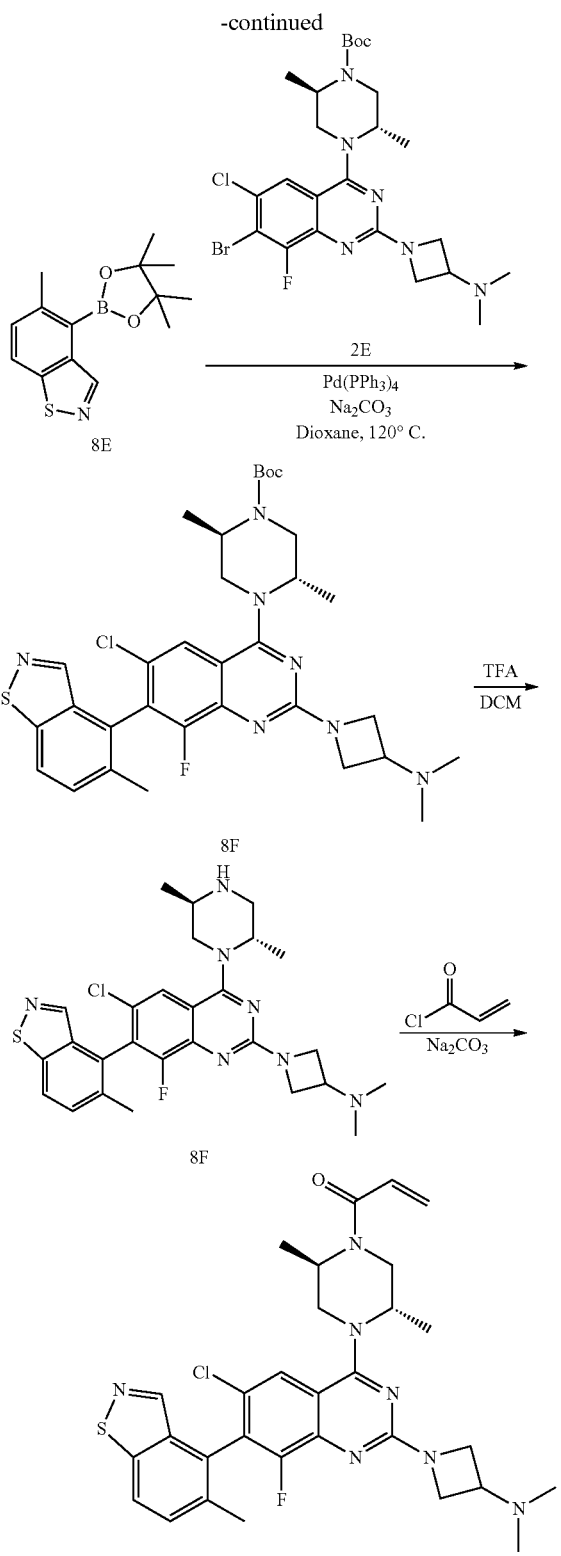

2-bromo-6-fluoro-3-methylbenzaldehyde (8B)

The mixture of 2-bromo-4-fluoro-1-methylbenzene (10 g, 53 mmol), and LDA (32 mL, 64 mmol) in 250 mL of THF was purged with nitrogen for 1 h and stirred at −78° C., and then DMF (11.6 g, 158 mmol) was added. The mixture was purged with nitrogen for 2 h and stirred at −78° C. overnight. The mixture was quenched, extracted with EA and concentrated to afford the crude product 8B. ESI-MS m/z: 216.9 [M+H]$^+$.

6-(tert-butylthio)-2-bromo-3-methylbenzaldehyde (8C)

The mixture of 2-bromo-6-fluoro-3-methylbenzaldehyde (5 g, 23.1 mmol), 2-methylpropane-2-thiol (7.6 mL, 67.5 mmol) and K$_2$CO$_3$ (4.7 g, 34.6 mmol) in 40 mL of DMF was purged with nitrogen and stirred at 50° C. overnight to afford the crude product 8C. ESI-MS m/z: 288.02 [M+H]$^+$.

4-bromo-5-methylbenzo[d]isothiazole (8D)

The mixture of 6-(tert-butylthio)-2-bromo-3-methylbenzaldehyde (6.8 g, 23.8 mmol) and H$_2$N—OH.HCl (8.26 g, 118 mmol) in propan-2-ol/H$_2$O (120 mL/20 mL) was stirred at 70° C. for 30 min. The mixture was diluted with water and NaHCO$_3$ and extracted with dichloromethane. The organic layer was dried over sodium sulfate and concentrated in vacuo. The residue was dissolved in butan-1-ol and then p-MeC$_6$H$_4$SO$_3$H was added. The resulting mixture was stirred at 120° C. overnight. The mixture was cooled to RT and concentrated in vacuo to afford the crude product 8D. ESI-MS m/z: 228.9 [M+H]$^+$.

5-methyl-4-(4,4,5,5-tetramethyl-1,3,2-dioxaborolan-2-yl)benzo[d]isothiazole (8E)

The mixture of 4-bromo-5-methylbenzo[d]isothiazole (1 g, 4.4 mmol), 4,4,5,5-tetramethyl-2-(4,4,5,5-tetramethyl-1,3,2-dioxaborolan-2-yl)-1,3,2-dioxaborolane (2.2 g, 8.8 mmol), KOAc (1.3 g, 13.1 mmol) and Pd(dppf)Cl$_2$CH$_2$Cl$_2$ (0.36 g, 0.44 mmol) in 30 mL of dioxane was stirred at 110° C. overnight to afford the product 8E. ESI-MS m/z: 271.2 [M+H]$^+$.

(2R,5S)-tert-butyl 4-(6-chloro-2-(3-(dimethylamino) azetidin-1-yl)-8-fluoro-7-(5-methylbenzo[d]isothiazol-4-yl)quinazolin-4-yl)-2,5-dimethylpiperazine-1-carboxylate (8F)

To above reaction mixture of dioxane/H$_2$O (20 mL/5 mL) containing compound 8E, (2R,5S)-tert-butyl 4-(7-bromo-6-chloro-2-(3-(dimethylamino)azetidin-1-yl)-8-fluoroquinazolin-4-yl)-2,5-dimethylpiperazine-1-carboxylate (0.162 g, 0.28 mmol), Pd(PPh$_3$)$_4$(0.033 g, 0.028 mmol) and Na$_2$CO$_3$ (0.15 g, 1.42 mmol) were added. The mixture was purged with nitrogen for 5 min and then stirred at 120° C. overnight. The mixture was diluted with water and extracted with ethyl acetate. The organic layer was dried over sodium sulfate and concentrated in vacuo. The residue was purified by column chromatography on silica gel (2.5% methanol in dichloromethane) to afford the desired product 2F (497 mg). ESI-MS m/z: 1089.7 [M+H]$^+$.

1-(6-chloro-8-fluoro-7-(5-methylbenzo[d]isothiazol-4-yl)-4-((2S,5R)-2,5-dimethylpiperazin-1-yl)quinazolin-2-yl)-N,N-dimethylazetidin-3-amine (8G)

The above obtained compound 2F (497 mg) was dissolved in 5 mL of 20% trifluoroacetic acid in dichloromethane. The mixture was stirred for 10 min. The concentrated in vacuo to afford the desired product 2G. The crude product 2G was used in the next step without further purification. ESI-MS m/z: 540.3 [M+H]⁺.

1-((2R,5S)-4-(6-chloro-2-(3-(dimethylamino)azetidin-1-yl)-8-fluoro-7-(5-methylbenzo[d]isothiazol-4-yl)quinazolin-4-yl)-2,5-dimethylpiperazin-1-yl)prop-2-en-1-one (8H)

To a solution of above obtained compound 2G in dichloromethane (5 mL), was added 0.5 mL of trimethylamine followed by addition of acryloyl chloride (1.75 eq). The resulting mixture was stirred for 10 min. The reaction mixture was diluted with water and extracted with ethyl acetate. The organic layer was dried over sodium sulfate, filtered and concentrated in vacuo. The residue was purified to afford the desired product 8H (62.7 mg). ESI-MS m/z: 594.4 [M+H]⁺; ¹HNMR (400 MHz, DMSO-d₆): δ 8.56 (d, J=19.2 Hz, 1H), 8.27 (d, J=8.4 Hz, 1H), 7.82 (s, 1H), 7.68 (d, J=8.4 Hz, 1H), 6.89-6.79 (m, 1H), 6.24-6.09 (m, 1H), 5.76-5.73 (m, 1H), 4.74-4.65 (m, 3H), 4.46-4.44 (m, 2H), 4.28 (m, 1H), 4.13-4.00 (m, 4H), 3.23-3.15 (m, 1H), 2.25-2.23 (m, 3H), 2.23-2.09 (m, 6H), 1.40-1.19 (m, 6H).

Example 9

Synthesis of 1-((2R,5S)-4-(6-chloro-2-(3-(dimethylamino)azetidin-1-yl)-8-fluoro-7-(1-methyl-1H-indol-7-yl)quinazolin-4-yl)-2,5-dimethylpiperazin-1-yl)prop-2-en-1-one

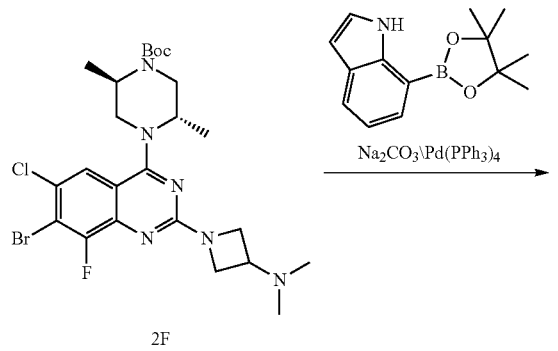

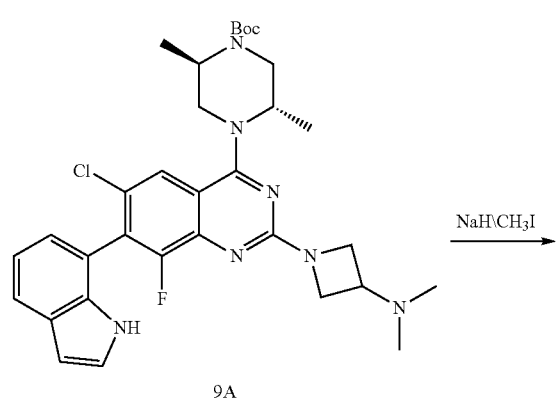

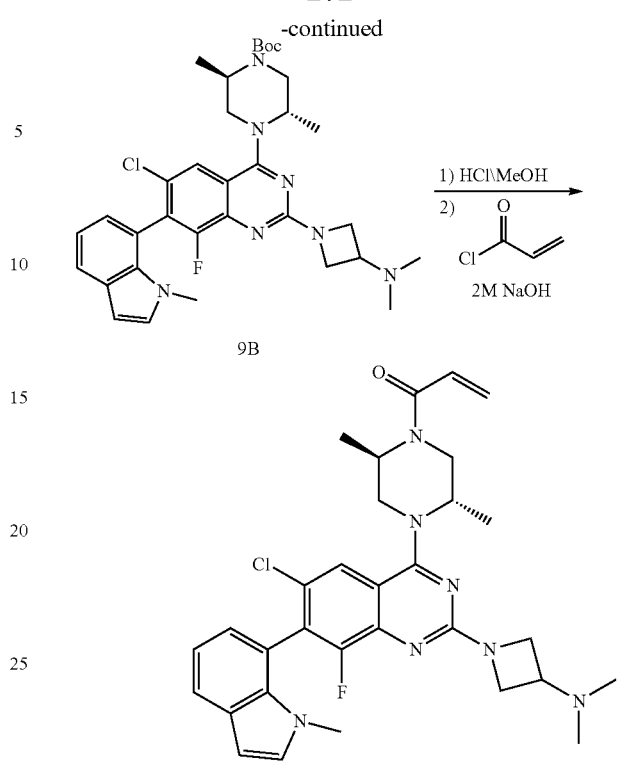

(2R,5S)-tert-butyl 4-(6-chloro-2-(3-(dimethylamino)azetidin-1-yl)-8-fluoro-7-(1H-indol-7-yl)quinazolin-4-yl)-2,5-dimethylpiperazine-1-carboxylate (9A)

To a solution of 2F (180 mg, 0.315 mmol) in dioxane (4 mL) and H₂O (1 mL), 7-(4,4,5,5-tetramethyl-1,3,2-dioxaborolan-2-yl)-1H-indole (76 mg, 0.945 mmol), Pd(PPh₃)₄ (36 mg, 0.03 mmol) and Na₂CO₃ (133 mg, 1.26 mmol) were added. The mixture was purged with nitrogen and stirred at 120° C. for 16 h. The mixture was diluted with water and extracted with EA. The organic layer was dried over sodium sulfate and concentrated in vacuo. The residue was purified by flash column chromatography on silica gel (0-10% methanol in DCM) to afford the desired product (150 mg, 78.4% yield). ESI-MS m/z: 608.5 [M+H]⁺.

(2R,5S)-tert-butyl 4-(6-chloro-2-(3-(dimethylamino)azetidin-1-yl)-8-fluoro-7-(1-methyl-1H-indol-7-yl)quinazolin-4-yl)-2,5-dimethylpiperazine-1-carboxylate (9B)

To a stirred solution of (2R,5S)-tert-butyl 4-(6-chloro-2-(3-(dimethylamino)azetidin-1-yl)-8-fluoro-7-(1H-indol-7-yl)quinazolin-4-yl)-2,5-dimethylpiperazine-1-carboxylate (150 mg, 0.25 mmol) in DMF (5 mL) in DMF at 0° C., was added NaH (20 mg, 0.49 mmol, 60%). The mixture was stirred for 30 min and then MeI (38 mg, 0.271 mmol) was added to the mixture. The mixture was stirred for another 30 min at 0° C. The mixture was poured into ice water, extracted with EA and water. The solvent was removed and the residue was used directly in the next step (150 mg). ESI-MS m/z: 621.4 [M+H]⁺.

1-((2R,5S)-4-(6-chloro-2-(3-(dimethylamino)azetidin-1-yl)-8-fluoro-7-(1-methyl-1H-indol-7-yl)quinazolin-4-yl)-2,5-dimethylpiperazin-1-yl)prop-2-en-1-one (9C)

A solution of (2R,5S)-tert-butyl 4-(6-chloro-2-(3-(dimethylamino)azetidin-1-yl)-8-fluoro-7-(1-methyl-1H-indol-7-yl)quinazolin-4-yl)-2,5-dimethylpiperazine-1-carboxylate (150 mg, 0.24 mmol) in HCl\MeOH (5 mL) was stirred at RT for 1 h. The solvent was removed, the residue was dissolved in THF (3 mL) and cooled to 0° C. To this mixture, 2M NaOH (3 mL) was added followed by acryloyl chloride (109 mg, 1.2 mmol). The mixture was stirred for 30 min, extracted by EA and washed with water. The organic layer was dried and concentrated in vacuo. The residue was purified by flash column chromatography on silica gel (0-10% methanol in DCM) followed by prep-TLC to give the desire product (14 mg, 10% yield) ESI-MS m/z: 576.3 [M+H]$^+$; $^1$HNMR (400 MHz, DMSO-$d_6$): δ 7.76-7.74 (m, 1H), 7.67-7.65 (m, 1H), 7.30 (m, 1H), 7.15-7.11 (m, 1H), 6.97-6.93 (m, 1H), 6.84-6.78 (m, 1H), 6.53-6.52 (m, 1H), 6.21-6.16 (m, 1H), 5.76-5.72 (m, 1H), 4.74-4.46 (m, 2H), 4.12-4.09 (m, 2H), 3.88-3.85 (m, 4H), 3.32-3.30 (m, 3H), 3.13 (m, 1H), 2.12 (s, 6H), 1.32-1.24 (m, 6H).

Example 10

Synthesis of 1-((2R,5S)-4-(6-chloro-7-(1,6-dimethyl-1H-indazol-7-yl)-8-fluoro-2-(((S)-4-methylmorpholin-2-yl)methoxy)quinazolin-4-yl)-2,5-dimethylpiperazin-1-yl)prop-2-en-1-one

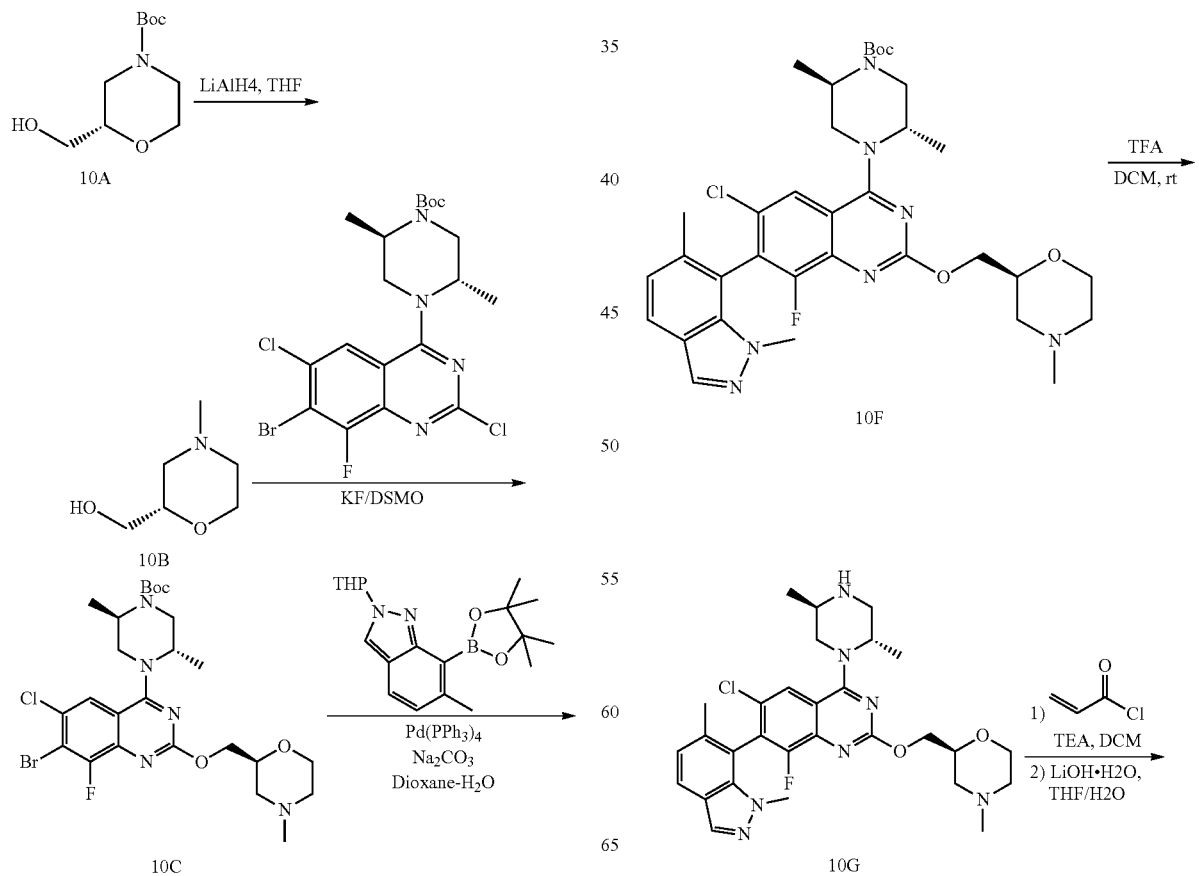

-continued

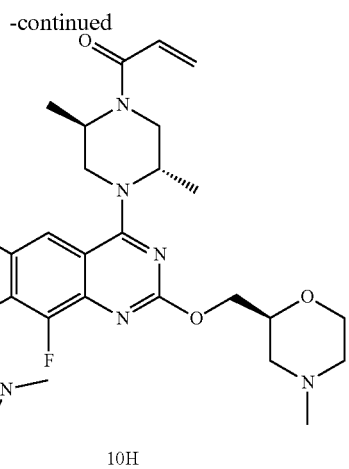

10H

Example 10 provides an exemplary procedure according to General Method D.

(S)-(4-methylmorpholin-2-yl)methanol (10B)

A mixture of compound 10A (500 mg, 2.3 mmol) in THF (20 mL) at 0° C., was added LiAlH$_4$ (524 mg, 13.8 mmol) and the resulting mixture was stirred at reflux for 16 h. Water (5 mL) was added. The mixture was filtered and the filtrate was dried over Na$_2$SO$_4$ and concentrated in vacuo to afford the desired product (290 mg, 96% yield). ESI-MS m/z: 133.25 [M+H]$^+$.

(2R,5S)-tert-butyl-4-(7-bromo-6-chloro-8-fluoro-2-(((S)-4-methylmorpholin-2-yl)methoxy)quinazolin-4-yl)-2,5-dimethylpiperazine-1-carboxylate (10C)

A mixture of compound 10B (374 mg, 0.736 mmol) in DMSO (20 mL) at RT, (S)-(4-methylmorpholin-2-yl)methanol (290 g, 2.21 mmol) and KF (342 g, 5.88 mmol) were added and the resulting mixture was stirred at 120° C. under nitrogen for 16 h. The mixture was poured to ice water and then extracted with EA. The organic layer was washed with brine, dried over Na$_2$SO$_4$ and concentrated in vacuo. The residue was purified by flash column chromatography on silica gel (DCM: CH$_3$OH=60:1) to afford the desired product (253 mg, 57% yield).

(2R,5S)-tert-butyl-4-(6-chloro-8-fluoro-7-(6-methyl-2-(tetrahydro-2H-pyran-2-yl)-2H-indazol-7-yl)-2-(((S)-4-methylmorpholin-2-yl)methoxy)quinazolin-4-yl)-2,5-dimethylpiperazine-1-carboxylate (10D)

To a solution of 10C (500 mg, 0.83 mmol) in 1,4-dioxane/H$_2$O (16 mL/4 mL) at RT, 6-methyl-2-(tetrahydro-2H-pyran-2-yl)-7-(4,4,5,5-tetramethyl-1,3,2-dioxaborolan-2-yl)-2H-indazole (369 mg, 1.078 mmol), Tetrakis(triphenylphosphine) palladium (96 mg, 0.083 mmol) and Na$_2$CO$_3$ (264 mg, 2.49 mmol) were added and the resulting mixture was stirred at 100° C. under nitrogen overnight. The mixture was partitioned between water and ethyl acetate. The organic layer was dried over anhydrous Na$_2$SO$_4$, filtered and concentrated in vacuo. The residue was purified by flash column chromatography on silica gel to afford the desired product (499 mg, 81.7% yield).

(2R,5S)-tert-butyl-4-(6-chloro-8-fluoro-7-(6-methyl-2H-indazol-7-yl)-2-(((S)-4-methylmorpholin-2-yl)methoxy)quinazolin-4-yl)-2,5-dimethylpiperazine-1-carboxylate (10E)

To a stirred solution of 10D (499 mg, 0.68 mmol) in CH$_3$OH (15 mL) at RT, PPTs (511 mg, 2.03 mmol) was added and the resulting mixture was stirred at reflux for 3 h. The mixture was concentrated in vacuo. The residue was partitioned between saturated NaHCO$_3$ aqueous solution and ethyl acetate. The organic layer was washed with brine, dried over Na$_2$SO$_4$ and concentrated in vacuo. The residue was purified by flash column chromatography on silica gel (DCM:CH$_3$OH=40:1) to afford the desired product (395 mg, 89% yield).

(2R,5S)-tert-butyl-4-(6-chloro-7-(1,6-dimethyl-1H-indazol-7-yl)-8-fluoro-2-(((S)-4-methylmorpholin-2-yl)methoxy)quinazolin-4-yl)-2,5-dimethylpiperazine-1-carboxylate (10F)

To a stirred solution of 10E (180 mg, 0.28 mmol) in DMF (15 mL) at 0° C., NaH (22 mg, 0.55 mmol) was added and the resulting mixture was stirred for 30 min. CH$_3$I (47 mg, 0.33 mmol) was added and then the mixture was stirred at 0° C. for 30 min. The mixture was poured into ice water, and extracted with EA. The organic layer was washed with brine, dried over Na$_2$SO$_4$ and concentrated in vacuo to afford the desired product (180 mg, 97.8% yield). ESI-MS m/z: 668.35 [M+H]$^+$.

6-chloro-7-(1,6-dimethyl-1H-indazol-7-yl)-4-((2S,5R)-2,5-dimethylpiperazin-1-yl)-8-fluoro-2-(((S)-4-methylmorpholin-2-yl)methoxy)quinazoline (10G)

To a stirred solution of 10F (153 mg, 0.17 mmol) in DCM (8 ml) at RT, CF$_3$COOH (2 mL) was added and the resulting mixture was stirred at RT for 1.5 h. The mixture was concentrated in vacuo and the residue was extracted by ethyl acetate. The organic layer was washed with NaHCO$_3$ and brine, dried over Na$_2$SO$_4$, filtered and concentrated in vacuo to afford the desired product (150 mg) which was used in the next step without purification.

1-((2R,5S)-4-(6-chloro-7-(1,6-dimethyl-1H-indazol-7-yl)-8-fluoro-2-(((S)-4-methylmorpholin-2-yl)methoxy)quinazolin-4-yl)-2,5-dimethylpiperazin-1-yl)prop-2-en-1-one (10H)

To a stirred solution of 10G (150 mg, 0.26 mmol) in DCM (10 mL) at 0° C., Et$_3$N (80 mg, 0.79 mmol) was added followed by acryloyl chloride (36 mg, 0.4 mmol). The resulting mixture was slowly warmed to RT under stirring. The mixture was partitioned between water and DCM. The organic layer was concentrated in vacuo. The residue was dissolved in THF and water, LiOH—H2O (89 mg, 2.11 mmol) was added and the resulting mixture was stirred at RT for 20 min. The mixture was partitioned between water and ethyl acetate. The organic layer was dried over Na$_2$SO$_4$, filtered and concentrated in vacuo. The residue was purified by flash column chromatography on silica gel (DCM/MeOH=30:1) to afford the desired product (56 mg, 34.1% yield). ESI-MS m/z: 622.40 [M+H]$^+$; $^1$HNMR (400 MHz, DMSO-d6): δ 8.09 (s, 1H), 8.01-8.02 (m, 1H), 7.80-7.82 (d, J=8.4 Hz, 1H), 7.20-7.22 (d, J=8.4 Hz, 1H), 6.79-6.89 (m, 1H), 6.17-6.22 (m, 1H), 5.74-5.78 (m, 1H), 4.79-4.80 (m, 2H), 4.33-4.39 (m, 2H), 4.09-4.18 (m, 2H), 3.82-3.90 (m, 3H), 3.44-3.58 (m, 4H), 2.82-2.83 (m, 1H), 2.65-2.68 (m, 1H). 2.24 (m, 3H), 2.17 (m, 3H), 2.00-2.02 (m, 2H), 1.20-1.33 (m, 8H).
Example 11
Synthesis of 1-((2R,5S)-4-(6-chloro-7-(3, 5-dimethyl-1H-indazol-4-yl)-8-fluoro-2(((R)-4-methylmorpholin-2-yl)methoxy)quinazolin-4-yl)-2, 5-dimethylpiperazin-1-yl)prop-2-en-1-one (Compound
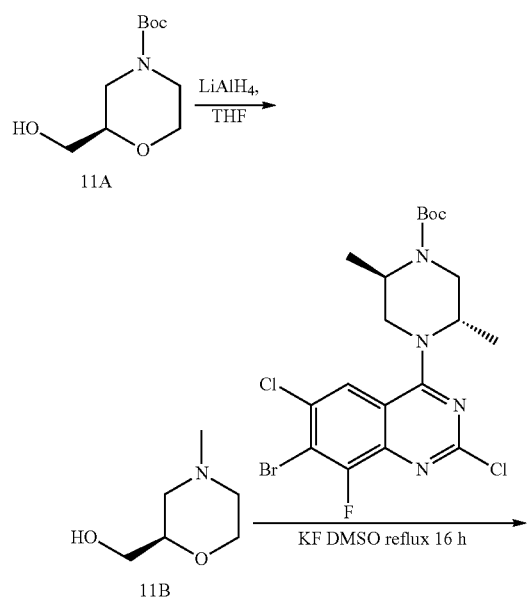
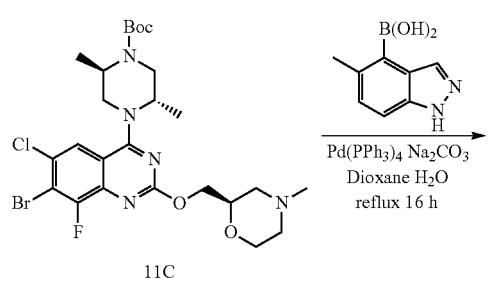
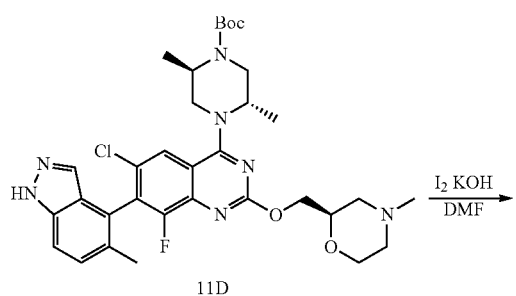
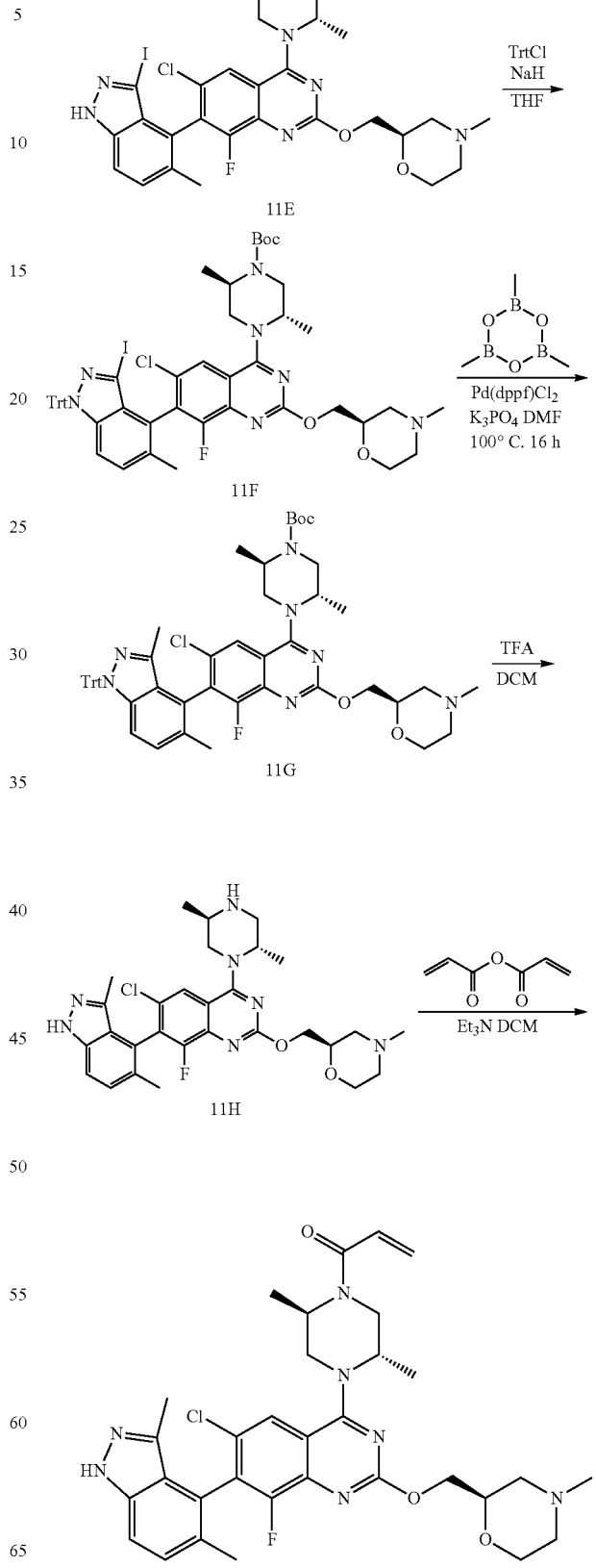

tert-butyl (R)-2-(hydroxymethyl)morpholine-4-carboxylate (11B)

To a solution of 11A (3.0 g, 13.8 mmol) in THF (30 mL) at −20° C. under argon, LiAlH$_4$ (1.5 g, 41.4 mmol) was added and the resulting mixture was stirred at −20° C. for 20 min and then stirred at reflux for 3 h. The mixture was cooled to −20° C., water (1 mL) was added slowly, NaOH (15%, 1 mL) was added slowly, water (3 mL) was added slowly and stirring was continued for 15 min. The mixture was dried over magnesium sulfate, filtered and concentrated in vacuo to afford the desired product 11B. ESI-MS m/z: 131.17 [M+H]$^+$. The crude product 11B was used in the next step without further purification.

tert-butyl(2R,5S)-4-(7-bromo-6-chloro-8-fluoro-2-(((R)-4-methylmorpholin-2-yl)methoxy)quinazolin-4-yl)-2,5-dimethylpiperazine-1-carboxylate (11C)

To a mixture of compound tert-butyl (2R,5S)-4-(7-bromo-2,6-dichloro-8-fluoroquinazolin-4-yl)-2,5-dimethylpiperazine-1-carboxylate (3.16 g, 6.22 mmol) in DMSO (20 mL) at RT, compound 11B (1.63 g, 12.43 mmol) and KF (2.89 g, 49.72 mmol) were added and the resulting mixture was stirred at 120° C. under argon for 16 h. The mixture was poured into ice water. The mixture was extracted with EA. The organic layer was washed with brine, dried over Na$_2$SO$_4$ and concentrated in vacuo. The residue was purified by flash column chromatography on silica gel to afford the desired product 11C (1.82 g, 48.5% yield). ESI-MS m/z: 602.8 [M+H]$^+$.

tert-butyl(2R,5S)-4-(6-chloro-8-fluoro-7-(5-methyl-1H-indazol-4-yl)-2-(((R)-4-methylmorpholin-2-yl)methoxy)quinazolin-4-yl)-2,5-dimethylpiperazine-1-carboxylate (11D)

To a solution of 11C (1.22 g, 2.02 mmol) in 1,4-dioxane/H$_2$O (20 mL/5 mL) at RT, 5-methyl-1H-indazol-4-ylboronic acid (1.78 g, 10.12 mmol), Tetrakis (triphenylphosphine) palladium (233.3 mg, 0.20 mmol) and Na$_2$CO$_3$ (1.07 g, 10.12 mmol) were added and the resulting mixture was at 100° C. under argon overnight. The mixture was partitioned between water and ethyl acetate. The organic layer was dried over anhydrous Na$_2$SO$_4$, filtered and concentrated in vacuo. The residue was purified by flash column chromatography on silica gel to afford the desired product 11D (1.0 g, 75.7% yield). ESI-MS m/z: 654 [M+H]$^+$.

tert-butyl(2R,5S)-4-(6-chloro-8-fluoro-7-(3-iodo-5-methyl-1H-indazol-4-yl)-2-(((R)-4-methylmorpholin-2-yl)methoxy)quinazolin-4-yl)-2,5-dimethylpiperazine-1-carboxylate (11E)

To a stirred solution of 11D (1.0 g, 1.53 mmol) in DMF (20 mL) at 0° C., 4N KOH (342.7 mg, 6.12 mmol) was added and the resulting mixture was stirred at RT for 10 min. I$_2$ (777.2 mg, 3.06 mmol) was added and then stirred at RT for 2 h. 50 mL of water was added to the mixture. The solid was collected by filtration and rinsed with water. The collected solid was dissolved in 50 mL of DCM, dried over Na$_2$SO$_4$ and concentrated in vacuo to afford the desired product 11E (800 mg, 67.3% yield). ESI-MS m/z: 780 [M+H]$^+$.

tert-butyl (2R,5S)-4-(6-chloro-8-fluoro-7-(3-iodo-5-methyl-1-trityl-1H-indazol-4-yl)-2-(((R)-4-methylmorpholin-2-yl)methoxy)quinazolin-4-yl)-2,5-dimethylpiperazine-1-carboxylate (11F)

To a stirred solution of 11E (800 mg, 1.03 mmol) in THF (20 mL) at 0° C., NaH (82.4 mg, 2.06 mmol) was added and the resulting mixture was stirred at RT for 0.5 h. TrtCl (574.3 mg, 2.06 mmol) was added and then the mixture was stirred at RT overnight. 50 mL of water was added to the mixture and then extracted with EA. The organic layer was washed with brine, dried over Na$_2$SO$_4$ and concentrated in vacuo. The residue was purified by flash column chromatography on silica gel to afford the desired product 11F (220 mg, 20.9% yield). ESI-MS m/z: 1022.4 [M+H]$^+$.

tert-butyl(2R,5S)-4-(6-chloro-7-(3,5-dimethyl-1-trityl-1H-indazol-4-yl)-8-fluoro-2-(((R)-4-methylmorpholin-2-yl)methoxy)quinazolin-4-yl)-2,5-dimethylpiperazine-1-carboxylate (11G)

To a solution of 11F (220 mg, 0.22 mmol), 2,4,6-trimethyl-1,3,5,2,4,6-trioxatriborinane (162 mg, 0.65 mmol), K$_3$PO$_4$ (228 mg, 1.08 mmol) in DMF (4 mL), was added Pd(dppf)Cl$_2$ (15.7 mg, 0.022 mmol) and the resulting mixture was stirred at 100° C. under argon for 16 h. The mixture was poured to ice water and extracted with EA. The organic layer was washed with brine, dried over Na$_2$SO$_4$ and concentrated in vacuo to afford the desired product 11G (120 mg, 61.4% yield). ESI-MS m/z: 910 [M+H]$^+$.

(2R)-2-(((6-chloro-7-(3,5-dimethyl-1H-indazol-4-yl)-4-((2S,5R)-2,5-dimethylpiperazin-1-yl)-8-fluoroquinazolin-2-yl)oxy)methyl)-4-methylmorpholine (11H)

To a stirred solution of 11G (120 mg, 0.13 mmol) in DCM (6 mL) at RT, CF$_3$COOH (3 mL) was added and the resulting mixture was stirred at RT for 1 h. The mixture was concentrated in vacuo. The residue was extracted with EA (2×50 mL), washed with NaHCO$_3$ and brine, dried over Na$_2$SO$_4$ and concentrated in vacuo to afford the desired product 11H (70 mg) which was used in the next step without purification.

1-((2R,5S)-4-(6-chloro-7-(3,5-dimethyl-1H-indazol-4-yl)-8-fluoro-2-(((R)-4-methylmorpholin-2-yl)methoxy)quinazolin-4-yl)-2,5-dimethylpiperazin-1-yl)prop-2-en-1-one (11I)

To a stirred solution of 11H (70 mg, 0.123 mmol) in DCM (10 ml) was added Et$_3$N (66 mg, 0.66 mmol) and cooled to 0° C., acrylic anhydride (18.1 mg, 0.144 mmol) was added. The reaction mixture was then slowly warmed to RT. LC-MS shows no SM left. Quenched with NaHCO$_3$ (10 ml), extracted with EtOAc washed with water, dried over Na$_2$SO$_4$, concentrated purified by flash column chromatography on silica gel (DCM/MeOH=10:1) to afford the desired product 11I (13 mg), ESI-MS m/z: 622.1 [M+H]$^+$.

Example 12

Synthesis of 1-((2R,5S)-4-(6-chloro-2-(3-(dimethylamino)azetidin-1-yl)-7-(3-(ethylamino)-5-methyl-1H-indazol-4-yl)-8-fluoroquinazolin-4-yl)-2,5-dimethylpiperazin-1-yl)prop-2-en-1-one

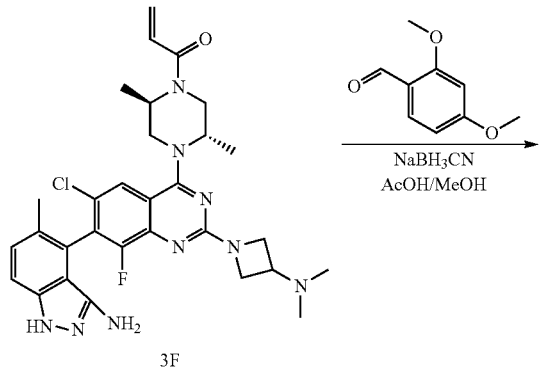

3F

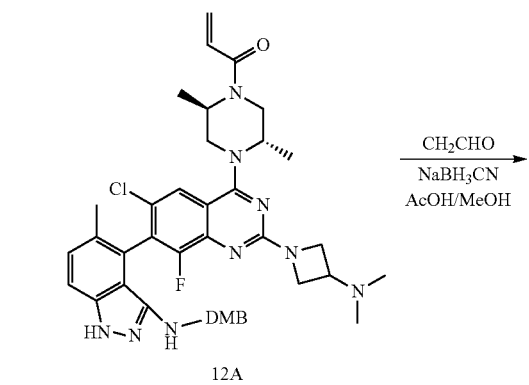

12A

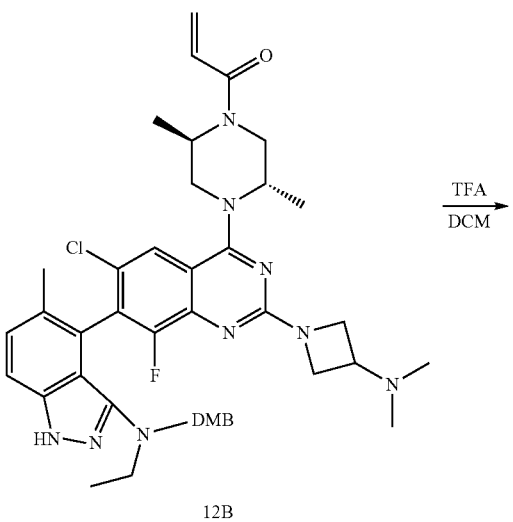

12B

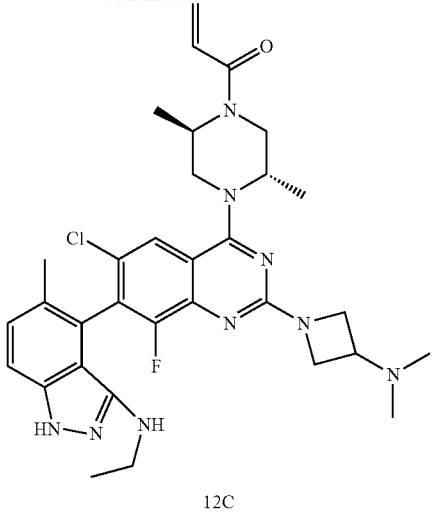

12C

1-((2R,5S)-4-(6-chloro-2-(3-(dimethylamino)azetidin-1-yl)-7-(3-((3,4-dimethylbenzyl)amino)-5-methyl-1H-indazol-4-yl)-8-fluoroquinazolin-4-yl)-2,5-dimethylpiperazin-1-yl)prop-2-en-1-one (12A)

To a solution of compound 3F (100 mg, 0.17 mmol) in MeOH (6 mL) at RT, 2,4-dimethoxybenzaldehyde (30 mg, 0.18 mmol) and AcOH (0.1 mL) were added and the resulting mixture was stirred at 50° C. for 1 h. NaBH$_3$CN (32 mg, 0.51 mmol) was added at 50° C. The resulting mixture was stirred at 50° C. overnight. The mixture was concentrated in vacuo and the residue was purified by flash column chromatography on silica gel to afford the desired product (120 mg, 90% yield). ESI-MS m/z: 710.4 [M+H]$^+$.

1-((2R,5S)-4-(6-chloro-2-(3-(dimethylamino)azetidin-1-yl)-7-(3-((3,4-dimethylbenzyl)(ethyl)amino)-5-methyl-1H-indazol-4-yl)-8-fluoroquinazolin-4-yl)-2,5-dimethylpiperazin-1-yl)prop-2-en-1-one (12B)

To a solution of compound 12A (70 mg, 0.094 mmol) in MeOH (6 mL) at RT, CH$_3$CHO (15 mg, 0.14 mmol, 40% in water), AcOH (0.1 mL) and NaBH$_3$CN (17 mg) were added and the resulting mixture was stirred at 60° C. overnight. The residue was concentrated in vacuo to afford the desired product 12B (68 mg, 94% yield). ESI-MS m/z: 772.5 [M+H]$^+$.

1-((2R,5S)-4-(6-chloro-2-(3-(dimethylamino)azetidin-1-yl)-7-(3-(ethylamino)-5-methyl-1H-indazol-4-yl)-8-fluoroquinazolin-4-yl)-2,5-dimethylpiperazin-1-yl)prop-2-en-1-one (12C)

To a solution of compound 12B (68 mg, 0.088 mmol) in DCM (3 mL) at RT, TFA (3 mL) was added and the resulting mixture was stirred at RT for 1 h. The mixture was concentrated in vacuo. The residue was partitioned between water and ethyl acetate. The organic layer was washed with brine, dried over Na$_2$SO$_4$, filtered and concentrated in vacuo. The residue was purified by flash column chromatography on silica gel to afford the desired product 12C (15 mg, 27% yield). ESI-MS m/z: 620.4 [M+H]$^+$; HNMR (400 MHz, DMSO-d$_6$) δ: 7.76 (s, 1H), 7.43-7.41 (d, 1H), 7.30-7.28 (d, 1H), 6.84-6.77 (m, 1H), 6.21-6.16 (m, 1H), 5.76-5.72 (m, 1H), 5.34-5.31 (m, 1H), 4.75-4.60 (m, 2H), 4.19-3.89 (m, 9H), 2.14 (s, 6H), 2.06-2.04 (d, 3H), 2.01-1.97 (m, 2H), 1.35-1.30 (m, 9H).

Example 13

Synthesis of 1-((2R,5S)-4-(6-chloro-2-(3-(dimethylamino)azetidin-1-yl)-8-fluoro-7-(3-hydroxy-6-methyl-1H-indazol-7-yl)quinazolin-4-yl)-2,5-dimethylpiperazin-1-yl)prop-2-en-1-one

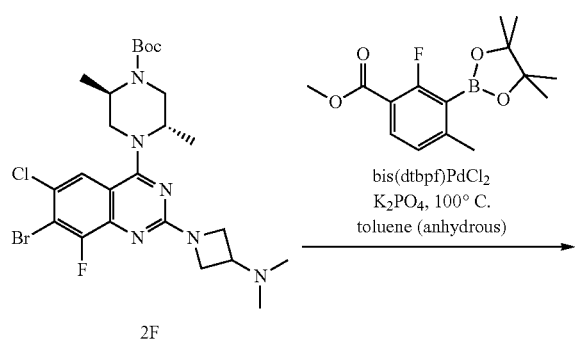

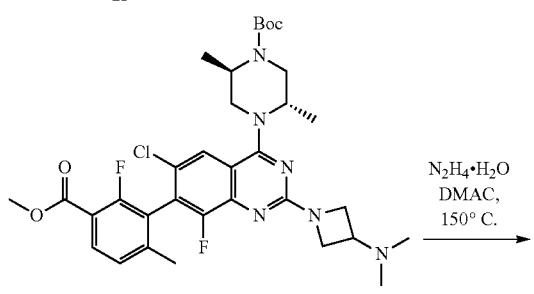

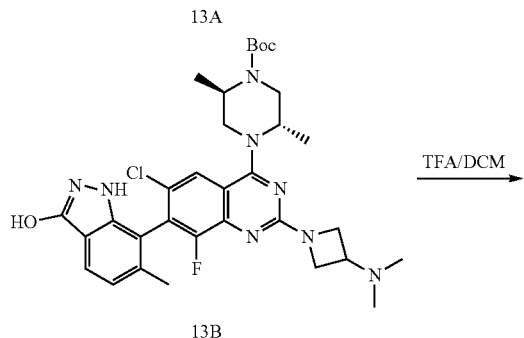

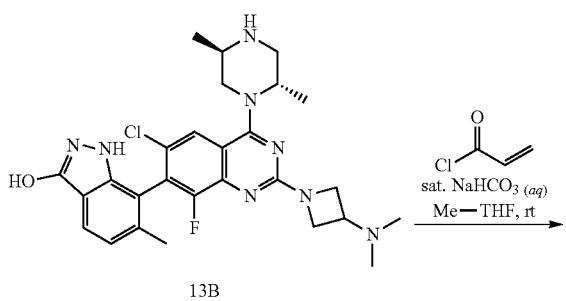

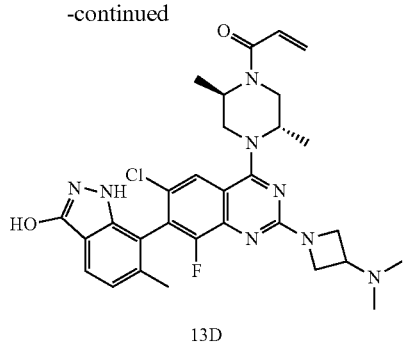

13D tert-Butyl (2R, 5S)-4-(6-chloro-2-[3-(dimethylamino)azetidin-1-yl] 8-fluoro-7-[methyl-2-fluoro-6-methyl-3-benzoate] quinazolin-4-yl)2,5 dimethyl piperazine-1-carboxylate (13A)

The reaction mixture of compound 2F (815 mg, 1.43 mmol), 2-fluoro-4-methyl-3-(4,4,5,5-tetramethyl-[1,3,2]dioxaborolan-2-yl)benzoic acid methyl ester (507 mg, 1.72 mmol) and K$_3$PO$_4$ (1.52 g, 7.14 mmol) in 15 mL of anhydrous toluene was purged with N$_2$ for 5 min, followed by addition of [1,1'-bis(di-tert-butyl phosphino) ferrocene] dichloropalladium (II) (184 mg, 0.28 mmol). The reaction vessel was sealed and the headspace connected to vacuum line for 5 min, before heating conventionally to 100° C. for 10 h. The reaction mixture was filtered, then diluted with water and extracted with EtOAc. The organic layer was combined, dried over Na$_2$SO$_4$, and concentrated in vacuo. The residue was purified via Isolera One Biotage (10% MeOH in DCM/0.0175N NH$_3$) to afford the desired product (401 mg, 43% yield). ESI-MS m/z=659.3 [M+H]$^+$.

tert-Butyl (2R, 5S-4-(6-chloro-8-fluoro-2-[3-(dimethylamino)azetidin-1-yl]-7-[2H-4-hydroxy-7-methyl indazol-1-yl]quinazolin-4-yl)2,5 dimethyl piperazine-1-carboxylate (13B)

To a mixture of compound 13A (259 mg, 0.39 mmol) in 7 mL of DMAC, hydrazine hydrate (55 wt %, 1.8 mL, 19.8 mmol) was added. The reaction mixture was heated to 150° C. with constant stirring for 17 h. The recation mixture was diluted in H$_2$O and extracted with DCM. The organic layers were combined, dried over Na$_2$SO$_4$ and concentrated in vacuo. The residue was purified via Isolera One Biotage ACI instrument (10% MeOH in DCM/0.0175N NH$_3$) to afford the desired product (54 mg, 22% yield). ESI-MS m/z=639.3 [M+H]$^+$.

1H (2R, 5S)-4-(6-chloro-8-fluoro-7-[2H-4-hydroxy-7-methyl indazol-1-yl]-2-[3-(dimethylamino)azetidin-1-yl] quinazolin-4-yl)2,5 dimethyl piperazine (13C)

To a solution of compound 13B (51 mg, 0.079 mmol) in 2 mL of DCM, 2 mL of TFA was added and the resulting mixture was stirred for 30 min. The solvent was removed in vacuo to afford TFA salt of compound 13C, which was used in the next step without purification. ESI-MS m/z=539.2 [M+H]$^+$.

1-((2R, 5S)-4-(6-chloro-2-[3-(dimethylamino)azetidin-1-yl]-8-fluoro-7-[2H-4-hydroxy-7-methyl indazol-1-yl] quinazolin-4-yl)2,5 dimethyl piperazin-1-yl)-prop-2-en-1-one (13D)

To a reaction vessel charged with TFA salt of compound 13C (0.079 mmol), 2 mL of saturated NaHCO$_3$ solution was added to neutralize the acid, followed by 2 mL of Me-THF. To above mixture was added acryloyl chloride (9 mg, 0.099 mmol), and the reaction mixture was stirred at room temperature for 30 min. The reaction mixture was diluted in DCM and washed with H$_2$O. The organic extractions were combined and dried over Na$_2$SO$_4$. The solvent was removed in vacuo, and the residues was purified via Isolera One Biotage (10% MeOH in DCM/0.0175N NH$_3$) to afford the desired product (6.2 mg, 13% yield in two steps). $^1$H NMR (500 MHz, DMSO-d$_6$) δ: 11.11 (s, 1H), 10.53 (s, 1H), 7.76 (s, 1H), 7.60 (d, J=8.3 Hz, 1H), 6.99 (d, J=8.5 Hz, 1H), 6.75-6.90 (m, 1H), 6.18 (d, J=15.0 Hz, 1H), 5.74 (t, J=8.5, 8.0 Hz, 1H), 4.35-4.80 (m, 2H), 3.7-4.20 (m, 8H), 3.45-3.55 (m, 1H), 2.50 (s, 6H), 2.13 (s, 3H), 1.13-1.35 (m, 6H). ESI-MS m/z=593.2 [M+H]$^+$.

Example 14

Comparative Biochemical Data

Representative compounds of embodiments of the invention were tested according to the above procedures and their potency compared to the following compound:

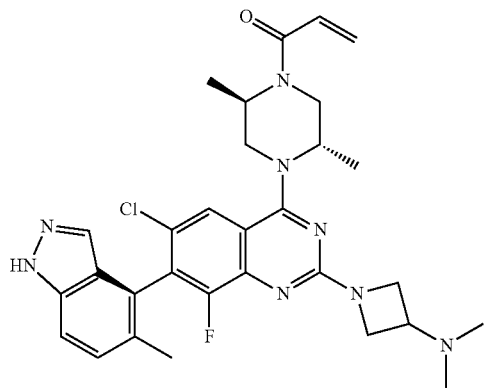

It was found that the above compound had binding activity of 71%, while representative compounds 35, 67, 104, 117, 136, 150 and 154 each had binding activity in excess of 80%.

All of the U.S. patents, U.S. patent application publications, U.S. patent applications, foreign patents, foreign patent applications and non-patent publications referred to in this specification or the attached Application Data Sheet are incorporated herein by reference, in their entirety to the extent not inconsistent with the present description.

From the foregoing it will be appreciated that, although specific embodiments of the invention have been described herein for purposes of illustration, various modifications may be made without deviating from the spirit and scope of the invention. Accordingly, the invention is not limited except as by the appended claims.

The invention claimed is:

1. A compound having one of the following structures:

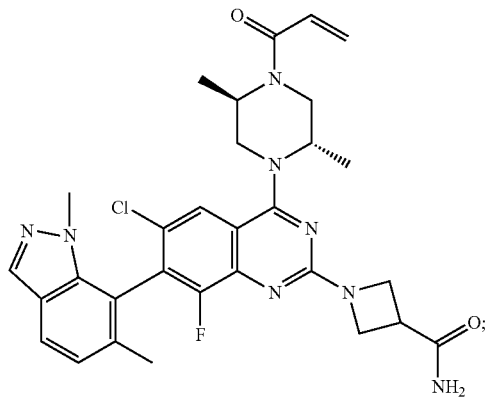

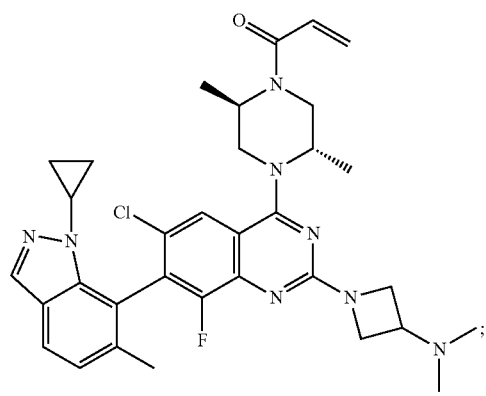

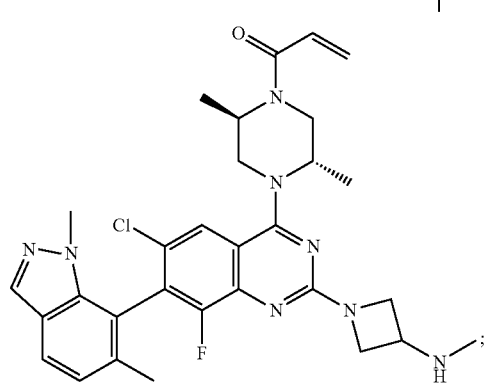

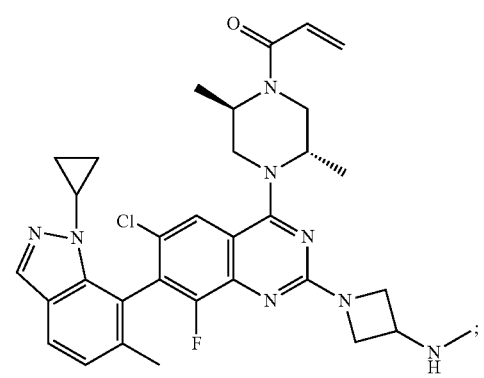

-continued

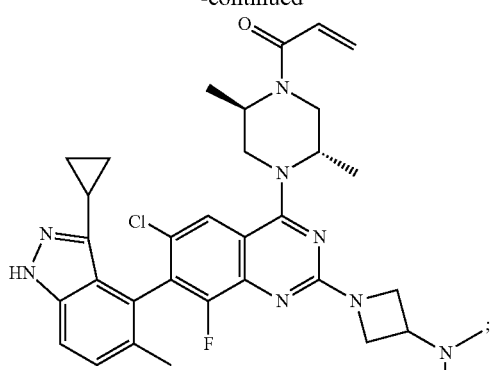

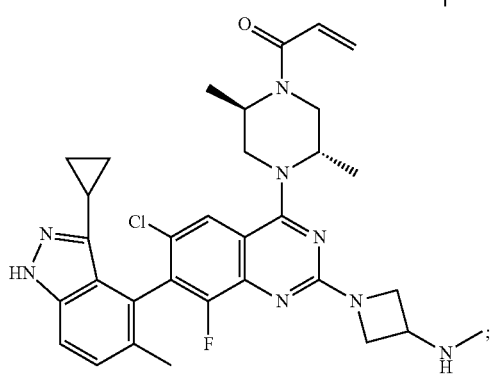

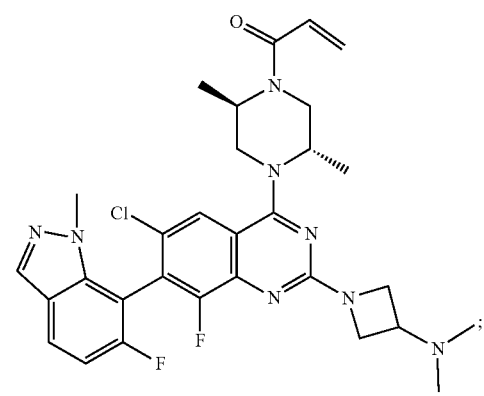

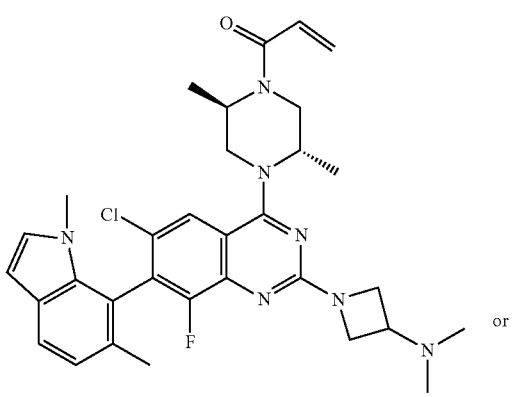

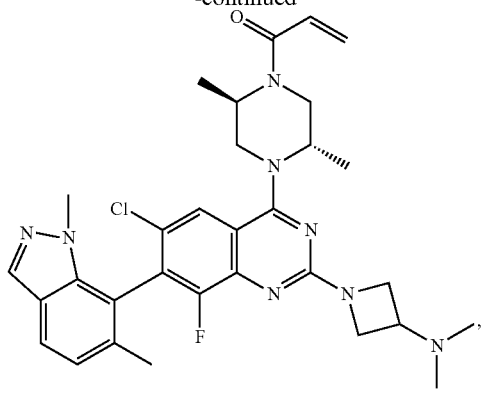

or an atropisomer thereof, or a pharmaceutically acceptable salt of the compound or atropisomer thereof.

2. A pharmaceutical composition comprising a compound of claim 1, or an atropisomer thereof, or a pharmaceutically acceptable salt of the compound or atropisomer thereof, and a pharmaceutically acceptable carrier.

3. The compound of claim 1, having one of the following structures:

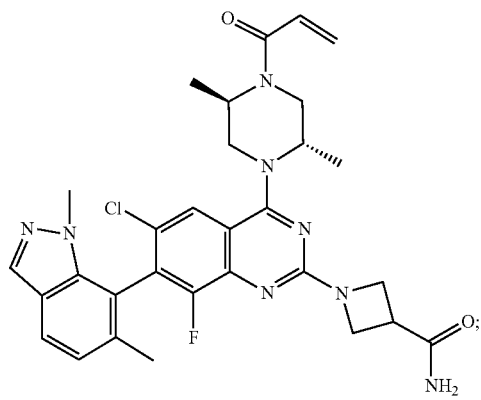

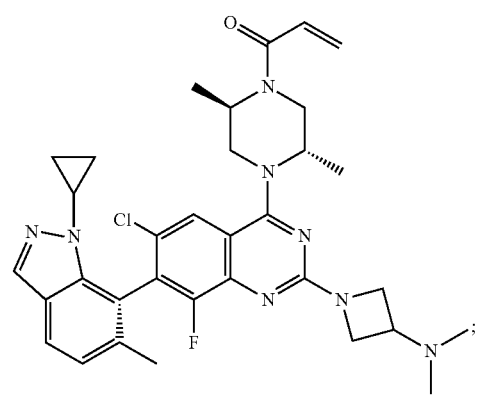

289
-continued
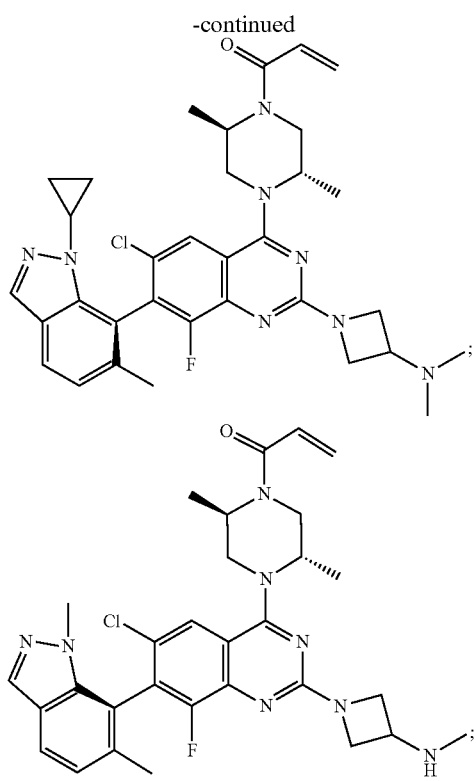
290
-continued
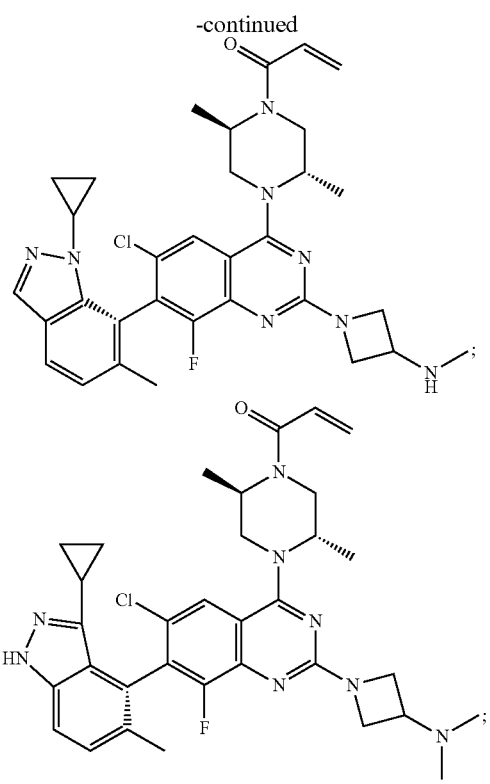
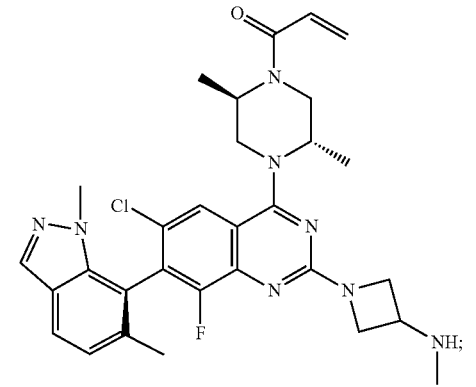
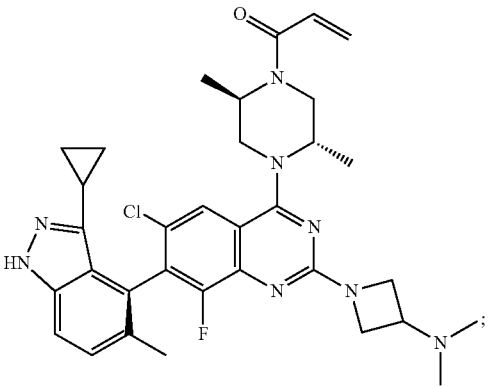
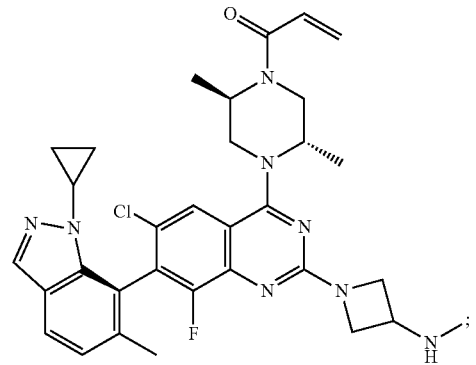
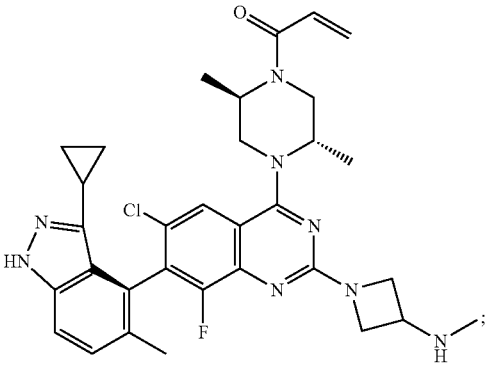

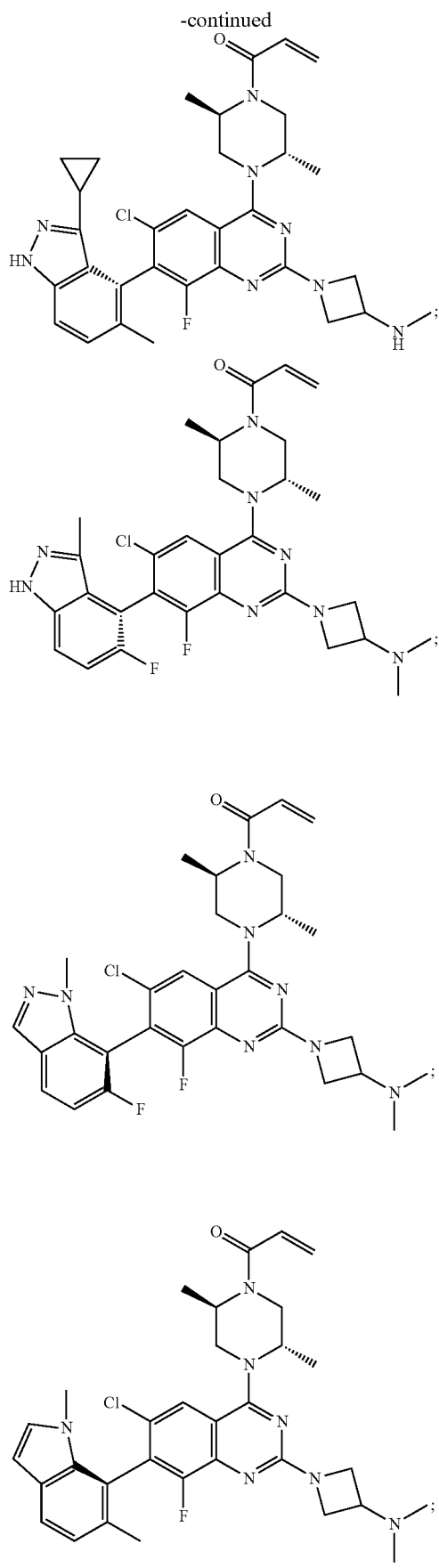
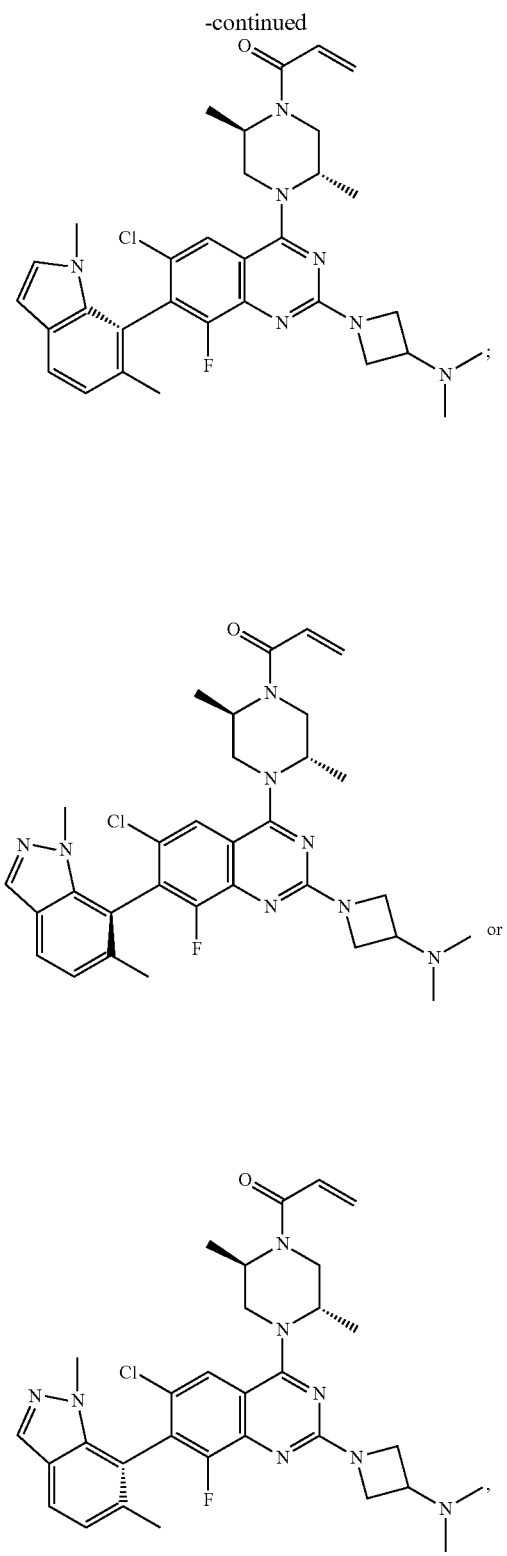
or a pharmaceutically acceptable salt thereof.
4. A pharmaceutical composition comprising a compound of claim 3, or a pharmaceutically acceptable salt thereof, and a pharmaceutically acceptable carrier.
5. The compound of claim 1, having the following structure:

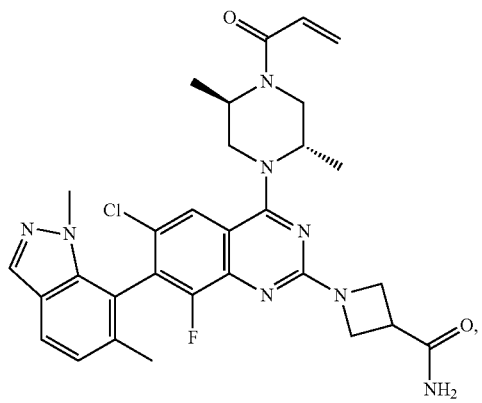 [SMILES: C=CC(=O)N1C[C@H](C)N(c2nc(N3CC(C(N)=O)C3)nc3c(F)c(-c4c(C)ccc5cnn(C)c45)c(Cl)cc23)C[C@H]1C]

or an atropisomer thereof, or a pharmaceutically acceptable salt of the compound or atropisomer thereof.

6. A pharmaceutical composition comprising the compound of claim 5, or an atropisomer thereof, or a pharmaceutically acceptable salt of the compound or atropisomer thereof, and a pharmaceutically acceptable carrier.

7. The compound of claim 1, having the following structure:

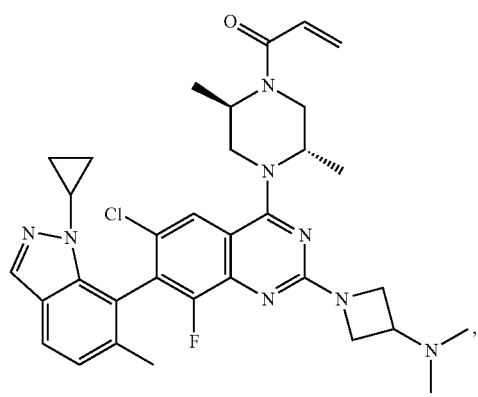 [SMILES: C=CC(=O)N1C[C@H](C)N(c2nc(N3CC(N(C)C)C3)nc3c(F)c(-c4c(C)ccc5cnn(C6CC6)c45)c(Cl)cc23)C[C@H]1C]

or an atropisomer thereof, or a pharmaceutically acceptable salt of the compound or atropisomer thereof.

8. A pharmaceutical composition comprising the compound of claim 7, or an atropisomer thereof, or a pharmaceutically acceptable salt of the compound or atropisomer thereof, and a pharmaceutically acceptable carrier.

9. The compound of claim 1, having the following structure:

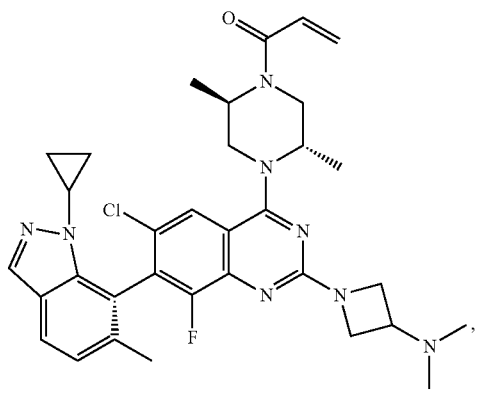

or a pharmaceutically acceptable salt thereof.

10. A pharmaceutical composition comprising the compound of claim 9, or a pharmaceutically acceptable salt thereof, and a pharmaceutically acceptable carrier.

11. The compound of claim 1, having the following structure:

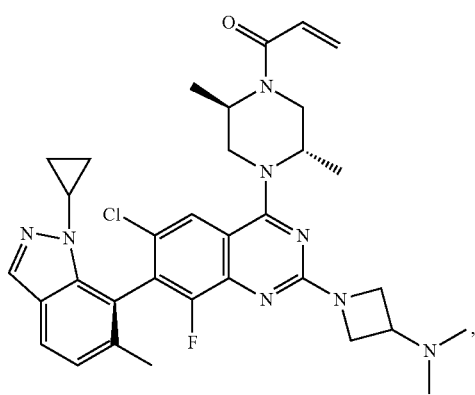

or a pharmaceutically acceptable salt thereof.

12. A pharmaceutical composition comprising the compound of claim 11, or a pharmaceutically acceptable salt thereof, and a pharmaceutically acceptable carrier.

13. The compound of claim 1, having the following structure:

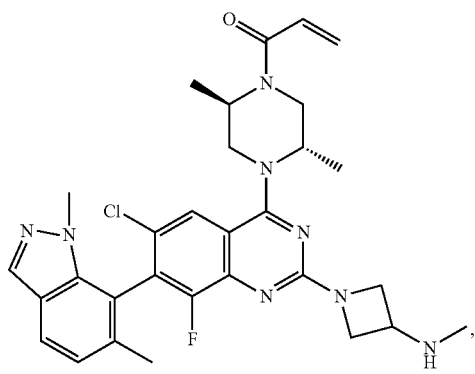 [SMILES: C=CC(=O)N1C[C@H](C)N(c2nc(N3CC(NC)C3)nc3c(F)c(-c4c(C)ccc5cnn(C)c45)c(Cl)cc23)C[C@H]1C]

or an atropisomer thereof, or a pharmaceutically acceptable salt of the compound or atropisomer thereof.

14. A pharmaceutical composition comprising the compound of claim 13, or an atropisomer thereof, or a pharmaceutically acceptable salt of the compound or atropisomer thereof, and a pharmaceutically acceptable carrier.

15. The compound of claim 1, having the following structure:

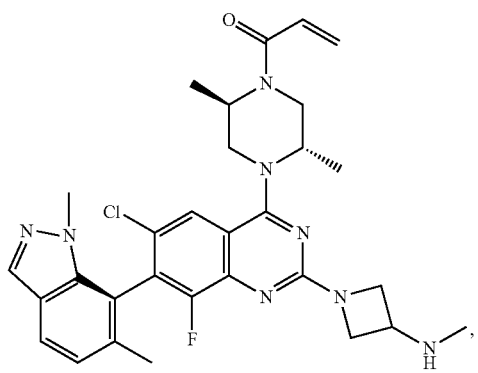

or a pharmaceutically acceptable salt thereof.

16. A pharmaceutical composition comprising the compound of claim 15, or a pharmaceutically acceptable salt thereof, and a pharmaceutically acceptable carrier.

17. The compound of claim 1, having the following structure:

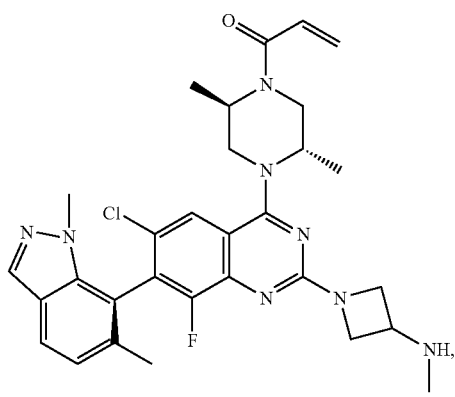

or a pharmaceutically acceptable salt thereof.

18. A pharmaceutical composition comprising the compound of claim 17, or a pharmaceutically acceptable salt thereof, and a pharmaceutically acceptable carrier.

19. The compound of claim 1, having the following structure:

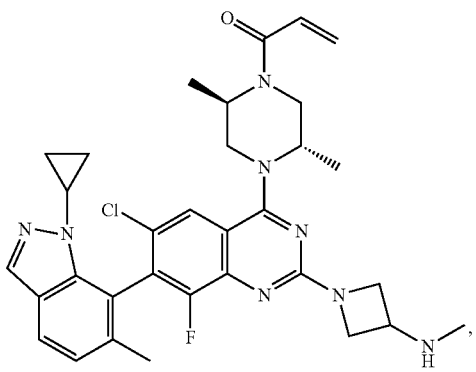 [SMILES: C=CC(=O)N1C[C@H](C)N(c2nc(N3CC(NC)C3)nc3c(F)c(-c4c(C)ccc5cnn(C6CC6)c45)c(Cl)cc23)C[C@H]1C]

or an atropisomer thereof, or a pharmaceutically acceptable salt of the compound or atropisomer thereof.

20. A pharmaceutical composition comprising the compound of claim 19, or an atropisomer thereof, or a pharmaceutically acceptable salt of the compound or atropisomer thereof, and a pharmaceutically acceptable carrier.

21. The compound of claim 1, having the following structure:

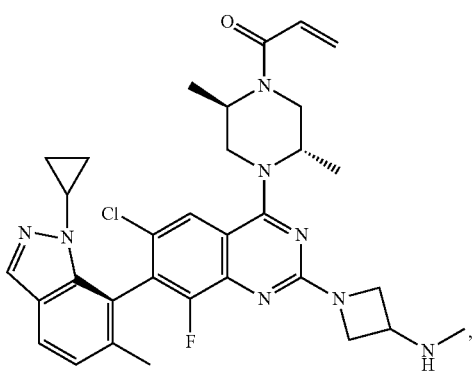

or a pharmaceutically acceptable salt thereof.

22. A pharmaceutical composition comprising the compound of claim 21, or a pharmaceutically acceptable salt thereof, and a pharmaceutically acceptable carrier.

23. The compound of claim 1, having the following structure:

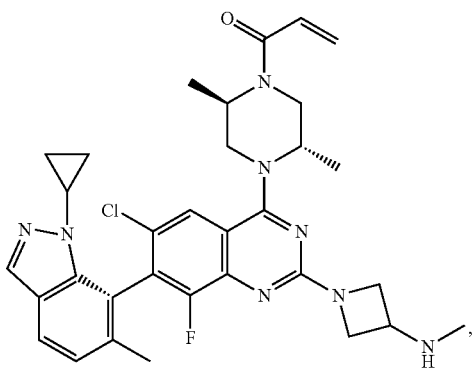

or a pharmaceutically acceptable salt thereof.

24. A pharmaceutical composition comprising the compound of claim 23, or a pharmaceutically acceptable salt thereof, and a pharmaceutically acceptable carrier.

25. The compound of claim 1, having the following structure:

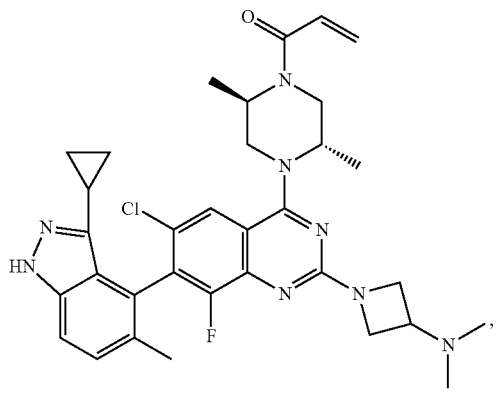 [SMILES: C=CC(=O)N1C[C@H](C)N(c2nc(N3CC(N(C)C)C3)nc3c(F)c(-c4c(C)ccc5[nH]nc(C6CC6)c45)c(Cl)cc23)C[C@H]1C]

or an atropisomer thereof, or a pharmaceutically acceptable salt of the compound or atropisomer thereof.

26. A pharmaceutical composition comprising the compound of claim 25, or an atropisomer thereof, or a pharmaceutically acceptable salt of the compound or atropisomer thereof, and a pharmaceutically acceptable carrier.

27. The compound of claim 1, having the following structure:

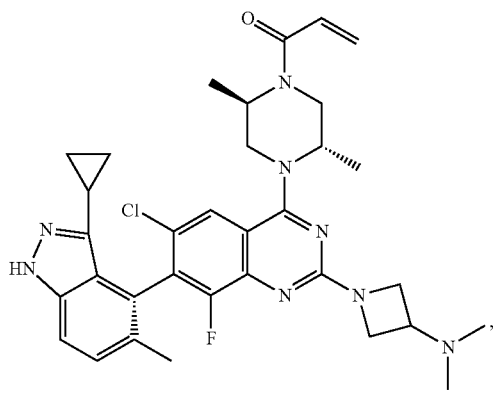

or a pharmaceutically acceptable salt thereof.

28. A pharmaceutical composition comprising the compound of claim 27, or a pharmaceutically acceptable salt thereof, and a pharmaceutically acceptable carrier.

29. The compound of claim 1, having the following structure:

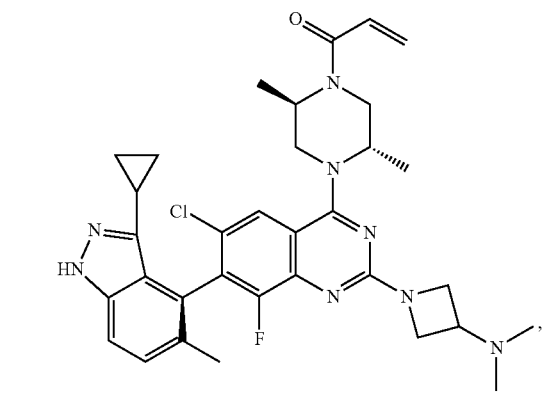

or a pharmaceutically acceptable salt thereof.

30. A pharmaceutical composition comprising the compound of claim 29, or a pharmaceutically acceptable salt thereof, and a pharmaceutically acceptable carrier.

31. The compound of claim 1, having the following structure:

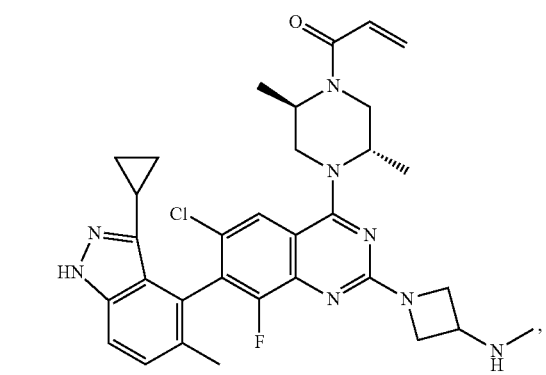 [SMILES: C=CC(=O)N1C[C@H](C)N(c2nc(N3CC(NC)C3)nc3c(F)c(-c4c(C)ccc5[nH]nc(C6CC6)c45)c(Cl)cc23)C[C@H]1C]

or an atropisomer thereof, or a pharmaceutically acceptable salt of the compound or atropisomer thereof.

32. A pharmaceutical composition comprising the compound of claim 31, or an atropisomer thereof, or a pharmaceutically acceptable salt of the compound or atropisomer thereof, and a pharmaceutically acceptable carrier.

33. The compound of claim 1, having the following structure:

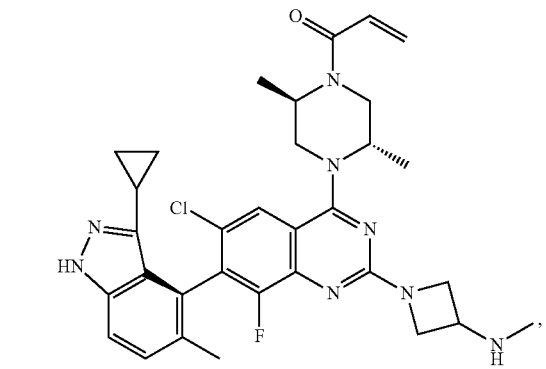

or a pharmaceutically acceptable salt thereof.

34. A pharmaceutical composition comprising the compound of claim 33, or a pharmaceutically acceptable salt thereof, and a pharmaceutically acceptable carrier.

35. The compound of claim 1, having the following structure:

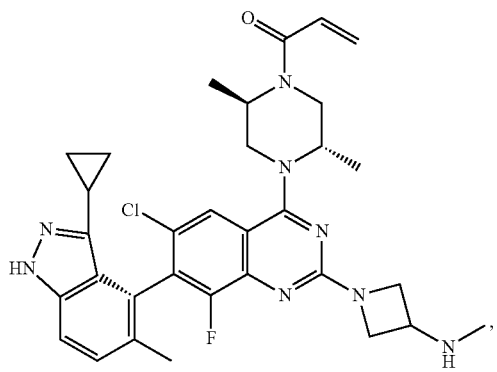

or a pharmaceutically acceptable salt thereof.

36. A pharmaceutical composition comprising the compound of claim 35, or a pharmaceutically acceptable salt thereof, and a pharmaceutically acceptable carrier.

37. The compound of claim 1, having the following structure:

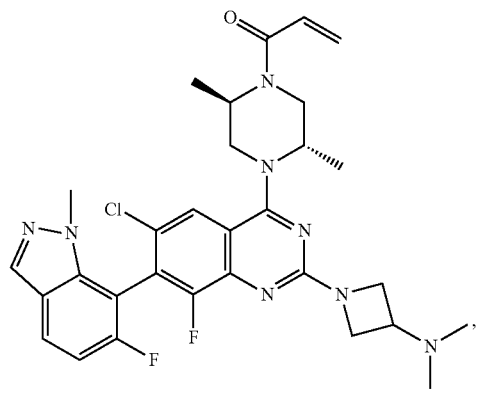 [SMILES: C=CC(=O)N1C[C@H](C)N(c2nc(N3CC(N(C)C)C3)nc3c(F)c(-c4c(F)ccc5cnn(C)c45)c(Cl)cc23)C[C@H]1C]

or an atropisomer thereof, or a pharmaceutically acceptable salt of the compound or atropisomer thereof.

38. A pharmaceutical composition comprising the compound of claim 37, or an atropisomer thereof, or a pharmaceutically acceptable salt of the compound or atropisomer thereof, and a pharmaceutically acceptable carrier.

39. The compound of claim 1, having the following structure:

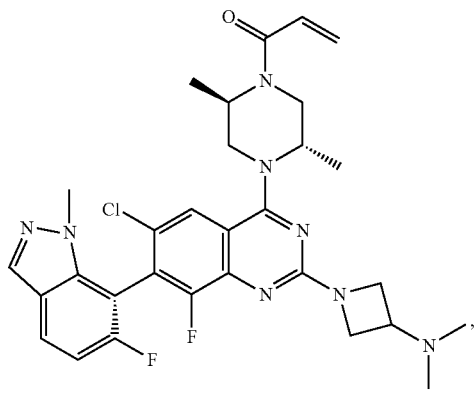

or a pharmaceutically acceptable salt thereof.

40. A pharmaceutical composition comprising the compound of claim 39, or a pharmaceutically acceptable salt thereof, and a pharmaceutically acceptable carrier.

41. The compound of claim 1, having the following structure:

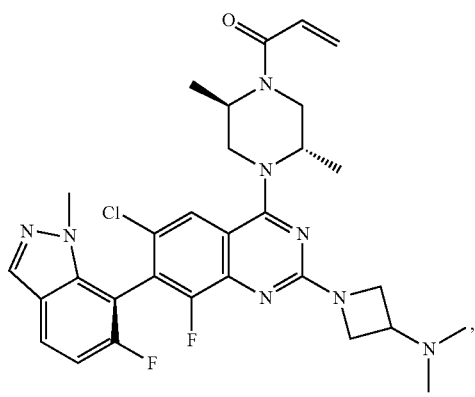

or a pharmaceutically acceptable salt thereof.

42. A pharmaceutical composition comprising the compound of claim 41, or a pharmaceutically acceptable salt thereof, and a pharmaceutically acceptable carrier.

43. The compound of claim 1, having the following structure:

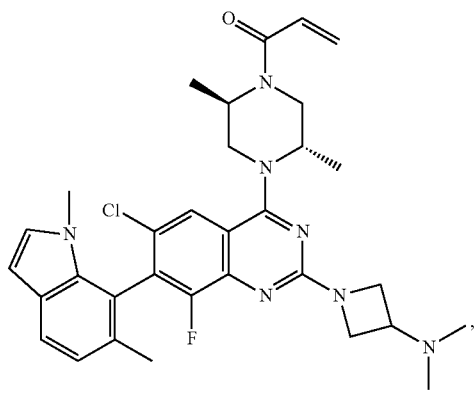 [SMILES: C=CC(=O)N1C[C@H](C)N(c2nc(N3CC(N(C)C)C3)nc3c(F)c(-c4c(C)ccc5ccn(C)c45)c(Cl)cc23)C[C@H]1C]

or an atropisomer thereof, or a pharmaceutically acceptable salt of the compound or atropisomer thereof.

44. A pharmaceutical composition comprising the compound of claim 43, or an atropisomer thereof, or a pharmaceutically acceptable salt of the compound or atropisomer thereof, and a pharmaceutically acceptable carrier.

45. The compound of claim 1, having the following structure:

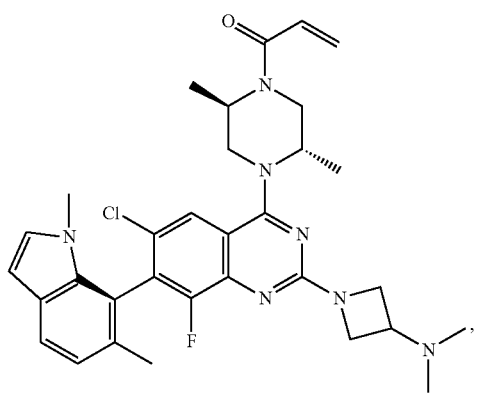

or a pharmaceutically acceptable salt thereof.

46. A pharmaceutical composition comprising the compound of claim 45, or a pharmaceutically acceptable salt thereof, and a pharmaceutically acceptable carrier.

47. The compound of claim 1, having the following structure:

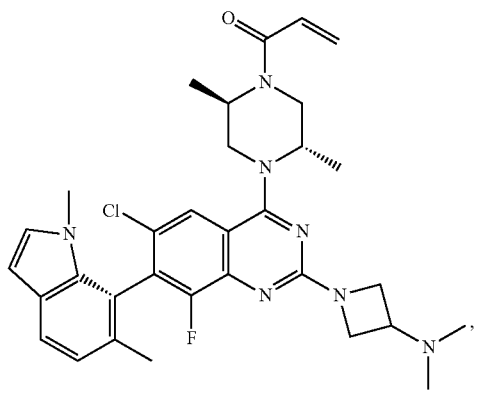

or a pharmaceutically acceptable salt thereof.

48. A pharmaceutical composition comprising the compound of claim 47, or a pharmaceutically acceptable salt thereof, and a pharmaceutically acceptable carrier.

49. The compound of claim 1, having the following structure:

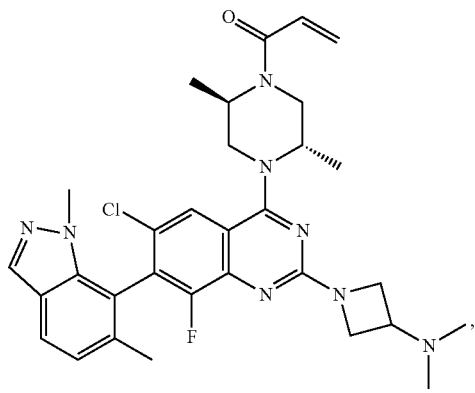 [SMILES: C=CC(=O)N1C[C@H](C)N(c2nc(N3CC(N(C)C)C3)nc3c(F)c(-c4c(C)ccc5cnn(C)c45)c(Cl)cc23)C[C@H]1C]

or an atropisomer thereof, or a pharmaceutically acceptable salt of the compound or atropisomer thereof.

50. A pharmaceutical composition comprising the compound of claim 49, or an atropisomer thereof, or a pharmaceutically acceptable salt of the compound or atropisomer thereof, and a pharmaceutically acceptable carrier.

51. The compound of claim 1, having the following structure:

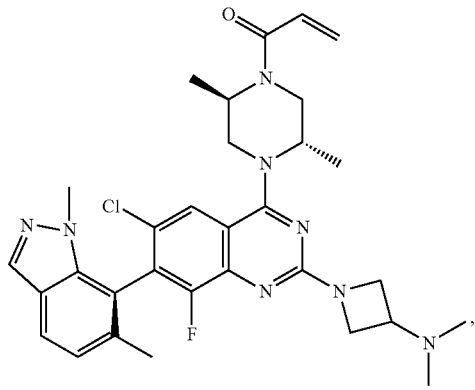

or a pharmaceutically acceptable salt thereof.

52. A pharmaceutical composition comprising the compound of claim 51, or a pharmaceutically acceptable salt thereof, and a pharmaceutically acceptable carrier.

53. The compound of claim 1, having the following structure:

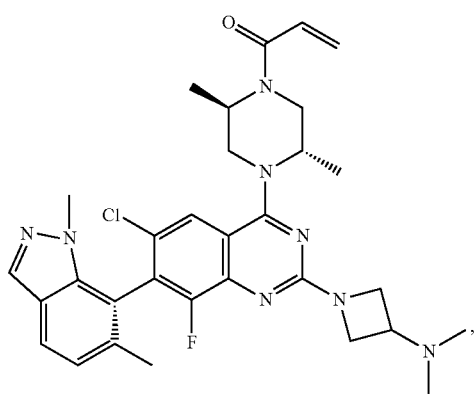

or a pharmaceutically acceptable salt thereof.

54. A pharmaceutical composition comprising the compound of claim 53, or a pharmaceutically acceptable salt thereof, and a pharmaceutically acceptable carrier.

* * * * *